(12) United States Patent
Gramer et al.

(10) Patent No.: US 11,492,371 B2
(45) Date of Patent: *Nov. 8, 2022

(54) PRODUCTION OF HETERODIMERIC PROTEINS

(71) Applicant: GENMAB A/S, Copenhagen V (DK)

(72) Inventors: Michael Gramer, Lino Lakes, MN (US); Amitava Kundu, Maple Grove, MN (US); Ewald T. J. Van Den Bremer, Eindhoven (NL); Muriel Van Kampen, Utrecht (NL); Patrick Priem, Utrecht (NL); Aran Frank Labrijn, Nigtevecht (NL); Joyce I. Meesters, Utrecht (NL); Joost J. Neijssen, Werkhoven (NL); Janine Schuurman, Diemen (NL); Paul Parren, Odijk (NL); Patrick Van Berkel, Utrecht (NL); Werner L. Vos, Utrecht (NL); Arnout F. Gerritsen, Utrecht (NL)

(73) Assignee: GENMAB A/S, Copenhagen V (DK)

( * ) Notice: Subject to any disclaimer, the term of this patent is extended or adjusted under 35 U.S.C. 154(b) by 58 days.

This patent is subject to a terminal disclaimer.

(21) Appl. No.: 16/426,647

(22) Filed: May 30, 2019

(65) Prior Publication Data

US 2020/0048304 A1 Feb. 13, 2020

Related U.S. Application Data

(63) Continuation of application No. 14/353,962, filed as application No. PCT/EP2012/071294 on Oct. 26, 2012, now Pat. No. 10,344,050.

(60) Provisional application No. 61/552,272, filed on Oct. 27, 2011.

(30) Foreign Application Priority Data

Oct. 27, 2011 (DK) .............................. PA201100826

(51) Int. Cl.
*C07K 1/113* (2006.01)
*C07K 16/28* (2006.01)
*C07K 16/46* (2006.01)

(52) U.S. Cl.
CPC ........ *C07K 1/1133* (2013.01); *C07K 16/2863* (2013.01); *C07K 16/2887* (2013.01); *C07K 16/468* (2013.01); *C07K 2317/24* (2013.01); *C07K 2317/31* (2013.01); *C07K 2317/41* (2013.01); *C07K 2317/524* (2013.01); *C07K 2317/526* (2013.01); *C07K 2317/53* (2013.01); *C07K 2317/55* (2013.01); *C07K 2317/732* (2013.01); *C07K 2317/734* (2013.01); *C07K 2317/90* (2013.01)

(58) Field of Classification Search
CPC .............. C07K 1/1133; C07K 16/2863; C07K 16/2887; C07K 16/468; C07K 2317/24; C07K 2317/31; C07K 2317/41; C07K 2317/524; C07K 2317/526; C07K 2317/53; C07K 2317/55; C07K 2317/732; C07K 2317/734; C07K 2317/90

See application file for complete search history.

(56) References Cited

U.S. PATENT DOCUMENTS

| | | |
|---|---|---|
| 2,592,668 A | 4/1952 | Dufour |
| 5,292,668 A | 3/1994 | Paulus |
| 5,731,168 A | 3/1998 | Carter et al. |
| 5,807,706 A | 9/1998 | Carter et al. |
| 6,528,286 B1 | 3/2003 | Ryll |
| 6,737,056 B1 | 5/2004 | Presta |
| 6,822,075 B2 | 11/2004 | Bjorck et al. |
| 7,537,930 B2 | 5/2009 | Goldenberg et al. |
| 7,723,485 B2 | 5/2010 | Junutula et al. |
| 8,911,726 B2 | 12/2014 | Takahashi et al. |
| 9,150,663 B2 * | 10/2015 | Labrijn ............... C07K 16/468 |
| 9,212,230 B2 | 12/2015 | Schuurman et al. |
| 10,344,050 B2 * | 7/2019 | Gramer ............... C07K 16/468 |
| 10,597,464 B2 | 3/2020 | Labrijn et al. |
| 10,906,991 B2 | 2/2021 | Schuurman et al. |
| 2004/0038894 A1 | 2/2004 | Daeron et al. |
| 2006/0074225 A1 | 4/2006 | Chamberlain et al. |
| 2006/0194280 A1 | 8/2006 | Dillon et al. |
| 2008/0051469 A1 | 2/2008 | Brahmbhatt et al. |
| 2009/0042253 A1 | 2/2009 | Hiller |
| 2009/0202546 A1 | 8/2009 | Harris et al. |
| 2010/0015133 A1 | 1/2010 | Igawa et al. |
| 2010/0105874 A1 | 4/2010 | Schuurman et al. |
| 2010/0331527 A1 | 12/2010 | Davis et al. |
| 2014/0141000 A1 | 5/2014 | Chiu et al. |
| 2014/0170148 A1 | 6/2014 | De Goeij et al. |
| 2014/0170149 A1 | 6/2014 | Neijssen et al. |

(Continued)

FOREIGN PATENT DOCUMENTS

| | | |
|---|---|---|
| DE | 19859115 A1 | 3/2000 |
| EP | 1693386 A1 | 8/2006 |

(Continued)

OTHER PUBLICATIONS

Aalberse, Rob C. et al., "IgG4 breaking the rules," Immunology, vol. 105:9-19 (2002).
Aalberse, Rob C. et al., "Serologic Aspects of IgG4 Antibodies. I. Prolonged Immunization Results in an IgG4-Restricted Response," The Journal of Immunology, vol. 130(2):722-726 (1983).
Aalberse, Rob C. et al., "The Apparent Monovalency of Human IgG4 Is Due to Bispecificity," Int. Arch. Allergy Immunol., vol. 118:187-189 (1999).
Aalberse, Rob C., "Physiological Fab arm exchange of IgG4 generates an anti-inflammatory antibody," Genmab, European Antibody Congress, 36 pages (2008).

(Continued)

*Primary Examiner* — Phuong Huynh
(74) *Attorney, Agent, or Firm* — Nelson Mullins Riley & Scarborough LLP; Jane E. Remillard, Esq.; Christopher L. Frank

(57) ABSTRACT

The present invention relates to an in vitro method for production of heterodimeric proteins.

21 Claims, 115 Drawing Sheets

Specification includes a Sequence Listing.

(56) References Cited

U.S. PATENT DOCUMENTS

| | | |
|---|---|---|
| 2014/0303356 A1 | 10/2014 | Gramer et al. |
| 2015/0353636 A1 | 12/2015 | Parren et al. |
| 2016/0046727 A1 | 2/2016 | Labrijn et al. |
| 2016/0159930 A1 | 6/2016 | Schuurman et al. |
| 2017/0233497 A1 | 8/2017 | Labrijn et al. |
| 2020/0262932 A1 | 8/2020 | Labrijn et al. |

FOREIGN PATENT DOCUMENTS

| | | | |
|---|---|---|---|
| EP | 1870459 | A1 | 12/2007 |
| WO | 96/27011 | A1 | 9/1996 |
| WO | 98/04592 | A1 | 2/1998 |
| WO | 98/50431 | A2 | 11/1998 |
| WO | 9955369 | A1 | 11/1999 |
| WO | 02/100348 | A2 | 12/2002 |
| WO | 2004/035607 | A2 | 4/2004 |
| WO | 2005/000899 | A2 | 1/2005 |
| WO | 2005/062916 | A2 | 7/2005 |
| WO | 2006/047340 | A2 | 5/2006 |
| WO | 2006/106905 | A1 | 10/2006 |
| WO | 2007/059782 | A1 | 5/2007 |
| WO | 2007/103112 | A2 | 9/2007 |
| WO | 2007/110205 | A2 | 10/2007 |
| WO | 2007147901 | A1 | 12/2007 |
| WO | 2008/119353 | A1 | 10/2008 |
| WO | 2008/145140 | A2 | 12/2008 |
| WO | 2008/145142 | A1 | 12/2008 |
| WO | 2009/089004 | A1 | 7/2009 |
| WO | 2010/001251 | A2 | 1/2010 |
| WO | 2010/063785 | A2 | 6/2010 |
| WO | 2010/129304 | A2 | 11/2010 |
| WO | 2010/151792 | A1 | 12/2010 |
| WO | 2011/131746 | A2 | 10/2011 |
| WO | 2011/133886 | A2 | 10/2011 |
| WO | 2011/143545 | A1 | 11/2011 |
| WO | 2012/058768 | A1 | 5/2012 |
| WO | 2012/116453 | A1 | 9/2012 |

OTHER PUBLICATIONS

Angal, S. et al., "A Single Amino Acid Substitution Abolishes the Hetergeneity of Chimeric Mouse/Human (IgG4) Antibody," Molecular Immunology, vol. 30(1):105-108 (1993).
Bloom, James W. et al., "Interchain disulfide bond in the core hinge region of human IgG4," Protein Science, vol. 6:407-415 (1997).
Brusco et al., "Molecular characterization of immunoglobulin G4 gene isoallotypes," Eur J Immnogene, 25:349-355 (1998).
Carlring, Jennifer et al., "A Novel Redox Method for Rapid Production of Functional Bi-Specific Antibodies For Use in Early Pilot Studies," PLoS One, vol. 6(7):e22533, pp. 1-6 (2011).
Chames, P. et al, "Bispecific Antibodies for Cancer Therapy" Curr. Opin Drug Discvo. Devel, vol. 12(2), pp. 276-283 (2009).
Ciccimarra, F. et al., "Localization of the IgG effector site for monocyte receptors," PNAS, 72:2081-2083(1975).
Dall'Acqua, William et al., "Contribution of Domain Interface Residues to the Stability of Antibody CH3 Domain Homodimers," Biochemistry, vol. 37:9266-9273 (1998).
Deng, Liang et al., "Detection and quantification of the human IgG4 half-molecule, HL, from unpurified cell-culture supernatants," Biotechnol. Appl. Biochem., vol. 40:261-269 (2004).
Dick et al., Biotechnology and Bioengineering 100(6): 1132-1143, Aug. 15, 2008.
Genmab, "Better Antibodies by Design," www.genmab.com, 2 pages (2011).
Genmab, "Building for a Commercial Future: Research, Development and Business Update," slideshow, 65 pages (2006).
Genmab, "DuoBody, Genmab's proprietary bispecifiic antibody platform," slideshow, 13 pages (2011).
Genmab, "DuoBody, The next generation of therapeutic antibodies," www.genmab.com, 2 pages (2011).
Genmab, "DuoBody: Innovative Bispecific Antibody Platform," Poster for R&D Day, 1 page (2011).
Genmab, "Genmab, Beter Antibodies by Design," slideshow, 18 pages (2011).
Genmab, "The physiological generation of bispecific IgG4 antibodies," Sanquin Spring Symposium, slideshow, 54 pages (2007).
Genmab, "Therapeutic IgG4 antibodies engage in Fab-arm exchange with patients' IgG4 in vivo," Antibodies as Drugs, Poster #214, 14 pages (2009).
International Preliminary Report on Patentability, PCT/EP2012/071294, dated Apr. 29, 2014, pp. 1-13.
International Search Report and Written Opinion, PCT/EP2012/071294, dated Apr. 26, 2013, pp. 1-20.
Labrijn, A. et al.,"Efficient generation of stable bispecific IgG 1 by controlled Fab-arm exchange," Proc. Nat'l Acad. Sci., vol. 110(13), pp. 5145-5150 (2013).
Labrijn, Aran F. et al., "Species-Specific Determinants in the IgG CH3 Comain Enable Fab-Arm Exchange by Affecting the Noncovalent CH3-CH3 Interaction Strength," The Journal of Immunology, vol. 187, 9 pages (2011).
Labrijn, Aran F. et al., "Species-specific determinants in the immunoglobulin CH3 domain enable Fab-arm exchange by affecting the non-covalent CH3-CH3 interaction strength," Keystone Symposium, Antibodies as Drugs Poster Presentation, 1 page (2011).
Labrijn, Aran F. et al., "Therapeutic IgG4 antibodies engage in Fab-arm exchange with endogenous human IgG4 in vivo," Nature Biotechnology, vol. 27:767-771 (2009).
Lewis, Kenneth B. et al., "Comparison of the ability of wild type and stabilized human IgG4 to undergo Fab arm exchange with endogenous IgG4 in vitro and in vivo," Molecular Immunology, vol. 46:3488-3494 (2009).
Marvin, Jonathan S. et al., "Recombinant approaches to IgG-like bispecific antibodies," Acta Pharmacologica Sinica, vol. 26(6):649-658 (2005).
Merchant, A. Margaret et al., "An efficient route to human bispecific IgG," Nature Biotechnology, vol. 16:677-681 (1998).
Mori, Katsuhiro et al., "Non-fucosylated therapeutic antibodies: the next generation of therapeutic antibodies," Cytotechnology, vol. 55:109-114 (2007).
Ooijevaar-De Heer, Pleuni G. et al., "Fc binding activity of IgG4 is a confounding factor in the measurement of IgG4 bispecificity," Sanquin Spring Symposium, 1 page (2007).
Parren, Paul, "UniBody, a novel nonactivating antibody format," Beyond Antibodies, slideshow, 35 pages (2009).
Rispens, Theo et al., "Human IgG1 Binds to IgG4 and Conformationally Altered IgG1 via Fc-Fc Interactions," The Journal of Immunology, vol. 182:4275-4281 (2009).
Rispens, Theo, "IgG4: an odd antibody, Fc interactions and the relation to half-molecule exchange," Sanquin, slideshow, 41 pages (2009).
Santora et al., Analytical Biochemistry 275: 98-108, 1999.
Schuurman, J. et al., "Normal human immunoglobulin G4 is bispecific: it has two different antigen-combining sites," Immunology, vol. 97:693-698 (1999).
Schuurman, Janine et al., "Anti-Inflammatory Activity of Human IgG4 Antibodies by Dynamic Fab Arm Exchange," World BioPharm Forum, Poster, 1 page (2009).
Schuurman, Janine et al., "The inter-heavy chain disulfide bonds of IgG4 are in equilibrium with intra-chain disulfide bonds," Molecular Immunology, vol. 38:1-8 (2001).
Schuurman, Janine, "IgG4 therapeutic antibodies," World BioPharm Forum, slideshow, 26 pages (2009).
Schuurman, Janine, "Post-Transcriptional Modifications," Genmab, slideshow, 43 pages (2008).
Schuurman, Janine, "The impact of Fab-arm exchange on the development of antibody therapeutics," Antibody Engineering and Design, slideshow, 29 pages (2011).
Schuurman, Janine, "The impact of Fab-arm exchange on the development of antibody therapeutics," Genmab, slideshow, 26 pages (2010).
Scinicariello, F. et al., "Rhesus macaque antibody molecules: sequences and heterogeneity of alpha and gamma constant regions," Immunol, vol. 111, pp. 66-74 (2011).

(56) References Cited

OTHER PUBLICATIONS

Stubenrauch, Kay et al., "Impact of Molecular Processing in the Hinge Region of Therapeutic IgG4 Antibodies on Disposition Profiles in Cynomolgus Monkeys," Drug Metabolism and Disposition, vol. 38(1):84-91 (2010).
Van Berkel, Patrick H.C., "Development of a production process for DuoBody: a novel human bispecific platform," Informa/IBC Life Sciences' Bioproduction Conference, Poster, 1 page (2011).
Van De Winkel, Jan et al., "Better Antibodies by Design, 2011 R&D Day," slideshow, 109 pages (2011).
Van Der Neut Kolfschoten, Marijn et al., "Anti-Inflammatory Activity of Human IgG4 Antibodies by Dynamic Fab Arm Exchange," Science, vol. 317:1554-1557 (2007).
Van Der Zee, J.S. et al., "Inhibition of complement activation by IgG4 antibodies," Clin. exp. Immunol., vol. 64:415-422 (1986).
Van Der Zee, Jaring S. et al., "Serologic Aspects of IgG4 Antibodies. II. IgG4 Antibodies Form Small, Nonprecipitating Immune Complexes Due to Functional Monovalency," The Journal of Immunology, vol. 137(11):3566-3571 (1986).
Zuckier et al., "Chimeric human-mouse IgG antibodies with shuffled constant region exons demonstrate that multiple domains contribute to in vivo half-life," Cancer Research, 58:3905-3908 (1998).
U.S. Appl. No. 14/353,962, filed Apr. 24, 2014, Michael Gramer.
U.S. Appl. No. 12/593,759, filed Jan. 6, 2010, Janine Schuurman.
U.S. Appl. No. 14/934,956, filed Nov. 6, 2015, Janine Schuurman.
U.S. Appl. No. 16/777,053, filed Jan. 30, 2020, Aran Frank Labrijn.
U.S. Appl. No. 15/414,122, filed Jan. 24, 2017, Aran Frank Labrijn.
U.S. Appl. No. 14/830,336, filed Aug. 19, 2015, Aran Frank Labrijn.
U.S. Appl. No. 13/642,253, filed Oct. 24, 2012, Aran Frank Labrijn.
U.S. Appl. No. 14/760,135, filed Jul. 9, 2015, Paul Parren.
U.S. Appl. No. 12/593,759, Aug. 4, 2015.
U.S. Appl. No. 12/593,759, Oct. 14, 2014.
U.S. Appl. No. 12/593,759, Apr. 23, 2014.
U.S. Appl. No. 12/593,759, Aug. 3, 2012.
U.S. Appl. No. 14/934,956, Oct. 1, 2020.
U.S. Appl. No. 14/934,956, Dec. 26, 2019.
U.S. Appl. No. 14/934,956, May 30, 2019.
U.S. Appl. No. 14/934,956, Nov. 1, 2018.
U.S. Appl. No. 14/934,956, Feb. 7, 2018.
U.S. Appl. No. 14/934,956, Aug. 1, 2017.
U.S. Appl. No. 15/414,122, Jan. 27, 2020.
U.S. Appl. No. 15/414,122, Dec. 13, 2019.
U.S. Appl. No. 15/414,122, Apr. 9, 2019.
U.S. Appl. No. 15/414,122, Sep. 13, 2018.
U.S. Appl. No. 15/414,122, Apr. 20, 2018.
U.S. Appl. No. 14/830,336, Oct. 27, 2016.
U.S. Appl. No. 14/830,336, Jun. 23, 2016.
U.S. Appl. No. 13/642,253, May 22, 2015.
U.S. Appl. No. 13/642,253, Jan. 22, 2015.
U.S. Appl. No. 13/642,253, Sep. 11, 2014.
U.S. Appl. No. 13/642,253, Apr. 23, 2014.
U.S. Appl. No. 14/353,962, Mar. 1, 2019.
U.S. Appl. No. 14/353,962, Jul. 20, 2018.
U.S. Appl. No. 14/353,962, Nov. 6, 2017.
U.S. Appl. No. 14/353,962, May 30, 2017.
U.S. Appl. No. 14/353,962, Sep. 13, 2016.
U.S. Appl. No. 14/353,962, Mar. 23, 2016.
U.S. Appl. No. 14/353,962, Sep. 23, 2015.
U.S. Appl. No. 14/760,135, Dec. 24, 2020.
U.S. Appl. No. 14/760,135, Jul. 10, 2019.
U.S. Appl. No. 14/760,135, Sep. 13, 2018.
U.S. Appl. No. 14/760,135, Jan. 24, 2018.
U.S. Appl. No. 14/760,135, Oct. 5, 2017.
U.S. Appl. No. 14/760,135, Jul. 30, 2021.

\* cited by examiner

FIG. 2

| Species (common name) | Isotype | Amino-acid position* | | | | | | | | | | | | | | | | | | |
|---|---|---|---|---|---|---|---|---|---|---|---|---|---|---|---|---|---|---|---|---|
| | | Core-hinge | | | | | CH3-CH3 interface | | | | | | | | | | | | | |
| | | 226 | 227 | 228 | 229 | 230 | 347 | 349 | 350 | 351 | 366 | 368 | 370 | 392 | 394 | 395 | 397 | 398 | 399 | 405 | 407 | 409 |
| Homo sapiens | IgG1 | C | P | P | C | P | Q | Y | T | L | T | L | K | K | T | P | V | L | D | F | Y | K |
| | IgG2 | - | - | - | - | - | - | - | - | - | - | - | - | - | - | - | M | - | - | - | - | - |
| | IgG3 | - | - | R | - | - | - | - | - | - | - | - | - | N | - | - | M | - | - | - | - | - |
| | IgG4 | - | - | S | - | - | - | - | - | - | - | - | - | - | - | - | - | - | - | - | - | R |
| Macaca mulatta (Rhesus Monkey) | IgG1 | - | - | - | - | - | - | - | - | - | - | - | - | - | - | - | - | - | - | - | - | - |
| | IgG2 | - | - | - | - | - | - | - | - | - | - | - | - | - | - | - | - | - | - | - | - | - |
| | IgG3 | - | - | - | - | - | - | - | I | - | - | - | T | - | - | - | - | - | - | - | - | - |
| | IgG4 (In)** | - | - | - | - | - | - | - | I | - | - | - | T | - | - | - | - | - | - | L | - | - |
| | IgG4 (Ch)*** | - | - | A | - | - | - | - | I | - | - | - | T | - | - | - | - | - | - | L | - | - |

*EU numbering; In, Indian; *Ch, Chinese

Peak results:

| | RT (min) | Area | Height | % Height |
|---|---|---|---|---|
| 1 | 5.362 | 18309 | 448 | 0.21 |
| 2 | 7.584 | 82197 | 2876 | 1.36 |
| 3 | 8.869 | 4431069 | 207416 | 98.42 |

FIG. 16

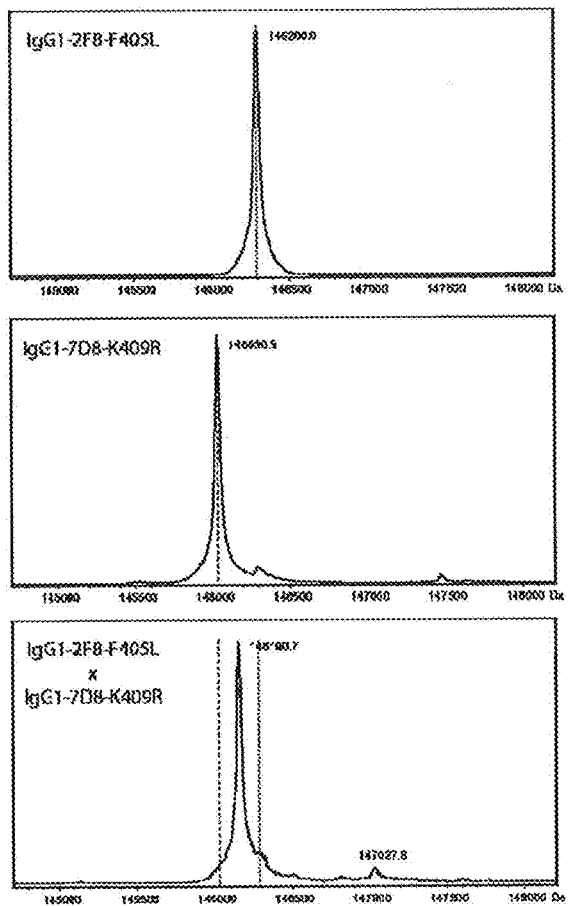

Non-reduced

Reduced

1) IgG1 control B12
2) IgG1-7D8-K409R
3) IgG1-2F8-F405L
4) IgG1-7D8-K409R + IgG1-2F8-F405L (1:1)
5) IgG1-7D8-K409R x IgG1-2F8-F405L (Exchanged)

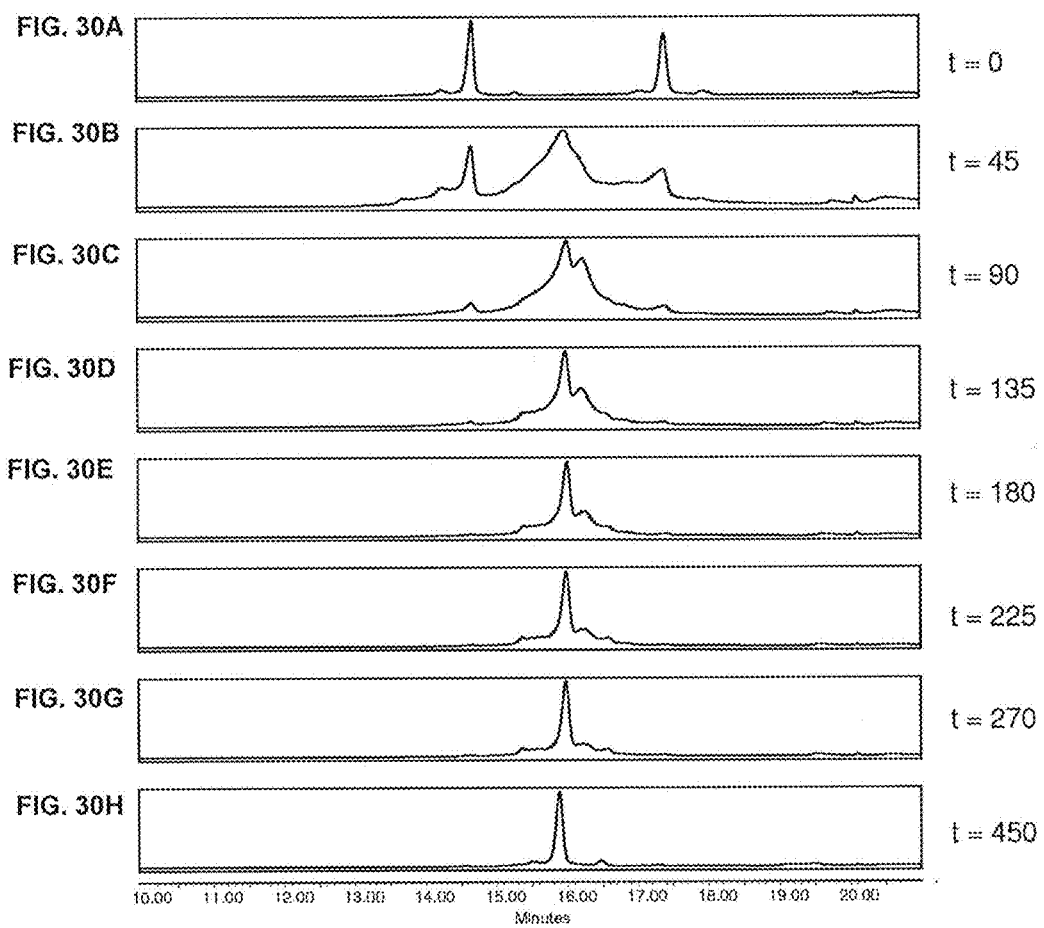

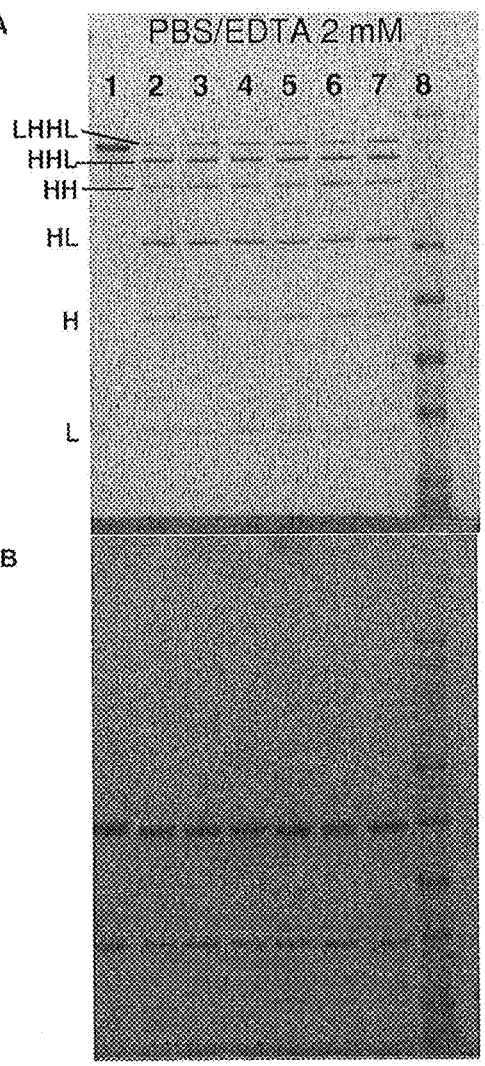
FIG. 61A
FIG. 61B
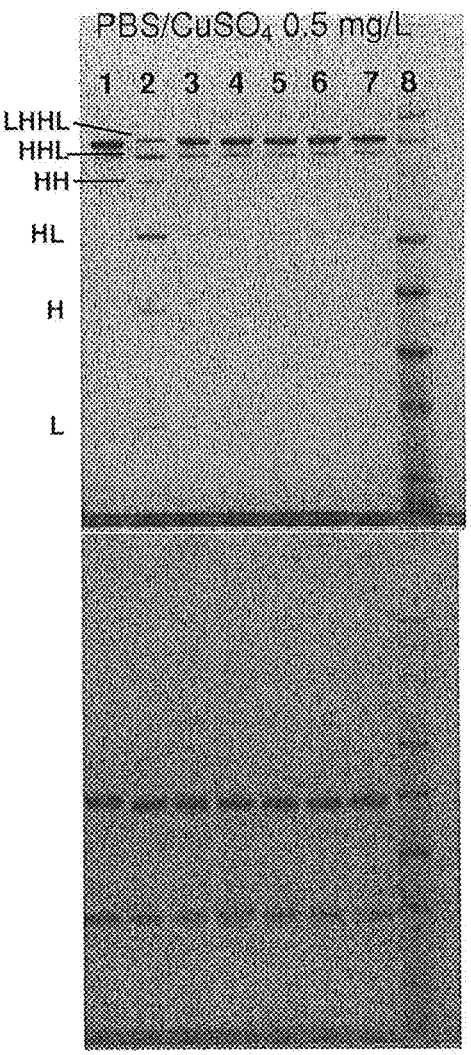
FIG. 61C
FIG. 61D

SEQUENCE LISTING

<160> NUMBER OF SEQ ID NOS: 12

<210> SEQ ID NO 1
<211> LENGTH: 107
<212> TYPE: PRT
<213> ORGANISM: homo sapiens

<400> SEQUENCE: 1

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

```
Asn Asn Tyr Lys Thr Thr Pro Pro Val Leu Asp Ser Asp Gly Ser Phe
             50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 2
<211> LENGTH: 107
<212> TYPE: PRT
<213> ORGANISM: homo sapiens

<400> SEQUENCE: 2

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
             50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 3
<211> LENGTH: 107
<212> TYPE: PRT
<213> ORGANISM: homo sapiens

<400> SEQUENCE: 3

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
             50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Gly Leu His Asn His Tyr
                 85                  90                  95

Thr Gln Lys Ser Leu Ser Leu Ser Pro Gly Lys
            100                 105

<210> SEQ ID NO 4
<211> LENGTH: 440
<212> TYPE: PRT
<213> ORGANISM: homo sapiens

<400> SEQUENCE: 4
```

```
Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
    195                 200                 205

Asn Val Asn His Lys Pro Ser Asn Thr Lys Val Asp Lys Arg Val Ala
210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser His Glu Asp Pro Glu Val Lys Phe Asn Trp Tyr Val
        260                 265                 270

Asp Gly Val Glu Val His Asn Ala Lys Thr Lys Pro Arg Glu Glu Gln
    275                 280                 285

Tyr Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
            325                 330                 335

Arg Glu Pro Gln Val Tyr Thr Leu Pro Pro Ser Arg Glu Glu Met Thr
        340                 345                 350

Lys Asn Gln Val Ser Leu Thr Cys Leu Val Lys Gly Phe Tyr Pro Ser
    355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
```

```
                420             425             430
Ser Leu Ser Leu Ser Pro Gly Lys
        435             440

<210> SEQ ID NO 5
<211> LENGTH: 24
<212> TYPE: PRT
<213> ORGANISM: homo sapiens

<400> SEQUENCE: 5

Ser Cys Ser Val Met His Glu Ala Leu His Asn His Tyr Thr Gln Lys
1               5                   10                  15

Ser Leu Ser Leu Ser Leu Gly Lys
            20

<210> SEQ ID NO 6
<211> LENGTH: 24
<212> TYPE: PRT
<213> ORGANISM: Macaca mulatta

<400> SEQUENCE: 6

Thr Cys Ser Val Met His Glu Ala Leu His Asn His Tyr Thr Gln Lys
1               5                   10                  15

Ser Leu Ser Val Ser Pro Gly Lys
            20

<210> SEQ ID NO 7
<211> LENGTH: 106
<212> TYPE: PRT
<213> ORGANISM: Macaca mulatta

<400> SEQUENCE: 7

Ala Val Ala Ala Pro Ser Val Phe Ile Phe Pro Pro Ser Glu Asp Gln
1               5                   10                  15

Val Lys Ser Gly Thr Val Ser Val Cys Leu Leu Asn Asn Phe Tyr
            20                  25                  30

Pro Arg Glu Ala Ser Val Lys Trp Lys Val Asp Gly Val Leu Lys Thr
        35                  40                  45

Gly Asn Ser Gln Glu Ser Val Thr Glu Gln Asp Ser Lys Asp Asn Thr
    50                  55                  60

Tyr Ser Leu Ser Ser Thr Leu Thr Leu Ser Ser Thr Asp Tyr Gln Ser
65                  70                  75                  80

His Asn Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 330
<212> TYPE: PRT
<213> ORGANISM: homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
   50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Arg Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Ala Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Arg Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 10
<211> LENGTH: 455
<212> TYPE: PRT
<213> ORGANISM: HOMO SAPIENS

<400> SEQUENCE: 10

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Thr Tyr
            20                  25                  30
Gly Met His Trp Val Arg Gln Ala Pro Gly Lys Gly Leu Glu Trp Val
        35                  40                  45
Ala Val Ile Trp Asp Asp Gly Ser Tyr Lys Tyr Tyr Gly Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Gly Ile Thr Met Val Arg Gly Val Met Lys Asp Tyr Phe
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
```

```
            130                 135                 140
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 11
<211> LENGTH: 97
<212> TYPE: PRT
<213> ORGANISM: HOMO SAPIENS

<400> SEQUENCE: 11

Asn Val Asn His Lys Pro Ser Asn Thr Lys Val Asp Lys Arg Val Glu
1               5                   10                  15

Leu Lys Thr Pro Leu Gly Asp Thr Thr His Thr Cys Pro Arg Cys Pro
            20                  25                  30

Glu Pro Lys Ser Cys Asp Thr Pro Pro Cys Pro Arg Cys Pro Glu
        35                  40                  45
```

```
Pro Lys Ser Cys Asp Thr Pro Pro Cys Pro Arg Cys Pro Glu Pro
    50                  55                  60

Lys Ser Cys Asp Thr Pro Pro Cys Pro Arg Cys Pro Ala Pro Glu
65                  70                  75                  80

Leu Leu Gly Gly Pro Ser Val Phe Leu Phe Pro Pro Lys Pro Lys Asp
                85                  90                  95

Thr
```

<210> SEQ ID NO 12
<211> LENGTH: 452
<212> TYPE: PRT
<213> ORGANISM: HOMO SAPIENS

<400> SEQUENCE: 12

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
                35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205

Asn Val Asp His Lys Pro Ser Asn Thr Lys Val Asp Lys Arg Val Glu
        210                 215                 220

Ser Lys Tyr Gly Pro Pro Cys Pro Ser Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320
```

-continued

```
Gly Lys Glu Tyr Lys Cys Lys Val Ser Asn Lys Gly Leu Pro Ser Ser
                325             330                 335

Ile Glu Lys Thr Ile Ser Lys Ala Lys Gly Gln Pro Arg Glu Pro Gln
            340             345                 350

Val Tyr Thr Leu Pro Pro Ser Gln Glu Glu Met Thr Lys Asn Gln Val
        355             360                 365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395                 400

Pro Val Leu Asp Ser Asp Gly Ser Phe Phe Leu Tyr Ser Arg Leu Thr
                405             410             415

Val Asp Lys Ser Arg Trp Gln Glu Gly Asn Val Phe Ser Cys Ser Val
                420             425             430

Met His Glu Ala Leu His Asn His Tyr Thr Gln Lys Ser Leu Ser Leu
            435             440                 445

Ser Leu Gly Lys
    450
```

PRODUCTION OF HETERODIMERIC PROTEINS

RELATED APPLICATIONS

This application is a continuation of U.S. patent application Ser. No. 14/353,962, filed Apr. 24, 2014 (now U.S. Pat. No. 10,344,050), which is a 35 U.S.C. 371 national stage filing of International Application No. PCT/EP2012/071294, filed Oct. 26, 2012, which claims priority to U.S. Provisional Application No. 61/552,272, filed Oct. 27, 2011, and Danish Patent Application No. PA 2011 00826, filed Oct. 27, 2011. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on May 30, 2019, is named GMI_146USCN_Sequence_Listing.txt and is 23,225 bytes in size.

FIELD OF THE INVENTION

The present invention relates to an in vitro method for production of a heterodimeric protein comprising a first step of incubating a first and a second homodimeric protein under reducing conditions and a second step of subjecting the composition obtained from the first step to oxidizing conditions. The method of the present invention is particularly suitable for large-scale production of heterodimeric proteins including antibodies.

BACKGROUND OF THE INVENTION

Monoclonal antibodies have in recent years become successful therapeutic molecules, in particular for the treatment of cancer. Bispecific antibodies may further be able to increase the potency and efficacy of monoclonal antibody therapies, e.g. they could be used to direct a drug or toxic compound to target cells, to redirect effector mechanisms to disease-associated sites or to increase specificity for tumor cells, for example by binding to a combination of target molecules that is exclusively found on tumor cells. Furthermore, by combining the specificity of two monoclonal antibodies in one, bispecific antibodies could potentially engage a greater array of mechanisms of action c.q. their combined mechanisms of actions.

Different formats and uses of bispecific antibodies have recently been reviewed by Chames and Baty (2009) Curr Opin Drug Disc Dev 12: 276. One of the major obstacles in the development of bispecific antibodies has been the difficulty of producing the material in sufficient quality and quantity by traditional technologies, such as the hybrid hybridoma and chemical conjugation methods (Marvin and Zhu (2005) Acta Pharmacol Sin 26:649). Co-expression in a host cell of two antibodies, consisting of different heavy and light chains, leads to a mixture of possible antibody products in addition to the desired bispecific antibody.

Several strategies have been described to favor the formation of a heterodimeric, i.e. bispecific, product upon co-expression of different antibody constructs.

Lindhofer et al. (1995 J Immunol 155:219) disclose preferential species-restricted heavy/light chain pairing in rat/mouse quadromas.

A technique for formation of bispecific antibodies is the so-called "knob-into-hole" strategy (U.S. Pat. No. 5,731,168). EP1870459 (Chugai) and WO 2009089004 (Amgen) describe other strategies for favoring heterodimer formation upon co-expression of different antibody domains in a host cell. In these methods, one or more residues that make up the heavy chain constant domain 3 (CH3), CH3-CH3 interfaces in both CH3 domains are replaced with a charged amino acid such that homodimer formation is electrostatically unfavorable and heterodimerization is electrostatically favorable. WO2007110205 (Merck) describes yet another strategy, wherein differences between IgA and IgG CH3 domains are exploited to promote heterodimerization.

Dall'Acqua et al. (1998 Biochemistry 37:9266) have identified five energetically key amino-acid residues (366, 368, 405, 407 and 409) that are involved in the CH3-CH3 contact at the interface of a CH3 homodimer.

WO 2008119353 (Genmab) describes an ex vivo method for the generation of an antibody.

WO 11/131746 (Genmab) discloses heterodimeric antibody Fc-containing proteins and methods for production thereof.

The present invention relates to a method for production of heterodimeric proteins, such as stable IgG1 bispecific antibodies, wherein said method is particularly suitable for large-scale production of stable heterodimeric proteins wherein disulfide bonds are re-oxidized. By introduction of asymmetrical mutations in the CH3 domains of the homodimers, the Fab-arm exchange reaction can be forced to become directional due to complementarity of the CH3 domains, and thereby yield highly stable heterodimeric proteins.

SUMMARY OF THE INVENTION

In one aspect, the present invention relates to an in vitro method for production of a heterodimeric protein comprising the steps of:
  a) incubating a first homodimeric protein with a second homodimeric protein under reducing conditions sufficient to allow reduction of the inter-chain disulfide bonds in the hinge region and
    wherein said first homodimeric protein comprises an Fc region of an immunoglobulin, said Fc region comprising a first CH3 region, and said second homodimeric protein comprises an Fc region of an immunoglobulin, said Fc region comprising a second CH3 region, and wherein the sequences of said first and second CH3 regions are different and are such that the heterodimeric interaction between said first and second CH3 regions is stronger than each of the homodimeric interactions of said first and second CH3 regions,
  b) subjecting the composition obtained from step a) to oxidizing conditions sufficient to allow oxidation of cysteines in the heterodimeric protein to inter-chain disulfide bonds In another aspect the present invention step a) is replaced with the steps of:
x) providing a first nucleic-acid construct encoding a first polypeptide comprising a first Fc region of an immunoglobulin, said first Fc region comprising a first CH3 region,
y) providing a second nucleic-acid construct encoding a second polypeptide comprising a second Fc region of an immunoglobulin, said second Fc region comprising a first CH3 region,
wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407.

and/or wherein the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.

z) co-expressing said first and second nucleic-acid constructs in a host cell.

BRIEF DESCRIPTION OF THE DRAWINGS

FIG. 2: Alignment of the amino acid sequences of the core hinge (i.e. the CPPC sequence in human IgG1 which includes the two cysteine residues that potentially form the inter-heavy chain disulphide bonds and corresponding residues in other human and rhesus monkey isotypes) and the CH3-CH3 interface of the human and rhesus antibody isotypes.

The generation of bispecific antibodies after 2-MEA-induced in vitro Fab-arm exchange between the indicated human EGFR (2F8) and CD20 (7D8) antibodies was determined by mass spectrometry for all samples of the concentration series of 0-40 mM 2-MEA. (FIG. 6A) Representative examples of the mass spectrometry profiles for samples of Fab-arm exchange reactions between IgG1-2F8-ITL×IgG4-7D8-CPPC with 0 mM, 7 mM and 40 mM 2-MEA are shown. (FIG. 6B) After quantification of the mass spectrometry data, the percentage bispecific antibody was calculated and plotted against the concentration 2-MEA in the Fab-arm exchange reaction. IgG4-2F8×IgG4-7D8 resulted in maximally approximately 50% bispecific antibody. IgG1-2F8-ITL×IgG4-7D8-CPPC resulted in maximally approximately 95% bispecific antibody.

(FIG. 7A) Bispecific binding of the 2-MEA-induced bispecific product derived from IgG1-2F8-ITL×IgG4-7D8-CPPC was preserved, indicating a stable product that did not participate in Fab-arm exchange under GSH conditions. (FIG. 7B) Bispecific EGFR/CD20 binding of the 2-MEA-induced bispecific product derived from IgG4-2F8×IgG4-7D8 was diminished, indicating that the product participated in Fab-arm exchange with the irrelevant IgG4 under GSH conditions.

(FIG. 8A) Total antibody concentrations over time, determined by ELISA. The curves of the total antibody plasma concentrations were the same for all antibodies. (FIG. 8B) Bispecific antibody concentration as determined by an ELISA. The bispecificity of the injected antibody was the same with and without the addition of an excess irrelevant IgG4. (*) Bispecific binding for the IgG1-2F8-ITL+IgG4-7D8-CPPC mixture was below the detection limit and therefore the corresponding symbols could not be plotted in this graph. Mean values of two ELISA experiments are shown.

(FIG. 9A) Reducing SDS-PAGE (a) shows bands of the heavy and light chains for both the bispecific sample and the IgG1 control sample. Non-reducing SDS-PAGE (b) shows intact IgG. (FIG. 9B) The peak results from the HP-SEC analysis shows that >98% of the bispecific sample is homogenous, and practically no antibody aggregates were detectable. (FIG. 9C) Mass spectrometry shows that Fab-arm exchange resulted in approximately 100% bispecific product.

(FIG. 13A) A concentration series (total antibody) of 0-20 µg/mL was analyzed. The positive control is a purified batch of bispecific antibody, derived from IgG1-2F8-ITL×IgG4-7D8-CPPC. (FIG. 13B) The exchange is presented as bispecific binding at 20 µg/mL relative to the positive control (black bar). Dark grey bars represents the bispecific binding between the IgG4 control (IgG4-7D8×IgG4-2F8), the negative control (IgG1-2F8×IgG1-7D8-K409R) and between IgG1-2F8-ITL and IgG4-7D8-CPPC. Light grey bars represent results from simultaneously performed Fab-arm-exchange reactions between the indicated IgG1-7D8-K409X mutants and IgG1-2F8-ITL.

(FIG. 15A), (FIG. 15B) and (FIG. 15C) Generation of bispecific antibodies by GSH-induced Fab-arm exchange between IgG1-2F8 and IgG1-7D8 (FIG. 15A) or IgG4-2F8 and IgG4-7D8 (FIGS. 15B and 15C) constructs with the indicated mutations, presented as bispecific binding in an ELISA over time. Bispecificity is presented relative to the IgG4-2F8×IgG4-7D8 control after 24 h. (FIG. 15D) and (FIG. 15E) Relation between apparent $K_D$ (Table 2) and bispecific antibody generation after 24 hours (FIGS. 15A/15B/15C) for IgG1-based (FIG. 15D) or IgG4-based (FIG. 15E) molecules.

FIG. 16: Sequence alignment of anti-EGFr antibody 2F8 in an IgG1, IgG4 and (partial) IgG3 backbone. Amino acid numbering according to Kabat and according to the EU-index are depicted (both described in Kabat et al., Sequences of Proteins of Immunological Interest, 5th Ed. Public Health Service, National Institutes of Health, Bethesda, Md. (1991)). 2F8-G1 is given in SEQ ID NO:10, 2F8-G3 (partially) is given in SEQ ID NO:11, and 2F8-G4 is given in SEQ ID NO:12.

(FIG. 18A) The generation of bispecific antibodies after 2-MEA-induced in vitro Fab-arm exchange was determined by an ELISA. The presented graph shows the result of the ELISA in which a total antibody concentration of 20 µg/mL was used. 2-MEA efficiently induced Fab-arm exchange between human IgG1-2F8-F405L and IgG1-7D8-K409R. (FIG. 18B) The generation of bispecific antibodies after 2-MEA-induced in vitro Fab-arm exchange was determined by mass spectrometry for all samples of the concentration series of 0-40 mM 2-MEA. After quantification of the mass spectrometry data, the percentage bispecific antibody was calculated and plotted against the concentration of 2-MEA in the Fab-arm exchange reaction. Fab-arm exchange between IgG1-2F8-F405L and IgG1-7D8-K409R resulted in ~100% bispecific antibody at the highest 2-MEA concentration tested, confirming the ELISA data.

FIG. 19: Purity of bispecific antibody generated by Fab-arm exchange between human IgG1-2F8-F405L×IgG1-7D8-K409R. Mass spectrometry shows that Fab-arm exchange resulted in approximately 100% bispecific product.

(FIG. 20A) Total antibody concentrations over time, determined by ELISA. The curves of the total antibody plasma concentrations were the same for all antibodies. (FIG. 20B) Bispecific antibody concentration as determined by an ELISA. The bispecificity of the injected antibody was the same with and without the addition of an excess irrelevant IgG4.

(FIG. 23A) A concentration series (total antibody) of 0-20 µg/mL was analyzed in the ELISA. The positive control is a purified batch of bispecific antibody, derived from IgG1-2F8-F405L×IgG1-7D8-K409R. (FIG. 23B) The exchange is presented as bispecific binding at 20 µg/mL antibody concentration relative to the positive control (black bar). Dark grey bars represent the bispecific binding between the IgG4 control (IgG4-7D8×IgG4-2F8) and the negative control (IgG1-2F8×IgG1-7D8-K409R). Light grey bars represent results from simultaneously performed Fab-arm exchange reactions between the indicated IgG1-2F8-F405X mutants and IgG1-7D8-K409R or controls.

(FIG. 24A) A concentration series (total antibody) of 0-20 µg/mL was analyzed in the ELISA. The positive control is a purified batch of bispecific antibody, derived from IgG1-2F8-F405L×IgG1-7D8-K409R. (FIG. 24B) The exchange is presented as bispecific binding at 20 µg/mL antibody concentration relative to the positive control (black bar). Dark grey bars represents the bispecific binding for the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-Y407X mutants and IgG1-7D8-K409R or controls.

FIGS. 30A-30H: Exchange reaction of the homodimers IgG1-2F8-F405L and IgG1-7D8-K409R as monitored by High Pressure Liquid Chromatography Cation Exchange (HPLC-CIEX) after injection at different time points.

FIG. 35B shows the bispecific binding at 20 μg/mL relative to the positive control (black bar). Dark grey bars represent the bispecific binding of the IgG4 control (IgG4-7D8×IgG4-2F8) and the negative control (IgG1-2F8×IgG1-7D8-K409R). Light grey bars represent results from simultaneously performed Fab-arm exchange reactions between the indicated IgG1-2F8-L368X mutants and IgG1-7D8-K409R.

FIG. 36B shows the bispecific binding at 20 μg/mL relative to the positive control (black bar). Dark grey bars represent the bispecific binding of the IgG4 control (IgG4-7D8×IgG4-2F8) and the negative control (IgG1-2F8×IgG1-7D8-K409R). Light grey bars represent results from simultaneously performed Fab-arm exchange reactions between the indicated IgG1-2F8-D370X mutants and IgG1-7D8-K409R.

FIG. 37B shows the bispecific binding at 20 μg/mL antibody concentration relative to the positive control (black bar). Dark grey bars represent the bispecific binding of the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-D399X mutants and IgG1-7D8-K409R.

FIG. 38B shows the bispecific binding at 20 μg/mL antibody concentration relative to the positive control (black bar). Dark grey bars represent the bispecific binding of the IgG4 control (IgG4-7D8×IgG4-2F8) and the negative control (IgG1-2F8×IgG1-7D8-K409R). Light grey bars represent results from simultaneously performed Fab-arm exchange reactions between the indicated IgG1-2F8-T366X mutants and IgG1-7D8-K409R.

(FIG. 53A) Redox potential and oxygen saturation during reduction and oxidation phase were followed using a redox probe and a dissolved oxygen (DO) probe. The left y axis and the solid line show redox potential; the right y axis and the dashed line show oxygen saturation as measured in the solution during the different phases of the process, as indicated by the arrows. (FIG. 53B) Comparison of DO drop in the presence and absence of EDTA (taken from example 46 [without EDTA] and 47 [with EDTA]).

FIGS. 61A-61D: SDS-PAGE analysis during re-oxidation process. Samples were taken after different incubation times in PBS containing EDTA or $Cu^{2+}$ and analyzed by SDS-PAGE under non-reducing (FIG. 61A, FIG. 61C) and reducing (FIG. 61B, FIG. 61D) conditions. Lane 1: IgG1, internal assay control, lane 2: 0 h sample, lane 3: 1 h sample, lane 4: 2 h sample, lane 5: 3 h sample, lane 6: 4 h sample, lane 7: 24 h sample, lane 8: MW marker.

Bill of Materials
1) ½" zero-static tee diaphragm valve, SED, 316L SS
2) 50 L bag, Sartoruis Stedim, model FFB207004, on 50 L Wave Mixer, model EHT rev A
3) Twin beam scale, Intercomp, model TB830
4) ½" ID tubing, platinum cured silicone, Masterflex 96410-82
5) ⅜" ID tubing, platinum cured silicone, Tygon 3350
6) Tubing pinch clamp
7) 1" ID high pressure hose, reinforced platinum cured silicone, 316L SS TC ends, Page International, model SWPV
8) 0-30 psig pressure gauge, Anderson, model EM066010041025A
9) 1" gauge tee, 316L SS
10) ½' gauge tee, 316L SS
11) ½"×1" TC reducer, 316L SS
12) Feed peristaltic pump, Watson Marlow, model 720 DUN/RE, Stapure tubing element, model 960.0254.PFT, 0-33 LPM
13) Dissolved oxygen sensor and transmitter, Metter-Toledo, model 4100e and Inpro 6800/12/120 (sensor)
14) Redox sensor and transmitter, Mettler Toledo, model 2100e and 3250SG (sensor)
15) 1" Wedgewood flow cell, 316L SS
16) ½" tee, Kynar, Cole-Parmer model EW-30703-78
17) ½" diaphragm valve, SED, 316L SS
18) Millipore UF membrane holder with Pall disposable polypropylene inserts, and Pall Omega 30kD PES membrane, model OS030F26
19) Male Kleenpak HT Connector, Pall, model KPCHT02M6
20) Female Kleenpak HT Connector, Pall, model KPCHT02F6
21) Diafilter peristaltic pump, Watson Marlow, model 620 Di/R, Stapure tubing element, model 960.0170.PFT, 0-9 LPM
22) 0.2 micron filter, Pall, model KA3NFP1
23) 500 L bag, Sartoruis Stedim, model FXB211905
24) 200 L bag, Sartoruis Stedim, model PDL200LWS
25) 20 L bag, Sartoruis Stedim, model FFB208721
26) 5 L bag, Sartoruis Stedim, model FFB208723

All TC gaskets were platinum cured silicone.
All 5/20/50 L Sartorius Stedim bags use a multilayer film with EVA (ethylene vinyl acetate) product contact and an EVOH (ethylene vinyl alcohol) gas barrier layers.
All 200/500 L Sartorius Stedim bags use a multilayer film with ULDPE (ultra-low density polyethylene) product contact and an EVOH gas barrier layers.

Figure 64:
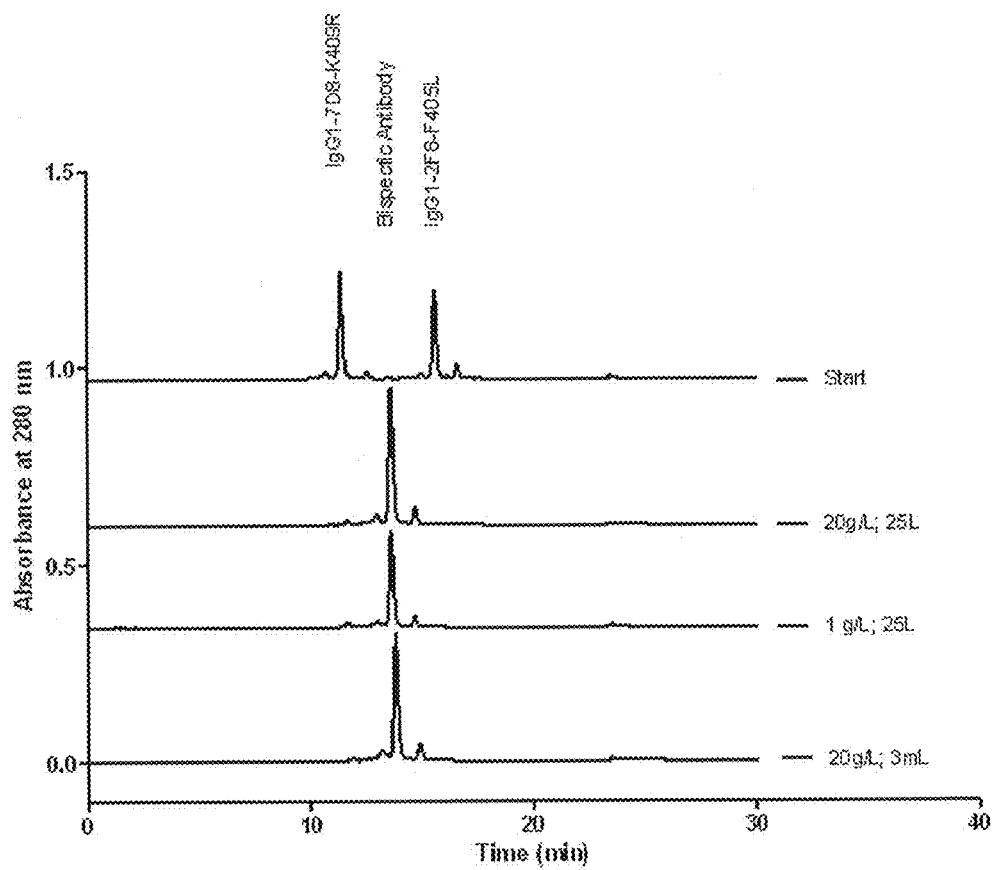

FIG. 64: CIEX profiles of the initial and final product from the three different conditions.

Figure 65:
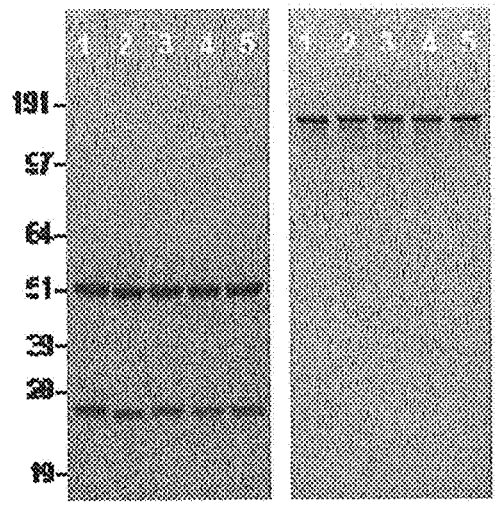

FIG. 65: Reduced (left) and non-reduced (right) SDS-PAGE analysis of the initial and final products. Lane 1: IgG1-b12 assay control. Lane 2: initial IgG1-F405L-2F8.

Lane 3: initial IgG1-K409R-7D8. Lane 4: final 25-L run at 1 g/L. Lane 5: final 25-L run at 20 g/L.

Figure 66:
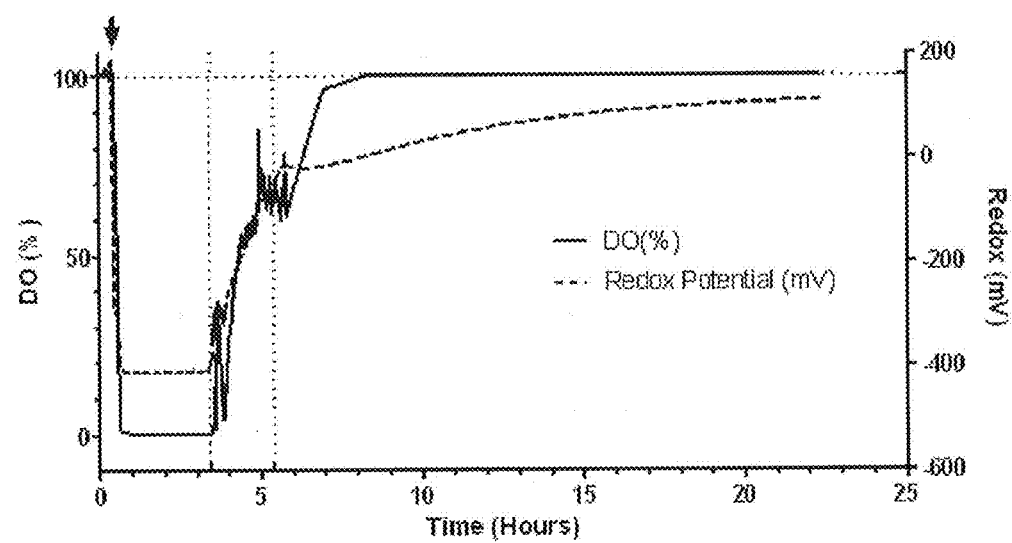

FIG. 66: Dissolved oxygen and redox potential during reduction and re-oxidation. Oxygen saturation and redox potential during reduction and re-oxidation of IgG1-2F8-F405L and IgG1-7D8-K409R (1:1 mixture) were followed using a redox probe and a DO probe. The horizontal dashed line shows the initial value of both DO and redox. The addition of 2-MEA (indicated by the arrow) coincided with a large drop in DO and redox at the beginning of the run. The vertical dashed lines show the start and stop of diafiltration.

Figure 67:
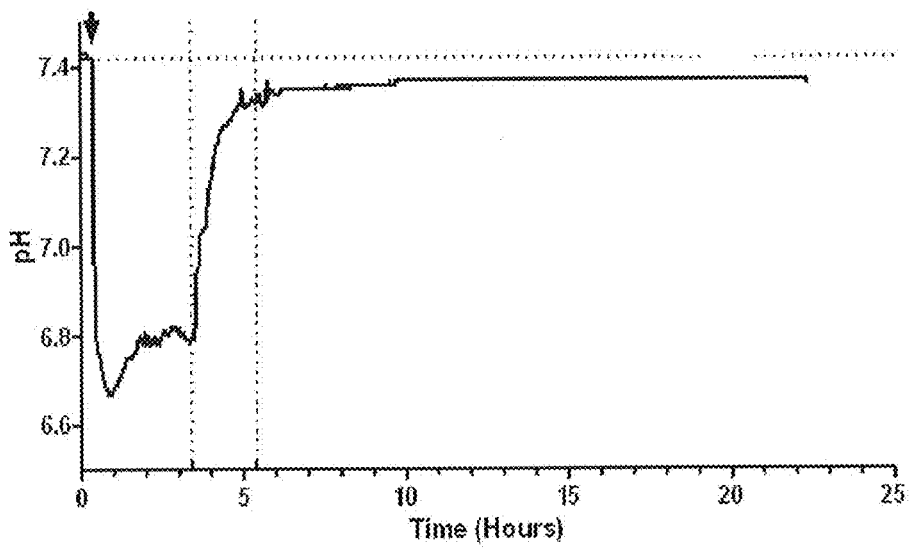

FIG. 67: pH profile during reduction and re-oxidation. pH during reduction and re-oxidation of IgG1-2F8-F405L and IgG1-7D8-K409R (1:1 mixture) was measured by a pH probe. The horizontal dashed line shows the initial pH value. The addition of 2-MEA (indicated by the arrow) coincided with a large drop in pH at the beginning of the run. The vertical dashed lines show start and stop of diafiltration.

Figure 68:
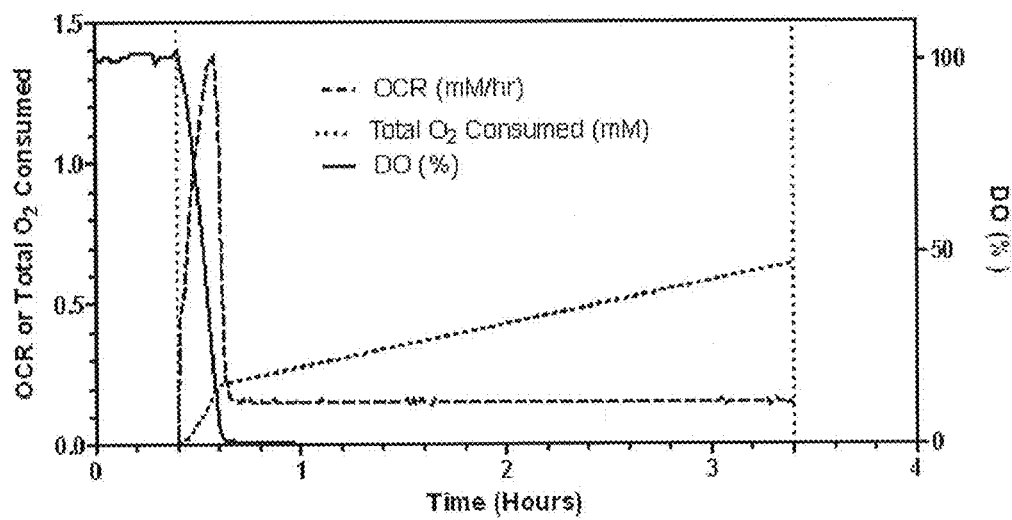

FIG. 68: Oxygen consumption rate (OCR [mM/h]), total $O_2$ consumed (mM) and DO (%) during reduction phase. Oxygen consumption rate and total $O_2$ consumed were calculated, DO was measured. The vertical dotted lines represent start and finish of reduction.

Figure 69:
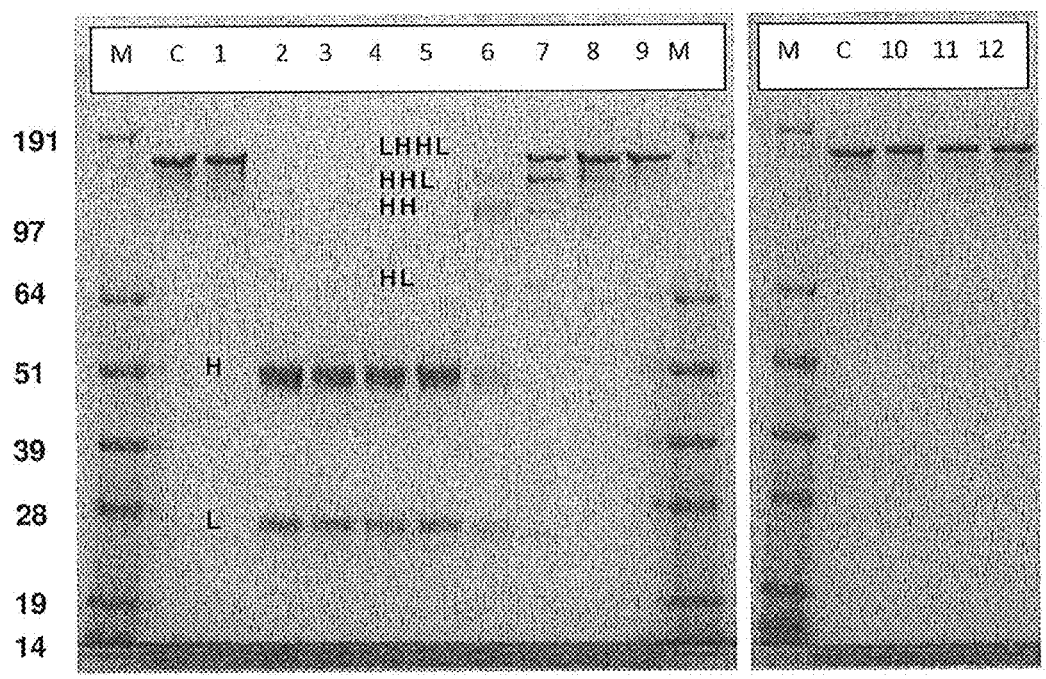

FIG. 69: SDS-PAGE (non-reduced) analysis during reduction and re-oxidation. Samples taken during reduction and re-oxidation of IgG1-2F8-F405L and IgG1-7D8-K409R (1:1 mixture) were analyzed by non-reduced SDS-PAGE analysis. M: MW marker; C: IgG1 control; lane 1: prior to 2-MEA addition; lanes 2, 3, 4 and 5: after 30 min, 1 hour, 2 hours and 3 hours of reduction, lanes 6, 7, 8, 9 and 10: diafiltration results after 1, 2, 3, 5, and 7 L diafiltered buffer, lanes, 11 and 12: 1 hour and O/N incubation after diafiltration. The masses of the molecular weight markers are indicated on the left. Reduced/re-oxidized IgG species are indicated by H (heavy chain) and/or L (light chain) and combinations thereof.

Figure 70:
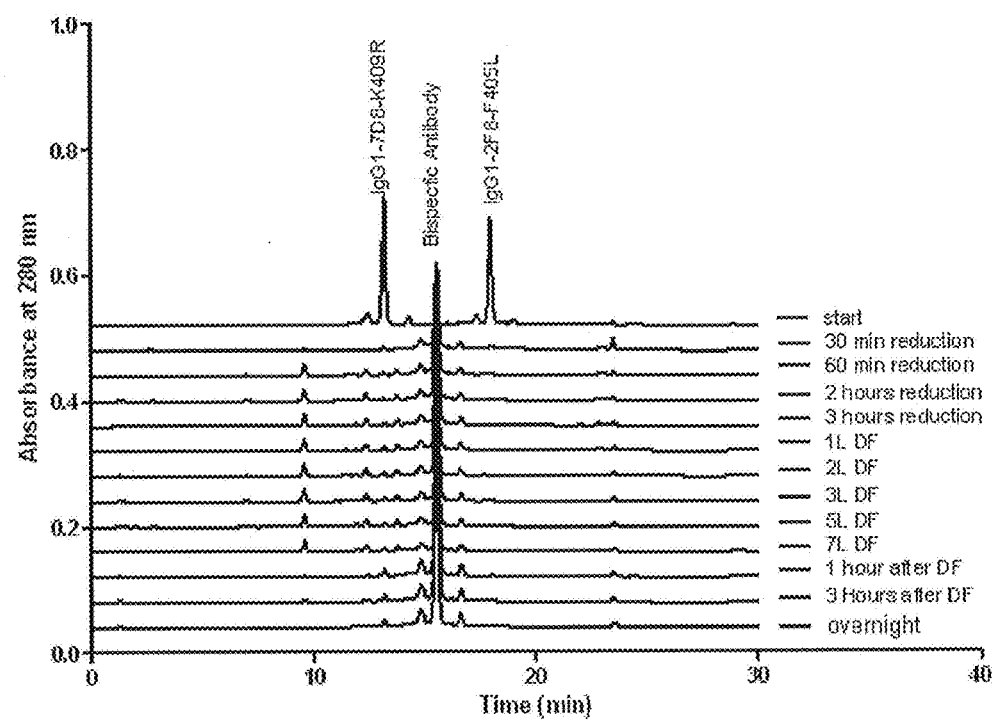

FIG. 70: CIEX profiles during reduction and re-oxidation. Samples were taken and snap frozen during reduction and re-oxidation of IgG1-2F8-F405L and IgG1-7D8-K409R (1:1 mixture) at the indicated time points and were analyzed by analytical CIEX.

Figure 71:
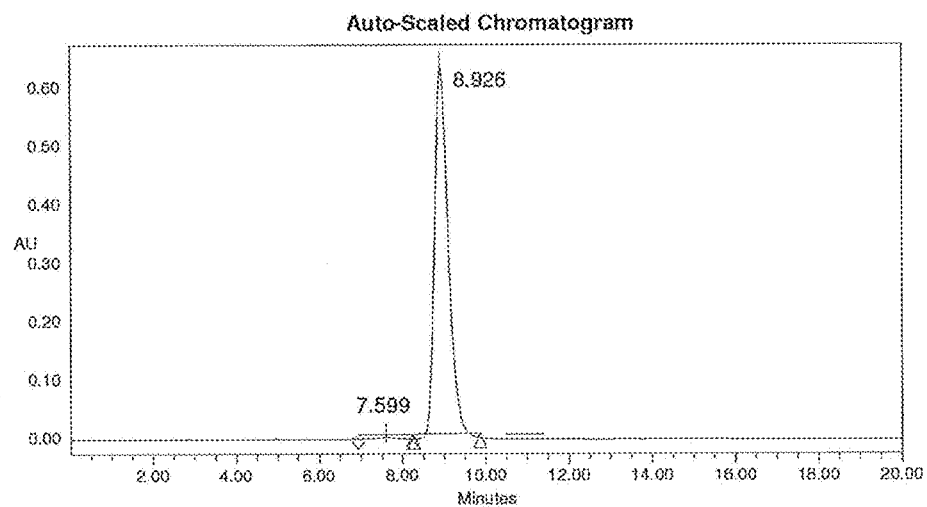

FIG. 71: HP-SEC analysis of end sample after O/N incubation. The sample taken after O/N incubation after diafiltration was analyzed by HP-SEC. The peaks at 7.599 and 10.792 represent dimeric and monomeric IgG, respectively.

Figure 72:
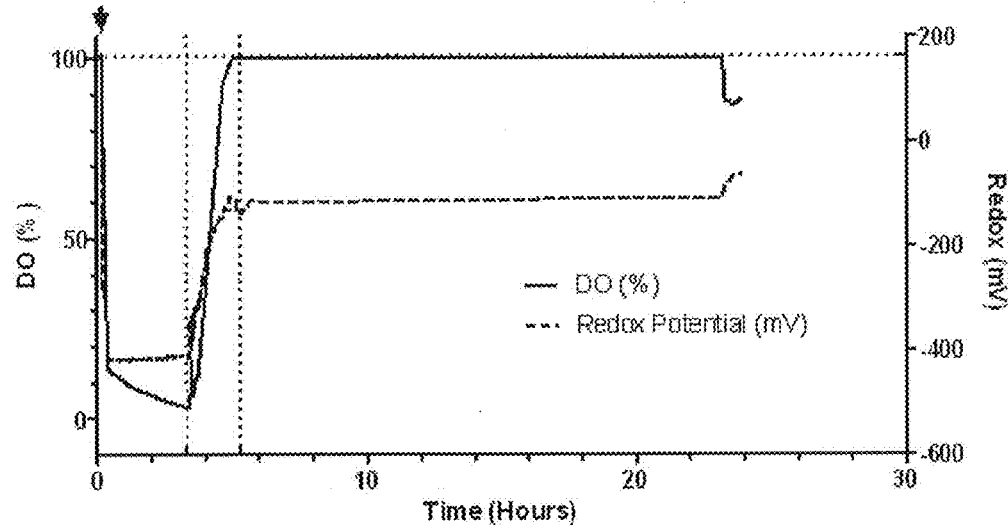

FIG. 72: Dissolved oxygen and redox potential during reduction and re-oxidation. Oxygen saturation and redox potential during reduction and re-oxidation of IgG1-2F8-F405L and IgG1-7D8-K409R (1:1 mixture) in the presence of 2 mM EDTA were followed using a redox probe and a DO probe. The horizontal dashed line shows the initial value of both redox and DO. The addition of 2-MEA coincided (indicated by the arrow) with a large drop in DO and redox at the beginning of the run. The vertical dashed lines show start and stop of diafiltration. The rise in redox and drop in DO late in the run (t=24 h) coincide with the addition of $CuSO_4$.

Figure 73:
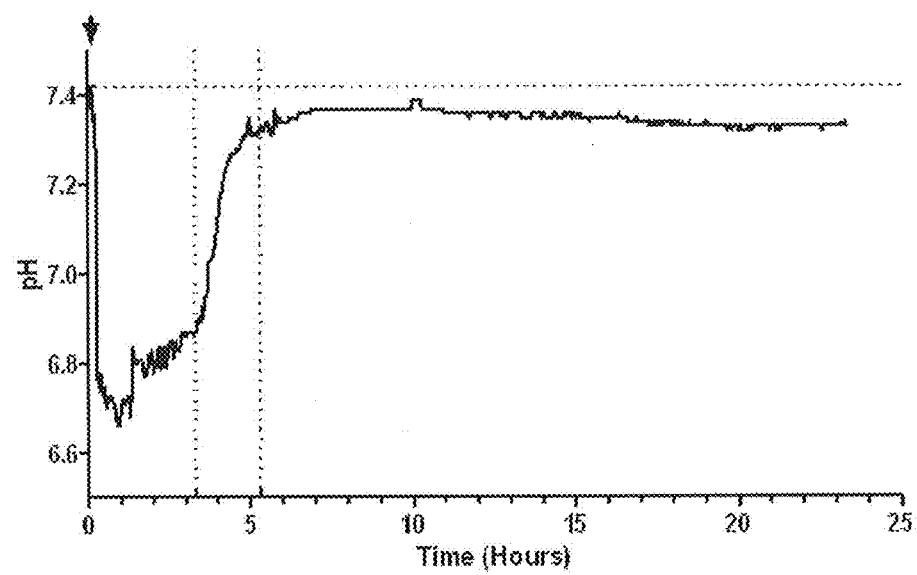

FIG. 73: pH profile during reduction and re-oxidation. pH during reduction and re-oxidation of IgG1-2F8-F405L and IgG1-7D8-K409R (1:1 mixture) in the presence of 2 mM EDTA was followed using a pH probe. The horizontal dashed line shows the initial pH value. The addition of 2-MEA (indicated by the arrow) coincided with a large drop in pH at the beginning of the run. The vertical dashed lines show start and stop of diafiltration.

Figure 74:
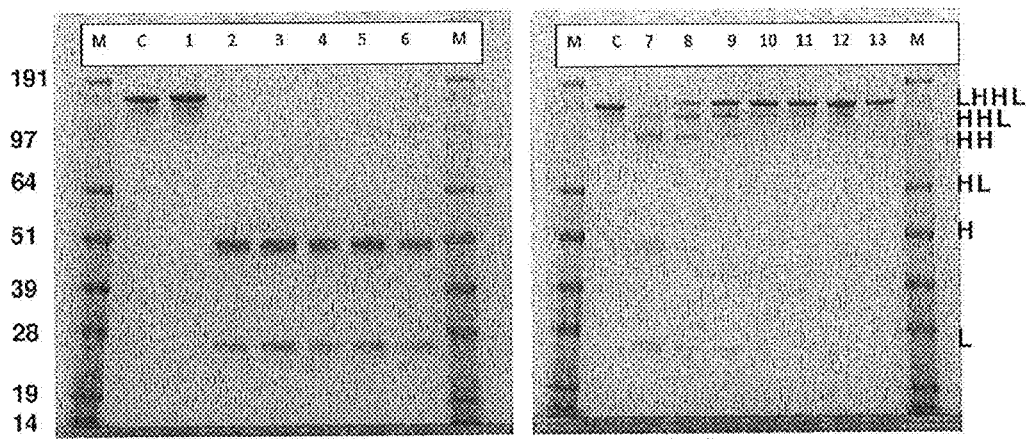

FIG. 74: SDS-PAGE analysis during reduction and re-oxidation. Samples taken during reduction and re-oxidation of IgG1-2F8-F405L and IgG1-7D8-K409R (1:1 mixture) in the presence of 2 mM EDTA were analyzed by non-reduced SDS-PAGE analysis. M: MW marker; C: IgG1 control; lane 1: prior to 2-MEA addition; lanes 2, 3, 4 and 5: after 30 min, 1 hour, 2 hours and 3 hours of reduction, lanes 6, 7, 8, 9 and 10 diafiltration results after 1, 2, 3, 5, and 7 L diafiltered buffer, lanes, 11 and 12: 1 hour and O/N incubation after diafiltration, lane 13: 10 min after addition of $CuSO_4$. The masses of the molecular weight markers are indicated on the left. Reduced/re-oxidized IgG species are indicated by H (Heavy chain) and/or L (light chain) and combinations thereof.

Figure 75:
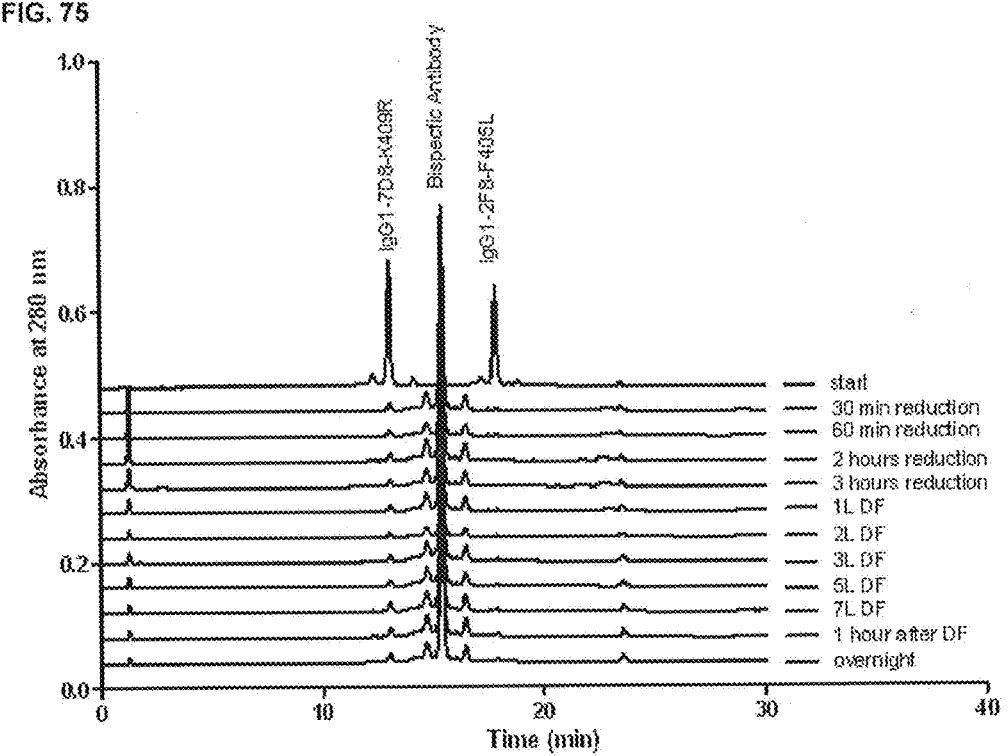

FIG. 75: CIEX profiles during reduction and re-oxidation. Samples taken during reduction and re-oxidation of IgG1-2F8-F405L and IgG1-7D8-K409R (1:1 mixture) in the presence of 2 mM EDTA were analyzed by analytical CIEX. Samples were taken at the indicated time points and snap frozen until CIEX analysis.

Figure 76:
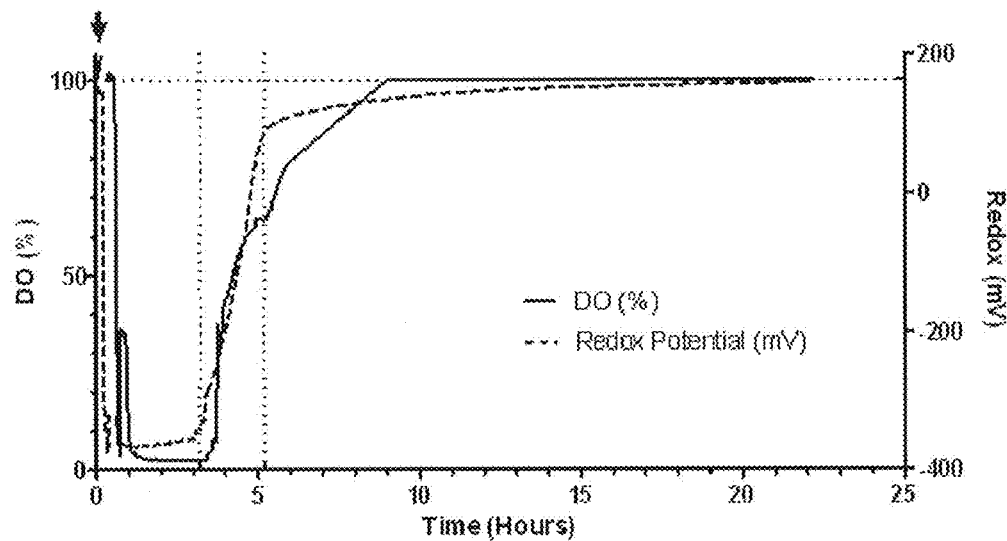

FIG. 76: Dissolved oxygen and redox potential during reduction and re-oxidation. Oxygen saturation and redox potential during reduction and re-oxidation of IgG1-2F8-F405L and IgG1-7D8-K409R (1:1 mixture) were followed using a redox probe and a DO probe. The addition of 2-MEA (indicated by the arrow) coincided with a large drop in DO and redox at the beginning of the run. The horizontal dashed line shows the initial value of both redox and DO. The vertical dashed lines show the start and stop of diafiltration.

Figure 77:
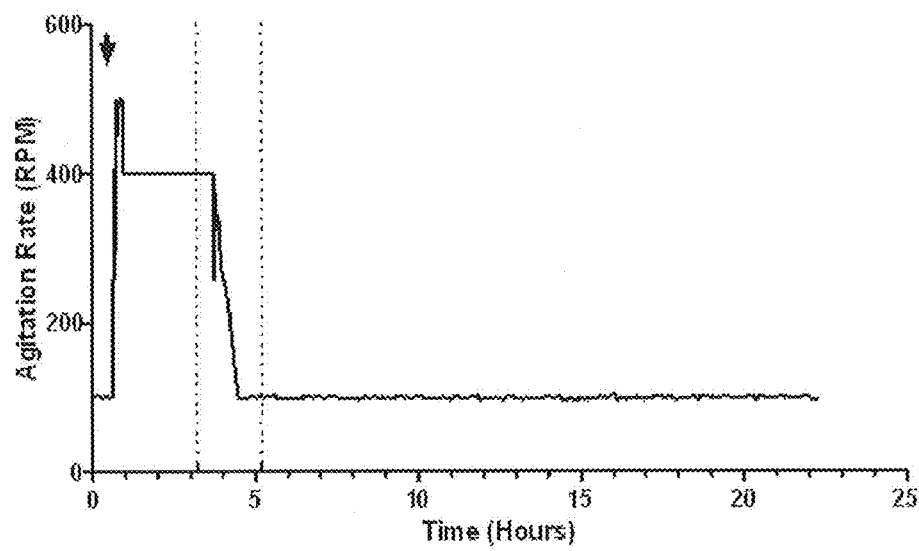

FIG. 77: Agitation rate during reduction and re-oxidation. The addition of 2-MEA (indicated by the arrow) coincided with a large increase in agitation rate near the beginning of the run. The vertical dashed lines show start and stop of diafiltration.

Figure 78:
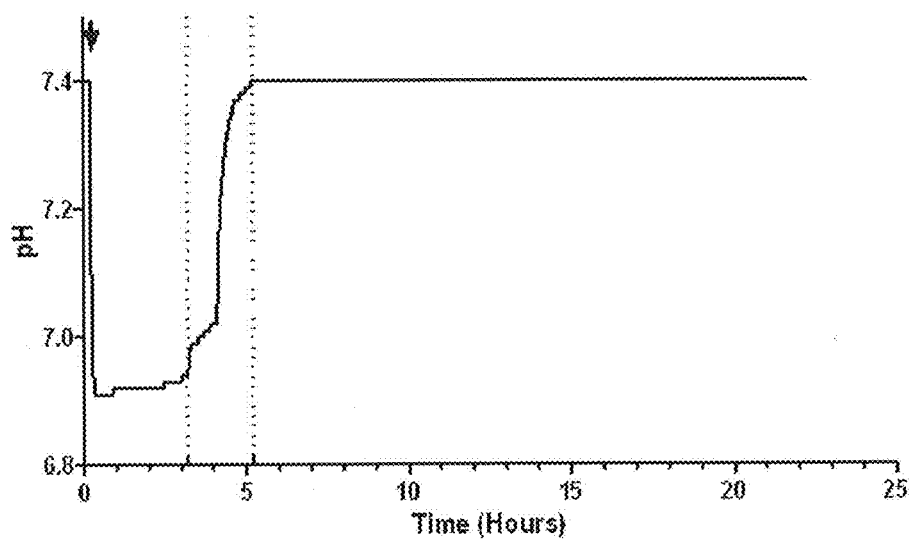

FIG. 78: pH profile during reduction and re-oxidation. pH during reduction and re-oxidation of IgG1-2F8-F405L and IgG1-7D8-K409R (1:1 mixture) was measured by a pH probe. The addition of 2-MEA (indicated by the arrow) coincided with a large drop in pH at the beginning of the run. The vertical dashed lines show start and stop of diafiltration.

Figure 79:
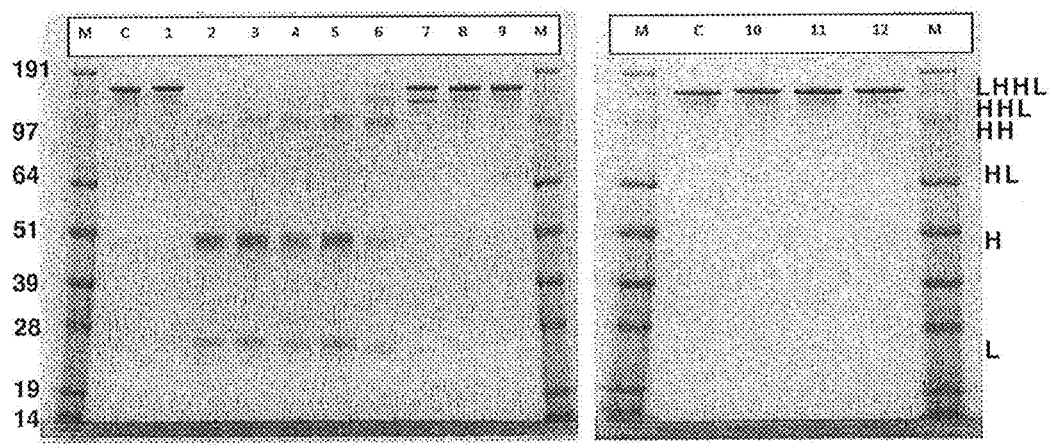

FIG. 79: SDS-PAGE (non-reduced) analysis during reduction and re-oxidation. Samples taken during reduction and re-oxidation of IgG1-2F8-F405L and IgG1-7D8-K409R (1:1 mixture) were analyzed by non-reduced SDS-PAGE analysis. M: MW marker; C: IgG1 control; lane 1: prior to 2-MEA addition; lanes 2, 3, 4 and 5: after 30 min, 1 hour, 2 hours and 3 hours of reduction, lanes 6, 7, 8, 9 and 10: diafiltration results after 1, 2, 3, 5, and 7 L diafiltered buffer, lanes, 11 and 12: 1 hour and O/N incubation after diafiltration. The masses of the molecular weight markers are indicated on the left. Reduced/re-oxidized IgG species are indicated by H (Heavy chain) and/or L (light chain) and combinations thereof.

Figure 80:
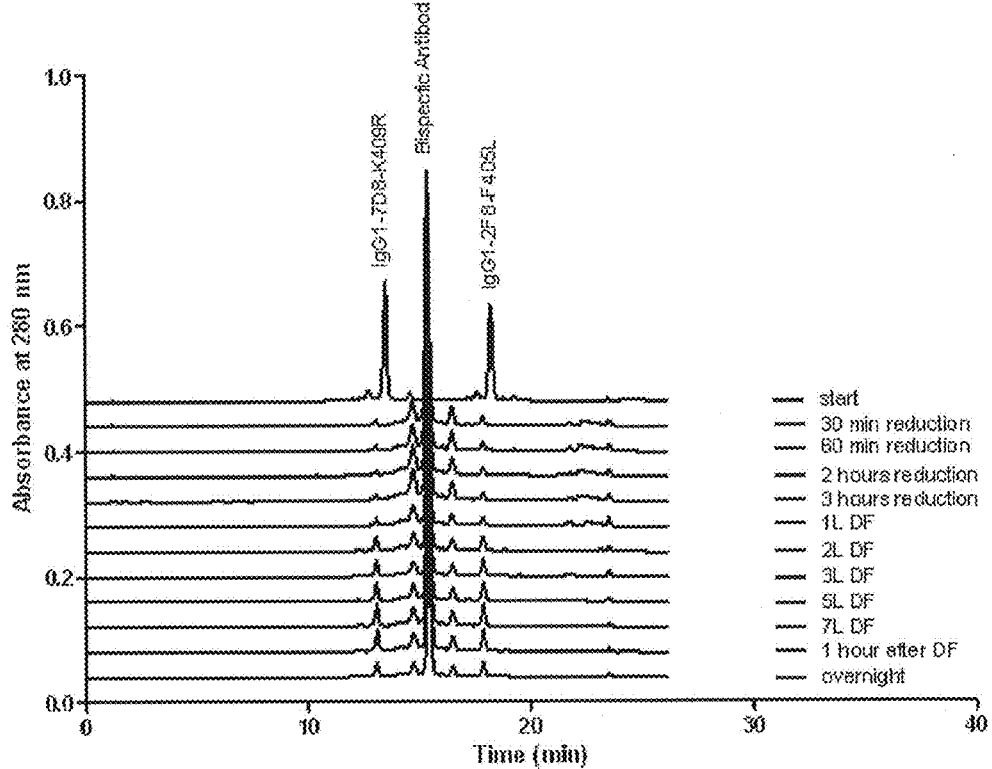

FIG. 80: CIEX profiles during reduction and re-oxidation. Samples taken during reduction and re-oxidation of IgG1-2F8-F405L and IgG1-7D8-K409R (1:1 mixture) were analyzed by analytical CIEX. Samples were taken at the indicated time points and snap frozen until CIEX analysis.

Figure 81:
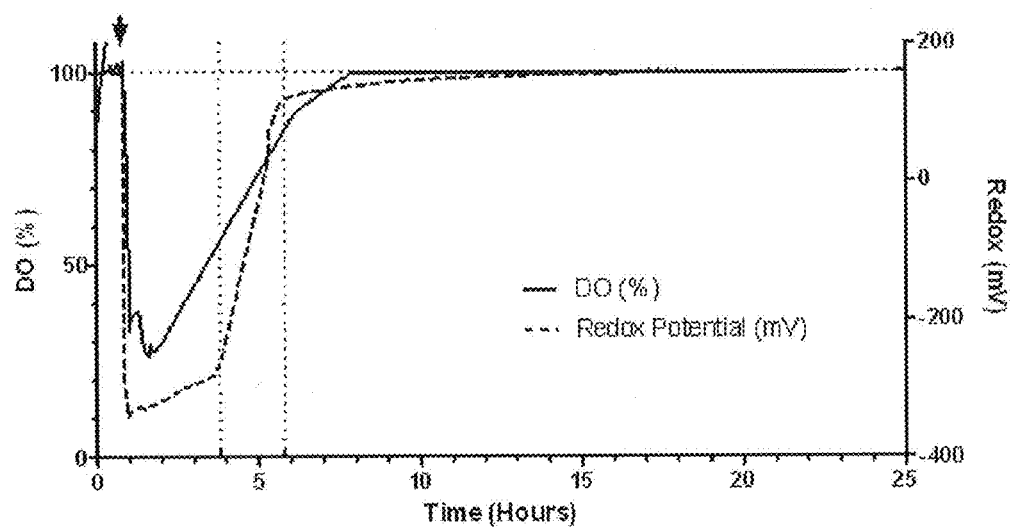

FIG. 81: Dissolved oxygen and redox potential during reduction and re-oxidation. Oxygen saturation and redox potential during reduction and re-oxidation of IgG1-2F8-F405L and IgG1-7D8-K409R (1:1 mixture) were followed using a redox probe and a DO probe. The horizontal dashed line shows the initial values for both redox and DO. The addition of 2-MEA (indicated by the arrow) coincided with a large drop in DO and redox at the beginning of the run. The horizontal dashed line shows the initial value of both redox and DO. The vertical dashed lines show start and stop of diafiltration.

Figure 82:
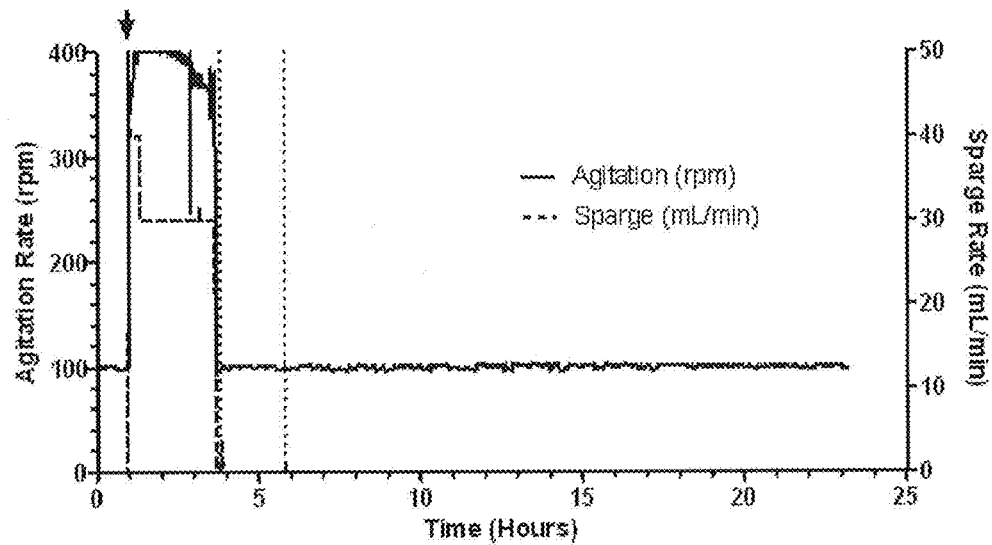

FIG. 82: Agitation rate during reduction and re-oxidation. The addition of 2-MEA (indicated by the arrow) coincided with a large increase in agitation rate near the beginning of the run. The vertical dashed lines show start and stop of diafiltration.

Figure 83:
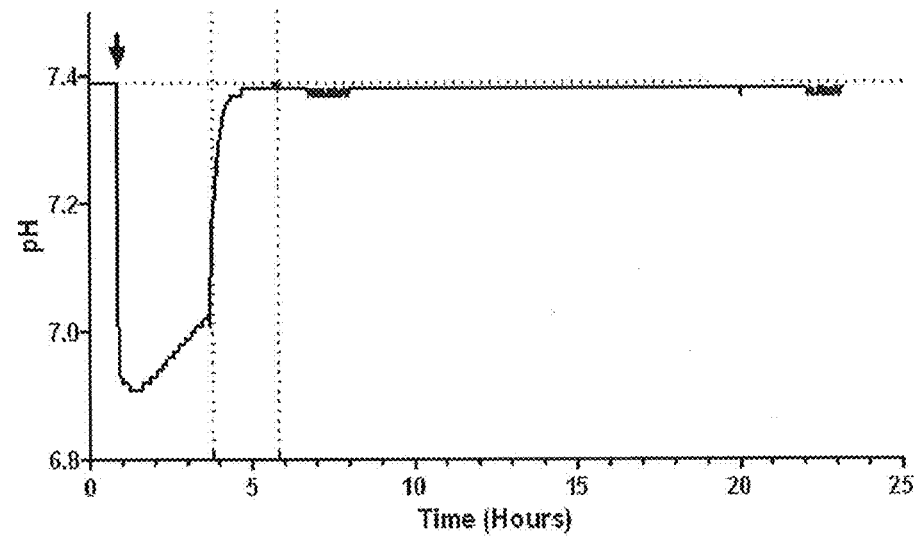

FIG. 83: pH profile during reduction and re-oxidation. pH during reduction and re-oxidation of IgG1-2F8-F405L and IgG1-7D8-K409R (1:1 mixture) was measured by a pH probe. The horizontal dashed line shows the initial value. The addition of 2-MEA (indicated by the arrow) coincided with a large drop in pH at the beginning of the run. The horizontal dashed line shows the initial pH value. The vertical dashed lines show start and stop of diafiltration.

Figure 84:
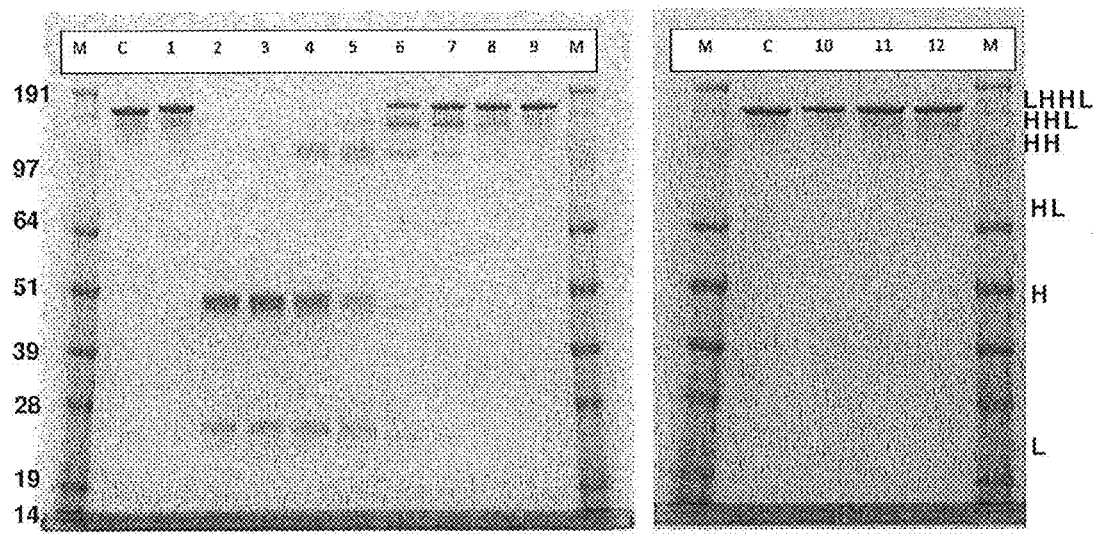

FIG. 84: SDS-PAGE (non-reduced) analysis during reduction and re-oxidation. Samples taken during reduction and re-oxidation of IgG1-2F8-F405L and IgG1-7D8-K409R (1:1 mixture) were analyzed by non-reduced SDS-PAGE analysis. M: MW marker; C: IgG1 control; lane 1: prior to 2-MEA addition; lanes 2, 3, 4 and 5: after 30 min, 1 hour, 2 hours and 3 hours of reduction, lanes 6, 7, 8, 9 and 10: diafiltration results after 1, 2, 3, 5, and 7 L diafiltered buffer, lanes, 11 and 12: 1 hour and O/N incubation after diafiltration. The masses of the molecular weight markers are indicated on the left. Reduced/re-oxidized IgG species are indicated by H (Heavy chain) and/or L (light chain) and combinations thereof.

Figure 85:
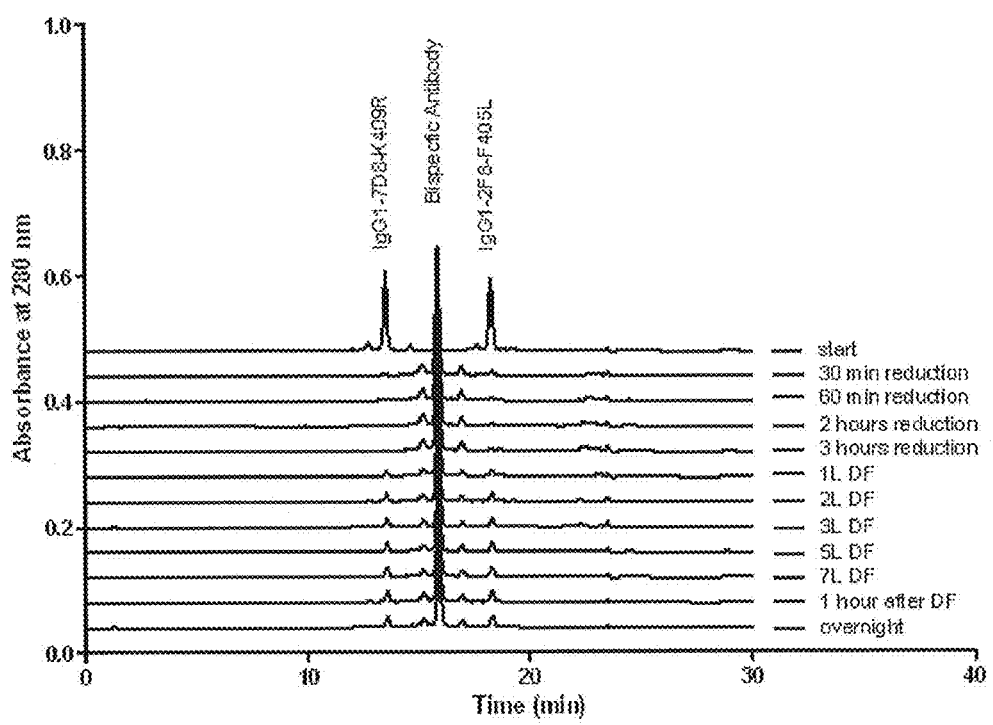

FIG. 85: CIEX profiles during reduction and re-oxidation. Samples taken during reduction and re-oxidation of IgG1-2F8-F405L and IgG1-7D8-K409R (1:1 mixture) were analyzed by analytical CIEX. Samples were taken at the indicated time points and snap frozen until CIEX analysis.

Figure 86:
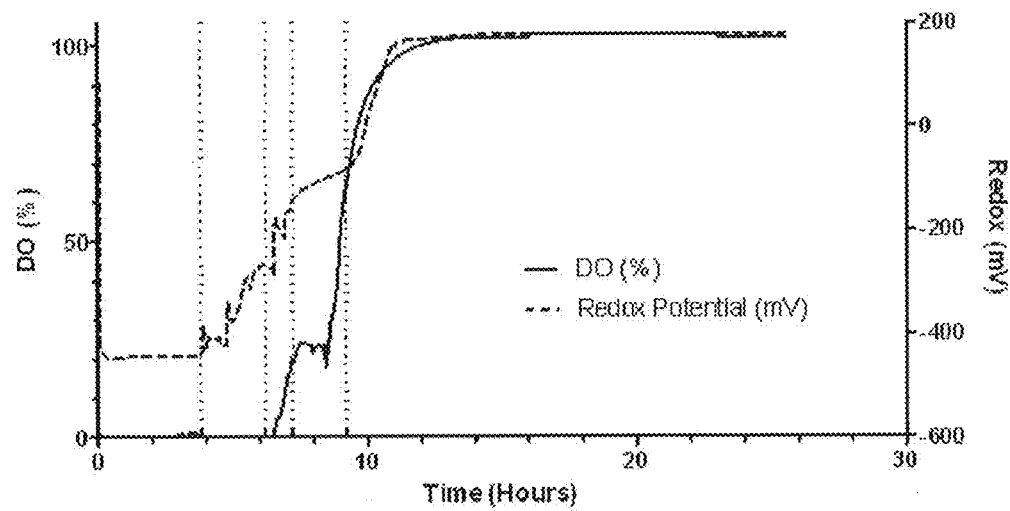

FIG. 86: Dissolved oxygen and redox potential during reduction and re-oxidation. Oxygen saturation and redox potential during reduction and re-oxidation of IgG1-2F8-F405L and IgG1-7D8-K409R (1:1 mixture) in the presence of nitrogen were followed using a redox probe and a DO probe. The addition of 2-MEA at time 0 coincided with a large drop in redox at the beginning of the run. The vertical dashed lines show the start of diafiltration, the end of diafiltration, the 1-hr post diafiltration sample point, and the 3-hr post diafiltration sample point. The headspace was flushed with air at the end of diafiltration.

Figure 87:
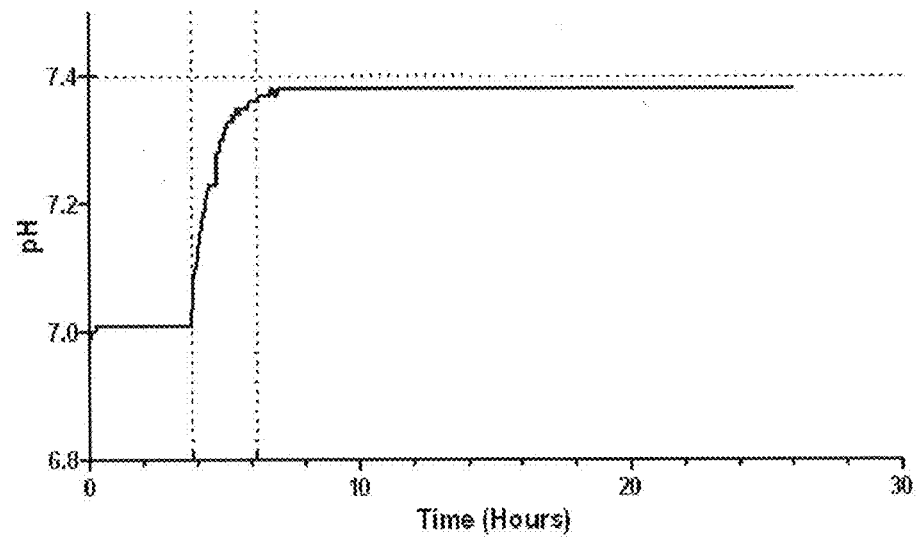

FIG. 87: pH profile during reduction and re-oxidation. pH during reduction and oxidation of IgG1-2F8-F405L and IgG1-7D8-K409R (1:1 mixture) in the presence of nitrogen was measured by a pH probe. The horizontal dashed line shows the initial pH value. The addition of 2-MEA at time 0 coincided with a large drop in pH at the beginning of the run. The vertical dashed lines show start and stop of diafiltration.

Figure 88:
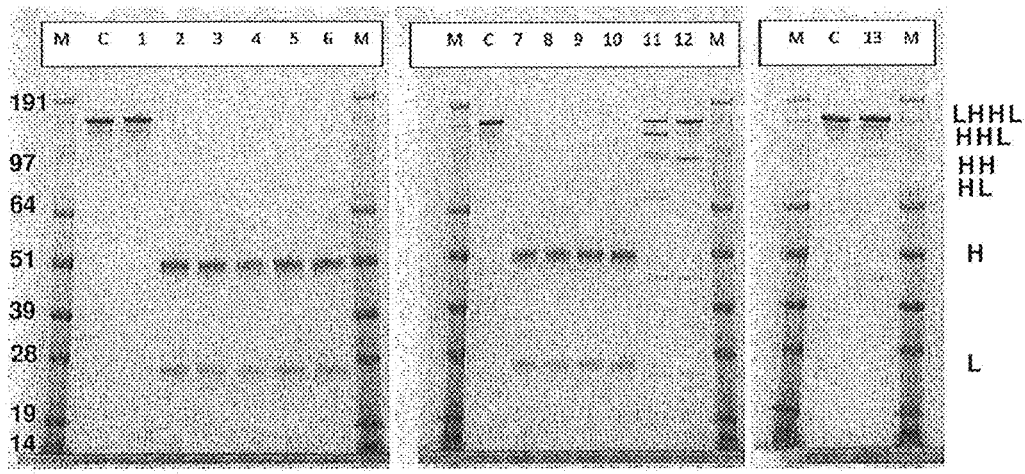

FIG. 88: SDS-PAGE (non-reduced) analysis during reduction and re-oxidation. Samples taken during reduction and re-oxidation of IgG1-2F8-F405L and IgG1-7D8-K409R (1:1 mixture) in the presence of nitrogen were analyzed by non-reduced SDS-PAGE analysis. M: MW marker; C: IgG1 control; lane 1: prior to 2-MEA addition; lanes 2, 3, 4 and 5: after 30 min, 1 hour, 2 hours and 3 hours of reduction, lanes 6, 7, 8, 9 and 10: diafiltration results after 1, 2, 3, 5, and 7 L diafiltered buffer, lanes, 11 and 12: 1 and 3 hour after diafiltration, lane 13: O/N incubation after diafiltration. The masses of the molecular weight markers are indicated on the left. Reduced/re-oxidized IgG species are indicated by H (Heavy chain) and/or L (light chain) and combinations thereof.

Figure 89:
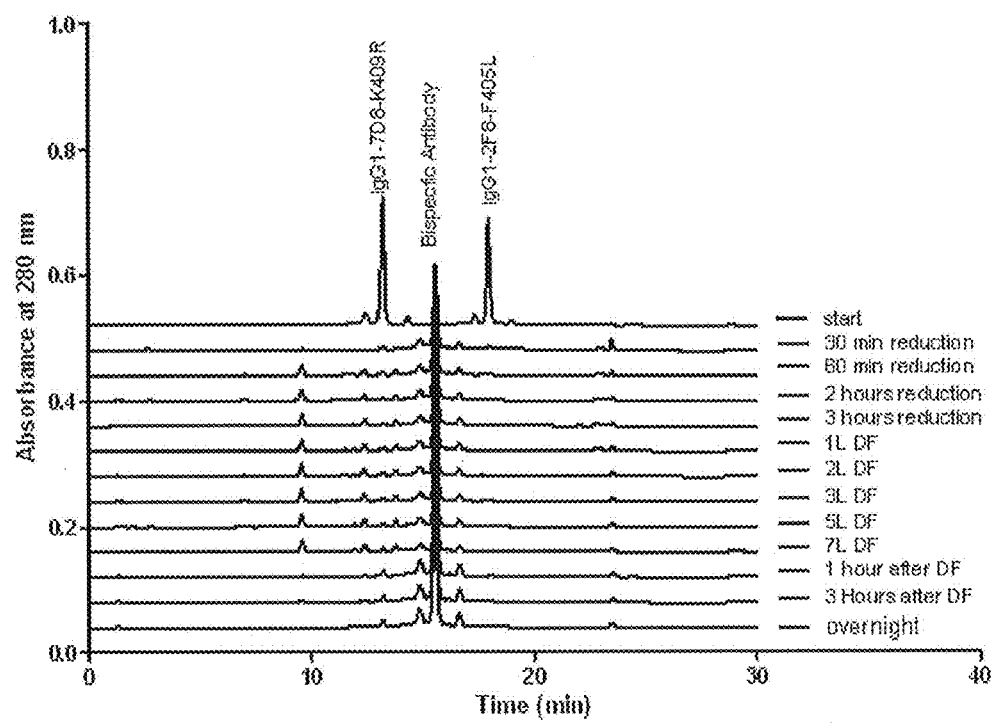

FIG. 89: CIEX profiles during reduction and re-oxidation. Samples taken during reduction and re-oxidation of IgG1-2F8-F405L and IgG1-7D8-K409R (1:1 mixture) in the presence of nitrogen were analyzed by analytical CIEX. Samples were taken at the indicated time points and snap frozen until CIEX analysis.

Figure 90:
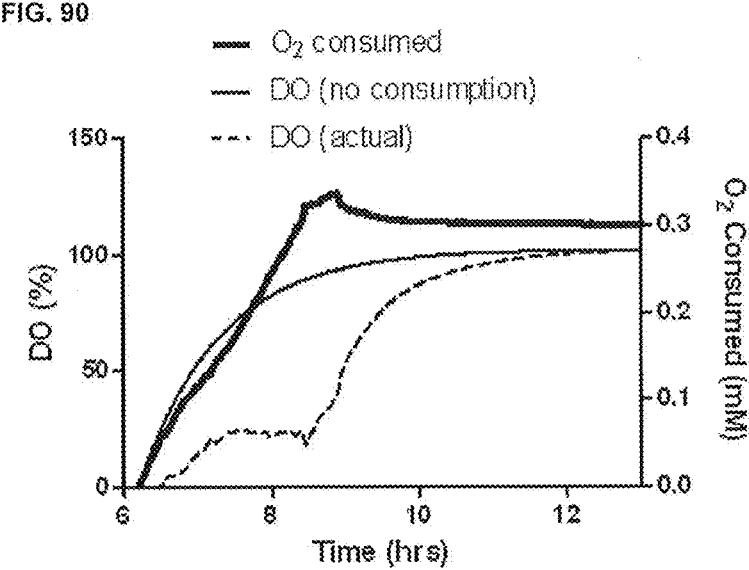

FIG. 90: Oxygen consumption after introduction of air. The graph shows the values from just after diafiltration, upon the addition of air. The actual DO is the DO measured in the system. DO (no consumption) is a calculated value assuming no oxygen consumption. $O_2$ consumed is the calculated amount of oxygen consumed using a previously determined kla and assuming the saturation of oxygen in the system is 0.2 mM.

Figure 91:
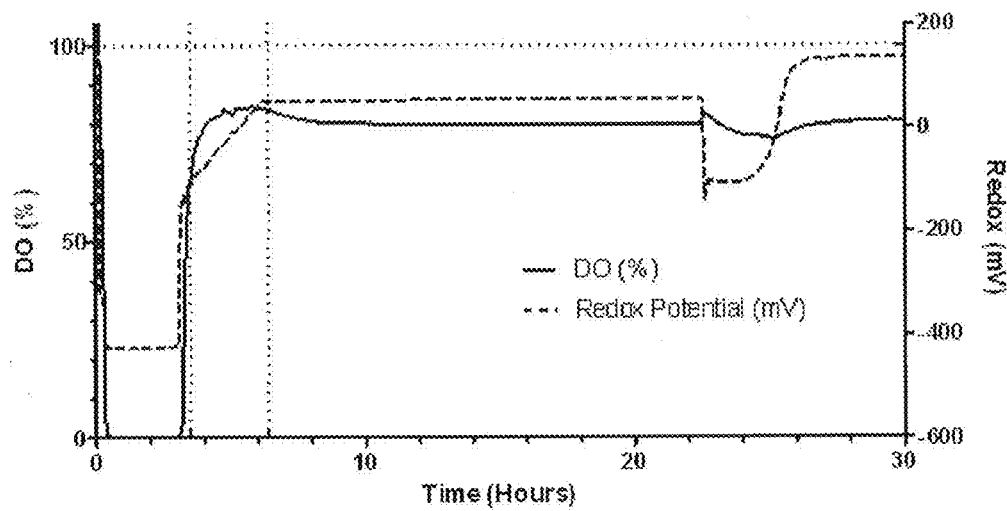

FIG. 91: Dissolved oxygen and redox potential during reduction and re-oxidation. Oxygen saturation and redox potential during reduction and re-oxidation of IgG1-2F8-F405L and IgG1-7D8-K409R (1:1 mixture) were followed using a redox probe and a DO probe. The horizontal dashed line shows the initial values for redox and DO. The vertical dashed lines show start and stop of diafiltration. The addition of 2-MEA coincided with a large drop in DO and redox at the beginning of the run. The pH was adjusted to 5.0 just prior to diafiltration. The pH was adjusted back to 7.4 after O/N incubation.

Figure 92:
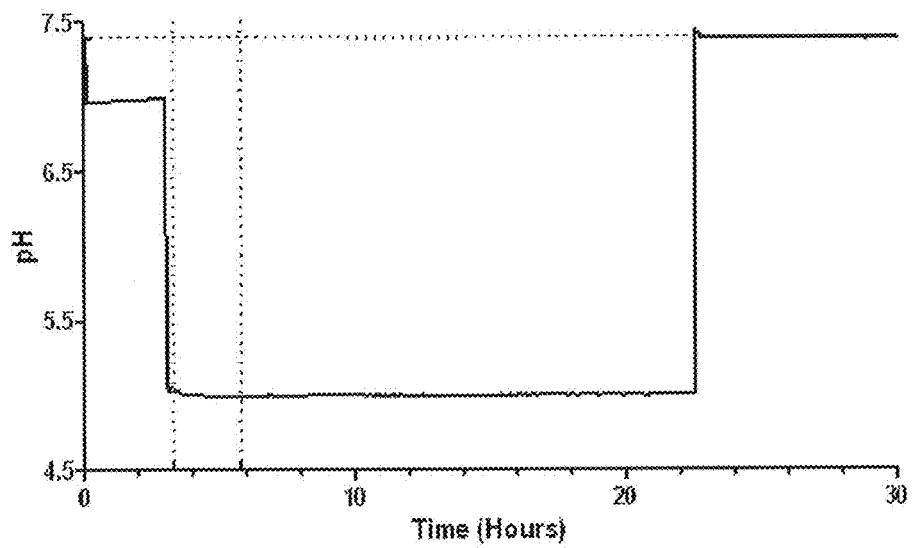

FIG. 92: pH profile during reduction and re-oxidation. pH during reduction and re-oxidation of IgG1-2F8-F405L and IgG1-7D8-K409R (1:1 mixture) was measured by a pH probe. The horizontal dashed line shows the initial value. The vertical dashed lines show start and stop of diafiltration. The addition of 2-MEA coincided with a drop in pH at the beginning of the run. The pH was adjusted to 5.0 just prior to diafiltration against pH 5.0 buffer. The pH was readjusted to 7.4 after O/N incubation.

Figure 93:
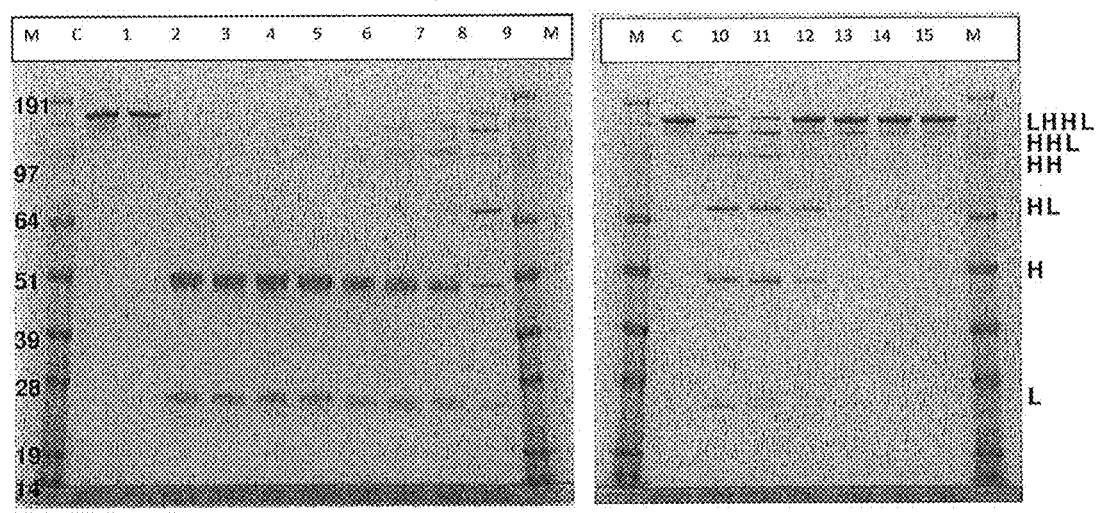

FIG. 93: SDS-PAGE (non-reduced) analysis during reduction and re-oxidation. Samples taken during reduction and re-oxidation of IgG1-2F8-F405L and IgG1-7D8-K409R (1:1 mixture) were analyzed by non-reduced SDS-PAGE analysis. M: MW marker; C: IgG1 control; lane 1: prior to 2-MEA addition; lanes 2, 3, 4 and 5: after 30 min, 1 hour, 2 hours and 3 hours of reduction, lanes 6, 7, 8, 9 and 10: diafiltration results after 1, 2, 3, 5, and 7 L diafiltered buffer, lanes 11 and 12: 1 hour and O/N incubation after diafiltration, lanes, 13, 14 and 15: immediately and 1 and 2 hours after Tris addition. The masses of the molecular weight markers are indicated on the left. Reduced/re-oxidized IgG species are indicated by H (Heavy chain) and/or L (light chain) and combinations thereof.

Figure 94:
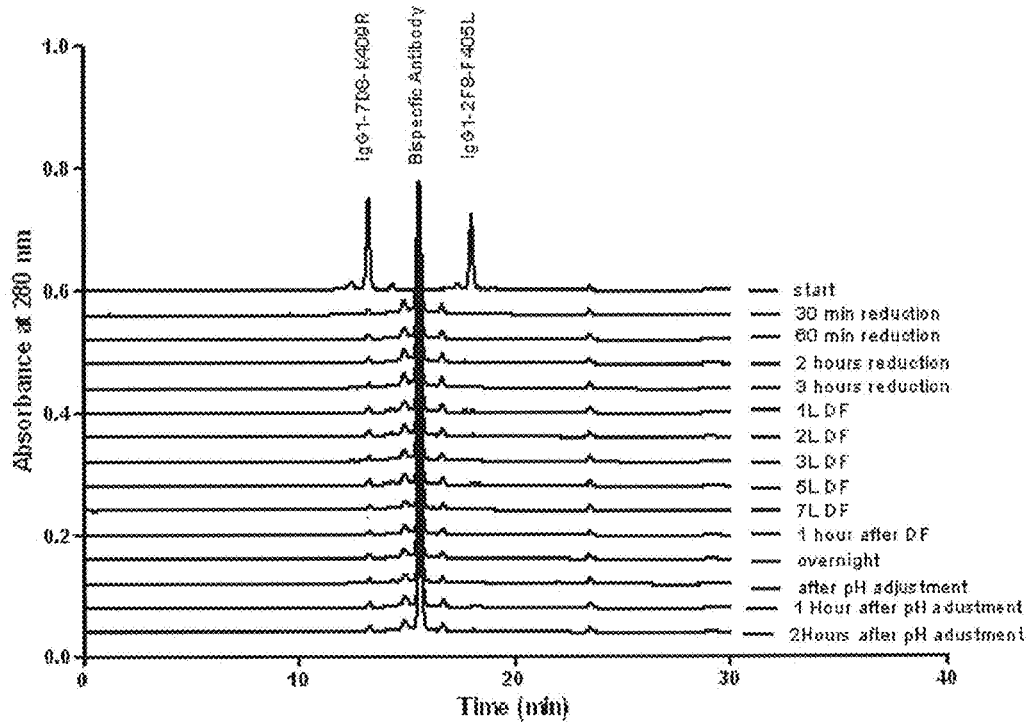

FIG. 94: CIEX profiles during reduction and re-oxidation. Samples taken during reduction and re-oxidation of IgG1-2F8-F405L and IgG1-7D8-K409R (1:1 mixture) were analyzed by analytical CIEX. Samples were taken at the indicated time points and snap frozen until CIEX analysis.

Figure 95:
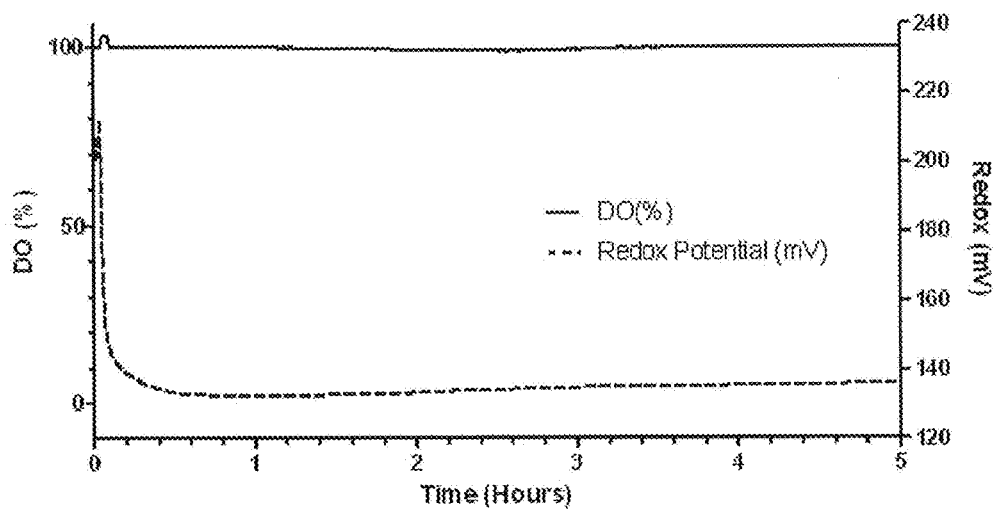

FIG. 95: Dissolved oxygen and redox potential after cystamine addition. Oxygen saturation and redox potential after addition of cystamine to IgG1-2F8-F405L and IgG1-7D8-K409R 1:1 mixture were followed using a redox probe and a DO probe.

Figure 96:
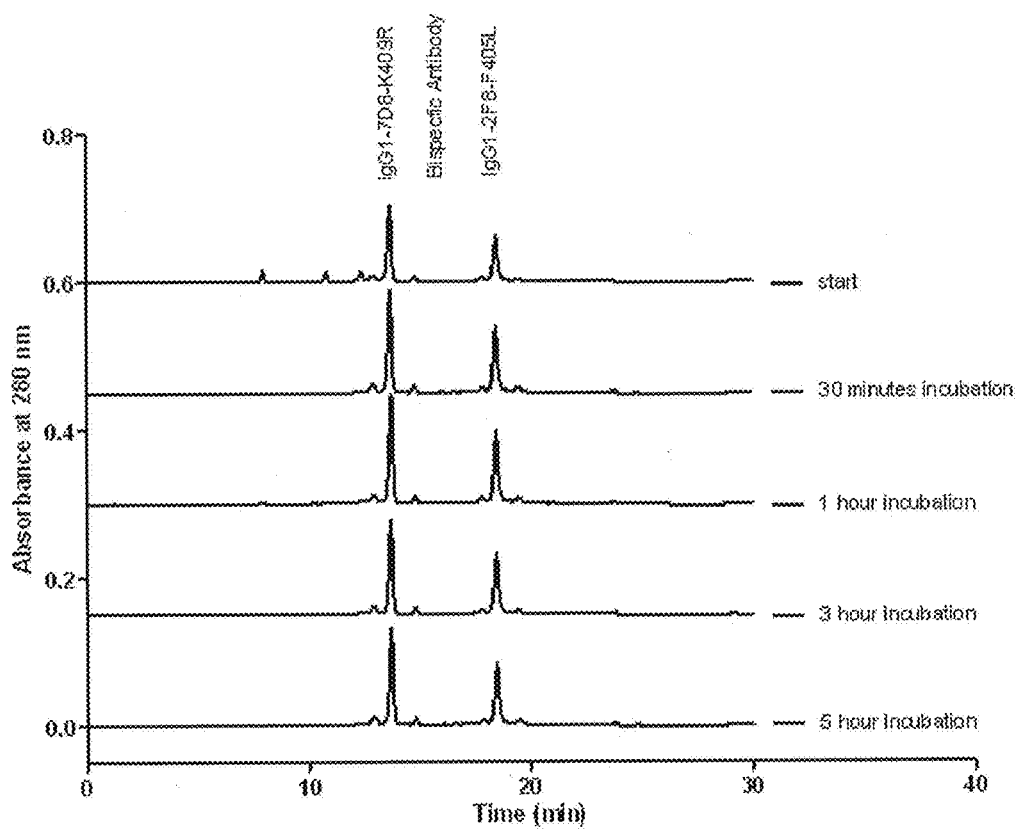

FIG. 96: CIEX profiles after addition of cystamine. Samples taken after addition of cystamine to IgG1-2F8-F405L and IgG1-7D8-K409R were analyzed by analytical CIEX. Samples were taken at the indicated time points.

Figure 97:
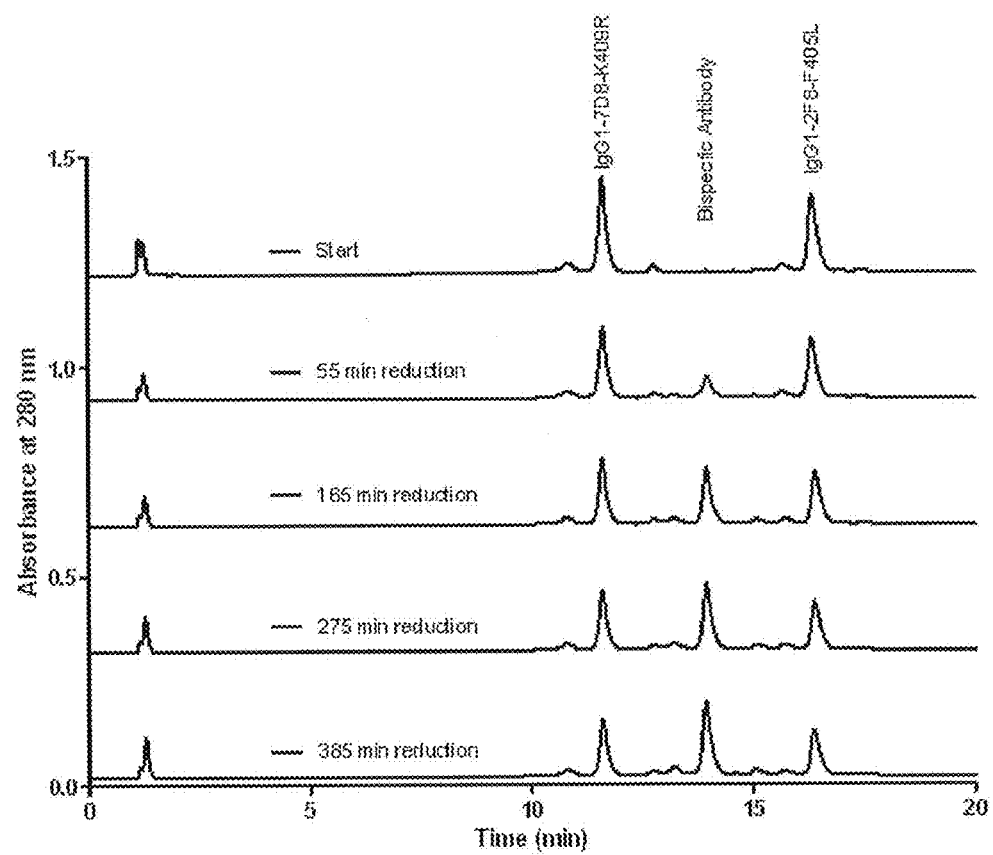

FIG. 97: CIEX profiles of reduction using 10 mM cysteine. Samples were loaded on the column every 55 min and analyzed by analytical CIEX. Selected profiles are shown, incubation times are indicated.

Figure 98:
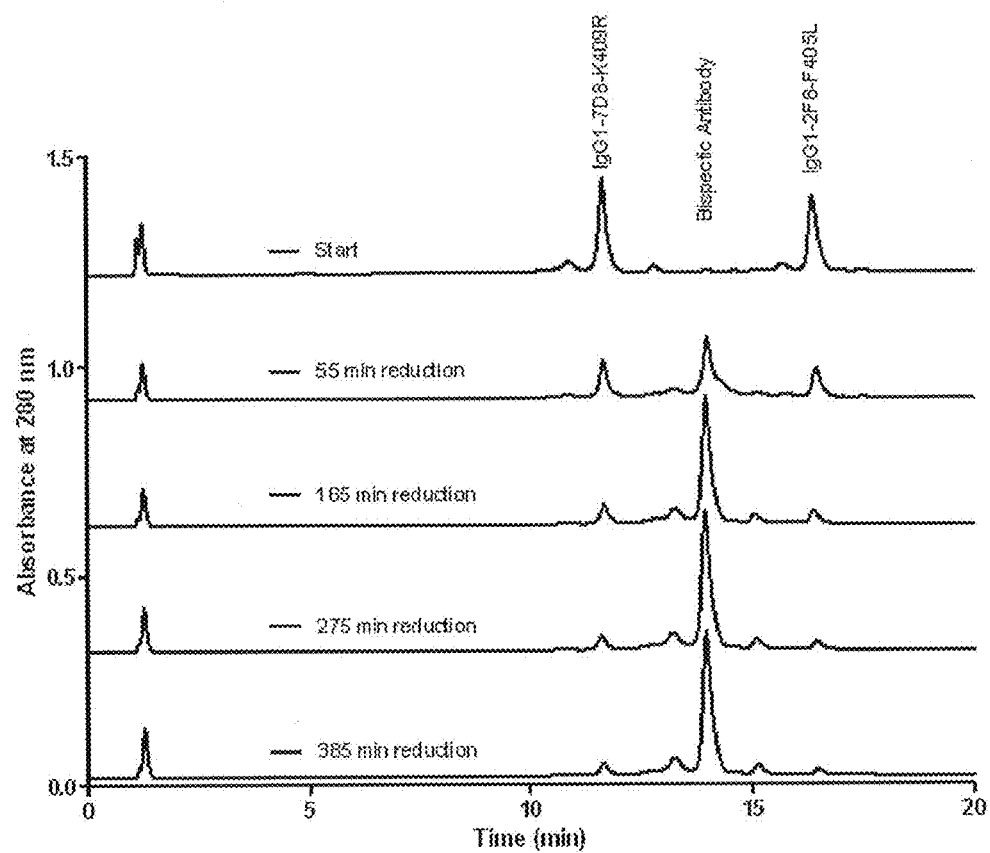

FIG. 98: CIEX profiles of reduction at 25 mM cysteine. Samples were loaded on the column every 55 min and analyzed by analytical CIEX. Selected profiles are shown, incubation times are indicated.

Figure 99:
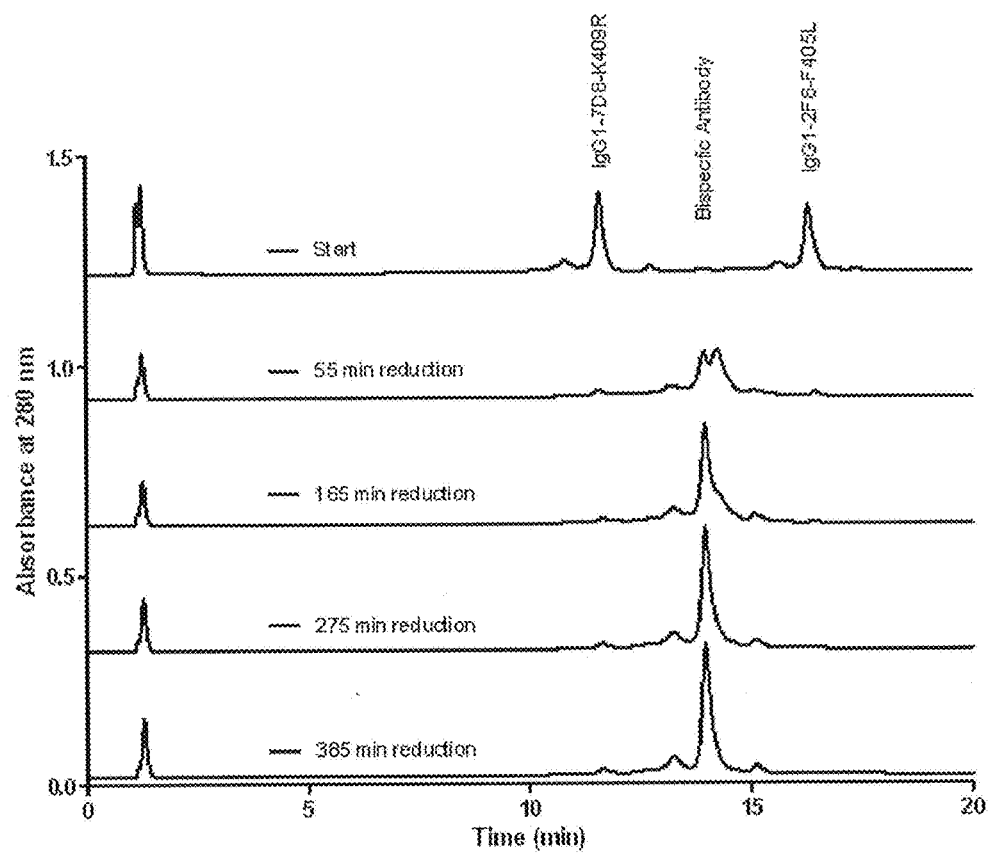

FIG. 99: CIEX profiles of reduction at 50 mM cysteine. Samples were loaded on the column every 55 min and analyzed by analytical CIEX. Selected profiles are shown, incubation times are indicated.

Figure 100:
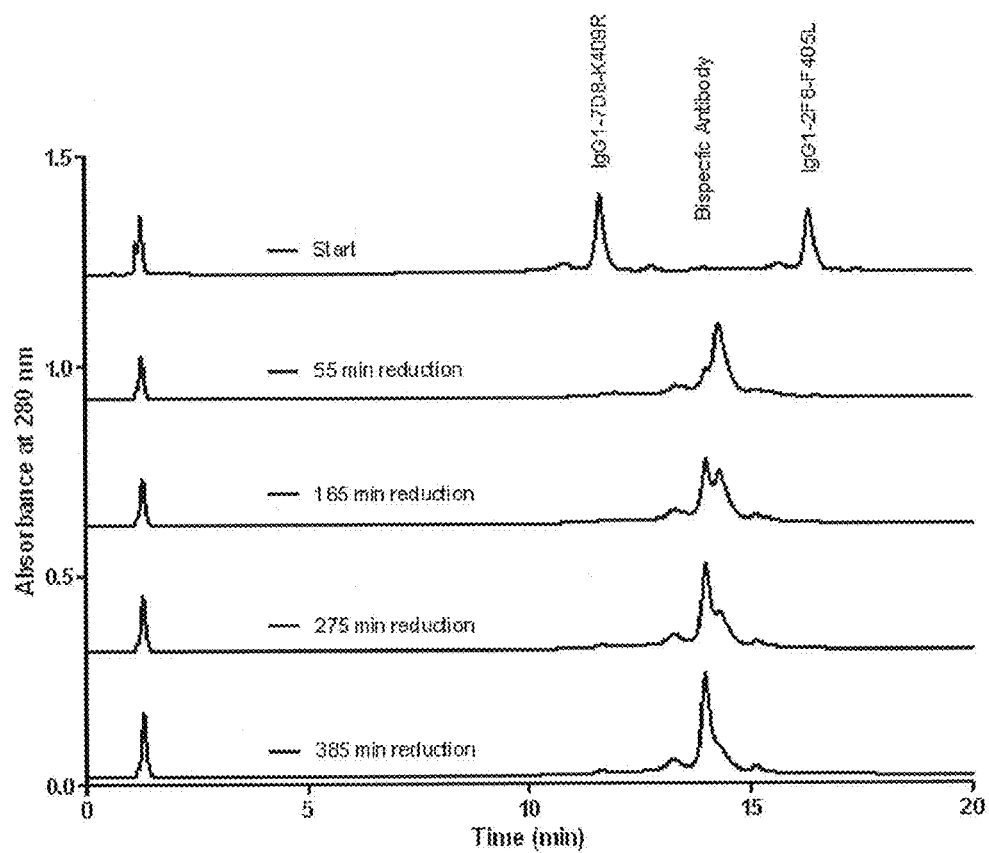

FIG. 100: CIEX profiles of reduction at 75 mM cysteine. Samples were loaded on the column every 55 min and analyzed by analytical CIEX. Selected profiles are shown, incubation times are indicated.

Figure 101:
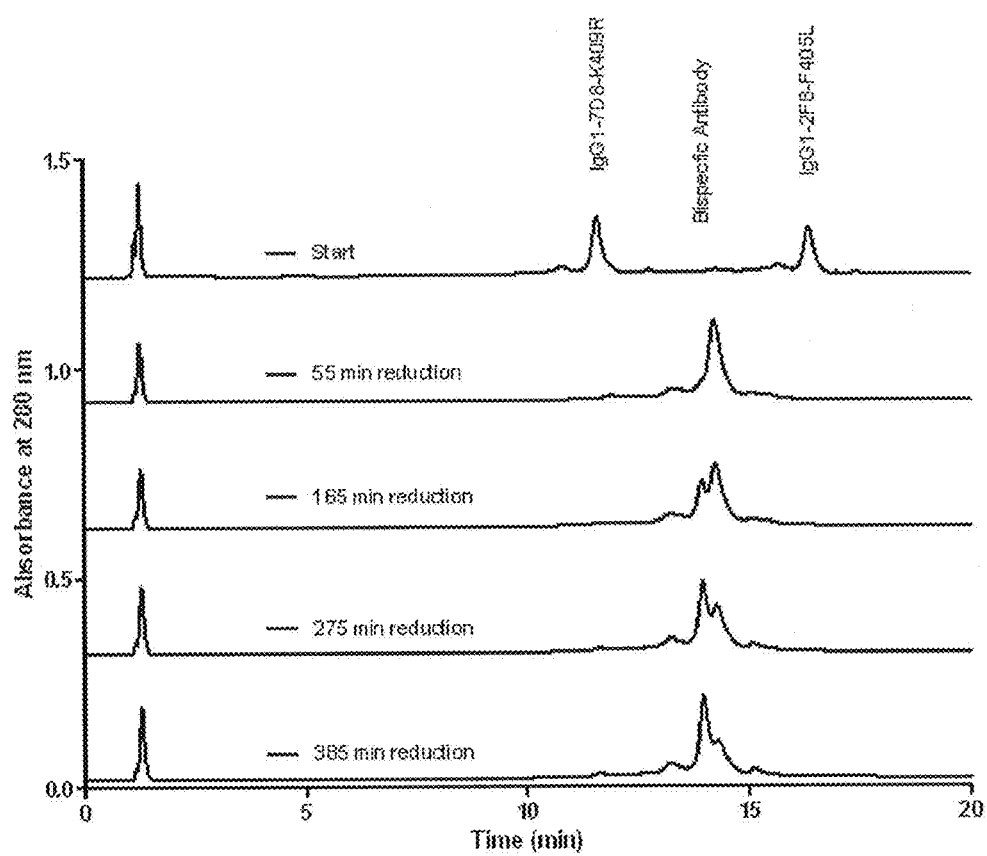

FIG. 101: CIEX profiles of reduction at 100 mM cysteine. Samples were loaded on the column every 55 min and analyzed by analytical CIEX. Selected profiles are shown, incubation times are indicated.

Figure 102:
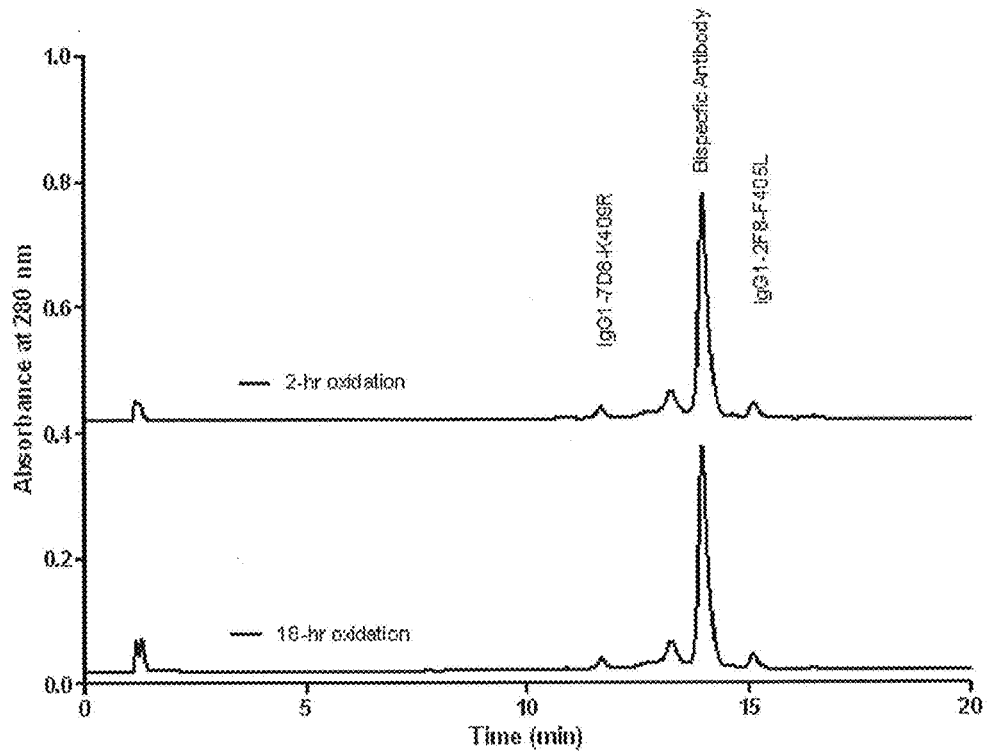

FIG. 102: CIEX profile after reduction using cysteine, removal of cysteine, and incubation. Shown is the CIEX profile after reduction for 385 minutes in 50 mM cysteine at 30° C., followed by removal of cysteine using a desalting column and subsequent incubation for 2 hours and 18 hours.

Figure 103:
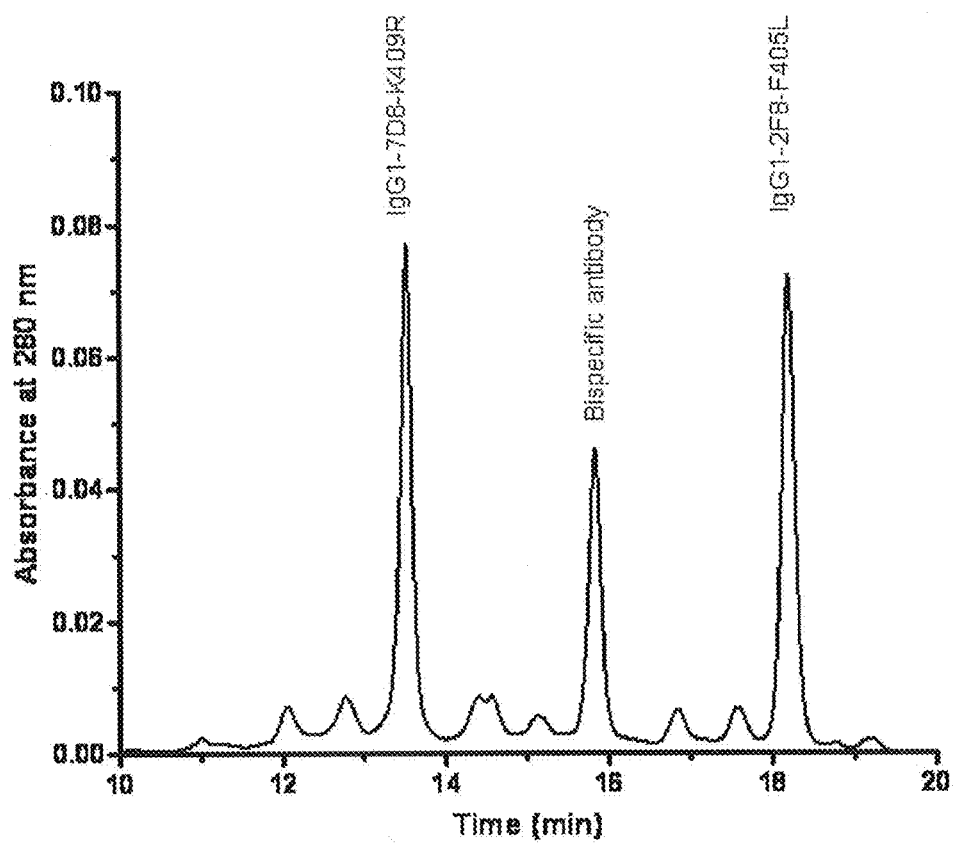

FIG. 103: CIEX profile of remaining homodimers and the newly formed bispecific antibody after elution from the immobilized reductant column. A mixture of homodimers IgG1-2F8-F405L and IgG1-7D8-K409R were added to an immobilized reductant column, incubated and eluted. Formation of bispecific antibodies was analyzed by analytical CIEX.

Figure 104:
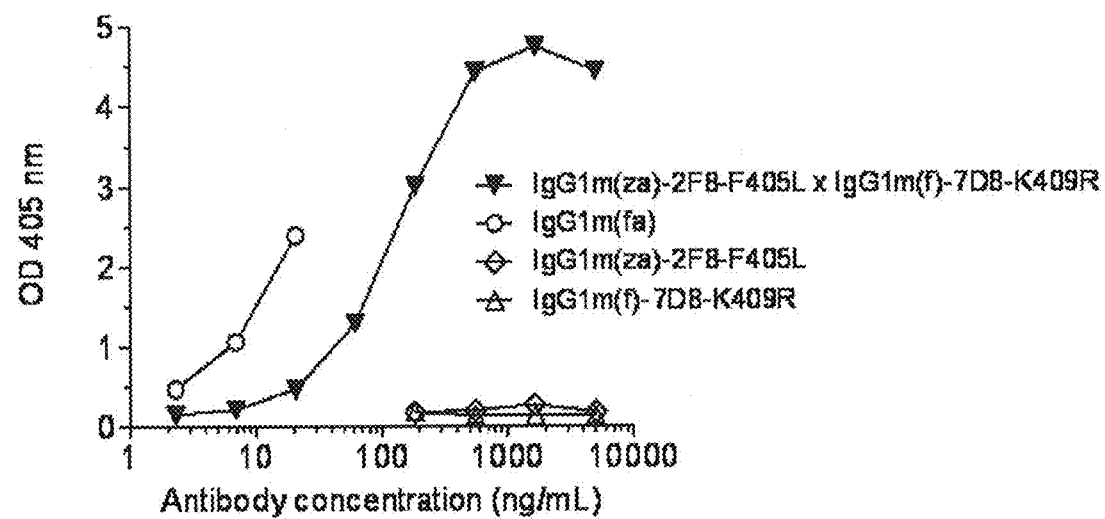

FIG. 104: Allotype ELISA for the detection of bispecific antibodies. A mixture of IgG1m(f)-K409R-CD20 and IgG1m(za)-F405L-EGFR was incubated with 25 mM 2-MEA at 37° C. for 90 min. The formation of bispecific antibodies was measured in a sandwich ELISA. The optical density at 405 nm is plotted on the Y-axis as a measure for the formation of bispecific IgG1m(f,za)-CD20×EGFR antibodies. An IgG1m(fa) antibody was included as positive control.

Figure 105:
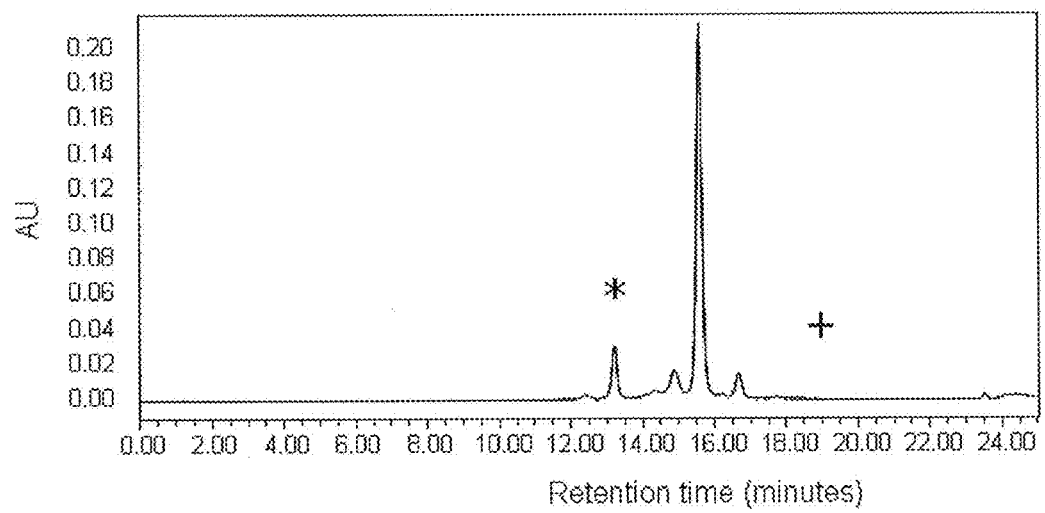

FIG. 105: CIEX analysis after the SNEEP. CIEX analysis was performed after SNEEP in which IgG1-7D8-AAA-K409R was added in excess. Quantification showed that 11.4% of IgG1-7D8-AAA-K409R (*), 88.5% bispecific antibody and only 0.1% IgG1-2F8-F405L (+) homodimer was present after the exchange reaction.

Figure 106:
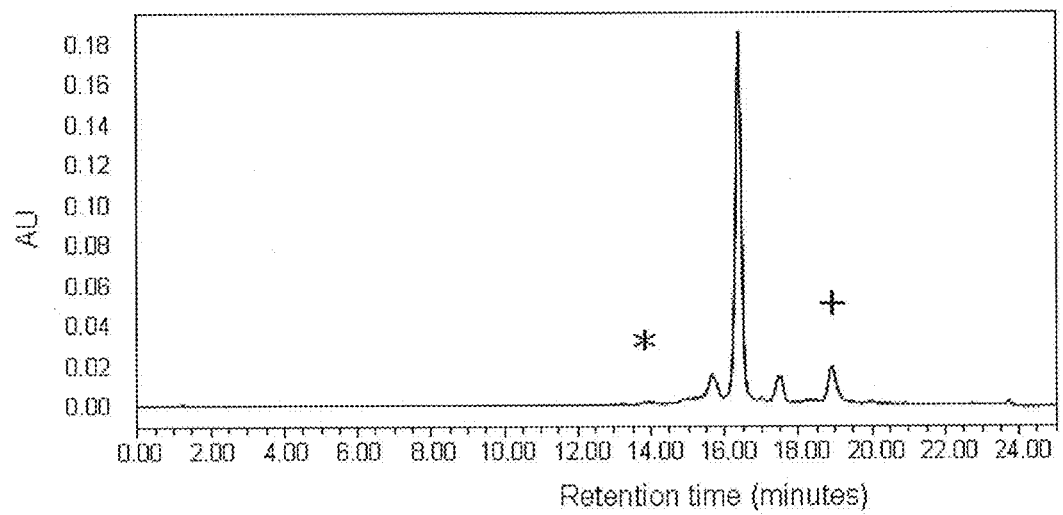

FIG. 106: CIEX analysis after SNEEP. CIEX analysis was performed after SNEEP in which IgG1-2F8-F405R was used in excess. Quantification showed that 0.4% IgG1-7D8-K409R (*), 88.4% bispecific antibody, and 11.2% IgG1-2F8-F405L (+) were present after the exchange reaction.

Figure 107:
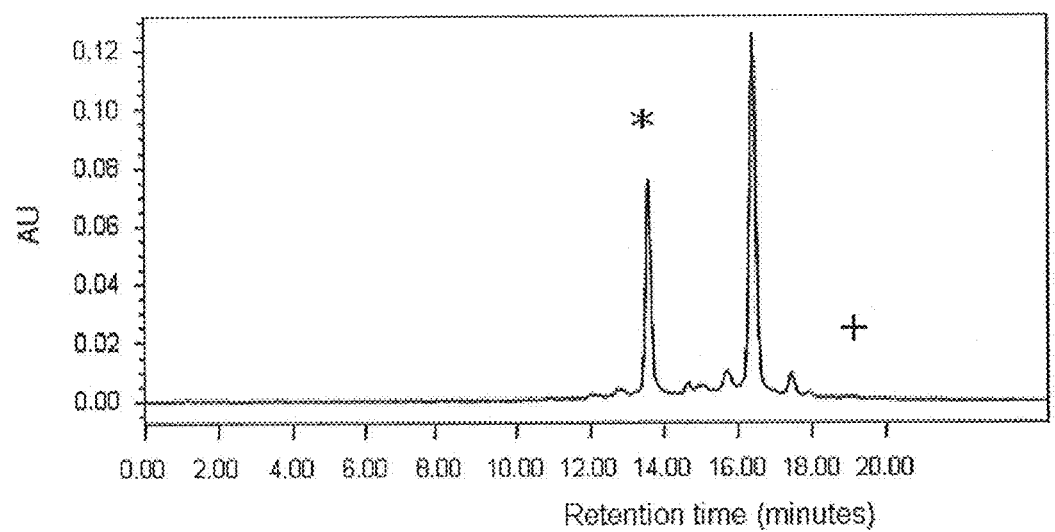

FIG. 107: CIEX analysis after SNEEP. CIEX analysis was performed after SNEEP in which an excess of IgG1-7D8-AAA-K409R was used. Quantification indicated that 25.5% IgG1-7D8-AAA-K409R (*), 73.3% bispecific antibody and 1.2% of IgG1-2F8-F405L (+) was present after the exchange reaction. Note that the percentage of IgG1-2F8-F405L homodimer was reduced further under optimal exchange conditions (FIG. 105).

Figure 108:
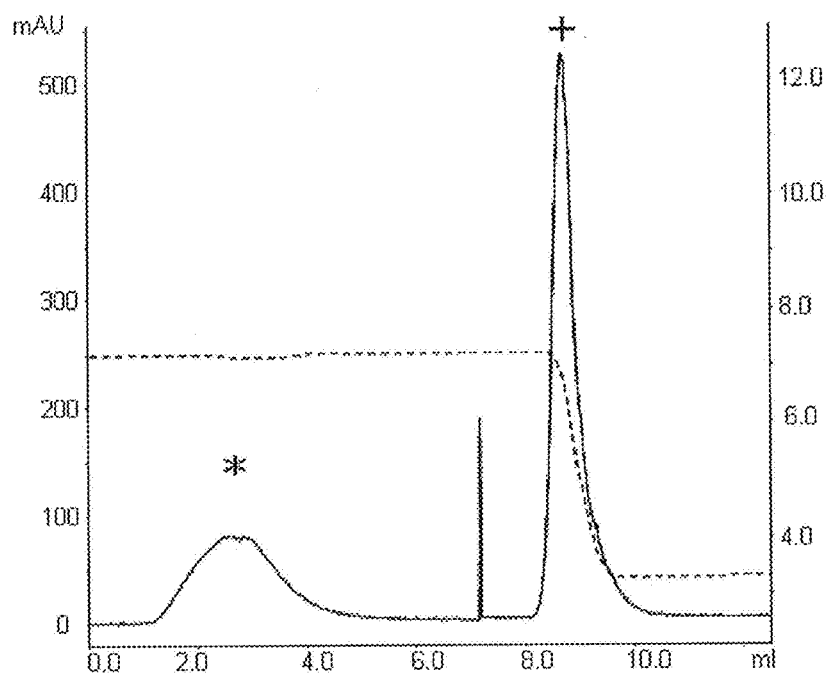

FIG. 108: Protein A fast protein liquid chromatography (FPLC) profile. Protein A FPLC profile of bispecific antibody produced after exchange using a 50% excess of the IgG1-7D8-AAA-K409R homodimer. On the left axis the $A_{280}$ signal in mAU is shown (black trace), on the right axis the pH (grey trace). The spike between the two marked peaks represents an air bubble at the start of the fractionation.

Figure 109:
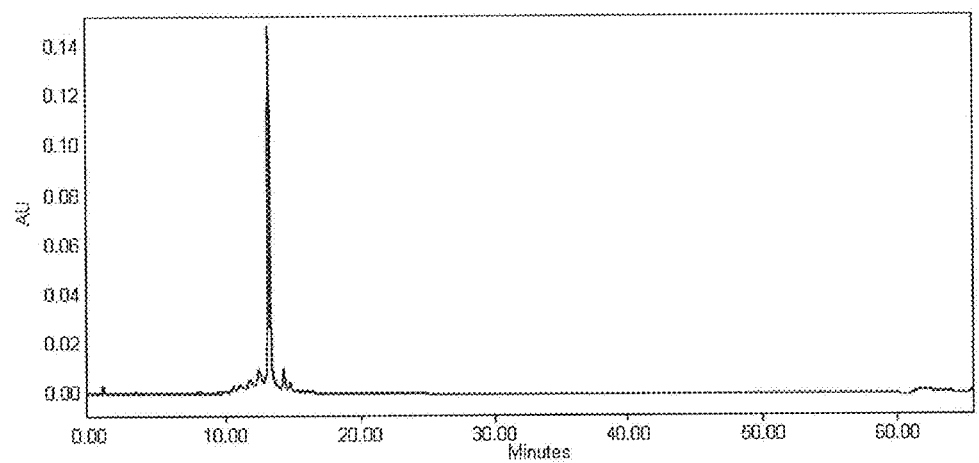

FIG. 109: CIEX analysis of the flow-through fraction (peak indicated with * in FIG. 108. No bispecific antibody (retention time ~16.4 minutes) nor IgG1-2F8-F405L (retention time ~19.2 minutes) were detected; the peak at 13.6 minutes corresponds to the (non-binding) IgG1-7D8-AAA-K409R homodimer.

Figure 110:
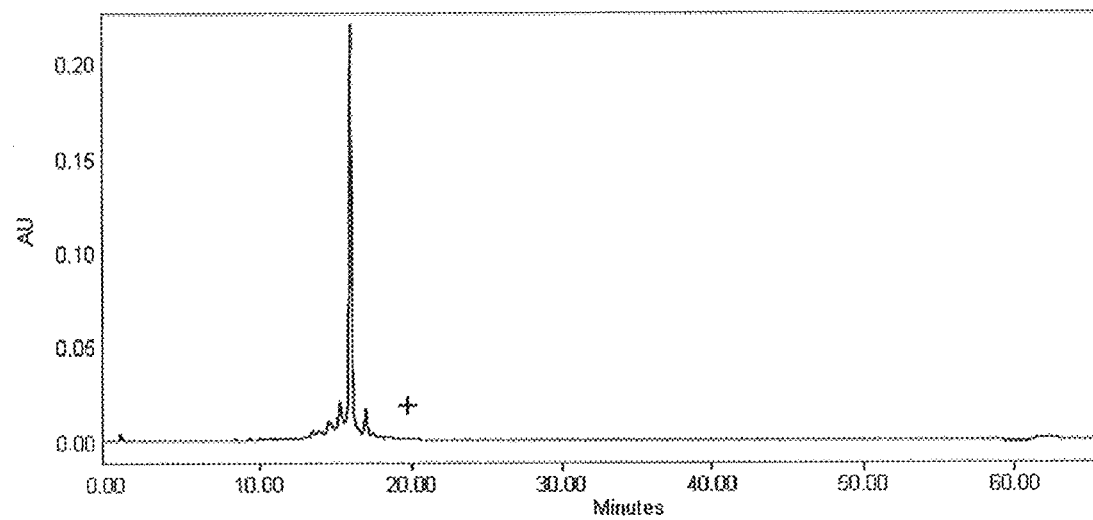

FIG. 110: CIEX analysis of the eluted product (peak indicated with + in FIG. 108). The peak at 16.4 minutes corresponds to bispecific antibody, no peak was detected at 13.6 (IgG1-7D8-AAA-K409R) and a small peak at 19.2 minutes (IgG1-2F8-F405L) was detected (1.4%). This demonstrated that a SNEEP in combination with Protein A polishing can be used to remove residual homodimer.

Figure 111:
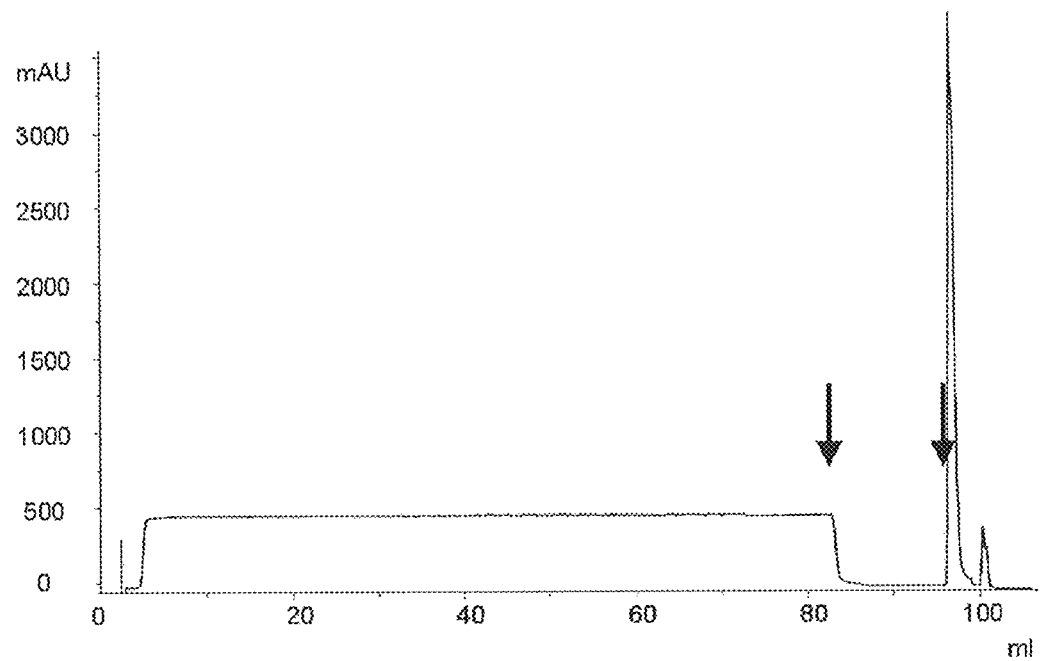

FIG. 111: FPLC chromatogram of jointly Protein A-purified IgG1-b12-F405L and IgG1-058-K409R. The trace shows the A280 signal. Loading is observed as an increase in A280 signal after ~5 mL. The start of the wash and elution steps is marked with an arrow. A post-elution peak at 100 mL was observed during the first low pH regeneration step. This peak was not analyzed, but indicates minor protein impurities.

Figure 112:
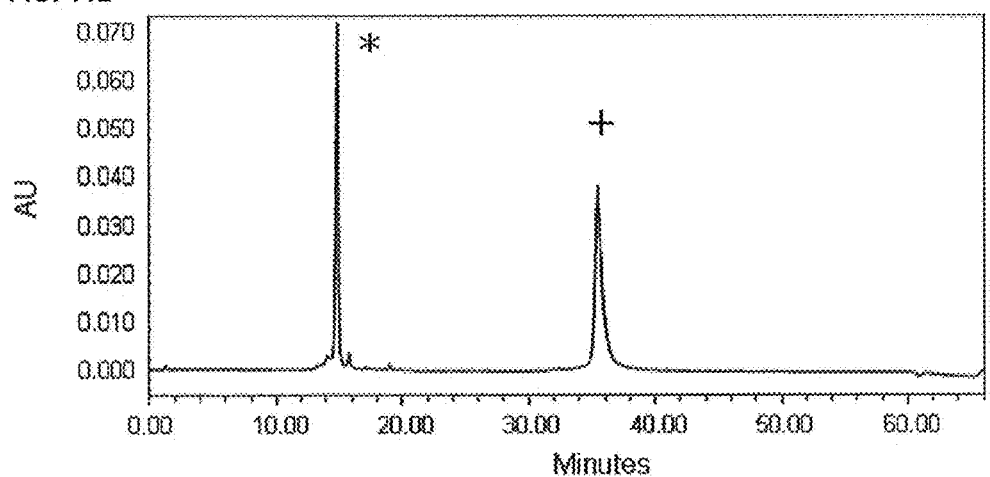

FIG. 112: CIEX profile of jointly Protein A-purified IgG1-058-K409R (*) and IgG1-b12-F405L (+).

Figure 113:
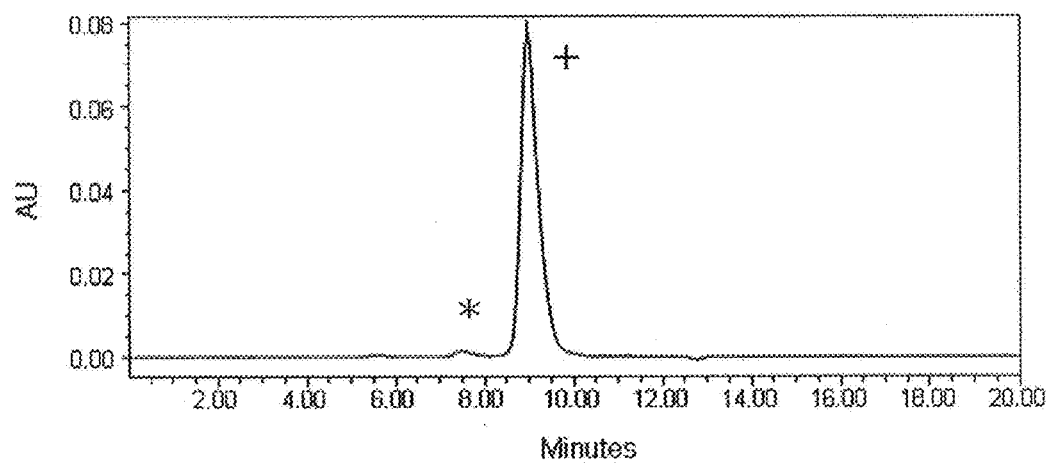

FIG. 113: HP-SEC profile of bispecific antibody produced from jointly Protein A-purified IgG1-b12-F405L and IgG1-058-K409R. The peak at 7.5 minutes (*) corresponds to dimeric species, the peak at 9.0 minutes to monomeric species (+).

Figure 114:
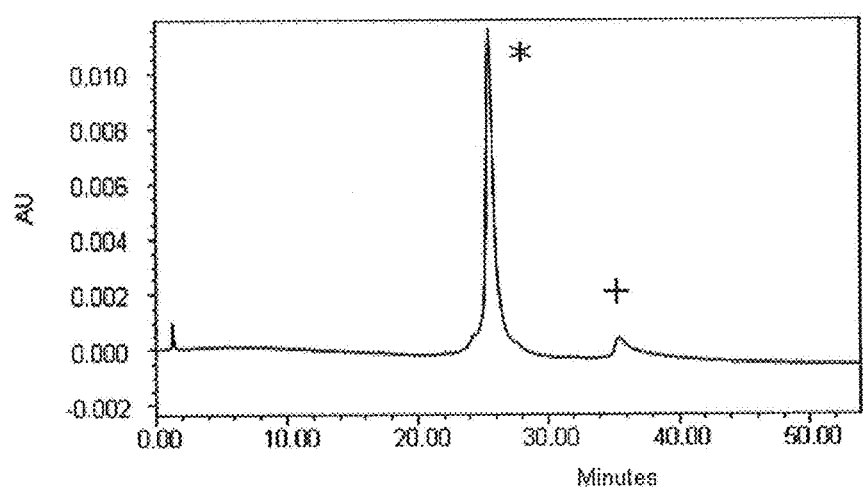

FIG. 114: CIEX profile of bispecific antibody produced from jointly Protein A-purified IgG1-b12-F405L and IgG1-058-K409R. The peak at 26 minutes (*) corresponds to bispecific antibody; the peak at 36 minutes corresponds to IgG-b12-F405L homodimer (+). No IgG1-058-K409R was detected.

Figure 115:
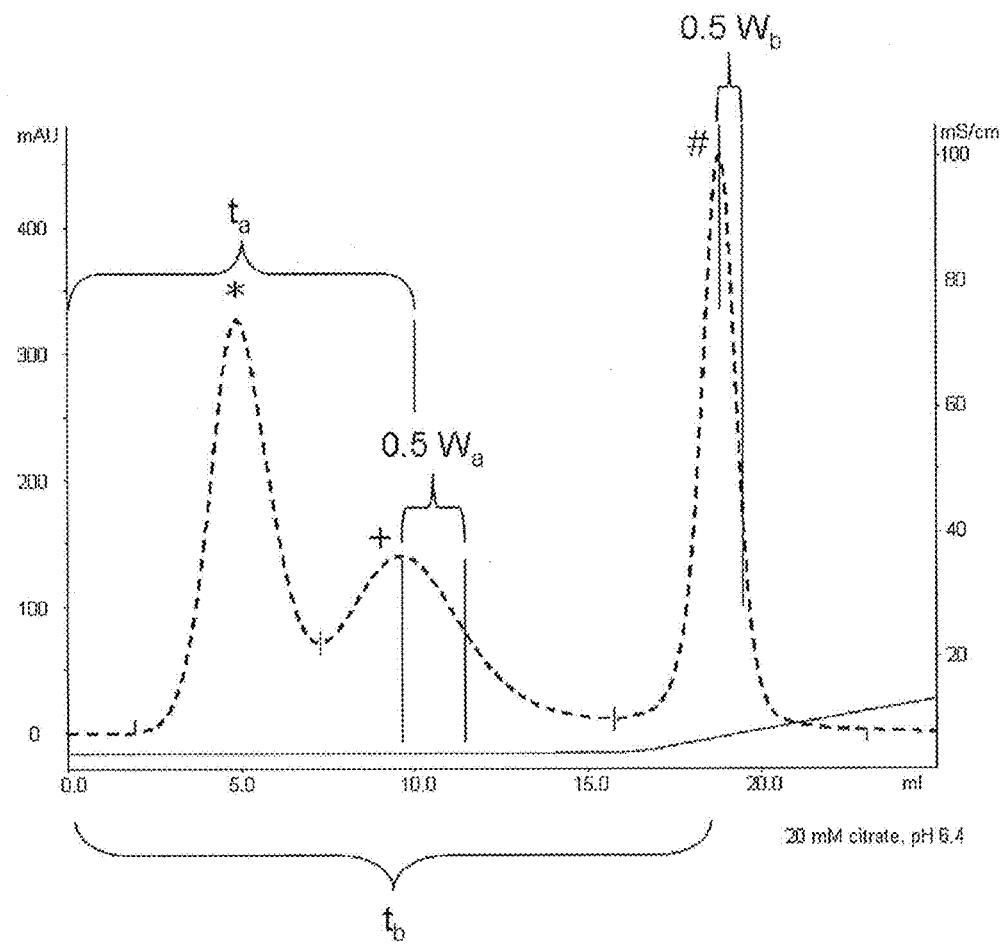

FIG. 115: FPLC profile of a 1:1:1 mixture of bispecific antibody and homodimers. FPLC profile of 1:1:1 mixture of IgG1-7D8-K409R (*), bispecific antibody (+), and IgG1-2F8-F405L (#) separated on a WCIEX column under near isocratic conditions (only the elution of the IgG1-2F8-F405L was slightly accelerated by a shallow gradient).

Figure 116:
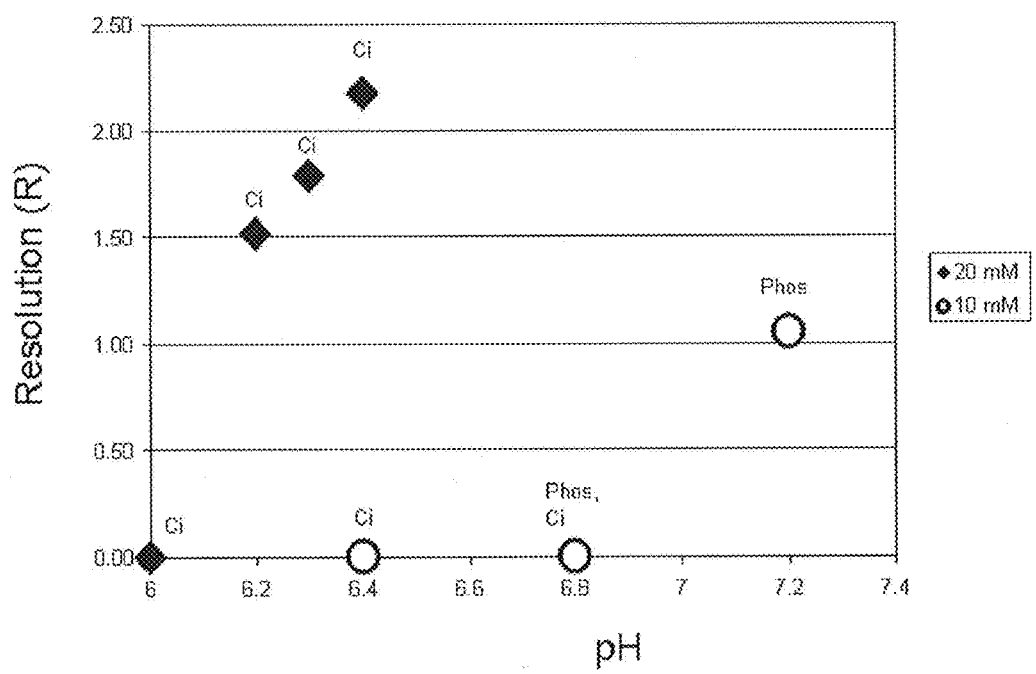

FIG. 116: Calculated resolution. Calculated resolution (R, calculated using Equation 5) is shown for citrate and phosphate buffers. Optimal resolution was found for 20 mM citrate pH 6.4. A resolution of 1.75-2.00 was thought to be acceptable for satisfactory separation (John W. Dolan, Peak Tailing and Resolution, LC Resources Inc., Walnut Creek, Calif., USA).

Figure 117:
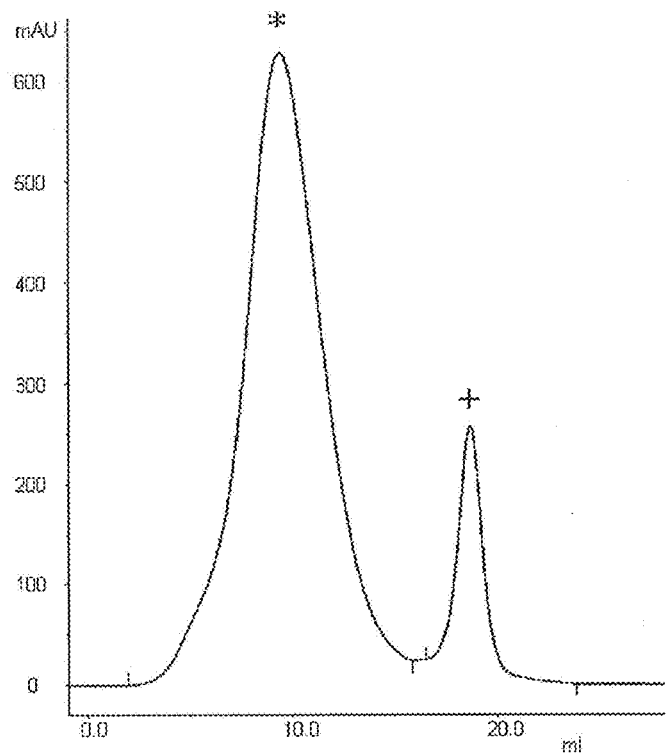

FIG. 117: FPLC profile. FPLC profile of IgG1-2F8-F405L×IgG1-7D8-K409R (*) bispecific antibody spiked with 10% of the IgG1-2F8-F405L homodimer (+) at pH 6.4, 20 mM citrate. Loading was 4.4 mg/mL resin.

Figure 118:
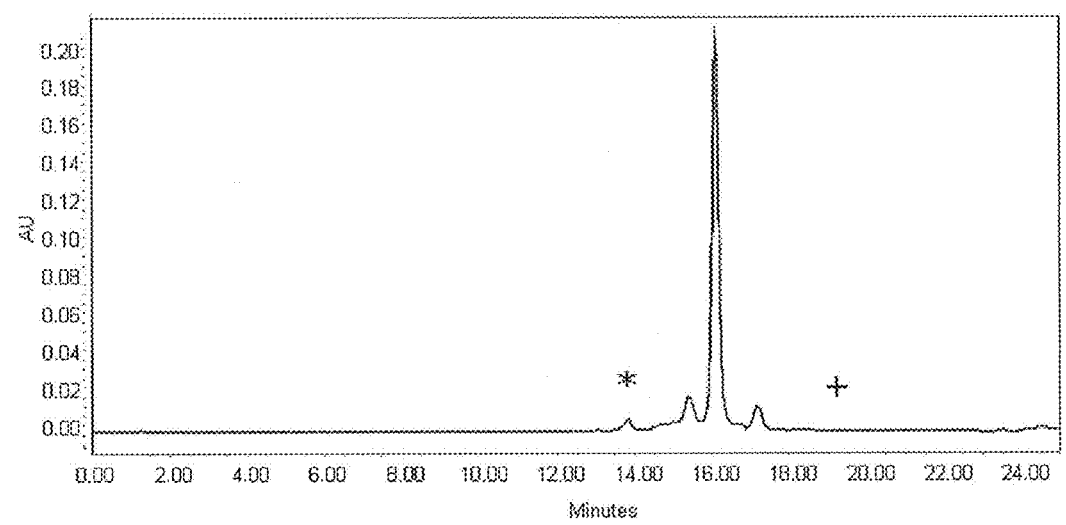

FIG. 118: CIEX profile of IgG1-2F8-F405L×IgG17D8-K409R bispecific antibody. Shown is the CIEX profile of IgG1-2F8-F405L×IgG1-7D8-K409R indicated by the asterisk (*) in FIG. 117. Percentages of IgG1-7D8-K409R homodimer (*), bispecific antibody, and IgG1-2F8-F405L homodimer (+) were 4.3, 94.8, and 0.9. The IgG1-7D8-K409R homodimer was residual homodimer from the original batch that was spiked with IgG1-2F8-F405L.

Figure 119A:
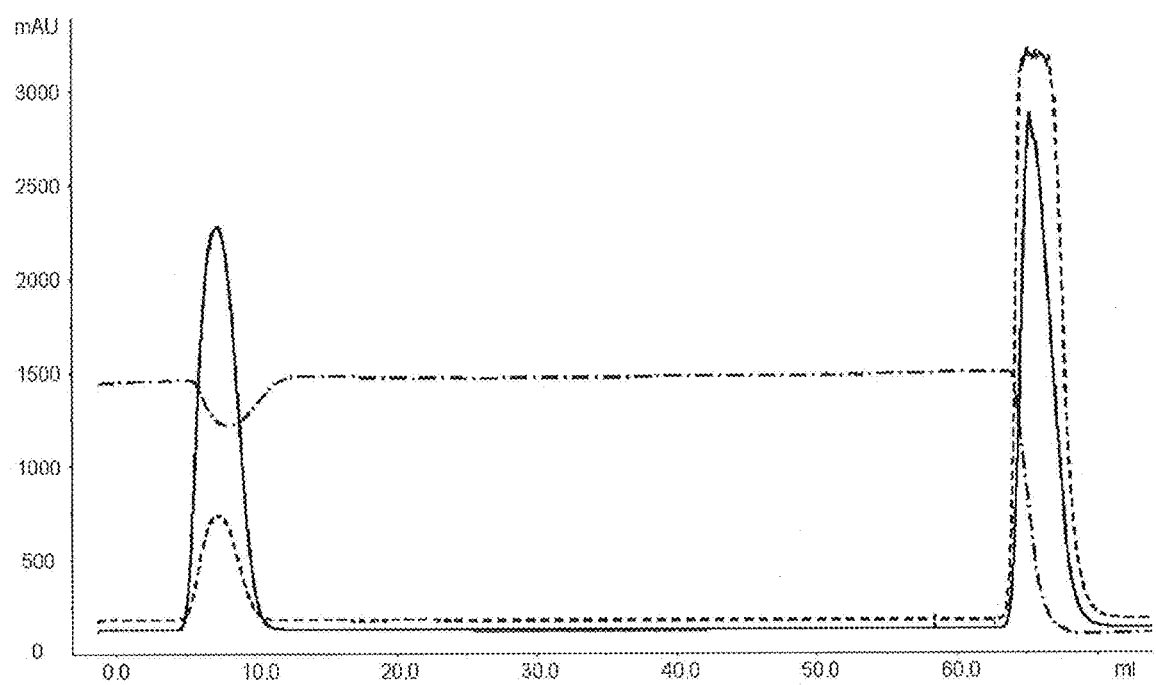
Figure 119B:
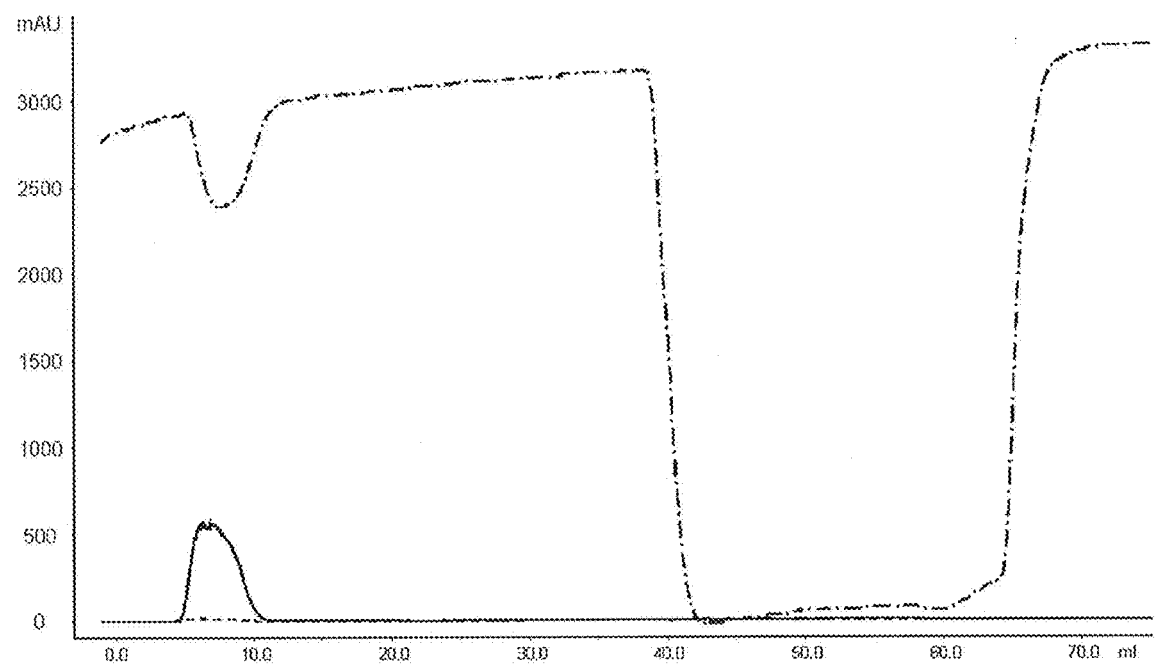

FIGS. 119A and 119B: FPLC chromatogram. FIG. 119A) Protein A elution profile of 20 mg bispecific antibody in PBS with 75 mM 2-MEA (total volume 3 mL). The solid line is the $A_{254}$ signal (left axis), the dashed line the $A_{280}$ (left axis) signal, the long dash-dotted line is the pH (values not shown, the pH dropped from 7.4 to 3.0 at ~65 mL and is indicated for reference only). FIG. 119B) PBS with 75 mM 2-MEA (total volume 3 mL) loaded on protein A. The solid line is the $A_{254}$ signal (left axis), the dashed line the $A_{280}$ (left axis)

signal, the long dash-dotted line is the pH (values not shown, the pH dropped from 7.4 to 3.0 at ~40 mL and is indicated for reference only).

Figure 120A:
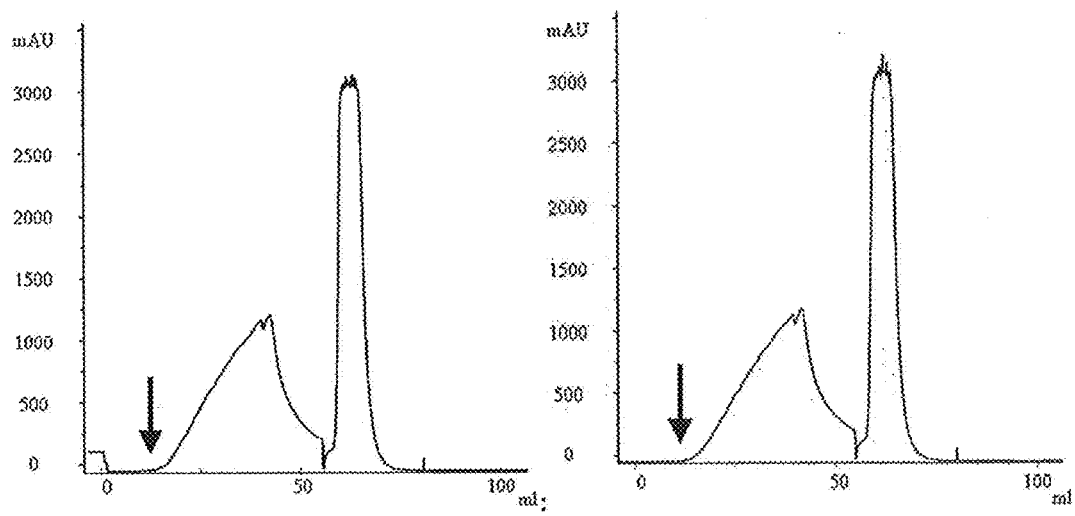
Figure 120B:
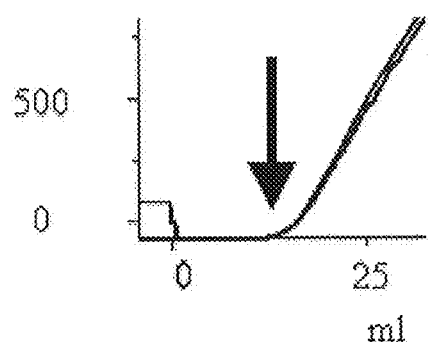

FIGS. 120A and 120B: Point of breakthrough determination. FIG. 120A) Point of breakthrough (indicated in the figure with an arrow) was determined before (left panel) and after (right panel) exposure of the protein A column to 2-MEA. IgG1-7D8-K409R (5 mg/mL) was loaded using a residence time of 1 minute. Both before and after exposure to 75 mM 2-MEA the point of breakthrough was ~15 mL indicating that the column performance was not strongly affected by the presence of 2-MEA. Data shown are A280 values (mAU). FIG. 120B) Zoom of FIG. 120A) with both traces superimposed.

Figure 121:
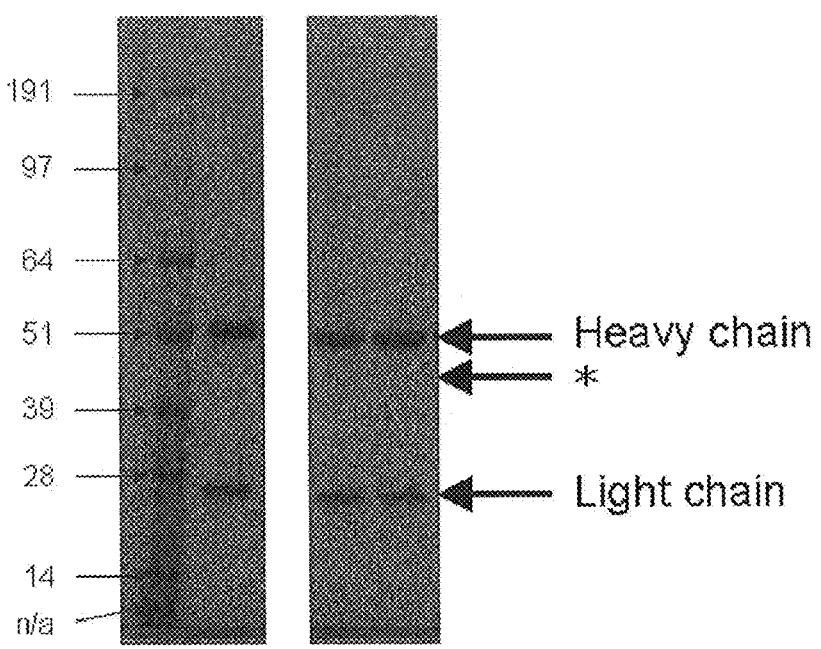

FIG. 121: Reduced SDS-PAGE analysis of the eluted protein after 2-MEA removal. Lanes contain marker, control antibody (IgG1-b12), the bispecific reaction mixture in the presence of 2-MEA before column loading, and end product after 2-MEA removal. No protein A was detected, indicating that the column remained intact. Heavy and light chains are indicated by arrows, the expected molecular weight of protein A (45 kDa) is indicated by an asterisk (*).

Figure 122:
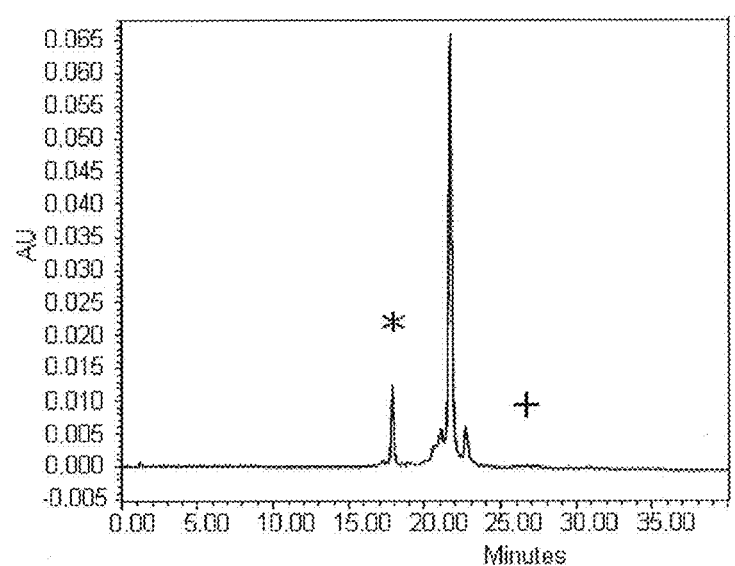

FIG. 122: CIEX profile of bispecific lambda-kappa antibody. The place where the BMA 031-K409R antibody containing a λ light chain was expected is indicated by a plus sign (+) and no peak was detected, the IgG12F8-F405L antibody with a κ light chain is indicated by an asterisk (*). The bispecific antibody is in the middle. Percentages of BMA 031-K409R, bispecific antibody, and IgG12F8-F405L were 11.2, 88.8, and 0, respectively.

Figure 123:
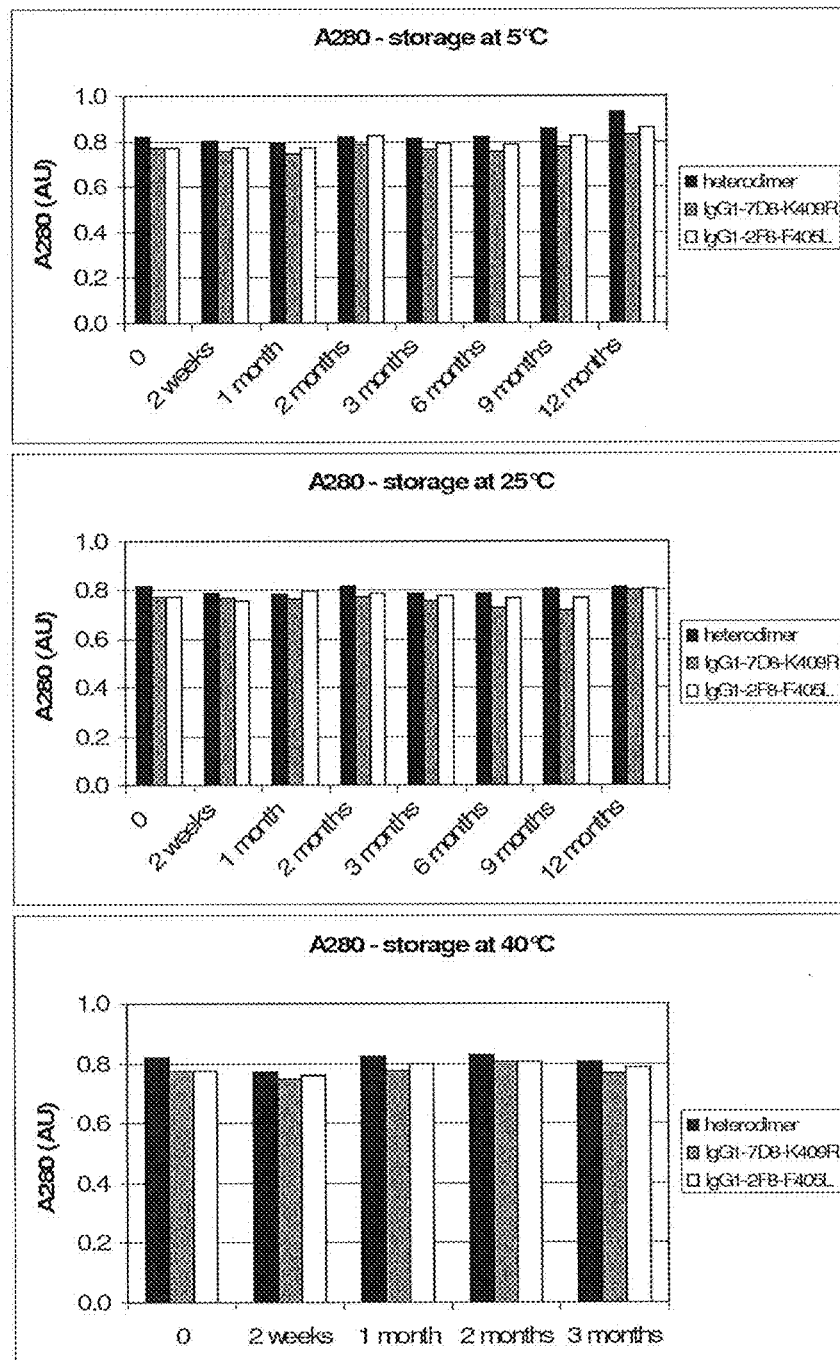

FIG. 123: A280 data of bispecific antibody (black), IgG1-7D8-K409R (grey) and IgG1-2F8-F405L (white) after storage for different time periods and at different temperatures. A280 measurements were performed on the Nanodrop and results are given as A280 (AU) at 1 mm path length.

Figure 124:
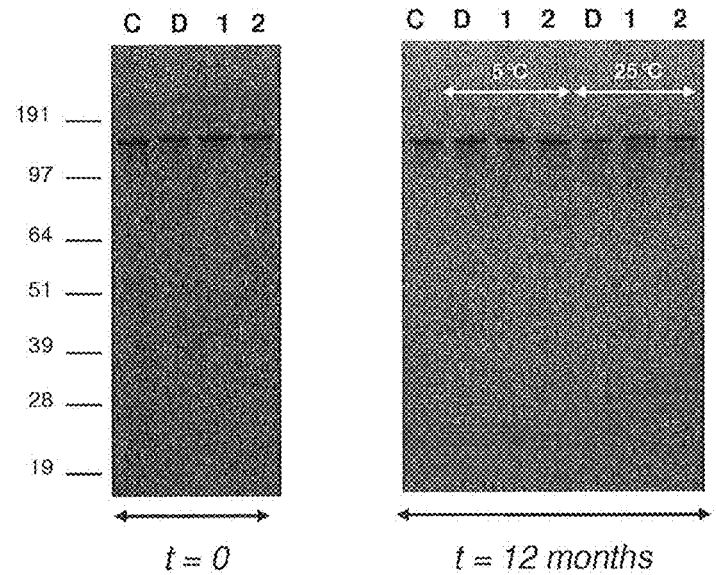

FIG. 124: Non-reduced SDS-PAGE of bispecific antibody (D), IgG1-7D8-K409R (1) and IgG1-2F8-F405L (2) at t=0 and t=12 months at 2-8° C. and at 25° C. C=internal IgG1 assay control.

Figure 125:
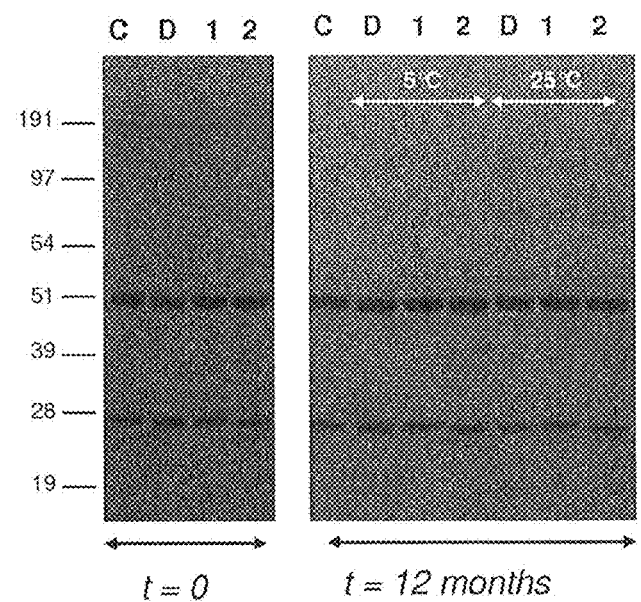

FIG. 125: Reduced SDS-PAGE of bispecific antibody (D), IgG1-7D8-K409R (1) and IgG1-2F8-F405L (2) at t=0 and t=12 months at 2-8° C. and at 25° C. C=internal IgG1 assay control.

Figure 126:
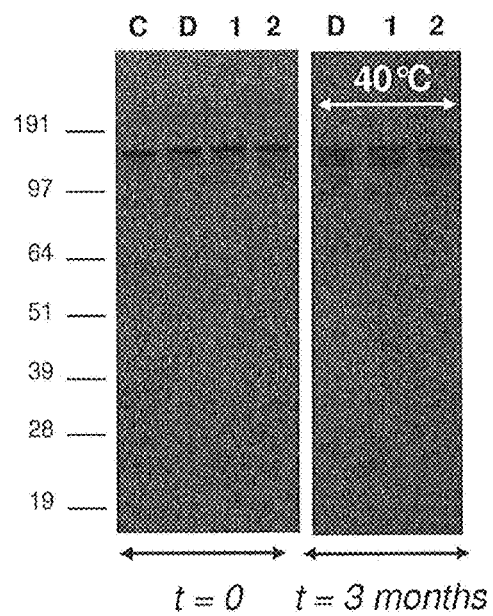

FIG. 126: Non-reduced SDS-PAGE of bispecific (D), IgG1-7D8-K409R (1) and IgG1-2F8-F405L (2) at t=0 and t=3 months at 40° C. C=internal IgG1 assay control.

Figure 127:
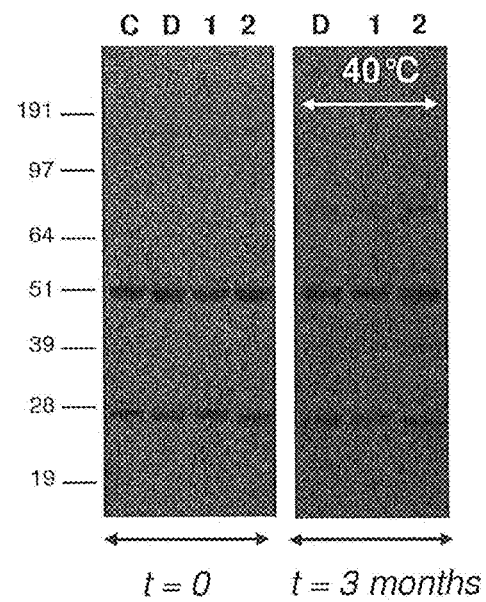

FIG. 127: Reduced SDS-PAGE of bispecific antibody (D), IgG1-7D8-K409R (1) and IgG1-2F8-F405L (2) at t=0 and t=3 months at 40° C. C=internal IgG1 assay control.

Figure 128:
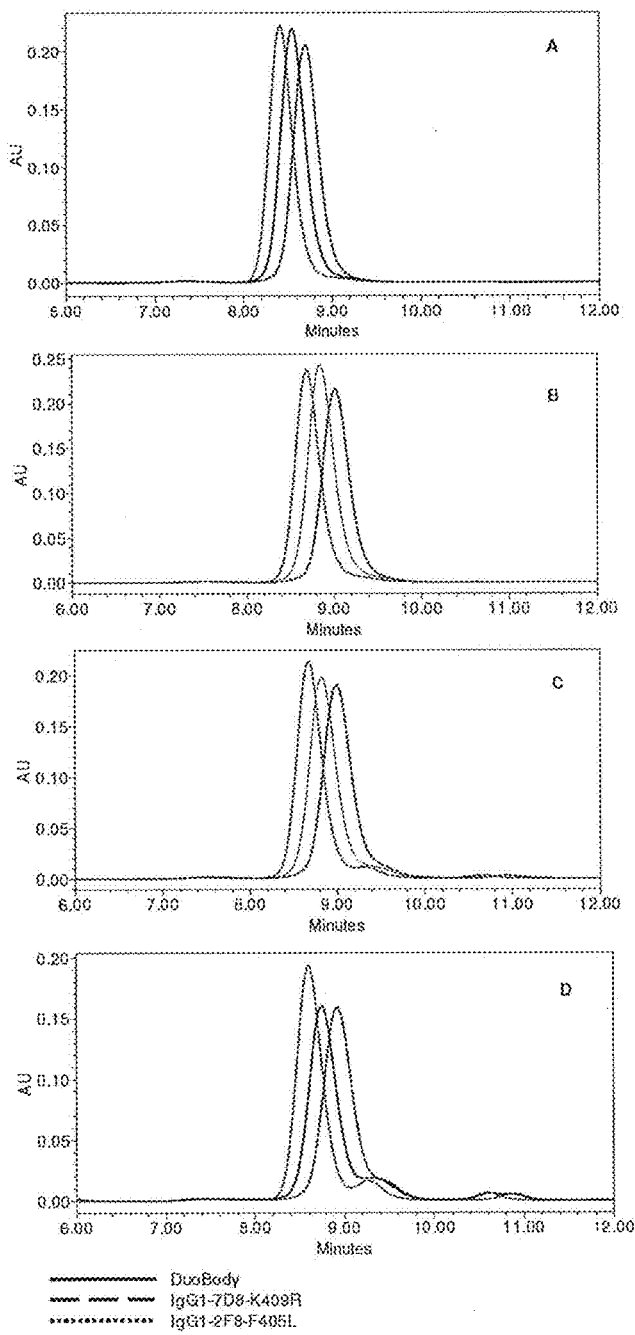

FIG. 128: HP-SEC chromatograms of bispecific antibody (solid), IgG1-7D8-K409R (striped) and IgG1-2F8-F405L (dotted). Storage conditions were A: t=0; B: t=12 months at 2-8° C.; C: t=12 months at 25° C. and D: t=3 months at 40° C.

Figure 129:
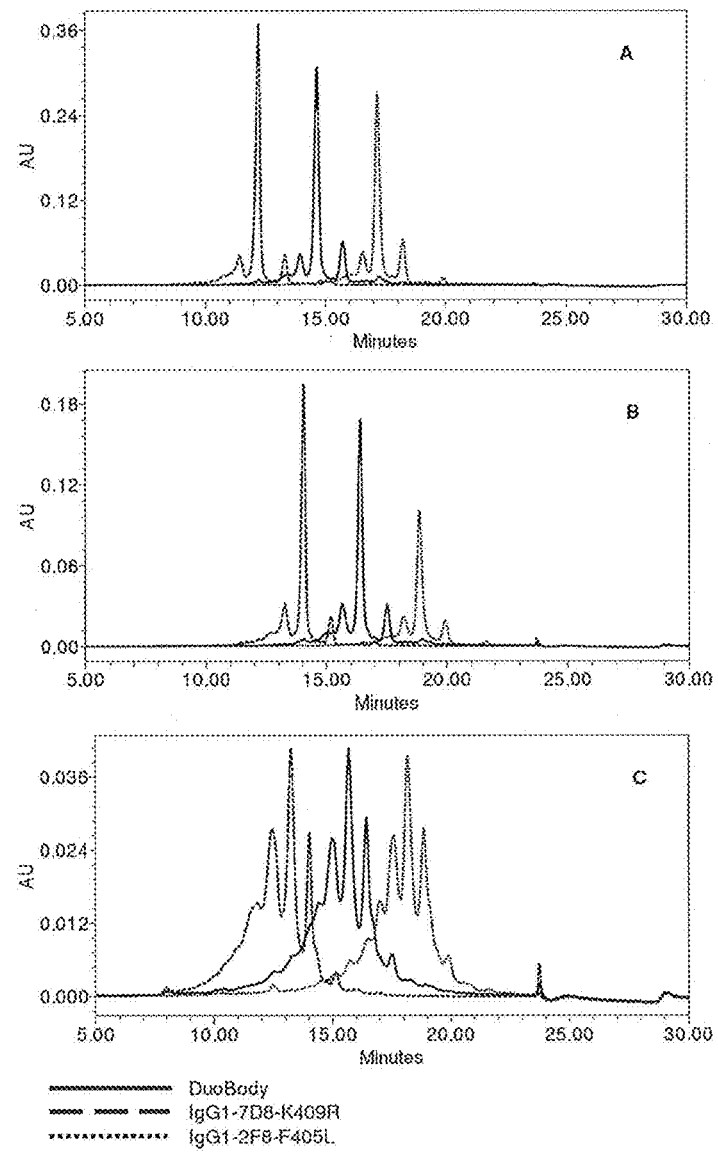

FIG. 129: CIEX chromatograms of bispecific antibody (solid), IgG1-7D8-K409R (striped) and IgG1-2F8-F405L (dotted). Storage conditions are A: t=0; B: t=12 months at 2-8° C.; C: t=12 months at 25° C. (Note: the difference in retention time of the materials at t=0 compared to t=12 months could be due to small changes in buffer composition and/or the use of a different column lot. Analysis of an internal IgG1 control in each run also showed a shift of +1.64 min at t=12 months compared to t=0, data not shown).

DETAILED DESCRIPTION OF THE INVENTION

Definitions

Figure 16:
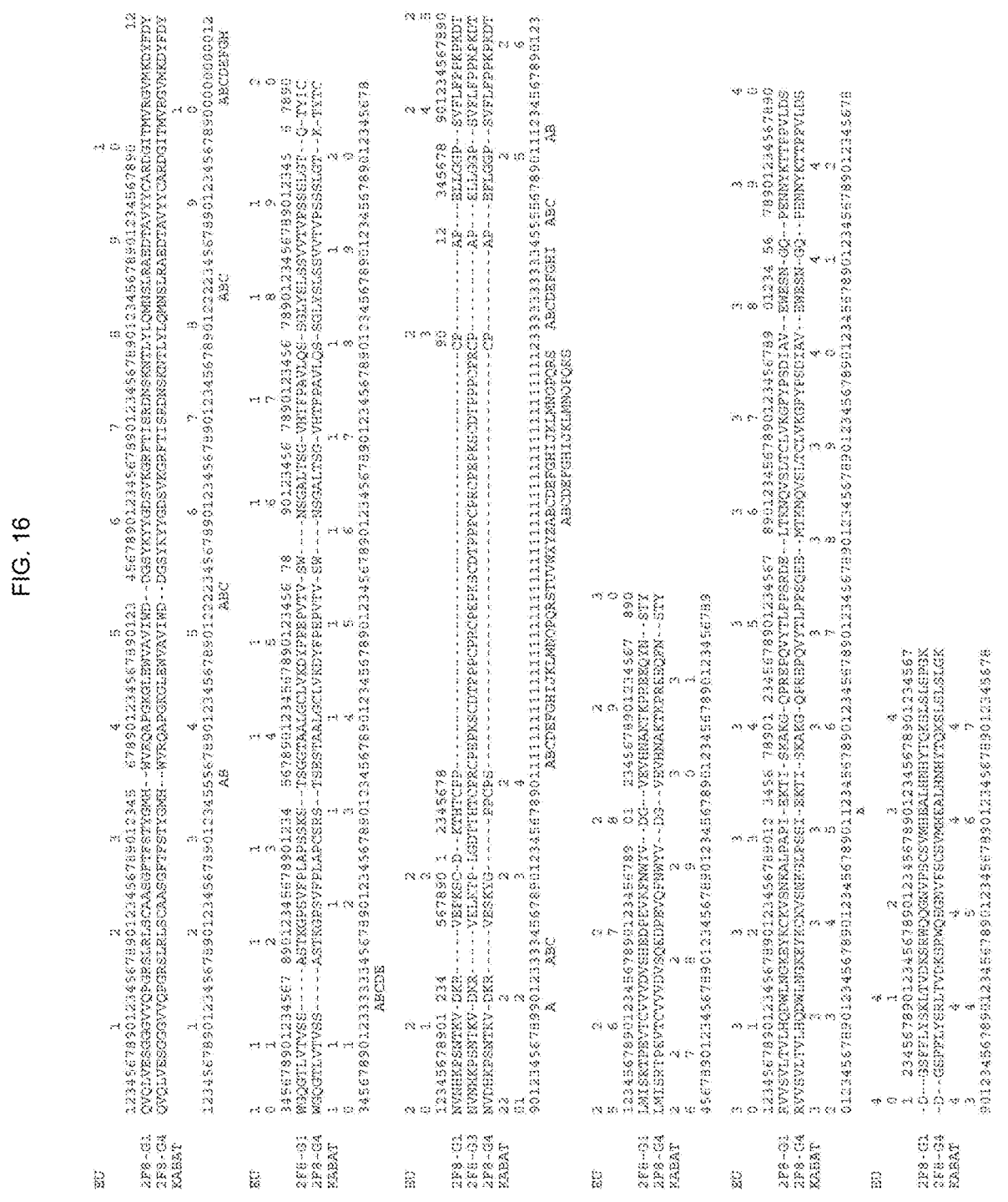

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are interconnected via disulfide bonds in the so-called "hinge region". Each light chain typically is comprised of a light chain variable region (abbreviated herein as VL) and a light chain constant region. The light chain constant region typically is comprised of one domain, CL. Typically, the numbering of amino acid residues in the constant region is performed according to the EU-index as described in Kabat et al., Sequences of Proteins of Immunological Interest, 5th Ed. Public Health Service, National Institutes of Health, Bethesda, Md. (1991). FIG. 16 gives an overview of the EU and Kabat numbering for different isotype forms of antibody 2F8 (WO 02/100348). The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)).

When used herein, the term "Fab-arm" refers to one heavy chain-light chain pair of an antibody.

When used herein, the term "Fc region" or "Fc domain" refers to an antibody region comprising at least the hinge region, a CH2 domain and a CH3 domain (see e.g. Kabat E A, in US Department of Health and Human Services, NIH publication no 91-3242, Edn. $5^{th}$ edition 662, 680, 689 (1991). The Fc region may be generated by digestion of an antibody with papain, where the Fc region is the fragment obtained thereby, which includes the two CH2-CH3 regions of an immunoglobulin and a hinge region. The constant domain of an antibody heavy chain defines the antibody isotype, e.g. IgG1, IgG2, IgG3, IgG4, IgA1, IgA2, IgE. The Fc-domain mediates the effector functions of antibodies with cell surface receptors called Fc receptors and proteins of the complement system.

The term "CH2 region" or "CH2 domain" as used herein is intended to refer to the CH2 region of an immunoglobulin. Thus for example the CH2 region of a human IgG1 antibody corresponds to amino acids 228-340 according to the EU numbering system. However, the CH2 region may also be any of the other antibody isotypes as described herein.

The term "CH3 region" or "CH3 domain" as used herein is intended to refer to the CH3 region of an immunoglobulin. Thus for example the CH3 region of a human IgG1 antibody corresponds to amino acids 341-447 according to the EU numbering system. However, the CH3 region may also be any of the other antibody isotypes as described herein.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, or similar molecule. The term "bispecific antibody" refers to an antibody having specificities for at least two different epitopes, typically non-overlapping epitopes or an antibody that contains two distinct antigen-binding sites. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. Fab or F(ab')2 fragments. It also should be understood that the term antibody, unless specified otherwise, also includes polyclonal antibodies, monoclonal antibodies (mAbs), antibody-like polypeptides, such as chimeric antibodies and humanized antibodies. An antibody as generated can possess any isotype.

The term "full-length antibody" when used herein, refers to an antibody which contains all heavy and light chain constant and variable domains that are normally found in an antibody of that isotype.

As used herein, "isotype" refers to the immunoglobulin class (for instance IgG1, IgG2, IgG3, IgG4, IgD, IgA, IgE, or IgM) that is encoded by heavy chain constant region genes.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

When used herein, the term "heavy chain antibody" or "heavy-chain antibody" refers to an antibody which consists only of heavy chains and lacks the light chains usually found in antibodies. Heavy chain antibodies, which naturally occur in e.g. camelids, can bind antigens despite having only VH domains.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked by the antigen binding peptide (in other words, the amino acid residue is within the footprint of the antigen binding peptide).

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000-fold. The term "$K_D$" (M), as used herein, refers to the dissociation equilibrium constant of a particular antibody-antigen interaction.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

An "isolated antibody", as used herein, denotes that the material has been removed from its original environment (e.g., the natural environment if it is naturally occurring or the host cell if it is recombinantly expressed). It is also advantageous that the antibodies are in purified form. The term "purified" does not require absolute purity; rather, it is intended as a relative definition, indicating an increase of the antibody concentration relative to the concentration of contaminants in a composition as compared to the starting material.

The term "host cell", as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

When used herein, the term "co-expression" of two or more nucleic acid constructs, refers to expression of the two constructs in a single host cell.

The term "tumor cell protein", as used herein, refers to a protein located on the cell surface of a tumor cell.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells, including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell. In some embodiments, an effector cell may phagocytose a target antigen or target cell.

The term "reducing conditions" or "reducing environment" refers to conditions sufficient to allow reduction of the inter-chain disulfide bonds in the hinge region of an antibody.

Reference to amino acid positions in the present invention is, unless contradicted by the context, according to the EU-index as described in Kabat et al., Sequences of Proteins of Immunological Interest, 5th Ed. Public Health Service, National Institutes of Health, Bethesda, Md. (1991).

The term "rpm" or "RPM" refers to revolutions per minute, and may be indicated as rpm or RPM in the context of the present invention.

Method of the Present Invention

The present invention relates to an in vitro method for production of a heterodimeric protein comprising the steps:
a) incubating a first homodimeric protein with a second homodimeric protein under reducing conditions sufficient to allow reduction of the inter-chain disulfide bonds in the hinge region and
wherein said first homodimeric protein comprises an Fc region of an immunoglobulin, said Fc region comprising a first CH3 region, and said second homodimeric protein comprises an Fc region of an immunoglobulin, said Fc region comprising a second CH3 region, and wherein the sequences of said first and second CH3 regions are different and are such that the heterodimeric interaction between said first and second CH3 regions is stronger than each of the homodimeric interactions of said first and second CH3 regions,
b) subjecting the composition obtained from step a) to oxidizing conditions sufficient to allow oxidation of cysteines in the heterodimeric protein to inter-chain disulfide bonds Step a) of the present invention may alternatively comprise the steps of:
z) providing a first nucleic-acid construct encoding a first polypeptide comprising a first Fc region of an immunoglobulin, said first Fc region comprising a first CH3 region,
y) providing a second nucleic-acid construct encoding a second polypeptide comprising a second Fc region of an immunoglobulin, said second Fc region comprising a first CH3 region,
wherein the sequences of said first and second CH3 regions are different and are such that the heterodimeric interaction between said first and second CH3 regions is stronger than each of the homodimeric interactions of said first and second CH3 regions, and
wherein said first homodimeric protein has an amino acid other than Lys, Leu or Met at position 409 and said second homodimeric protein has an amino-acid substitution at a position selected from the group consisting of: 366, 368, 370, 399, 405 and 407.
and/or
wherein the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.
z) co-expressing said first and second nucleic-acid constructs in a host cell.

In a further embodiment, step z) further comprises co-expressing one or more nucleic-acid constructs encoding a light chain in said host cell.

The method of the present invention is particularly suitable when larger volumes of heterodimeric protein are produced.

Hence in a particular embodiment step b) may comprise:
b) subjecting at least 10 mL of the composition obtained from step a) to oxidizing conditions sufficient to allow oxidation of cysteines in the heterodimeric protein to inter-chain disulfide bonds.

In one embodiment the method of the present invention further comprises a step of obtaining the heterodimeric protein, e.g. the method of the present invention may comprise a step c):
c) obtaining the heterodimeric protein.

In a further embodiment step a) of the present invention may comprise the steps of:
i) providing a first homodimeric protein comprising an Fc region of an immunoglobulin, said Fc region comprising a first CH3 region,
ii) providing a second homodimeric protein comprising an Fc region of an immunoglobulin, said Fc region comprising a second CH3 region,
wherein the sequences of said first and second CH3 regions are different and are such that the heterodimeric interaction between said first and second CH3 regions is stronger than each of the homodimeric interactions of said first and second CH3 regions,
iii) incubating said first protein together with said second protein under reducing conditions sufficient to allow reduction of the inter-chain disulfide bonds in the hinge region.

The first and second homodimeric proteins may be produced and/or purified together or separately. For example, if the first and second homodimeric protein are produced by expression in a host cell, the first and second homodimeric protein may be produced in the same reaction vessel, e.g. same bioreactor. If the first and second homodimeric protein are produced in the same reaction vessel, said first and second homodimeric protein may be produced in the same host cell or by different host cells. Alternatively, the first and second homodimeric protein may be produced in two separate reaction vessels, e.g. in two separate bioreactors. If the first and second homodimeric proteins are produced by different host cells, such host cells may be derived from the same or from different cell types. Production in the same reaction vessel may be advantageous for cost or timing considerations or to take advantage of redox enzymes, such as cytosolic thioredoxin 1 and 2 (TXN1 and TXN2), released by the host cells expressing the first and/or second homodimeric protein, which may under certain conditions, e.g. by lysis of a high number of viable cells so that the enzymes and the co-factors required for reduction are released combined with a very low oxygen concentration, catalyze reduction of the inter-chain disulfide bonds in the hinge region of the first and second homodimeric protein and thereby facilitate that heavy chain swapping occurs in the bioreactor or in the subsequent harvest step (Kao et al., 2010, Biotechnol. Bioeng 107; 622-632). Thus in a further embodiment, step a) of the present invention may be performed in the same reaction vessel as production of the first and/or second homodimeric protein. In a further embodiment step b) may also be performed in the same reaction vessel as step a), or in the same reaction vessel as both step a) and the production of the first and/or second homodimeric protein. In this case oxygen and divalent metal ions already present in the reaction may also stimulate the re-oxidation process of step b).

Further conditions for the production of the first and/or second homodimeric protein include any of those described in relation to step a). Production of the first and second homodimeric protein in separate batches may be advantageous from a control viewpoint (easier to reproduce and/or to determine the quality of each homodimer) or if one of the homodimers is used to create multiple different bispecific antibodies by combining it with a number of different other homodimers.

In a further embodiment the first and/or second homodimeric protein may be purified prior to incubation in step a). Methods for purification of homodimeric proteins include but are not limited to protein A and protein G chromatography (or other ways of affinity chromatography), affinity chromatography based on e.g. antigen-binding or anti-idiotypic antibodies, ion exchange, hydrophobic interaction, kappa or lambda select, thioaffinity, and hydroxyapatite chromatography and other mixed mode resins. Other methods of purification include but are not limited to precipitation with for example salts or polyethylene glycol to obtain purified protein. Combination of different purification methods is also envisioned.

If the first and second homodimeric proteins are produced separately the first and second homodimeric proteins may also be purified separately.

In alternative embodiment, if the first and second homodimeric protein are produced separately they may be purified together, e.g. by Protein A purification. Purification of the first and second homodimeric protein together may provide some operational and/or economical efficiency.

If the first and second homodimeric proteins are produced together the first and second homodimeric proteins may also be purified together, e.g. by Protein A purification.

By purification of the first and/or second homodimeric proteins prior to step a) it may be possible to remove components which may impact the rate or extent of one or more steps of the method; such as the reduction and/or exchange process of step a) and/or the oxidation process of step b), or which may further or alternatively impact the quality of the heterodimeric protein. As described above, the first and second homodimeric protein may be produced separately or together. Thus if the first and second homodimeric proteins are produced together, said first and second homodimeric protein may in particular be purified together.

If the first and second homodimeric protein are produced separately, the first and/or second homodimeric protein may purified separately or together, e.g. by combining the first and second homodimeric protein and subsequently purifying them.

In a further embodiment, the first and/or second homodimeric protein may be present in a solution or buffer. If for example this buffer is not optimal for performance of the reduction and exchange process taking place in step a), the buffer may be replaced with another solution or buffer. Thus, in a further embodiment, the method of the present invention may further comprise a step of replacing the solution or buffer which the first and/or second homodimeric protein is in to another solution or buffer prior to step a).

In a further embodiment the heterodimeric protein may be purified. Methods for purification of the heterodimeric protein may include, but is not limited to, any of those described herein. Methods relevant for purification of the heterodimeric protein include but are not limited to protein A and protein G chromatography (or other ways of affinity chromatography), affinity chromatography based on e.g. antigen-binding or anti-idiotypic antibodies, ionic exchange, hydrophobic interaction, kappa or lambda select, thioaffinity, and hydroxyapatite chromatography and other mixed mode resins. Other methods use precipitation with for example salts or polyethylene glycol rather than chromatography to obtain purified protein.

Hence the method of the present invention may further comprise a step of purifying the heterodimeric protein. By purifying the heterodimeric protein it is possible to remove excess reagents, such as the reducing agent, and impurities. Purifying the heterodimeric protein may also include removal of residual first and/or second homodimeric protein. As described below excess of either the first or second homodimeric protein may be used in step a) to facilitate removal of residual first and/or second homodimeric protein.

The step of purifying the heterodimeric protein may be in between steps a) and b) but for most purposes it may typically be after step b).

If the first or second homodimeric protein has been modified, e.g. the first or second CH3 region has been modified, to reduce or eliminate Protein A or Protein G binding the heterodimeric protein of the present invention may in particular be purified by protein A or protein G chromatography. Other methods for purification may also be used, e.g. in combination with protein A and/or protein G chromatography, such other methods include, but are not limited to, or other ways of affinity chromatography, affinity chromatography based on e.g. antigen-binding or anti-idiotypic antibodies, kappa or lambda select, thioaffinity, ionic exchange, hydrophobic interaction, hydroxyapatite chromatography and other mixed mode resins. Other methods use precipitation with for example salts or polyethylene glycol rather than chromatography to obtain purified protein.

The heterodimeric protein may, by the purification or subsequent to the purification, be formulated suitable for storage of the heterodimeric protein, e.g. conditions that ensure stability of the heterodimeric protein. For heterodimeric antibodies such a formulation may typically be solution or buffer. Alternatively, the heterodimeric protein may be freeze-dried.

Equipment suitable for the process of the method of the present invention is well known to a person skilled in the art. Expression of homodimeric antibodies by a host cell may for example typically be performed in a reaction vessel, such as a bioreactor. The reducing and oxidizing steps a) and b) may, as described above, take place in the same bioreactor as expression of the first and/or second homodimeric protein or it may take place in separate reactor vessel. Similarly, the reducing and oxidizing steps a) and b) may also take place in the same reaction vessel, or they may be performed in separate reactor vessels. If the reducing and oxidizing steps a) and b) take place in the same reaction vessel the conditions may be changed from step a) to step b) as described herein. The reaction vessel and supporting process piping may be disposable or re-usable and made from standard materials (plastic, glass, stainless steel etc). The reaction vessel may be equipped with mixing, sparging, headspace gassing, temperature control and/or be monitored with probes for measurement of temperature, weight/volume, pH, dissolved oxygen (DO), and redox potential. All such techniques are common within standard unit operations of a manufacturing plant and well known to a person skilled in the art.

The individual steps of the method of the present invention may be performed as described herein.

In one embodiment the method of the present invention is an extracellular method. As described above production of the first and second homodimeric protein may suitably be performed by expression in a host cell. Hence steps a), b) and c) may in a particular embodiment be performed extracellularly. In a further embodiment step a), step b), step c), and any steps in between any of steps a), b) and c) and any subsequent steps may also be performed extracellularly.

First and Second Homodimeric Protein

The method of the present invention may be used in many ways to generate desired combinations of heterodimeric proteins, and it is particularly suitable for large-scale production of bispecific antibodies. In addition to being able to combine antibodies targeting different antigens to obtain selective binding, it can be used to change a desired property, e.g. to increase CDC, by combining two different antibodies targeting the same antigen. Furthermore, it can be used to remove partial agonistic activity of an antagonistic antibody or convert an agonistic antibody into an antagonistic antibody by making an asymmetrical antibody thereof with an irrelevant (inactive) antibody.

In one embodiment, the homodimeric proteins are selected from the group consisting of (i) an Fc region, (ii) an antibody, (iii) a fusion protein comprising an Fc region, such as an Fc region fused to a receptor, cytokine or hormone, and (iv) an Fc region conjugated to a prodrug, peptide, drug or a toxin.

In some embodiments, said first and/or second homodimeric protein comprise, in addition to the Fc region, one or more or all of the other regions of an antibody, i.e. a CH1 region, a VH region, a CL region and/or a VL region. Thus, in one embodiment, said first homodimeric protein is a full-length antibody. In another embodiment, said second homodimeric protein is a full-length antibody.

In an important embodiment, said first and second homodimeric proteins are both antibodies, preferably full-length antibodies, and bind different epitopes. In such an embodiment, the heterodimeric protein that is generated is a bispecific antibody. Said epitopes may be located on different antigens or on the same antigen.

In other embodiments, however, only one of the homodimeric proteins is a full-length antibody and the other homodimeric protein is not a full-length antibody, but e.g. an Fc region, expressed in conjunction to another protein or peptide sequence like a receptor, cytokine or hormone, or conjugated to a prodrug, peptide, a drug or a toxin. If the first and/or second homodimeric protein is an antibody, e.g. full-length antibody, it may in one embodiment be conjugated to a prodrug, peptide, a drug or a toxin or contains an acceptor group for the same. In a further embodiment, neither of the homodimeric proteins is a full-length antibody. For example, both homodimeric proteins may be Fc regions that are fused to another protein or peptide sequence like a receptor, cytokine or hormone, or conjugated to a prodrug, peptide, a drug or a toxin. This may for example be used to produce a heterodimeric protein which is conjugated to two different, compounds; e.g. prodrugs, peptides, drugs or toxins, by using a first and second homodimeric protein in the method of the present invention which are conjugated to two different compounds; e.g. prodrugs, peptides, drugs or toxins. This may also be relevant in case the process or chemistry of adding drug is not compatible with adding the other drug, then the process of adding each of the two drugs to the first and second homodimeric protein, respectively may be performed separately and prior to the method of the present invention.

In one embodiment, the Fc region of the first homodimeric protein, is similar or identical to an Fc region derived from, or is of, an isotype selected from the group consisting of IgG1, IgG2, IgG3 and IgG4 (with at least the exception of the mutation(s) indicated in here) and the Fc region of the second homodimeric protein is similar or identical to an Fc region derived from, or is of, an isotype selected from the group consisting of IgG1, IgG2, IgG3 and IgG4 (with at least the exception of the mutation(s) indicated in here). In a preferred embodiment, the Fc regions of both said first and said second homodimeric protein are similar or identical to an Fc region derived from, or is of, the IgG1 isotype (with at least the exception of the mutation(s) indicated in here). In another preferred embodiment, one of the Fc regions of said homodimeric proteins is similar or identical to an Fc region derived from, or is of, the IgG1 isotype and the other is similar or identical to an Fc region derived, or is of, from the IgG4 isotype (with at least the exception of the mutation(s) indicated in here). In the latter embodiment, the resulting heterodimeric protein comprises an Fc region of an IgG1 and an Fc region of an IgG4 and may thus have interesting intermediate properties with respect to activation of effector functions. A similar product can be obtained if said first and/or said second homodimeric protein comprises a mutation removing the acceptor site for Asn-linked glycosylation or is otherwise manipulated to change the glycosylation properties.

In a further embodiment, one or both of the homodimeric proteins is glyco-engineered to reduce fucose and thus enhance ADCC, e.g. by addition of compounds to the culture media during homodimeric protein, e.g. antibody, production as described in US2009317869 or as described in van Berkel et al. (2010) Biotechnol. Bioeng. 105:350 or by using FUT8 knockout cells, e.g. as described in Yamane-Ohnuki et al (2004) Biotechnol. Bioeng 87:614. ADCC may alternatively be optimized using the method described by Umana et al. (1999) Nature Biotechnol 17:176. Alternatively, the first and/or second homodimeric protein may be expressed in a host cell which does not add fucose, e.g. Biowa/KHK.

In a further embodiment, one or both of the homodimeric proteins has been engineered or modified to enhance complement activation, e.g. as described in Natsume et al. (2009) Cancer Sci. 100:2411.

In a further embodiment, one or both of the homodimeric proteins has been engineered to reduce or increase the binding to the neonatal Fc receptor (FcRn) in order to manipulate the serum half-life of the heterodimeric protein.

In a further embodiment, one of the homodimeric starting proteins has been engineered or modified not to bind Protein A or Protein G, or combinations of Protein A and G, thus allowing separation of the heterodimeric protein from said homodimeric starting protein by passing the product over a Protein A or Protein G column. This may in particular be useful for embodiments wherein an excess of one homodimeric protein is used relative to the other homodimeric protein as starting material. In such embodiments, it may be useful to engineer or modify the Protein A or Protein G binding site of the homodimeric protein that will be used in excess so that its ability to bind such resins is disrupted. This type of modification includes but is not limited to the modifications in the CH3 domain which are disclosed in WO 2010/151792, incorporated herein by reference. Thus, the first or second homodimeric protein of the present invention may comprise one or more of the modifications in the CH3 domain described in WO 2010/151792 which reduces or eliminates binding of the IgG to Protein A. Thus in a particular embodiment the first or second homodimeric protein of the present invention may comprise a modification selected from the group consisting of but not limited to a) 435R and b) 435R and 436F. In another embodiment the first or second homodimeric protein may comprise the following mutations: I253A, H310A, and H435A (AAA), which also eliminates binding to Protein A. Following the heterodimerization reaction, the heterodimeric protein may then be separated from a surplus of unexchanged homodimeric protein by passage over a protein A column. If Protein G is used for purification of the heterodimeric protein, the first or second homodimeric protein of the present invention may comprise a modification selected from the group consisting of, but not limited to, I253, S254, H433 and N434 (Sloan, D., et al., Prot. Sci. 1999; 8: 1643-1648; Sauer-Eriksson, E., et al., Structure 1995; 3: 265-278). Following the heterodimerization reaction, the heterodimeric protein may then be separated from a surplus of unexchanged homodimeric protein by passage over a Protein G column. Other methods of purification include any of those described herein. Hence in one embodiment the first and second homodimeric proteins may comprise different light chains, such as kappa and lambda light chains, or the first and second homodimeric protein may be of different allotypes such as described herein.

In a further embodiment, one of the homodimeric proteins is (1) an Fc region or (2) a full-length antibody recognizing a non-relevant epitope.

Variable regions to be used for homodimeric starting material of the present invention may e.g. be produced by the hybridoma method first described by Kohler et al., Nature 256, 495 (1975), or may be produced by recombinant DNA methods. Variable regions may also be isolated from phage antibody libraries using the techniques described in, for example, Clackson et al., Nature 352, 624 628 (1991) and Marks et al., J. Mol. Biol. 222, 581 597 (1991). Variable regions may be obtained from any suitable source. Thus, for example, variable regions may be obtained from monoclonal antibodies of hybridomas prepared from murine splenic B cells obtained from mice immunized with an antigen of interest, for instance in form of cells expressing the antigen on the surface, or a nucleic acid encoding an antigen of interest. Variable regions may also be obtained from monoclonal antibodies of hybridomas derived from antibody-expressing cells of immunized humans or non-human mammals such as rats, dogs, primates, etc.

The first and/or second homodimeric protein may be e.g. a chimeric or a humanized antibody. In another embodiment, one or both of the homodimeric starting proteins, except for any specified mutations, is a human antibody. Human monoclonal antibodies may be generated using transgenic or transchromosomal mice, e.g. HuMAb mice or TC mice carrying a minichromosome encoding the complete or parts of the human heavy and light chain repertoire. The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., Nature 368, 856 859 (1994)). Accordingly, the mice exhibit reduced expression of mouse IgM or κ light chains and the introduced human heavy and light chain transgenes undergo class switching and somatic mutation to generate high affinity human IgG, κ monoclonal antibodies in response to immunization (Lonberg, N. et al. (1994), supra; reviewed in Lonberg, N. Handbook of Experimental Pharmacology 113, 49 101 (1994), Lonberg, N. and Huszar, D., Intern. Rev. Immunol. Vol. 13 65 93 (1995) and Harding, F. and Lonberg, N. Ann. N.Y. Acad. Sci 764 536 546 (1995)). The preparation of HuMAb mice is described in detail in Taylor, L. et al., Nucleic Acids Research 20, 6287 6295 (1992), Chen, J. et al., International Immunology 5, 647 656 (1993), Tuaillon et al., J. Immunol. 152, 2912 2920 (1994), Taylor, L. et al., International Immunology 6, 579 591 (1994), Fishwild, D. et al., Nature Biotechnology 14, 845 851 (1996). See also U.S. Pat. Nos. 5,545,806, 5,569, 825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187. Splenocytes from these transgenic mice may be used to generate hybridomas that secrete human monoclonal antibodies according to well known techniques.

Further, human antibodies of the present invention or antibodies of the present invention from other species may be identified through direct cloning or display-type technologies, including, without limitation, phage cloning or display, retroviral display, ribosomal display, mammalian display, and other techniques, using techniques well known in the art and the resulting molecules may be subjected to additional maturation, such as affinity maturation, as such techniques are well known in the art.

In a further embodiment of the invention, the antibody or a part thereof, e.g. one or more CDRs, is derived from a species in the family Camelidae, see WO2010001251, or from a species of cartilaginous fish, such as the nurse shark, or is a heavy-chain or domain antibody.

In one embodiment of the method of the invention, said first and second homodimeric proteins in step a) or provided in step a) are purified. Methods for purification of the homodimers may be any of those described herein, e.g. any of those described below.

In one embodiment, the first and/or second homodimeric protein is conjugated to a drug, a prodrug or a toxin or contains an acceptor group for the same. Such acceptor group may e.g. be an unnatural amino acid. In a particular embodiment the first and second homodimeric protein may be conjugated to different compounds, or contain different modifications, thereby resulting in production of a heterodimeric protein comprising both compounds or modifications.

As described above, the sequences of the first and second CH3 regions of the homodimeric starting proteins are different and are such that the heterodimeric interaction between said first and second CH3 regions is stronger than each of the homodimeric interactions of said first and second CH3 regions.

In one embodiment, the increased strength of the heterodimeric interaction as compared to each of the homodimeric interactions is due to CH3 modifications other than the introduction of covalent bonds, cysteine residues or charged residues.

In most embodiments, the product of the invention, the heterodimeric protein, is highly stable and does not undergo Fab-arm exchange under mildly reducing conditions in vitro or, importantly, in vivo upon administration to a human being or animal. Thus, in one embodiment, the heterodimeric interaction between said first and second proteins in the resulting heterodimeric protein is such that no Fab-arm exchange can occur at 0.5 mM GSH under the conditions described in Example 13.

In another embodiment, the heterodimeric interaction between said first and second proteins in the resulting heterodimeric protein is such that no Fab-arm exchange occurs in vivo in mice under the conditions described in Example 14.

In another embodiment, the heterodimeric interaction between said first and second proteins in the resulting heterodimeric protein is more than two times stronger, such as more than three times stronger, e.g. more than five times stronger than the strongest of the two homodimeric interactions, e.g. when determined as described in Example 30.

In a further embodiment, the sequences of said first and second CH3 regions are such that the dissociation constant of the heterodimeric interaction between said first and second proteins in the resulting heterodimeric protein is below 0.05 micromolar (µM) when assayed as described in Example 30.

In a further embodiment, the sequences of said first and second CH3 regions are such that the dissociation constants of both homodimeric interactions are above 0.01 µM, such as above 0.05 µM, preferably between 0.01 and 10 µM, such as between 0.05 and 10 µM, more preferably between 0.01 and 5 µM, such as between 0.05 and 5 µM, even more preferably between 0.01 and 1 µM, such as between 0.05 and 1 µM, or between 0.01 and 0.5 µM or between 0.01 and 0.1 µM when assayed as described in Example 21. Embodiments wherein the homodimeric starting proteins are relatively stable can have the advantage that it is easier to produce a large quantity of starting protein and e.g. avoid aggregation or misfolding.

In some embodiments, a stable heterodimeric protein can be obtained at high yield using the method of the invention on the basis of two homodimeric starting proteins containing only a few, fairly conservative, asymmetrical mutations in the CH3 regions.

Thus, in one embodiment, the sequences of said first and second CH3 regions contain amino acid substitutions at non-identical positions.

The amino acid substituents may be natural amino acids or unnatural amino acids. Examples of unnatural amino acids are e.g. disclosed in Xie J and Schultz P. G., Current Opinion in Chemical Biology (2005), 9:548-554, and Wang Q. et al., Chemistry & Biology (2009), 16:323-336.

In one embodiment, the amino acids are natural amino acids.

In one embodiment, said first homodimeric protein has no more than one amino acid substitution in the CH3 region, and the second homodimeric protein has no more than one amino acid substitution in the CH3 region relative to the wild-type, e.g. human IgG, such as human IgG1, CH3 regions.

In one embodiment, the first homodimeric protein has an amino acid substitution at a position selected from the group consisting of: 366, 368, 370, 399, 405, 407 and 409, and said second homodimeric protein has an amino acid substitution at a position selected from the group consisting of: 366, 368, 370, 399, 405, 407 and 409, and wherein said first homodimeric protein and said second homodimeric protein are not substituted at the same positions.

In one embodiment, the first homodimeric protein has an amino acid substitution at position 366, and said second homodimeric protein has an amino acid substitution at a position selected from the group consisting of: 368, 370, 399, 405, 407 and 409. In one embodiment the amino acid at position 366 is selected from Arg, Lys, Asn, Gln, Tyr, Glu and Gly.

In one embodiment, the first homodimeric protein has an amino acid substitution at position 368, and said second homodimeric protein has an amino acid substitution at a position selected from the group consisting of: 366, 370, 399, 405, 407 and 409.

In one embodiment, the first homodimeric protein has an amino acid substitution at position 370, and said second homodimeric protein has an amino acid substitution at a position selected from the group consisting of: 366, 368, 399, 405, 407 and 409.

In one embodiment, the first homodimeric protein has an amino acid substitution at position 399, and said second homodimeric protein has an amino acid substitution at a position selected from the group consisting of: 366, 368, 370, 405, 407 and 409.

In one embodiment, the first homodimeric protein has an amino acid substitution at position 405, and said second homodimeric protein has an amino acid substitution at a position selected from the group consisting of: 366, 368, 370, 399, 407 and 409.

In one embodiment, the first homodimeric protein has an amino acid substitution at position 407, and said second homodimeric protein has an amino acid substitution at a position selected from the group consisting of: 366, 368, 370, 399, 405, and 409.

In one embodiment, the first homodimeric protein has an amino acid substitution at position 409, and said second homodimeric protein has an amino acid substitution at a position selected from the group consisting of: 366, 368, 370, 399, 405, and 407.

Accordingly, in one embodiment, the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment, the first or second homodimeric protein has an amino other than Lys, Leu or Met at position 409. In a further embodiment the first or second homodimeric protein has an amino acid selected from the group consisting of Ala, Asp, Glu, Phe, Gly, His, Ile, Asn, Gln, Arg, Ser, Thr, Val, Trp and Tyr at position 409. In an even further embodiment the first or second homodimeric protein has an amino acid selected from the group consisting of Arg, Gly, His, Val and Ile at position 409. In an even further embodiment the first or second homodimeric protein has an amino acid selected from the group consisting of Arg, His, Ile, and Val at position 409. In an even further embodiment the first or second homodimeric protein has Arg at position 409.

In one embodiment, the first or second homodimeric protein has an amino acid other than Phe at position 405. In a further embodiment the first or second homodimeric protein has an amino acid other than Phe, Arg or Gly at position 405. In an even further embodiment the first or second homodimeric protein has an amino acid selected from the group consisting of Ala, Asp, Glu, Gly, His, Ile, Lys, Leu, Met, Asn, Gln, Arg, Ser, Thr, Val, Trp and Tyr at position 405. In an even further embodiment the first or second homodimeric protein has Leu at position 405.

In one embodiment the first or second homodimeric protein has an amino acid other than Lys, Arg, Ser, Thr or Trp at position 366. In a further embodiment the first or second homodimeric protein has an amino acid other than Phe, Gly, Ile, Lys, Leu, Met, Arg, Ser, Thr, Trp or Tyr at position 366. In an even further embodiment the first or second homodimeric protein has an amino acid selected from the group consisting of Ile and Val at position 366.

In one embodiment the first or second homodimeric protein has an amino acid other than Phe, Leu, or Met at position 368. In a further embodiment the first or second homodimeric protein has an amino acid other than Phe, Leu, Lys, or Met at position 368. In an even further embodiment the first or second homodimeric protein has an amino acid selected from the group consisting of Ala, Asp, Glu, Gly, His, Ile, Asn, Gln, Arg, Ser, Thr, Val, and Trp at position 368. In an even further embodiment the first or second homodimeric protein has an amino acid selected from the group consisting of Asp and Glu at position 368.

In one embodiment, the first homodimeric protein has an amino acid other than Lys, Leu or Met at position 409 and said second homodimeric protein has an amino-acid substitution at a position selected from the group consisting of: 366, 368, 370, 399, 405 and 407.

In one such embodiment, said first homodimeric protein has an amino acid other than Lys, Leu or Met at position 409 and said second homodimeric protein has an amino acid other than Phe at position 405. In a further embodiment hereof, said first homodimeric protein has an amino acid other than Lys, Leu or Met at position 409 and said second homodimeric protein has an amino acid other than Phe, Arg or Gly at position 405. In a further embodiment said first homodimeric protein has an amino acid selected from the group consisting of Ala, Asp, Glu, Phe, Gly, His, Ile, Asn, Gln, Arg, Ser, Thr, Val, Trp and Tyr at position 409 and said second homodimeric protein has an amino acid selected from the group consisting of Ala, Asp, Glu, Gly, His, Ile, Lys, Leu, Met, Asn, Gln, Arg, Ser, Thr, Val, Trp and Tyr at position 405. In an even further embodiment the first homodimeric protein has an amino acid selected from the group consisting of Arg, Gly, His, Val and Ile at position 409, and said second homodimeric protein has Leu at position 405. In an even further embodiment the first homodimeric protein has an amino acid selected from the group consisting of Arg, His, Ile and Val at position 409, and said second homodimeric protein has Leu at position 405. In an even further embodiment said first homodimeric protein has Arg at position 409 and said second homodimeric protein has Leu at position 405.

In another embodiment the first homodimeric protein has an amino acid other than Lys, Arg, Ser, Thr or Trp at position 366 and the second homodimeric protein has an amino acid other than Phe at position 405. In a further embodiment the first homodimeric protein has an an amino acid other than Phe, Gly, Ile, Lys, Leu, Met, Arg, Ser, Thr, Trp or Tyr at position 366 and said second homodimeric protein has an amino acid other than Phe, Arg or Gly at position 405. In an even further embodiment said first homodimeric protein has an amino acid selected from the group consisting of Ile and Val at position 366 and the second homodimeric protein has an amino acid selected from the group consisting of Ala, Asp, Glu, Gly, His, Ile, Lys, Leu, Met, Asn, Gln, Arg, Ser, Thr, Val, Trp and Tyr at position 405. In an even further embodiment said first homodimeric protein has an amino acid selected from the group consisting of Ile and Val at position 366 and the second homodimeric protein has Leu at position 405.

In another embodiment, said first homodimeric protein comprises a Phe at position 405 and an amino acid other than Lys, Leu or Met at position 409 and said second homodimeric protein comprises an amino acid other than Phe at position 405 and a Lys at position 409. In a further embodiment hereof, said first homodimeric protein comprises a Phe at position 405 and an amino acid other than Lys, Leu or Met at position 409 and said second homodimeric protein comprises an amino acid other than Phe, Arg or Gly at position 405 and a Lys at position 409.

In another embodiment, said first homodimeric protein comprises a Phe at position 405 and an amino acid other than Lys, Leu or Met at position 409 and said second homodimeric protein comprises a Leu at position 405 and a Lys at position 409. In a further embodiment hereof, said first homodimeric protein comprises a Phe at position 405 and an Arg at position 409 and said second homodimeric protein comprises an amino acid other than Phe, Arg or Gly at position 405 and a Lys at position 409.

In another embodiment, said first homodimeric protein comprises Phe at position 405 and an Arg at position 409 and said second homodimeric protein comprises a Leu at position 405 and a Lys at position 409.

In a further embodiment, said first homodimeric protein comprises an amino acid other than Lys, Leu or Met at position 409 and said second homodimeric protein comprises a Lys at position 409, a Thr at position 370 and a Leu at position 405.

In a further embodiment, said first homodimeric protein comprises an Arg at position 409 and said second homodimeric protein comprises a Lys at position 409, a Thr at position 370 and a Leu at position 405.

In an even further embodiment, said first homodimeric protein comprises a Lys at position 370, a Phe at position 405 and an Arg at position 409 and said second homodimeric protein comprises a Lys at position 409, a Thr at position 370 and a Leu at position 405.

In another embodiment, said first homodimeric protein comprises an amino acid other than Lys, Leu or Met at position 409 and said second homodimeric protein comprises a Lys at position 409 and: a) an Ile at position 350 and a Leu at position 405, or b) a Thr at position 370 and a Leu at position 405.

In another embodiment, said first homodimeric protein comprises an Arg at position 409 and said second homodimeric protein comprises a Lys at position 409 and: a) an Ile at position 350 and a Leu at position 405, or b) a Thr at position 370 and a Leu at position 405.

In another embodiment, said first homodimeric protein comprises a Thr at position 350, a Lys at position 370, a Phe at position 405 and an Arg at position 409 and said second homodimeric protein comprises a Lys at position 409 and: a) an Ile at position 350 and a Leu at position 405, or b) a Thr at position 370 and a Leu at position 405.

In another embodiment, said first homodimeric protein comprises a Thr at position 350, a Lys at position 370, a Phe at position 405 and an Arg at position 409 and said second homodimeric protein comprises an Ile at position 350, a Thr at position 370, a Leu at position 405 and a Lys at position 409.

In another embodiment, said first homodimeric protein has an amino acid other than Lys, Leu or Met at position 409 and said second homodimeric protein has an amino acid other than Tyr, Asp, Glu, Phe, Lys, Gln, Arg, Ser or Thr at position 407.

In another embodiment, said first homodimeric protein has an amino acid other than Lys, Leu or Met at position 409 and said second homodimeric protein has an Ala, Gly, His, Ile, Leu, Met, Asn, Val or Trp at position 407.

In another embodiment, said first homodimeric protein has an amino acid other than Lys, Leu or Met at position 409 and said second homodimeric protein has a Gly, Leu, Met, Asn or Trp at position 407.

In another embodiment, said first homodimeric protein has a Tyr at position 407 and an amino acid other than Lys, Leu or Met at position 409 and said second homodimeric protein has an amino acid other than Tyr, Asp, Glu, Phe, Lys, Gln, Arg, Ser or Thr at position 407 and a Lys at position 409.

In another embodiment, said first homodimeric protein has a Tyr at position 407 and an amino acid other than Lys, Leu or Met at position 409 and said second homodimeric protein has an Ala, Gly, His, Ile, Leu, Met, Asn, Val or Trp at position 407 and a Lys at position 409.

In another embodiment, said first homodimeric protein has a Tyr at position 407 and an amino acid other than Lys, Leu or Met at position 409 and said second homodimeric protein has a Gly, Leu, Met, Asn or Trp at position 407 and a Lys at position 409.

In another embodiment, said first homodimeric protein has a Tyr at position 407 and an Arg at position 409 and said second homodimeric protein has an amino acid other than Tyr, Asp, Glu, Phe, Lys, Gln, Arg, Ser or Thr at position 407 and a Lys at position 409.

In another embodiment, said first homodimeric protein has a Tyr at position 407 and an Arg at position 409 and said second homodimeric protein has an Ala, Gly, His, Ile, Leu, Met, Asn, Val or Trp at position 407 and a Lys at position 409.

In another embodiment, said first homodimeric protein has a Tyr at position 407 and an Arg at position 409 and said second homodimeric protein has a Gly, Leu, Met, Asn or Trp at position 407 and a Lys at position 409.

In another embodiment, said first homodimeric protein has an amino acid other than Lys, Leu or Met at position 409, and the second homodimeric protein has an amino acid other than Lys, Arg, Ser, Thr or Trp at position 366. In a further embodiment said first homodimeric protein has an amino acid other than Lys, Leu or Met at position 409, and the second homodimeric protein has an amino acid other than Phe, Gly, Ile, Lys, Leu, Met, Arg, Ser, Thr, Trp or Tyr at position 366.

In one embodiment the first homodimeric protein has an amino acid other than Lys, Leu or Met at position 409, and the second homodimeric protein has an amino acid other than Phe, Leu, or Met at position 368. In a further embodiment the first homodimeric protein has an amino acid other than Lys, Leu or Met at position 409, and the second homodimeric protein has an amino acid other than Phe, Leu, Lys, or Met at position 368. In a even further embodiment the first homodimeric protein has an amino acid selected from the group consisting of Ala, Asp, Glu, Phe, Gly, His, Ile, Asn, Gln, Arg, Ser, Thr, Val, Trp and Tyr at position 409 and said second homodimeric protein has an amino acid selected from the group consisting of Ala, Asp, Glu, Gly, His, Ile, Asn, Gln, Arg, Ser, Thr, Val, and Trp at position 368. In an even further embodiment the first homodimeric protein has an amino acid selected from the group consisting of Arg, Gly, His, Val and Ile at position 409, and said second homodimeric protein has an amino acid selected from the group consisting of Ala, Asp, Glu, Gly, His, Ile, Asn, Gln, Arg, Ser, Thr, Val, and Trp at position 368. In an even further embodiment the first homodimeric protein has an amino acid selected from the group consisting of Arg, His, Val and Ile at position 409, and said second homodimeric protein has an amino acid selected from the group consisting of Asp and Glu at position 368. In an even further embodiment said first homodimeric protein has Arg at position 409 and said second homodimeric protein has an amino acid selected from the group consisting of Asp and Glu at position 368.

In one embodiment, the first homodimeric protein has an amino acid other than Lys, Leu or Met at position 409, and the second homodimeric protein has (i) an amino acid other than Phe, Leu and Met at position 368, or (ii) a Trp at position 370, or (iii) an amino acid other than Asp, Cys, Pro, Glu or Gln at position 399.

In one embodiment, the first homodimeric protein has an Arg, Ala, His or Gly at position 409, and the second homodimeric protein has (i) a Lys, Gln, Ala, Asp, Glu, Gly, His, Ile, Asn, Arg, Ser, Thr, Val, or Trp at position 368, or (ii) a Trp at position 370, or (iii) an Ala, Gly, Ile, Leu, Met, Asn, Ser, Thr, Trp, Phe, His, Lys, Arg or Tyr at position 399.

In one embodiment, the first homodimeric protein has an Arg at position 409, and the second homodimeric protein has (i) an Asp, Glu, Gly, Asn, Arg, Ser, Thr, Val, or Trp at position 368, or (ii) a Trp at position 370, or (iii) a Phe, His, Lys, Arg or Tyr at position 399.

In addition to the above-specified amino-acid substitutions, said first and second homodimeric protein may contain further amino-acid substitutions, deletion or insertions relative to wild type, e.g. human IgG, Fc sequences.

In a further embodiment, said first and second CH3 regions, except for the specified mutations, comprise the sequence set forth in SEQ ID NO:1 (IgG1m(a)):

```
SEQ ID NO: 1:
GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGK
```

In a further embodiment, said first and second CH3 regions, except for the specified mutations, comprise the sequence set forth in SEQ ID NO:2 (IgG1m(f)):

```
SEQ ID NO: 2:
GQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKS

LSLSPGK
```

In a further embodiment, said first and second CH3 regions, except for the specified mutations, comprise the sequence set forth in SEQ ID NO:3 (IgG1m(ax)):

SEQ ID NO: 3:
GQPREPQVYTLPPSRDELTKNQVSLTCLVKGFYPSDIAVEWESNGQPENN

YKTTPPVLDSDGSFFLYSKLTVDKSRWQQGNVFSCSVMHEGLHNHYTQKS

LSLSPGK

The production of heterodimeric proteins by the present invention comprises that the heterodimeric interaction between the CH3 region of the first and second homodimeric protein is stronger than each of the homodimeric interactions between said first and second CH3 region. This effect may in particular, as described above, be obtained with the above mentioned examples of CH3 modifications of the first and/or second homodimeric protein. However, it is foreseen that first and/or second homodimeric proteins comprising other mutations than those described herein may also be used in a method of the present invention. For example the first and second homodimeric proteins may be a rat antibody and a mouse antibody, as described by Lindhofer et al. (1995) J Immunol 155:219 (see above), or so-called knob-in-hole variant antibodies, as described in U.S. Pat. No. 5,731,168 (see above). Thus, in one embodiment of the present invention, the first and second homodimeric protein of the present invention may comprise the knob-in-hole single or double modifications described in U.S. Pat. No. 5,731,168.

The method of the present invention may also be used to produce bispecific antibodies as described in WO2011/143545.

Another suitable example of first and second homodimeric proteins useful in the present invention include those which are based on electrostatic interactions between the CH3 region of the first and second homodimeric protein, as those disclosed in WO 2009/089004. This technique may also be referred to as electrostatic steering.

In some cases, however, the latter homodimeric starting proteins may be more difficult to produce, because of too weak homodimeric CH3-CH3 interactions. Thus, the herein described variants having mutations at one or more of positions 366, 368, 370, 399, 405, 407 and 409 may be preferred. The herein described variants having mutations at one or more of positions 350, 370, 405 and 409, may be preferred.

The sequence of the hinge region of the homodimeric starting proteins may vary. However, the resulting heterodimeric protein may be more stable under some circumstances if the hinge region is not IgG4-like, and, preferably is IgG1-like.

Thus, in one embodiment, neither said first nor said second homodimeric protein comprises a Cys-Pro-Ser-Cys sequence in the (core) hinge region.

In a further embodiment, both said first and said second homodimeric protein comprise a Cys-Pro-Pro-Cys sequence in the (core) hinge region.

In many embodiments wherein first and said second homodimeric proteins are antibodies, said antibodies further comprise a light chain. As explained above, said light chains may be different, e.g. differ in sequence and each form a functional antigen-binding domain with only one of the heavy chains. In another embodiment, however, said first and second homodimeric proteins are heavy-chain antibodies, which do not need a light chain for antigen binding, see e.g. Hamers-Casterman (1993) Nature 363:446.

Step a)

As described above, step a) of the method of the present invention comprises incubating said first homodimeric protein together with said second homodimeric protein under reducing conditions sufficient to allow reduction of the inter-chain disulfide bonds in the hinge region. The term "sufficient" in the context of "reducing conditions sufficient to allow reduction of the inter-chain disulfide bonds in the hinge region" may in particular be in terms of allowing the Fab-arm exchange reaction to occur. Thus in a particular embodiment "reducing conditions sufficient to allow reduction of the inter-chain disulfide bonds in the hinge region" are conditions resulting in production of more than 50% heterodimeric protein, such as more than 60% heterodimeric protein, or more than 70% heterodimeric protein, or more than 80% heterodimeric protein, or more than 90% heterodimeric protein, or more than 95% heterodimeric protein, or more than 99% heterodimeric protein, or more than 99.5% heterodimeric protein, such as 100% heterodimeric protein. The percentage of heterodimeric protein is in this context in relation to total amount of first homodimeric protein, second homodimeric protein and heterodimeric protein. The amount or percentage of heterodimeric protein may for example be measured by CIEX as described in the examples herein.

In the context of the present invention reference to "reducing conditions of step a)" is intended to refer to "reducing conditions sufficient to allow reduction of the inter-chain disulfide bonds in the hinge region". Examples of suitable conditions are given herein. The minimal requirements for reduction of the inter-chain disulfide bonds in the hinge region may differ, depending on the homodimeric starting proteins, in particular depending on the exact sequence in the hinge region. Without being bound by any theory, the cysteine residues in the hinge region may, after reduction of the disulfide bonds, become e.g. bound to the reducing agent, such as 2-MEA, or form intra-chain disulfide bonds or react with unbound cysteine residues.

Formation of a heterodimeric protein in step a) is based on reduction of the disulfide bonds in the hinge region of the first and second homodimeric protein and an exchange of the Fc regions of said first and second homodimeric proteins.

Hence the reducing conditions of step a) may furthermore be enabling for exchange of the Fc regions of the first and second homodimeric protein, thereby producing a heterodimeric protein. Exchange of the Fc regions of two first or two second homodimeric proteins may also take place in step a) which will result in formation of a first or second homodimeric protein. The heterodimeric interaction between the CH3 regions of the first and second homodimeric protein is stronger than each of the homodimeric interactions of said CH3 regions. Without being bound by any theory exchange of the Fc regions of the heterodimeric protein may thereby be disfavoured compared to exchange of the Fc regions of first and second homodimeric proteins. Thus step a) may generally result in production of more heterodimeric protein than either of the first and second homodimeric protein. Hence generally the method of the present invention results in more than 50%, such as more than 60%, or more than 70%, or more than 80%, or more than 90%, or more than 95%, or more than 99%, of the product obtained, i.e. the total amount of first and second homodimeric protein and heterodimeric protein, being heterodimeric protein.

The first and second homodimeric protein may be produced together or separately, as also described above. If the first and second homodimeric protein are produced together, step a) may take place in the same container, e.g. bioreactor, as production of the first and second homodimeric protein.

Methods for production of the first and second homodimeric protein, such as antibodies, are well known to a person skilled in the art.

The concentration of the first homodimeric and second homodimeric protein in step a) does not have to be the same. In principle there is no limitation with respect to the concentration of the first and second homodimeric protein, but for most practical purposes the concentration of each of the first and second homodimeric protein in step a) may typically be in the range of 0.1 mg/mL to 100 mg/mL, such as in the range of 0.5-100 mg/mL, or in the range of 1-75 mg/mL, or in the range of 1-50 mg/mL. The total concentration of the first and the second homodimeric protein in step a) may be at least 0.25 mg/mL. The upper limit is mainly due that at concentrations above 200 mg/mL protein may be so viscous that they are difficult to handle, the limit of solubility may be reached, or the protein aggregation rate is too high. Hence the total concentration of first and the second homodimeric protein in step a) may typically be in the range of 0.2 mg/mL to 200 mg/mL, such as in the range of 0.5-100 mg/mL, or in the range of 1-50 mg/mL.

In one embodiment of the present invention an excess of either the first or second homodimeric protein may be used in step a) of the method. This may in particular be relevant if for example the first homodimeric protein has a strong impact on product safety or efficacy or is more difficult to separate from the heterodimeric protein than the second homodimeric protein, or vice versa or to simplify or ease purification of the heterodimeric protein produced by the method. Using an excess of one of the homodimeric proteins; i.e. the first or second homodimeric protein, may ease subsequent purification of the heterodimeric protein as described herein, because it will drive the exchange process in step a) closer to completion with respect to the under-abundant protein. Thus as the first or second homodimeric protein becomes a limitation, most of it will be used in step a) and the subsequent purification will then mainly reside in separating the heterodimeric protein from the homodimeric protein used in excess, rather than from both the first and second homodimeric protein. Hence using an excess of either the first or second homodimeric protein in step a) may in particular be combined with using a first and second homodimeric proteins which comprises differences that facilitate purification. Such differences include the ones described herein, e.g. non-binding to protein A or protein G, different light chains and/or different allotypes. Using non-equimolar amounts of the first and second homodimeric protein may be known as steered non-equimolar exchange process (SNEEP) and may e.g. be performed as described in Example 64 herein.

Thus in one embodiment the ratio of first to second homodimeric protein in step a) may be different from 1:1, e.g the ratio of the first to second homodimeric protein may have a ratio in the range of 1:1.03 to 1:2; such as in the range of 1:1.05 to 1:1.5, or in in the range of 1:1.1 to 1:1.5, or in the range of 1:1.1 to 1:1.4; or in the range of 1:1.15 to 1:1.35, or in the range of 1:1.2 to 1:1.3.

Hence in one embodiment the first and second homodimeric protein may in step a) be used with an excess of 5%-60% of either the first or second homodimeric protein, such as an excess of 15%-55% of either the first or second homodimeric protein, e.g. an excess of 20%-55% of either the first or second homodimeric protein, or an excess of 30-50% of either the first or second homodimeric protein, or in particular an excess of 15%-35% of either the first or second homodimeric protein, such as an excess of 20%-30% of either the first or second homodimeric protein.

The first and second homodimeric proteins in step a) may in particular be present in a solution, such as in a buffer. Thus, in one embodiment, step a) is performed in a solution, such as in a buffer. The solution may in particular be an aqueous solution. A suitable buffer may be one that supports the reduction and exchange process and which does not affect the first and second homodimeric proteins or the heterodimeric adversely, e.g. a buffer in which the first and second homodimeric proteins and the heterodimeric protein are stable. The buffer used in step a) may be the same as the buffer in which the first and/or second homodimeric proteins are present as a result of the previous processing step in order to minimize process manipulation. Alternatively, it could be a different buffer to enable standardized conditions or optimal reduction. For example the first and/or second homodimeric protein may have been purified prior to step a), and the buffer or solution may have been changed during the purification.

Examples of suitable buffers for step a) include, but are not limited to, PBS (phosphate-buffered saline), DPBS (Dulbecco's phosphate-buffered saline), PBS Braun (example 44), citrate buffer, acetate buffer, histidine buffer, phosphate buffer or Tris buffer. Specific examples of such buffers include those described in the examples of the present invention. As also shown in example 43, the choice of buffer may affect the kinetics of formation of the heterodimeric protein. Thus, in a particular embodiment, a Tris or a phosphate buffer may be used in step a) of the present invention. The buffer used in step a) may for example be the phosphate or Tris buffer described in Example 43 herein, or it may be the PBS buffer described in Example 53 herein.

In one embodiment the buffer in step a) may comprise in the range of 1-100 mM buffer, such as 1-50 mM buffer or in the range of 1-25 mM, or in the range of 5-20 mM.

In one embodiment the buffer in step a) may comprise in the range of 1-100 mM phosphate, such as 1-50 mM phosphate or in the range of 1-25 mM, or in the range of 5-20 mM.

The pH of the reducing conditions of step a) may be in the range of pH 3-10, such as pH 4-9, or in the range of pH 4.5-8.5. As seen from example 43, the pH value may affect the kinetics for formation of the heterodimeric protein. Thus, in a particular embodiment, the pH of the reducing conditions in step a) may be in the range of pH 5-8, such as between pH 6-8, or between pH 6.5-7.5, e.g. the pH may in particular be around 5.5, or 6, or 6.5, or 7, or 7.5, or 7.8 or 8.

Examples of suitable buffers include those of Example 43, in particular the ones selected from the group consisting of 1) 1× Dulbecco's phosphate-buffered saline (DPBS): 8.1 mM sodium phosphate ($Na_2HPO_4$-$7H_2O$), 1.5 mM potassium phosphate ($KH_2PO_4$), 138 mM sodium chloride (NaCl), 2.7 mM potassium chloride (KCl) pH 5.0; 2) 1×DPBS pH 7.0; 3) 20 mM Tris-HCl, pH 7.8

In an alternative embodiment the buffer in step a) may be selected from the group consisting of, but not limited to; a) 10 mM sodium phosphate, 2 mM potassium phosphate, 137 mM NaCl, pH 5.0; b) 10 mM sodium phosphate, 2 mM potassium phosphate, 137 mM NaCl, pH 7.0; c) 20 mM sodium citrate, pH 4.9; d) 20 mM sodium citrate, pH 6.0; and e) 20 mM Tris-HCl, 20 mM NaCl, pH 7.8.

In one embodiment, the reducing conditions in step a) comprise a reducing agent, e.g. a sulfhydryl reducing agent. The terms "reducing agent" and "reductant" may be used interchangeably in the context of the present invention. Typically, the reducing conditions in step a) comprises adding a reducing agent, e.g. a sulfhydryl-reducing agent.

The reducing agent may for example be selected from the group consisting of, but not limited to: 2-mercaptoethylamine (2-MEA), dithiothreitol (DTT), dithioerythritol (DTE), glutathione, tris(2-carboxyethyl)phosphine (TCEP), L-cysteine, D-cysteine, beta-mercapto-ethanol and chemical derivatives thereof, preferably a reducing agent selected from the group consisting of: 2-mercaptoethylamine, dithiothreitol, L-cysteine, D-cysteine and tris(2-carboxyethyl) phosphine. Thus the reducing agent may in one embodiment be selected from the group consisting of: 2-mercaptoethylamine (2-MEA), a chemical derivative of 2-mercaptoethylamine (2-MEA), L-cysteine, and D-cysteine. More particularly, the reducing agent is 2-mercaptoethylamine (2-MEA), or L-cysteine, or D-cysteine. The reducing agent 2-mercaptoethylamine has other chemical names such as 2-MEA, and cysteamine and such terms may be used interchangeably in the context of the present invention. The term 2-MEA is also used to describe 2-mercaptoethylamine-HCl, which is e.g. used in the examples of the present invention.

The choice of reducing agent, concentration thereof and the incubation time of step a) should be such that the inter-chain disulfide bonds in the hinge region become reduced and the exchange of the Fc regions of the first and second homodimeric protein is possible. However it may at the same time be an advantage to avoid using too harsh conditions, such as too high concentrations of the reducing agent or too long incubation times e.g. as it may be unnecessary and too harsh conditions may damage the first and/or second homodimeric protein or the heterodimeric protein. The optimal conditions may be affected by different parameters, such as temperature, pH, dissolved oxygen concentration, homodimer concentrations, choice of buffer, trace metals and chelators, and the choice and concentration of reducing agent.

A suitable concentration of the reducing agent may be in the range of 0.1 mM to 1 M. If the reducing agent is 2-MEA, the concentration may typically be in the range of 10-500 mM, such as in the range of 25-500 mM, or in the range of 40-350 mM, or in the range of 10-100 mM, e.g. in the range of 25-100 mM, or in the range of 10-75 mM, e.g. in the range of 25-75 mM, or in the range of 10-60 mM, e.g. in the range of 25-60 mM, or in the range of 10-50 mM, e.g. in the range of 25-50 mM, such as around 10 mM, or around 25 mM, or around 30 mM, around 40 mM, or around 50 mM. If the reducing agent is L-cysteine or D-cysteine the concentration may typically be in the range of 10-500 mM, such as in the range of 10-400 mM, or in the range of 10-300 mM, or in the range of 10-200 mM, or in the range of 20-150 mM, or in the range of 20-125 mM, or in the range of 25-100 mM, such as around 25 mM, or around 50 mM, or around 75 mM or around 100 mM.

In a further embodiment step a) comprises incubation for at least 15 minutes, such as at least 20 minutes or at least 30 minutes, or at least 60 minutes or at least 90 minutes, such as for 15 minutes to 10 hours, or for 15 minutes to 6 hours, or for 15 minutes to 5 hours, or for 15 minutes to 4.5 hours, or for 15 minutes to 4 hours, or 30 minutes to 10 hours, or for 30 minutes to 6 hours, or for 30 minutes to 5 hours, or for 30 minutes to 4.5 hours, or for 320 minutes to 4 hours, or for 90 minutes to 10 hours, or for 90 minutes to 6 hours, or for 90 minutes to 5 hours, or for 90 minutes to 4.5 hours, or for 90 minutes to 4 hours, such as for 2-5 hours, or for 2-4.5 hours, or for 2-4 hours, or for 3-5 hours, or for 3-4.5 hours, or for 3-4 hours, or for 3.5-5 hours, or for 3.5-4.5 hours, e.g for approximately 2 hours, 3 hours, 4 hours or 5 hours. As shown in example 45 and Example 53, reduction of the inter-chain disulfide bonds in the hinge region, and exchange of the Fc regions of the first and second homodimeric protein to produce the heterodimeric protein were under the given conditions completed within 4 hours.

The optimal temperature of step a) may depend on the choice of the reducing agent. Typically the temperature may be in the range of 2-45° C., such as in the range of 2-10° C., or in the range of 15-45° C., or in the range of 20-40° C., or in the range of 20-30° C., or in the range of 30-40° C., or in the range of 22-39° C., such as in the range of 21-26° C., or in the range of 22-25° C., such as around 25° C. or around 37° C. In one embodiment, step a) comprises incubation for at least 30 minutes at a temperature of at least 20° C. in the presence of at least 25 mM of a reducing agent selected from the group consisting of 2-mercaptoethylamine, L-cysteine and D-cysteine. In one embodiment, the reducing conditions enabling controlled Fab-arm exchange, i.e. the reduction of the inter-chain disulfide bonds in the hinge region of the first and second homodimeric protein and the subsequent exchange of the Fc regions of the first and second homodimeric protein, are described in terms of the required redox potential. The tripeptide glutathione (GSH) is the major low-molecular weight thiol in cells and controls thiol-disulphide redox state which is essential for normal redox signaling in vivo. The dynamics of cellular redox balance are achieved by maintenance of the thiol-to-disulphide status of reduced GSH and its oxidized form GSSG. The values for the reduction potential can be measured as in Rost and Rapoport, Nature 201: 185 (1964) and Aslund et al., J. Biol. Chem. 272:30780-30786 (1997). The redox potential $E_h$, which takes into consideration the stoichiometry of two GSH oxidized per GSSG is a quantitative measure for the redox state. $E_h$ is calculated by the Nernst equation (Equation 1): $E_h=E_0+(RT/nF)\ln([GSSG(ox)]/[GSH(red)]^2)$. $E_0$ is the standard potential for the redox couple at defined pH, R is the gas constant, T is the absolute temperature, F is Faraday's constant and n is the number of electrons transferred. In vivo estimates for Eh for the GSH/GSSG couple are in the range of −260 to −200 mV (Aw, T., News Physiol. Sci. 18:201-204 (2003)). Terminally differentiated cells thereby maintain an Eh in the order of −200 mV, whereas actively proliferating cells maintain a more reduced Eh of approximately −260 mV.

The standard redox potential for DTT is −330 mV (Cleland et al. Biochemistry 3: 480-482 (1964)). TCEP has been shown to reduce DTT in solution and therefore has a more negative redox potential than DTT. The precise value however has not been reported. Reducing conditions suitable for step a) of the present invention can therefore be described in terms of a required redox potential $E_h$, which is optimally below the value that is achieved under normal plasma conditions in vivo and that is above the redox potential which reduces antibody disulphide bonds outside those located in the hinge region and involved in inter-chain disulfide bond formation, or involved in disulfide bonds between the light and heavy chain.

Thus, in one or a further embodiment, step a) is performed under reducing conditions with a redox potential ranging below −50 mV, such as below −150 mV, preferably between −150 and −600 mV, such as between −200 and −500 mV, more preferably between −250 and −450 mV, such as between −250 and −400 mV, even more preferably between −350 and −450 mV.

In one or a further embodiment, step a) comprises incubation for at least 30 minutes, e.g. 90 minutes, at a temperature of at least 20° C. in the presence of at least 25 mM 2-mercaptoethylamine or in the presence of at least 0.5 mM dithiothreitol or in the presence of at least 25 mM L- or D-cysteine.

In one or a further embodiment, step a) comprises incubation for at least 30 minutes, e.g. 90 minutes, at a temperature of at least 20° C., at a pH of from 5 to 8, such as at pH 7.0 or at pH 7.4, in the presence of at least 25 mM 2-mercaptoethylamine or in the presence of at least 0.5 mM dithiothreitol or in the presence of at least 25 mM L- or D-cysteine.

In another or a further embodiment, step a) comprises incubation for at least 30 minutes, e.g. 90 minutes, at a temperature of at least 20° C. in the presence of at least 25 mM 2-mercaptoethylamine, or in the presence of at least 25 mM L- or D-cysteine. The incubation may be performed at a pH of from 6 to 8, such as at pH 7-8.

In a further embodiment, step a) comprises incubation for 4-6 hours at a temperature of 20-30° C. in the presence of 25-75 mM 2-mercaptoethylamine, or in the presence of 25-100 mM L- or D-cysteine. The incubation may be performed at a pH of from 6 to 8, such as at pH 7-8.

In an even further embodiment, step a) comprises incubation for 5 hours at a temperature of 25° C. in the presence of 50 mM 2-mercaptoethylamine, or in the presence of 25-100 mM L- or D-cysteine. The incubation may be performed at a pH of from 6 to 8, such as at pH 7-8.

In one or a further embodiment, step a) comprises adding a metal chelating agent, such as EDTA, EGTA or citric acid. The inventors of the present invention have shown that when 2-MEA is used as a reducing agent in step a) of the present invention adding or including EDTA in step a) decreases the rate of 2-MEA auto-oxidation in this step as observed by a lower oxidation rate (see e.g. example 47 and 54). Without being bound by any theory this may be due to metal ions present in step a) being chelated by EDTA, which may then decrease auto-oxidation of 2-MEA by metal ions. In general, auto-oxidation of a reducing agent consumes the reducing agent resulting in an effectively lower concentration of the reducing agent. Thus by adding a metal chelating agent the rate of reduction of the inter-chain disulfide bonds in the hinge region may be increased and/or less reducing agent may be needed to reduce the inter-chain disulfide bonds in the hinge region. Metal ions may e.g. be present in the solutions or buffers used in the reaction and/or they may be leached from the equipment used for the reaction.

Examples of suitable metal chelating agents which may be added or included in step a) include, but are not limited to, EDTA, EGTA and citric acid.

The concentration of the metal chelating agent depends on the concentration of metal ions in the composition in step a), which may e.g. be affected by the components used in step a). However, relevant concentrations of EDTA or EGTA may be in the range of 0.01 mM to 10 mM, such as in the range of 0.1 mM to 10 mM, such as in the range 0.5 mM to 5 mM, or in the range of 1 mM to 5 mM, such as around 1 mM, or around 2 mM, or around 3 mM, or around 4 mM or around 5 mM.

The concentration of oxygen, e.g. dissolved oxygen, in step a) may also affect reduction of the inter-chain disulfide bonds and/or exchange of the Fc regions of the first and second homodimeric proteins. Thus, in a further embodiment, the reducing conditions in step a) comprise reducing the amount of oxygen, e.g. dissolved oxygen, present in step a), e.g the amount of oxygen dissolved in the composition of step a).

The presence of oxygen or amount of oxygen, e.g. dissolved oxygen or oxidant, in the composition in step a) may be affected by different factors, such as the presence of different compounds or mechanical effects which can reduce or increase transfer of oxygen from the air into the solution. Thus, in a further embodiment, step a) of the present invention comprises limiting the mixing rate, limiting oxygen sparging, minimizing oxygen transfer from the head space or any combination of those. In one embodiment the mixing rate may for example be between 50-200 rpm, such as between 75-150 rpm, or between 75-125 rpm, e.g. around 100 rpm. The rate of head-space gassing may for example be in the range of 5-25 mL/min, e.g. in the range of 10-20 mL/min, e.g. around 15 mL/min.

The oxygen transfer rate can be determined with the following equation 2:

$$OTR = kla \times \ln(DO^* - DO) \times s,$$

wherein,
OTR=oxygen transfer rate (mM/hr)
kla=oxygen transfer coefficient (1/hour)
$DO^*$=equilibrium DO concentration (nitrogen=0%, air=100%, oxygen=500%)
DO=actual dissolved oxygen concentration
s=oxygen solubility (approximately 0.2 mM/100%)

The optimal range of the oxygen transfer range depends on the type and concentration of the reducing agent.

In example 57, nitrogen was used as the gas and the system DO was brought to 0% prior to the exchange reaction. According to the equation 2 with $DO^*=0$ and DO=0, OTR=0 mM/hr. This condition resulted in suitable exchange.

In example 53, air was used in the gas phase, so $DO^*=100\%$. The kla for example 53 (agitation at 100 RPM) was 0.76/hr. The DO of the system dropped from the saturation value of 100% to a steady state value of 0.2%. The oxygen transfer rate of this condition according to the equation 2 is then 0.15 mM/hr. This condition resulted in suitable exchange.

In example 55, air was used in the gas phase, so $DO^*=100\%$. The kla for example 55 (agitation at 400 RPM) was 4.0/hr. The DO of the system dropped from the saturation value of 100% to a steady state value of 3%. The oxygen transfer rate of this condition according to the equation 2 is then 0.78 mM/hr. This condition resulted in incomplete reduction and a low conversion to heterodimeric product.

These results demonstrate that an OTR of 0-0.15 mM/hr provides suitable results, whereas on OTR of 0.78 mM/hr or higher provides suboptimal results, when 50 mM 2-MEA was used as the reducing agent.

If air is used for transfer of oxygen, the oxygen transfer coefficient (kla) in step a) may be less than e.g. 3/hour, such as less than 2/hour, or less than 1/hour, or less than 0.90/hour, or less than 0.80/hour, e.g. less than 0.76/hour such as around 0.76/hour.

Another way of limiting or purging the amount of oxygen dissolved in the composition in step a), includes adding an inert gas, such as nitrogen to step a) to displace oxygen from the composition.

Thus, in a further embodiment the reducing conditions in step a) comprise displacing, purging or replacing oxygen dissolved in the composition of step a) with an inert gas, e.g. nitrogen. This may for example be accomplished through headspace gassing with nitrogen and/or sparging with sufficient agitation.

The progress of the reduction of the disulfide bonds in the hinge region of the first and second homodimeric protein may be followed by monitoring redox potential and/or by monitoring the concentration of dissolved oxygen. Means for such monitoring is well known to a person skilled in the art, and include e.g. different types of probes, such as any of those described or used herein.

In an alternative embodiment step a) may be performed by passing the first and second heterodimeric protein over a material comprising a reducing agent. An example of such a method may be a column comprising a reducing agent, e.g. an immobilized reductant column comprising e.g. a reducing agent described herein, such as the one described in Example 61.

The heterodimeric protein may then be obtained from the material, e.g. eluting it from the column. The heterodimeric protein obtained by this method may not comprise or only comprise trace amounts of the reducing agent as this is bound to the material, e.g. in the column. The temperature, the concentration of dissolved oxygen, the concentration of the first and second homodimeric protein, the redox potential and the pH may be similar to those described above.

Step b)

The method of the present invention further comprises a step of:

b) subjecting the composition obtained from step a) to oxidizing conditions sufficient to allow oxidation of cysteines in the heterodimeric protein to inter-chain disulfide bonds.

In a particular embodiment step b) of the present invention comprises:

b) subjecting at least 10 mL of the composition obtained from step a) to oxidizing conditions sufficient to allow oxidation of cysteines in the heterodimeric protein to inter-chain disulfide bonds.

The reducing conditions of step a) cause reduction of the inter-chain disulfide bonds in the hinge region of the first and second homodimeric protein. Besides the inter-chain disulfide bonds in the hinge region, there may also be other disulfide bonds in the first and/or second homodimeric protein, such as a disulfide bond between the heavy and light chain of an antibody or intra-chain disulfide bonds. The reducing conditions of step a) may also cause reduction of such other inter- or intra-chain disulfide bonds in the first and/or second homodimeric protein.

After exchange of the Fc regions of the first and second homodimeric protein in step a), it may be advantageous if the disulfide bonds in the hinge region between the first and second Fc region of the heterodimeric protein, and optionally other disulfide bonds, reform. Thereby resulting in production of a heterodimeric protein comprising at least disulfide bonds in the hinge region, and optionally also other disulfide bonds at places similar to those in the first and/or second homodimeric protein. The presence of such disulfide bonds increases the stability of the heterodimeric protein.

Example 41 shows that after buffer exchange of a bispecific antibody produced according to step a) of the present invention, the bispecific antibody was only partially re-oxidized. Hence example 41 indicates that the conditions of step a) in that example were not sufficient for re-oxidation of the disulfide bonds in the hinge region of the bispecific antibody. Furthermore, example 48 and example 57 also show that when the dissolved oxygen concentration is reduced by replacing it by addition of nitrogen, the re-oxidation of the cysteines in an antibody to disulfide bonds is inhibited. For oxidation of cysteines to disulfide bonds, two cysteines should be in close enough proximity of each other. The process of the present invention generally results in a natural re-assemblance of the heterodimeric protein. Thus, the cysteines in e.g. a bispecific antibody produced by the present method may generally be positioned as in the first and second antibodies (first and second homodimeric protein), so that disulfide bonds present in the antibodies are also formed in the bispecific antibody. In the context of the present invention reference to "oxidizing conditions of step b)" is intended to refer to "oxidizing conditions sufficient to allow oxidation of cysteines in the heterodimeric protein to inter-chain disulfide bonds". In a further embodiment the oxidizing conditions in step b) are sufficient for formation of all relevant disulfide bonds in the heterodimeric protein; e.g. both inter- and intra-chain disulfide bonds.

In the context of the present invention, conditions sufficient to allow oxidation of cysteines in the heterodimeric protein to inter-chain disulfide bonds means that at least 80%, such as at least 85%, or at least 90%, or at least 95%, or at least 99%, or 100% of the inter-chain disulfide bonds are formed. As described elsewhere herein the heterodimeric protein may comprise cysteine residues capable of forming both inter-chain and intra-chain disulfide bonds. The relevant time-frame for oxidation of the cysteines to disulfide bonds depends on e.g. manufacturing conditions and may typically be within 48 hours, such as within 24 hours, or within 15 hours, or within 10 hours, or within 5 hours, or within 4 hours, or within 3 hours, or within 2 hours.

For the purpose of industrial production, increasing the speed of production, without affecting the product adversely, is generally recognized as an advantage. Examples 55 and 56 indicate that increasing the amount of oxygen increases the rate of re-oxidation of the disulfide bonds. This may be particularly relevant for production of larger volumes of heterodimeric protein. Thus, the method of the present invention comprises a step b) subjecting at least 10 mL of the composition obtained from step a) to oxidizing conditions sufficient to allow oxidation of cysteines in the heterodimeric protein to inter-chain disulfide bonds.

In a further embodiment, the volume of the composition obtained from step a) which is used in step b) may be at least 15 mL, such as at least 20 mL, or at least 25 mL, or at least 30 mL, or at least 40 mL, or at least 50 mL, or at least 75 mL, or at least 100 mL, or at least 125 mL, or at least 150 mL, or at least 200 mL, or at least 250 mL, or at least 300 mL, or at least 350 mL, or at least 400 mL, or at least 450 mL, or at least 500 mL, or at least 550 mL, or at least 600 mL, or at least 650 mL, or at least 700 mL, or at least 750 mL, or at least 800 mL, or at least 850 mL, or at least 900 mL, or at least 950 mL, or at least 1 L, or at least 2 L, or at least 3 L, or at least 4 L, or at least 5 L, or at least 10 L. In principle there is no upper limit especially not if the process is run as a continuous process. However, for many process conditions a suitable reactor vessel for this type of production may be at the size of 1 L to 10,000 L.

In one or a further embodiment the concentration of the heterodimeric protein in the composition obtained from step a), e.g. which is used in step b), may be at least 0.1 mg/mL, such as at least 0.2 mg/mL, or at least 0.3 mg/mL, or at least 0.4 mg/mL, or at least 0.5 mg/mL, or at least 0.75 mg/mL, or at least 1 mg/mL, or at least 1.5 mg/mL, or at least 2 mg/mL, or at least 3 mg/mL, or at least 4 mg/mL, or at least 5 mg/mL, or at least 10 mg/mL, or at least 15 mg/mL, or at least 16 mg/mL, or at least 20 mg/mL. The upper limit for the concentration of the heterodimeric protein may be between 100-200 mg/mL, such as around 100 mg/mL, or around 150 mg/mL, or around 200 mg/mL. Hence the concentration of the heterodimeric protein in the composition obtained from step a) may in one embodiment be in the range of 0.1-200 g/L, such as in the range of 1-100 g/L. The present invention is not limited to particular concentrations of heterodimeric protein, however when the concentration of protein (whether it is first or second homodimeric protein or heterodimeric protein) is too high the composition may become unstable or too viscous making it difficult to work with and/or protein aggregates may form. In contrast too low concentrations of heterodimeric protein may not be economically feasible.

The amount of oxygen which is necessary, e.g. by supplying it in step b), to obtain oxidizing conditions sufficient to allow oxidation of cysteines in the heterodimeric protein to inter-chain disulfide bonds depends on different factors. Such factors include e.g. the volume of the composition obtained from step a), the concentration of the heterodimeric protein, the number of disulfide bonds requiring oxidation and the concentration of oxygen in the composition obtained from step a), which may depend on e.g. solubility of oxygen in the buffer, which can depend on the specific solution or buffer, the pH, the ionic strength, the temperature, the pressure and the ambient oxygen concentration. Subjecting the composition obtained from step a) to the oxidizing conditions of step b) of the present invention may increase the rate of oxidation of the cysteines in the heterodimeric protein to inter-chain disulfide bonds. Generally, the amount of oxygen in step b) that is sufficient or necessary for oxidation of cysteines in the heterodimeric protein to inter-chain disulfide bonds may be or is approximately 0.5 mole of oxygen ($O_2$) per mole of disulfide bond, e.g. in the range of 0.25-0.75 mole of oxygen ($O_2$) per mole of disulfide bond, such as 0.3-0.7 mole of oxygen ($O_2$) per mole of disulfide bond. This corresponds to one mole of oxygen ($O_2$) per two moles of cysteines, such as in the range 0.6-1.4 mole of oxygen ($O_2$) per two moles of cysteines. Thus, in one embodiment the "oxidizing conditions" in step b) comprise 0.3-0.7 mole of oxygen per mole of disulfide bond, such as 0.5 mole of oxygen present per mole of disulfide bond, or in the range of 0.6-1.4 mole of oxygen per two mole of cysteines, e.g. 1 mole of oxygen per two moles of cysteines.

Hence the relevant concentration of oxygen to obtain such a ratio of oxygen to disulfide bonds or cysteines depends on the concentration of heterodimeric protein in the composition obtained from step a).

In one embodiment the oxidizing conditions in step b) may comprise a concentration of at least 0.05 mM oxygen, such as at least 0.075 mM oxygen, or at least 0.1 mM oxygen, or at least 0.125 mM oxygen, or at least 0.15 mM oxygen, or at least 0.175 mM oxygen, or at least 0.2 mM oxygen.

The molecular solubility of oxygen is 0.206 mM in sea water, at 1 atm, 25° C. However, at the conditions of the present method, e.g. the buffers, temperature etc., the concentration of oxygen in the composition obtained from step a) may be less than 0.2 mM.

Since oxygen solubility is dependent on the partial pressure of oxygen in the gas phase, increased oxygen transfer can be obtained by increasing the pressure of air in the system. For example, a two-fold increase in pressure results in a two-fold increase in equilibrium dissolved oxygen concentration and increased oxygen transfer rate. Alternatively, the partial pressure of oxygen in the gas phase can be increased by using oxygen instead of air. Since air contains approximately 21% oxygen, the use of pure oxygen provides an approximately five-fold higher concentration of equilibrium dissolved oxygen and an increased oxygen transfer rate. Pressure and pure oxygen can be combined to further increase oxygen solubility and transfer rate.

In one embodiment the oxidizing conditions in step b) comprise saturating the composition obtained from step a) with oxygen.

The composition obtained from step a) generally comprises low amounts of oxygen, to ensure a proper reduction of the inter-chain disulfide bonds in the hinge region. Thus it may be necessary to supply oxygen in step b) of the method of the present invention.

In one embodiment, the first and second homodimeric protein may, as described above, be present in a solution, such as a buffer. Thus, the composition obtained from step a) may in a particular embodiment be a solution, e.g. a buffer. In this embodiment it is the amount of oxygen dissolved in the solution, i.e. the concentration of dissolved oxygen, which is important for the oxidation of the cysteines in the heterodimeric protein.

Thus in one embodiment, "the oxidizing conditions of step b)" refers to controlling the level of dissolved oxygen, which may e.g. comprise increasing the amount or concentration of dissolved oxygen in the composition obtained from step a).

Different means for obtaining or creating the oxidizing conditions of step b) may be used in the method of the present invention and include, but are not limited to, those described herein.

In one embodiment, the oxidizing conditions of step b) of the present invention comprise adding oxygen. The term "adding oxygen" is, in the context of the present invention, to be understood as increasing the amount oxygen, e.g. dissolved oxygen, in the composition obtained from step a), so that it is sufficient to allow oxidation of cysteines in the heterodimeric protein to inter-chain disulfide bonds. Means or methods of adding oxygen include, but are not limited to, mechanical means, changing the solution or buffer of the composition obtained from step a) to a solution of buffer comprising a higher amount of oxygen, such as one of the buffers used for diafiltration described herein, diluting the solution or buffer of the composition obtained from step a) with a solution or buffer comprising sufficient oxygen, adding compounds capable of generating oxygen, increasing pressure or by directly adding or including oxygen, e.g. oxygen gas. Combinations of such methods may also be used.

The amount or concentration of oxygen in step b) may be measured, e.g. continuously, so as to ensure that there is sufficient oxygen at all times during step b). Methods or equipment for measuring the oxygen are well known to a person skilled in the art and may for example include any of those described herein, such as the probes described in Example 44.

Oxygen may be added to step b) by for example sparging with oxygen or air or increasing pressure. Another method may be to increase the transfer of oxygen from the surroundings, e.g. air. This may for example be done by mechanical means, e.g. by stirring, agitating, increasing pressure or creating flow. For example if the composition in step b) is present in a container, such as a vessel, oxygen may e.g. be transferred into the composition of step b) from e.g. a head-space, or means for agitating or stirring the composition of step b) may be applied. By controlling the rate of agitation or stirring of the composition in step b), the transfer rate of oxygen from the surroundings may be controlled, i.e. the higher the agitation or stirring rate, or the flow, the more oxygen may be transferred into the composition obtained from step a). Means for increasing the pressure may also be applied. Adding oxygen to step b) may also be performed by a combination of different means, for example agitation and/or stirring may be combined with sparging and/or increasing the pressure of the composition in step b) with oxygen or air.

In another embodiment the oxidizing conditions in step b) of the present invention comprise an oxidizing agent. The oxidizing agent is preferably one that is able to ensure oxidation of the inter-chain disulfide bonds in the heterodimeric protein but at the same time avoid oxidizing other parts of the heterodimeric protein, such as amino acids like methionine and tryptophane, which are known to be sensitive to oxidation. An example of a suitable oxidizing agent is dehydroascorbic acid (dhAA). If dhAA is used to oxidize a reducing agent present in step a) typical concentrations of dhAA may be in the range of 1-2 times the concentration of the reducing agent, e.g. in the range of 50-100 mM. If the reducing agent present in step a) is removed prior to adding dhAA, the amount of oxidizing agent sufficient to allow oxidation of cysteines in the heterodimeric protein to inter-chain disulfide bonds, may be lower, such as in the range of 0.01-1 mM, e.g. 0.1-1 mM. If an oxidizing agent, such as dhAA is added in step b) of the present invention, it may be removed subsequently using standard filtration and/or chromatography techniques.

Different means or methods for adding or increasing oxygen in step b) may be used in combination.

For example, independent of how oxygen is added, e.g. by sparging with oxygen, stirring, agitating or creating flow, it may, in one embodiment, be combined with adding an oxidizing agent.

In one embodiment of the present invention, the reducing conditions of step a) comprise a reducing agent, which may also be present in the composition obtained from step a) and therefore subjected to the oxidizing conditions in step b). The presence of a reducing agent in step b) may be detrimental to the oxidizing conditions of step b). Thus, in one embodiment the heterodimeric protein may be separated from the reducing agent. As described below the inventors of the present invention have found that certain methods for separating the reducing agent from the heterodimeric protein result in or create oxidizing conditions sufficient to allow oxidation of cysteines in the heterodimeric protein to inter-chain disulfide bonds.

Removing the reducing agent or separating the heterodimeric protein from the reducing agent, may not necessarily be enough, depending on the method, to allow oxidation of the cysteines in the heterodimeric protein to inter-chain disulfide bonds, especially not when large amounts of heterodimeric protein, i.e. high concentrations and/or high volumes of heterodimeric protein, are produced in step a) (see e.g. examples 41, 52 and 53). However, it may be advantageous for other reasons to separate the heterodimeric protein from the reducing agent, and the method of the present invention may therefore further comprise a step of separating the heterodimeric protein from the reducing agent. Embodiments for separating the reducing agent from the heterodimeric protein are further described below.

Another method for decreasing the amount of reducing agent in the composition obtained from step a) is to increase the volume of said composition, thereby decreasing the concentration of the reducing agent in the composition obtained from step a). Hence, in a further embodiment the volume of the composition obtained from step a) may be increased, e.g. by adding the same buffer as the buffer of composition obtained from step a) with the exception that it does not contain the reducing agent of step a), or by adding a buffer different from the buffer of the composition obtained from step a), which does not contain the reducing agent of step a). Increasing the volume of the composition obtained from step a) may be used in combination with other embodiments described herein, including methods for separating the reducing agent and the heterodimeric protein.

Adding oxygen and/or an oxidizing agent to the composition in step b), as described above, may be sufficient to allow oxidation of the cysteines in the heterodimeric protein to inter-chain disulfide bonds. Furthermore, if step a) comprises a reducing agent, these conditions may also be sufficient for oxidation of the reducing agent so that it cannot further reduce the inter-chain disulfide bonds of the heterodimeric protein. Thus, in a further embodiment, the oxidizing conditions of step b) are sufficient to allow oxidation of the reducing agent of step a). For example, if 2-MEA is used as a reducing agent in step a), the oxidizing conditions of step b) may be so that the 2-MEA auto-oxidizes, so that it can not reduce any disulfide bonds (see e.g. Example 59). Independent of whether the reducing agent is oxidized or not, it may be relevant to subsequently separate the heterodimeric protein from the reducing agent. Hence, in a further embodiment, the method of the present invention may also include separation of the heterodimeric protein and the reducing agent. Methods for separating the heterodimeric protein from the reducing agent include any of those described herein, e.g. below. Separation of the heterodimeric protein and the reducing agent may be part of step b) or it may be a separate step.

Thus, in one embodiment step b) comprises adding oxygen or an oxidizing agent and optionally, subsequently separating the heterodimeric protein from the reducing agent. Separating the heterodimeric protein from the reducing agent may also be performed as a separate step, after step b).

Adding oxygen and/or an oxidizing agent in step b) may also result in oxidation of the reducing agent while the cysteines in the heterodimeric protein are not fully oxidized to disulfide bonds. In this case, the heterodimeric protein may be separated from the reducing agent and then subsequently the cysteines of the heterodimeric protein may be oxidized to inter-chain disulfide bonds by e.g., as described above, adding oxygen and/or an oxidizing agent. Thus, step b) may, in one embodiment, comprise subjecting the composition obtained from step a) to oxidizing conditions sufficient to oxidize the reducing agent, separating the heterodimeric protein from the reducing agent, and subjecting the heterodimeric protein to conditions sufficient to allow oxidation of cysteines in the heterodimeric protein to inter-chain disulfide bonds. Oxidation of the reducing agent and the cysteines in the heterodimeric protein to inter-chain disulfide bonds, may be done or performed similarly, e.g. as described above by adding oxygen and/or an oxidizing agent. However, there may be some differences with respect to the amount of oxygen needed, incubation times etc for oxidation of the reducing agent and oxidation of the cysteines in the heterodimeric protein to inter-chain disulfide bonds. Methods for separating the heterodimeric protein from the reducing agent include, but are not limited to, any of those described below, e.g. dialysis, precipitation, chromatography or filtration. Hence, in one embodiment, step b) may comprise subjecting the composition obtained from step a) to chromatography, e.g. column chromatography, or filtration, e.g. diafiltration, such as tangential flow filtration or normal flow filtration. Methods for performing chromatography or filtration include, but are not limited to, any of those described below.

In another embodiment, the oxidizing conditions of step b) may be such that cysteines of the heterodimeric protein are oxidized to inter-chain disulfide bonds concurrently with separating the heterodimeric protein and the reducing agent. In this case, step b) of the present invention may comprise adding oxygen and/or an oxidizing agent, as described above, concurrently with separating the heterodimeric protein and the reducing agent. Hence, in one embodiment, the method or conditions for separating the heterodimeric protein from the reducing agent may lead to or allow oxidization of cysteines in the heterodimeric protein to inter-chain disulfide bonds. Thus, step b) may, in one embodiment, comprise separating the heterodimeric protein and the reducing agent. Methods for separating the heterodimeric protein from the reducing agent include, but are not limited to, any of those described below, e.g. dialysis, precipitation, chromatography or filtration. Hence, in one embodiment, step b) may comprise subjecting the composition obtained from step a) to chromatography, e.g. column chromatography, or filtration, e.g. diafiltration, such as tangential flow filtration or normal flow filtration. Methods for performing chromatography or filtration include, but are not limited to, any of those described below.

In yet another embodiment, the method of the present invention may comprise separating the heterodimeric protein from the reducing agent and subsequently subjecting the heterodimeric protein to oxidizing conditions sufficient to allow oxidation of the cysteines to inter-chain disulfide bonds in the heterodimeric protein. In this embodiment, the step of separating the heterodimeric protein from the reducing agent may be regarded as a separate step prior to step b) or it may be regarded as part of step b). Methods for separating the heterodimeric protein from the reducing agent include, but are not limited to, any of those described below, e.g. dialysis, precipitation, chromatography or filtration. Oxidizing conditions sufficient to allow oxidation of the cysteines to inter-chain disulfide bonds in the heterodimeric protein may be obtained as described above, by e.g. adding oxygen and/or an oxidizing agent to the composition comprising the heterodimeric protein.

Methods for separating the heterodimeric protein from the reducing agent may in principle be any method which leads to or is capable of separating the two without harming the heterodimeric protein. Such methods include, but are not limited to, dialysis, precipitation, chromatography or filtration. Separating the heterodimeric protein and the reducing agent may be performed as a continuous process or it may be performed as a batch process.

The composition obtained from step a) which comprises the heterodimeric protein may in particular be a solution, such as a buffer. Separating the heterodimeric protein from the reducing agent may also be done by exchanging the buffer or the solution of the composition obtained from step a), with another buffer or solution without the reducing agent. With the exception of the presence of the reducing agent, the buffer or solution may be exchanged to the same buffer or solution as the composition obtained from step a), or it may be exchanged to another buffer or solution, such as a buffer or solution suitable for subsequent steps or for a final formulation of the heterodimeric protein. The solution or buffer, to which the solution or buffer of the composition obtained from step a) is exchanged, may in one embodiment also comprise oxygen, e.g. dissolved oxygen, or an oxidizing agent. Hence, exchange or dilution of the solution or buffer of the composition obtained from step a), in step b), may create "oxidizing conditions sufficient to allow oxidation of cysteines in the heterodimeric protein to inter-chain disulfide bonds". The oxidizing conditions of step b) may as described above be obtained by different means; e.g. adding oxygen, or an oxidizing agent, by removing the reducing agent (separation of the heterodimeric protein and reducing agent), mechanical means, e.g. chromatography or filtration method, and/or by exchange of the buffer or solution of the composition obtained from step a) to a buffer or solution which comprises a higher amounts of oxygen or an oxidizing agent. "Higher amounts of oxygen" is in this context to be understood as compared to the amount of oxygen present in the buffer or solution of the composition obtained from step a). Exchange of the buffer or solution of the composition obtained from step a) may for example be performed by chromatography or filtration. Thus, in one embodiment, the method of the present invention comprises a step of exchanging the solution, e.g. buffer, of the composition obtained from step a) by chromatography or filtration.

Exchanging the solution or buffer of the composition obtained from step a) may e.g. be done with at least 3 (three) volumes of buffer or solution without the reducing agent. In principle, there is no upper limit to the number of volumes that can be exchanged, but for most practical purposes 3-12 volumes of buffer or solution may be exchanged, such as in the range of 4-11 volumes, or in the range of 4-10 volumes, or in the range of 5-10 volumes, e.g. 5, 6, 7, 8, 9 or 10 volumes may be sufficient to reduce the concentration of the reducing agent adequately, or to remove the reducing agent from the composition obtained from step a).

Separating the heterodimeric protein and the reducing agent by chromatography or filtration may involve an exchange of the solution or buffer, i.e. a buffer or solution exchange as described above.

A suitable example of a chromatography method for separating the heterodimeric protein and the reducing agent may in a particular embodiment be a chromatography method based on bind and elute. The term "bind and elute" or "binding and elution" is based on binding of either the reducing agent or the heterodimeric protein to a chromatography material, whereas the other component does not bind. The component not binding to the chromatography material may be collected in the flow through and wash steps whereas the bound material may be collected separately after changing the buffer conditions so as to elute the component from the column. Different chromatography methods exist and the most suitable one depends on choice of reducing agent and the heterodimeric protein. Suitable examples include, but are not limited to, protein A and protein G chromatography (or other ways of affinity chromatography), affinity chromatography based on e.g. antigen-binding or anti-idiotypic antibodies, kappa or lambda select, cation exchange chromatography, mixed mode chromatography, e.g. hydroxyapatite, ionic exchange, hydrophobic interaction, immobilized metal affinity chromatography and thiophilic adsorption chromatography.

In one embodiment the chromatography may be column chromatography. The chromatography may, as described above, involve an exchange of the buffer or solution of the composition obtained from step a) with another buffer or solution without a reducing agent. This may for example involve in the range of 3-12 volumes of buffer or solution exchange. Chromatography methods are often performed as batch processes, thus, if the heterodimeric protein and the reducing agent are separated by chromatography, it may in one embodiment be performed as a batch process.

As described above, the heterodimeric protein and the reducing agent may also be separated by filtration. A suitable example of a filtration method is diafiltration. The inventors of the present invention have found that the conditions of diafiltration may be sufficient to allow oxidation of cysteines in the heterodimeric protein to inter-chain disulfide bonds even when large volumes of the composition obtained from step a) are used (see e.g. example 41). Thus, separating the heterodimeric protein and the reducing agent by diafiltration may be done concurrently with oxidation of the cysteines in the heterodimeric protein to inter-chain disulfide bonds. Thus, step b) of the present invention may in a particular embodiment comprise diafiltration of the composition obtained from step a). The diafiltration may involve at least three volumes of buffer or solution exchange, as described above. Methods of diafiltration include tangential flow filtration (TFF) and normal flow filtration (NFF), both of which may be used in the method of the present invention. Both TFF and NFF may be performed as continuous processes or as batch processes. Thus, in one embodiment step b) of the present invention comprises subjecting the composition obtained from step a) to one of the following methods: continuous TFF, batch TFF, continuous NFF or batch NFF.

Different methods of diafiltration are known to a person skilled in the art. For the purposes of the present invention, diafiltration may e.g. be performed with a membrane having a cut-off value in the range of 10-50 kDa, e.g. 20-40 kDa, such as around 30 kDa. The membrane may for example be made of a material such as polyethersulfone (PES), modified polyethersulfone (mPES), regenerated cellulose (RC), cellulose triacetate (CTA), hydrophilized polyvinylidene difluoride (PVDF), nitrocellulose or nylon. The configuration of the membrane may e.g. be hollow fiber, flat sheet or spirally wound.

In one embodiment, a hollow cartridge, such as a fiber cartridge, may be used for the diafiltration. The surface area of a hollow cartridge affects the rate of diafiltration, i.e. the larger the surface area the higher the rate of diafiltration. The rate of diafiltration may e.g. be measured as L/hour. The surface area may be in the range of 0.05-1 $m^2$, e.g. in the range of 0.05-0.5 $m^2$, such as around 0.1 $m^2$, or around 0.16 $m^2$, or around 0.4 $m^2$.

The cartridge inlet pressure may be in the range of 10-40 psig (70-280 kPa) preferably in the range of 20-30 psig (140-210 kPa).

The term "psig" refers to pounds per square inch above atmospheric pressure, and the correlation to the unit Pa (Pascal) is 101,325 Pa=14.7 psig.

The term "PSI" refers to pounds per square inch.

Diafiltration may be performed for the period of time necessary to perform a relevant number of volumes of buffer/solution exchange. A suitable period of time depends e.g. on the surface area of the membrane, the type of membrane, the concentration of heterodimeric protein, the system pressure, the circulation rate, the geometry of the filter cartridge, the temperature, the viscosity of the solution, the volume that is to be filtered, the amount of filter fouling caused by the solution, in the diafiltration process. Typically, the diafiltration may be performed for between 30 minutes to 20 hours.

In one embodiment the diafiltration may be performed by circulating the composition through a hollow fiber cartridge comprising a cut-off value in the range of 10-50 kDa, and with a surface area in the range of 0.05-1 $m^2$ with a cartridge inlet pressure in the range of 70-280 kPa, until one to seven, such as three to seven, or five to seven or seven volumes of buffer exchange have taken place.

In one embodiment the diafiltration may be performed by circulating the composition through a 30 kDa modified polyethersulfone hollow fiber cartridge with a surface area of 0.1 $m^2$ with a cartridge inlet pressure of 25 PSI (170 kPa), resulting in a permeate flow of 25 mL/min, until five to seven, such as seven (7) volumes of buffer exchange have taken place.

In one embodiment the diafiltration may be performed by circulating the composition through a 30 kDa modified polyethersulfone hollow fiber cartridge with a surface area of 0.4 $m^2$ with a cartridge inlet pressure of 25 PSI (170 kPa), resulting in a permeate flow of 100 mL/min, until five to seven, such as seven (7) volumes of buffer exchange have taken place.

In one embodiment the diafiltration may be performed by circulating the composition through a 30 kDa modified polyethersulfone hollow fiber cartridge with a surface area of 0.16 $m^2$ with a cartridge inlet pressure of 25 PSI (170 kPa), resulting in a permeate flow of 100 mL/min, until five to seven, such as seven (7) volumes of buffer exchange have taken place.

Performing filtration as a continuous process generally comprises adding buffer or solution to the system at the same rate as removing the permeate, thereby keeping the amount of solution/buffer in the system constant. Thus, in the context of the present invention this would mean that in step b) buffer/solution is added to the composition obtained from step a) at the same rate as the permeate, is removed. The heterodimeric protein may be collected from the retentate. Performing chromatography or filtration as batch processes in the method of the present invention, may on the other hand typically involve concentrating the heterodimeric protein present in the composition obtained from step a) while removing the solution of the composition obtained from step a). Alternatively, the composition obtained from step a) comprising the heterodimeric protein may be diluted and subsequently concentrated by chromatography or filtration. The concentrated heterodimeric protein may, if the process is performed more than once, subsequently be diluted in buffer or solution again before repeating the step of chromatography or filtration.

In one embodiment the composition obtained from step a) may be diluted prior to separating the reducing agent and the heterodimeric protein.

In one embodiment separating the heterodimeric protein and the reducing agent by chromatography or filtration, e.g. diafiltration may be performed once.

In some embodiments separating the heterodimeric protein and the reducing agent by chromatography or filtration may be repeated two or more times, e.g. with a different step in between. Thus, in one embodiment, the method of the present invention may comprise steps I)-III). In a particular embodiment step b) of the present invention may comprise steps I)-III):

I) separating the heterodimeric protein and the reducing agent of the composition obtained from step a), II) incubating the composition obtained from step I) comprising the heterodimeric protein, III) separating the heterodimeric protein and the reducing agent of the composition obtained from step II).

Separation of the heterodimeric protein and the reducing agent may not be complete in step I), so the composition comprising the heterodimeric protein obtained from step I) may still comprise reducing agent.

Separating the heterodimeric protein and the reducing agent in step I) and III) may be performed by a method described herein, such as described above. It may in particular be performed by diafiltration. The conditions of chromatography and filtration described above also apply to step I) and III). Incubating the heterodimeric protein obtained from step I) in step II) may e.g. be done for a period 1 hour to 10 days, or from 1 hour to 5 days, or from 1 hour to 3 days, or from 1 hour to 48 hours, such as a period of 5-24 hours, or 8-18 hours and at a temperature in the range of 10-45° C., e.g in the range of 15-40° C., or in the range of 15-35° C., or in the range of 20-40° C., or in the range of 20-35° C. In a further embodiment, incubating the heterodimeric protein obtained from step I) in step II) may be performed for a period of 1 to 24 hours and at a temperature in the range of 15-40° C.

In a further embodiment, step I) may comprise diafiltration of the composition obtained from step a). Thus, in a further embodiment, steps I), II) and III) may comprise:

I) diafiltration of the composition obtained from step a)
II) incubation of the retentate obtained from step I)
III) diafiltration of the composition obtained from step II).

In a further embodiment, the diafiltration in steps I) and/or III) may comprise a buffer exchange, such as in the range of 3-12 volumes of buffer exchange.

In an even further embodiment, step II) comprises incubation at a temperature in the range of 15-35° C. for a period of 12-48 hours.

As shown in example 45, repeating the separation of the heterodimeric protein and the reducing agent may for some conditions, e.g. depending on the reducing conditions of step a), assist in ensuring a complete re-oxidation of the cysteines in the heterodimeric protein to inter-chain disulfide bonds and/or further minimize the amount of reducing agent in the composition comprising the heterodimeric protein.

The inventors of the present invention have furthermore found that the presence of EDTA, a metal chelating agent (see examples 49), results in a decrease in the oxidation rate of cysteines in a homodimeric protein to inter-chain disulfide bonds, where the homodimeric protein is used as an example of a heterodimeric protein. Similar, observations were seen a heterodimeric protein (Example 54). This indicates that the presence of a metal ion in step b) increases the oxidation rate of the cysteines in the heterodimeric protein to inter-chain disulfide bonds, at least compared to the situation where there are no metal ions present. Thus, in a further embodiment, step b), e.g. the oxidizing conditions in step b), may comprise a metal ion. The metal ion may be added to the composition obtained from step a), in step b), or it may be present in the composition obtained from step a), e.g. by the choice of buffer or solution in step a). Hence, in one embodiment, the oxidizing conditions in step b) comprise adding a metal ion. Even if a metal ion is already present in the composition obtained from step a), further metal ions may be added to or during step b), especially if the concentration of the metal ion is so low that it may be rate-limiting for the oxidation of the cysteines in the heterodimeric protein to inter-chain disulfide bonds or if a metal chelating agent is present. Examples of suitable metal ions are in particular divalent transition metal ions, such as copper, e.g. in the form of copper sulphate, manganese, iron, nickel, magnesium and cobalt. The metal ion may suitably be present in or added to a concentration in the range of 0.01-100 ppm, or 0.1-100 µM. Copper may be added to step b) as e.g. copper sulphate.

Addition of a divalent transition metal, e.g. copper, e.g. in the form of copper sulphate, may in particular be added if a metal chelating agent was present in step a) of the method. Copper sulphate may function as a catalyst for oxidation with oxygen.

The inventors of the present invention have also found that the redox potential in step b) affects, in particular the rate but also to some extent the yield, of re-oxidation of the cysteines in the heterodimeric protein to inter-chain disulfide bonds. The inventors of the present invention have found that re-oxidation of the inter-chain disulfide bonds between the heavy chains starts at approximately −350 mV, whereas that of the inter-chain bonds between the heavy and light chains starts at approximately −280 mV. Complete formation of all disulfide bonds in the heterodimeric protein generally occurs when the redox potential is higher than −50 mV, while for the optimal process robustness the redox potential should preferably be at least 50 mV. Hence, in a further embodiment, the redox potential in step b) may be higher than −300 mV, such as higher than −280 mV, or higher than −75 mV, or higher than −50 mV, or higher than 0 mV, or higher than 25 mV, or higher than 50 mV. For oxidation of the cysteines in the heterodimeric protein to disulfide bonds, it is the lower limit of the redox potential which is relevant. The upper limit of the redox potential in step b) may be around 100-300 mV, e.g. 100-200 mV, such as around 100 mV, or around 200 mV or around 250 mV, or around 300 mV. Hence the redox potential of step b) may be in the range of −300 mV to 300 mV, or −300 mV to 200 mV, or in the range of −280 mV to 300 mV, or −280 mV to 200 mV, or in the range of −75 mV to 300 mV, or −75 mV to 200 mV, or in the range of −50 mV to 300 mV, or −50 mV to 200 mV, or in the range of 0 mV to 300 mV, or 0 mV to 200 mV, or in the range of 25 mV to 300 mV, or 25 mV to 200 mV, or in the range of 50 mV to 300 mV, or 50 mV to 200 mV.

The inventors of the present invention have furthermore found that in the embodiment where the composition obtained from step a) is a solution, the pH in step b) also affects oxidation of the cysteines in the heterodimeric protein to disulfide bonds. Hence, in a further embodiment, the pH in step b) may in a particular embodiment be in the range of pH 6-8.5, such as a range of pH 6.5-8, or in the range of pH 6.5-8.5, or in the range of pH 6-8, or a range of pH 6.5-7.5, or a range of pH 7-7.5, e.g. around pH 7.4.

Ensuring that the pH of the composition in step b) is within a certain range, e.g. pH 6-8.5, may for example be done by choosing a solution or buffer in step a) with a suitable pH, or by adding to the composition in step b) a component capable of adjusting the pH, for example a concentrated pH adjustment solution. Ensuring that the pH of the composition in step b) is within a particular range, may also be done by using one of the methods described above comprising a buffer exchange, so that the buffer or solution to which there is exchanged, comprises a pH within the relevant range.

The buffer or solution in step b), e.g. to which the composition obtained from step a) is changed to, e.g. by diafiltration, may include, but is not limited to any of those described herein, such as any of those described in the examples. Examples of such buffers include e.g. PBS (phosphate buffered saline), PBS, pH 7.4.

The progress of the reduction of the inter-chain disulfide bonds in the hinge region of the first and second homodimeric protein may be followed by monitoring redox potential and/or by monitoring the concentration of dissolved oxygen. Means for such monitoring are well known to a person skilled in the art, and include e.g. use of different types of probes, e.g. one of the probes described in Example 44.

In some embodiments, the method of the invention yields an antibody product wherein more than 80%, such as more than 90%, e.g. more than 95%, such as more than 99% of the antibody molecules are the desired bispecific antibodies.

The post-production process described herein, is more flexible and easier to control compared to methods based on co-expression.

Purification

Although, the method of the present invention often results in a high yield of heterodimeric protein, residual amounts of the first and/or second homodimeric protein may also be present in the product or composition obtained by the method of the present invention.

Furthermore, the product obtained by the method of the present invention may also comprise a reducing agent and/or other components such as buffers or salts which were present during the method. In certain cases it may be preferred to remove such components so that they are not present in the final product.

As described above, the reducing agent, buffer components, or salt may, in some embodiments, be removed in step b) of the present invention. Removal of these components may be performed as a separate method of the present method or concomitant with removal of the reducing agent, e.g. by any of the methods described above, such as any of the methods involving exchange of the buffer of the composition obtained from step a).

Hence, in a further embodiment, the method of the present invention may further comprise a step of purification of the heterodimeric protein. Purification of the heterodimeric protein may be regarded as step c) obtaining the heterodimeric protein. Hence, in one embodiment, step c) comprises subjecting the composition obtained from step b) to a purification method.

Examples of suitable purification methods include, but are not limited to, a method selected from the group consisting of protein A or protein G chromatography (or other ways of affinity chromatography), affinity chromatography based on e.g. antigen-binding or anti-idiotypic antibodies, ion exchange, hydrophobic interaction chromatography, kappa or lambda select, thioaffinity, mixed mode chromatography, e.g. hydroxyapatite, Immobilized Metal Affinity Chromatography or Thiophilic Adsorption Chromatography. Other methods of purification include but are not limited to precipitation with for example salts or polyethylene glycol to obtain purified protein. Combination of different purification methods is also envisioned.

Subjecting the heterodimeric protein to a step of purification, or a purification method, refers to any kind of purification of the heterodimeric protein; such as separating the heterodimeric protein from residual amounts of the first and/or second homodimeric protein, or separating the heterodimeric protein from other components, e.g. reducing agent, salts or buffers or other product- or process-related impurities.

Purification or separation of the heterodimeric protein from residual amounts of first and/or second homodimeric proteins may be complicated by the heterodimeric protein being very similar to first and second homodimeric protein. Thus, separation of the heterodimeric protein from residual amounts of the first and/or second homodimeric protein may be more difficult than separation of the heterodimeric protein from the other components present, e.g. reducing agent, buffer or salt.

As described elsewhere herein, the method of the present invention may be performed so that the amount of either the first or second homodimeric protein is limiting with respect to formation of the heterodimeric protein. An example of such a method is known as steered non-equimolar exchange process (SNEEP). Thus, either the first or second homodimeric protein may be present in step a) in an excess of the other homodimeric protein. The ratio of the first and second homodimeric protein in step a) may in particular be adjusted, by including an excess or limited amount of one homodimeric protein to the other, to result in the limited homodimeric protein being completely used in step a). This results in production of a composition, i.e. the composition obtained from step a), comprising the heterodimeric protein together with residual amounts of only one of the first and second homodimeric proteins, rather than both the first and second homodimeric protein. Subsequent purification of the heterodimeric protein from residual homodimeric protein is thereby made easier, as the heterodimeric protein only has to be separated from either the first or second homodimeric protein rather than both of them.

Hence, in one embodiment, the first homodimeric protein is present in step a) in excess of the second homodimeric protein, or vice versa. The ratio of first to second homodimeric protein may in particular be as described herein.

In a further embodiment, performing the method with an excess of either the first or second homodimeric protein may be combined with a purification step of isocratic elution.

In one embodiment performing the method with an excess of either the first or second homodimeric protein may be combined with a purification step based on antigen-binding or an anti-idiotypic antibody binding the homodimer which was used in excess.

In one embodiment, purification or separation of the heterodimeric protein from the first and/or second homodimeric protein may be performed by a method based on differences in the first and second homodimeric protein. Such methods may facilitate separation of the first and second homodimeric protein from each other and, depending on the method, also separation of the homodimeric proteins from the heterodimeric protein. Examples of such purification or separation methods based on differences in the first and second homodimeric protein include, but are not limited to, methods wherein either the first or second homodimeric protein does not bind to Protein A or Protein G, or wherein the first and second homodimeric protein comprise different light chains, e.g. kappa and lambda light chains, or wherein the Fc regions of the first and second homodimeric protein comprise different allotypes. Such methods may facilitate separation of either the first or second homodimeric protein from the heterodimeric protein. This may in a further embodiment be combined with a purification step of isocratic elution.

In one embodiment, the purification or separation method based on differences in the first and second homodimeric protein, may be combined with using an excess of the first or second homodimeric protein as described above. Subsequent purification or separation of the heterodimeric protein from the residual homodimer may then utilize the differences of the first and second homodimeric protein, as the heterodimeric protein differs from the residual homodimer by comprising an Fc region from the homodimer which was used in limiting amounts.

In one embodiment, either the first or second homodimeric protein may have been engineered or modified so that it does not bind Protein A or Protein G, or combinations of Protein A and G. Purification or separation of the heterodimeric protein from at least one of the first and second homodimeric proteins may then be performed by passing it over a Protein A or a Protein G column, to which only the heterodimeric protein and the homodimeric protein which has not been modified with respect to Protein A or Protein G binding, will bind. This facilitates separation of the homodimeric protein which does not to bind to Protein A or Protein G from the heterodimeric protein. If the first homodimeric protein does not bind to Protein A and the second homodimeric protein does not bind Protein G, or vice versa; the heterodimeric protein may be separated from the first and second homodimeric proteins, by passing the composition comprising the heterodimeric protein over Protein A and Protein G materials. The first and second homodimeric proteins may have been modified to not bind Protein A and/or Protein G as described herein. This may also be used to separate the reducing agent from the heterodimeric protein. This may be combined with other methods of purification as described herein.

Using a first or second homodimeric protein in step a) which has been modified so as not to bind to Protein A, or Protein G, or Protein A and Protein G, may in particular be useful for embodiments wherein an excess of either the first or second homodimeric protein is used relative to the other homodimeric protein in step a). In such embodiments, it may be useful to engineer or modify the Protein A or Protein G binding site of the homodimeric protein that will be used in excess so that its ability to bind such resins is disrupted. This type of modification includes, but is not limited to, the modifications in the CH3 domain which are disclosed in WO 2010/151792, incorporated herein by reference. Thus, the first or second homodimeric protein of the present invention may comprise one or more of the modifications in the CH3 domain described in WO 2010/151792 which reduces or eliminates binding of the IgG to Protein A. Thus, in a particular embodiment, the first or second homodimeric protein of the present invention may comprise a modification selected from the group consisting of, but not limited to, a) 435R and b) 435R and 436F. Alternatively, the first or second homodimeric protein may comprise the following mutations: I253A, H310A, and H435A, which eliminates binding to Protein A. The heterodimeric protein may then be separated from a surplus of unexchanged homodimeric protein by passage over a Protein A column. This may be combined with other methods of purification as described herein.

In another embodiment, wherein the first and second homodimeric protein comprise a light chain, the light chain of the first and second homodimeric protein in step a) may be different. For example, the first homodimeric protein may comprise a kappa light chain and the second homodimeric protein may comprise a lambda light chain, or vice versa. Materials or resins suitable for column chromatography to which only a kappa or lambda light chain is able to bind, may then be used for purification or separation of the heterodimeric protein from the first and/or second homodimeric protein. Examples of such materials or resins include e.g. the affinity media known as KappaSelect and LambdaFabSelect from GE Healthcare Life Sciences. Using a first and second homodimeric protein which comprises different light chains, e.g. a kappa and a lambda light chain, may be combined with using one of the homodimeric proteins in excess in step a). For example, step a) may be performed with the first homodimeric protein comprising a kappa light chain and the second homodimeric protein comprising a lambda light and with the first homodimeric protein being present in excess of the second homodimeric protein, or vice versa with respect to whether it is homodimeric protein comprising a kappa or lambda light chain which is used in excess. Step c) may then comprise passing the heterodimeric protein over a column to which the only the lambda light chain is able to bind. Step c) then results in separation of the heterodimeric protein from the residual first homodimeric protein comprising a kappa light chain. Similarly, step c) may comprise passing the heterodimeric protein over a column to which only the kappa light binds if it is the homodimer comprising the lambda light chain which is used in excess in step a). This may be combined with other methods of purification as described herein.

Alternatively, purification or separation of the heterodimeric protein based on the differences in binding of kappa of lambda light chains to different materials may also be performed without using one of the homodimeric proteins in excess. In this embodiment, step c) may comprise passing the heterodimeric protein over a material to which the kappa light chain binds and subsequently over a material to which the lambda light chain binds or vice versa. As the heterodimeric protein comprises both a kappa and a lambda light chain, while the first and the second homodimeric protein comprises either a kappa or a lambda light chain, the heterodimeric protein can thereby be separated from the first and second homodimeric protein. This may be combined with other methods of purification as described herein.

Purification of a heterodimeric protein produced by a method in which the first and second homodimeric protein comprise different light chains, e.g. kappa and lambda light chains, and wherein one of the homodimeric proteins is used in excess, by passing it over a material to which the light chain of the homodimeric protein used in non-excess amounts binds, may be applied to other methods for producing heterodimeric proteins than the present invention. For example methods based on co-expression of heavy and light chains in a host cells or other methods.

In another embodiment the constant region of the first and second homodimeric proteins may be of different allotypes. Allotypes are variations in the amino acid sequence which are found naturally within a population. For example different allotypes of human IgG1 heavy chain are known, G1m(f) [also called G1m(3)], G1m(z) [also called G1m(17)], G1m(a) [also called G1m(1)] and G1m(x) [also called G1m(2)] (Jefferis, R., mAbs 2009; 1:4, 1-7). Thus, in one embodiment of the present invention, the constant region of the first and second homodimeric protein may be different allotypes; e.g. they may be an IgG1 isotype and the constant region of the first homodimeric protein may be e.g. an IgG1m(za) [=IgG1m(1,17)] or IgG1m(zax) [=IgG1m(1,2,17)] allotype, while the constant region of the second homodimeric protein may be e.g. an IgG1m(f) [=IgG1m(3)] or IgG1m(fa) [=IgG1m(1,3)] allotype. Similarly, as the embodiment described above wherein a kappa and a lambda light chain are used, using first and second homodimeric proteins comprising constant regions of different allotypes, may be combined with using either the first or second homodimeric protein in excess in step a). In this embodiment, step c) may then comprise passing the heterodimeric protein over a material, e.g. beads coated with an allotype-specific antibody, to which the allotype present in the homodimeric protein which was not used in excess, binds. Thereby the heterodimeric protein can be purified from the homodimeric protein which was used in excess in step a). This may be combined with other methods of purification as described herein.

In an alternative embodiment, the ratio of the first or second homodimeric protein was not adjusted in step a), thus neither the first or second homodimeric protein was completely used in step a), resulting in production of a composition comprising both the heterodimeric protein, first and second homodimeric protein. In this embodiment, step c) may comprise passing the heterodimeric protein over a material to which one of the allotype binds and subsequently over another material to which the other allotype binds. This may be combined with other methods of purification as described herein.

The use of a first and second homodimeric protein comprising Fc regions of different allotypes combined with separation of the heterodimeric protein from the homodimeric proteins may also apply to other methods of producing heterodimeric proteins than the one of the present invention. Such methods may further include using either the first or second homodimeric protein in excess. Examples of such methods include those based on co-expression of the first and second homodimeric protein in the same host cell.

C-Terminal Lysine

Removal of C-terminal lysines by carboxypeptidases from the heavy chain is a commonly observed antibody modification, both upon recombinant expression of antibodies in mammalian cells, as well as in vivo in human serum (Cai et al. (2010) Biotechnol. Bioeng. September 9). Removal is often partial, resulting in a mixed population of antibodies with zero (K0), one (K1) or two (K2) C-terminal lysines. In particular, B-cell hybridomas produce mixtures of K0, K1 and K2 molecules (Dick et al. (2008) Biotech. Bioeng. 100:1132).

In one embodiment, the C-terminal lysine of the heterodimeric protein, e.g. bispecific antibody produced by the method of the present invention may be removed. The term "C-terminal lysine residue" refers to the lysine residue at the C-terminus of the CH3 region, e.g. the C-terminus of the heavy chain of an antibody, which is position 447 in IgG1.

Besides the various effects that the C-terminal lysine may have, removal of the C-terminal lysine results in a heterodimeric protein, e.g. a composition or population comprising more than one molecule of the heterodimeric protein, which is more homogeneous with respect to the presence of the C-terminal lysines.

Thus, in a further embodiment the first and/or second homodimeric protein does not contain a C-terminal lysine.

The C-terminal lysine may be removed by engineering the first and/or second homodimeric protein to not contain a C-terminal lysine, or by removing, e.g. by enzyme catalysis, the C-terminal lysine from the first and/or second homodimeric protein or by removing, such as by enzyme catalysis, the C-terminal lysines from the heterodimeric protein.

Hence, in a further embodiment, the first and/or second homodimeric proteins are genetically modified to not contain the C-terminal lysine, e.g. in the heavy chain.

In another embodiment, the method of the present invention further comprises a step of removing the c-terminal lysine, e.g. from the heavy chain, e.g. by incubation with a carboxypeptidase.

If the first and/or second homodimeric protein is engineered to not contain a C-terminal lysine, the first and/or second homodimeric protein may be produced by:

i) providing a nucleotide construct encoding an Fc region of an immunoglobulin, said Fc region comprising a first CH3 region and/or comprising an Fc region of an immunoglobulin, said Fc region comprising a second CH3 region, wherein said construct does not encode a lysine residue at the C-terminus of said first and/or second CH3 region, ii) expressing said nucleotide construct in a host cell, and iii) recovering said first and/or second homodimeric protein from a cell culture of said host cell.

The first and/or second homodimeric protein may, in one embodiment, be an antibody, which may, in most embodiments, also comprise a light chain and thus said host cell may further express a light chain-encoding construct, either on the same or a different vector.

Methods for preparing nucleotide constructs are well known to a person skilled in the art.

Similarly, methods for expression of nucleotide constructs in a host cell are also well known to a person skilled in the art.

In a further embodiment of the above method of the invention, the nucleotide construct provided in step i) is derived from, or designed based on, an original heavy-chain sequence having a codon for a C-terminal lysine residue. Thus, said nucleotide construct may comprise a deletion of the codon for the C-terminal lysine residue compared to said original heavy-chain sequence.

In another embodiment, the C-terminal lysine residue may be removed from the first and/or second homodimeric protein, e.g. by enzymatic cleavage. Thus, the C-terminal lysine may be removed from the first and/or second homodimeric protein after they are produced. Methods for enzymatic removal of the C-terminal lysine include, but are not limited to, subjecting the first and/or second homodimeric protein to incubation with a carboxypeptidase. Hence, the step of removing the C-terminal lysine, e.g. from the heavy chain, may be performed prior to step a). Thus, the method of the present invention may, in one embodiment, comprise a further step of subjecting the first and/or second homodimeric protein to a carboxypeptidase, prior to step a).

Similarly, the C-terminal lysine may be removed from the heterodimeric protein. Thus, in one embodiment the method of the present invention may, after step a), comprise a further step of subjecting the heterodimeric protein to a carboxypeptidase. This step may be in between steps a) and step b) or it may be after step b). Thus, in one embodiment, the step of removing the C-terminal lysine, e.g. from the heavy chain, may be performed after step a). In another embodiment, the step of removing the C-terminal lysine, e.g. from the heavy chain, may be performed after step b). In principle, the method of the present invention may comprise subjecting both the first and/or second homodimeric protein and the heterodimeric protein to a carboxypeptidase. However, for most purposes it should be enough to include one of the above mentioned steps to remove the C-terminal lysines. Examples of suitable carboxypeptidases include, but are not limited to, carboxypeptidase B or carboxypeptidase N (Cai et al. Biotechnol. Bioeng. September 9 (2010) Supra). Suitable conditions for treatment with a carboxypeptidase are well known to a person skilled in the art. Another method to remove the C-terminal lysines would be to express the first and/or second homodimeric protein in a host cell expressing a carboxypeptidase. Leaving the first and/or second homodimeric protein in the host cell culture media at a temperature where the carboxypeptidase is active for a sufficient amount of time would also result in removal of the C-terminal lysine (Luo J L, Ahang J, Ren D, Tsai W-L, Li F (2102) Probing of C-Terminal Lysine Variation in a Recombinant Monoclonal Antibody Production Using Chinese Hamster Ovary Cells with Chemically Defined Media. Biotechnol. Bioeng. 109:2306-2315).

Nucleic Acid Sequences

In a further aspect, the present invention also relates to a nucleic acid sequence encoding a first or second homodimeric protein of the present invention, wherein said first or second homodimeric protein does not comprise the C-terminal lysine. The first and second homodimeric protein may be any of those described above in relation to the method.

In further aspect, the present invention also relates to an expression vector encoding a first or second homodimeric protein of the present invention, wherein said first or second homodimeric protein do not comprise the C-terminal lysine.

In an even further embodiment, the present invention also relates to a host cell comprising an expression vector encoding a first or second homodimeric protein of the present invention, wherein said first or second homodimeric protein do not comprise the C-terminal lysine.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, the nucleic acid sequence encoding the Fc region of a first or second homodimeric protein of the present invention, wherein said first or second homodimeric protein do not comprise the C-terminal lysine, may be comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaP04-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

An expression vector may also or alternatively be a vector suitable for expression in mammalian cells, e.g. a vector comprising glutamine synthetase as a selectable marker, such as the vectors described in Bebbington (1992) Bio-technology (NY) 10:169-175.

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

In an expression vector of the invention, the nucleic acid sequence encoding a first or second homodimeric protein of the present invention, wherein said first or second homodimeric protein does not comprise the C-terminal lysine, may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the expression vector may be positioned in and/or delivered to the host cell or host animal via a viral vector.

In an even further aspect, the invention relates to a recombinant eukaryotic or prokaryotic host cell, such as a transfectoma, which produces a first or second homodimeric protein of the present invention, wherein said first or second homodimeric protein does not comprise the C-terminal lysine, as defined herein. Examples of host cells include yeast, bacterial and mammalian cells, such as CHO or HEK cells. For example, in one embodiment, the present invention provides a cell comprising a nucleic acid stably integrated into the cellular genome that comprises a sequence coding for expression of the Fc region of a first or second homodimeric protein of the present invention, wherein said first or second homodimeric protein does not comprise the C-terminal lysine. In another embodiment, the present invention provides a cell comprising a non-integrated nucleic acid, such as a plasmid, cosmid, phagemid, or linear expression element, which comprises a sequence coding for expression of a first or second homodimeric protein of the present invention, wherein said first or second homodimeric protein does not comprise a C-terminal lysine.

In a further aspect, the invention relates to a hybridoma which produces a first or second homodimeric protein of the present invention, wherein said first or second homodimeric protein does not comprise a C-terminal lysine. In an even further aspect, the invention relates to a transgenic non-human animal or plant comprising nucleic acids encoding a first or second homodimeric protein of the present invention, wherein said first or second homodimeric protein does not comprise a C-terminal lysine, wherein the animal or plant produces a first or second homodimeric protein of the present invention, wherein said first or second homodimeric protein does not comprise a C-terminal lysine.

Heterodimeric Proteins

The present invention also relates to a heterodimeric protein obtained by a method of the present invention.

The method of the invention enables the formation of asymmetrical molecules, molecules with different characteristics on each of the Fab-arms or on each of the CH3 domains or molecules with distinct modifications throughout the molecules, e.g. molecules with unnatural amino acid substitution(s) for conjugation. Such asymmetrical molecules can be generated in any suitable combination. This is illustrated further below by some non-limiting examples.

Bispecific antibodies can be used to deliver an imaging or immunotherapeutic agent to a target cell of interest, including but not limited to, a tumor cell.

In an embodiment of the method of the invention, the first Fab-arm of the bispecific molecule binds to a tumor cell, such as a tumor cell surface protein or tumor cell surface carbohydrate, such as one of the tumor cell surface proteins listed herein and the second Fab-arm recognizes a radioactive effector molecule including but not limited to, a radiolabel coupled or linked (via a chelator) to a peptide or hapten. An example of such radiolabelled peptide is indium-labeled diethylenetriaminepentaacetic acid (anti-DTPA(In) van Schaijk et al. Clin. Cancer Res. 2005; 11: 7230s-7126s). Another example is using hapten-labelled colloidal particles such as liposomes, nanoparticles of polymeric micelles carrying radionuclides such as for example technetium-99 (Jestin et al. Q *J Nucl Med Mol Imaging* 2007; 51:51-60).

In another embodiment, a hapten-coupled alternative cytostatic molecule such as a toxin is used as effector molecule recognized by the second Fab arm.

In a further embodiment of the method of the invention, the first Fab-arm of the bispecific molecule is glycosylated at position N297 (EU numbering) and the second Fab-arm of the bispecific molecules is aglycosylated (nonglycosylated for instance by mutating N297 to Q or A or E mutation (Bolt S et al., *Eur J Immunol* 1993, 23:403-411)). Asymmetrical glycosylation in the Fc-region impacts the interaction with Fcγ-receptors and has impact on antibody-dependent cell cytotoxicity effect of the antibody (Ha et al., *Glycobiology* 2011, 21(8): 1087-1096), as well as interaction with other effector function molecules such as C1q.

In another embodiment of the method of the invention, the first Fab-arm of the bispecific molecule interacts with FcRn, the neonatal Fc receptor (Roopenian D C, et al. Nat. Rev. Immunol. 2007, 7:715-725) and the second Fab-arm is impaired in binding to FcRn by mutation of the FcRn interaction site on the molecules for instance by making a H435A mutation (Shields, R. L., et al, J Biol Chem, 2001, Firan, M., et al, Int Immunol, 2001).

In another embodiment, the binding to C1q is improved or decreased on one of the two Fab-arms of the bispecific molecule.

In another embodiment, the protein has been engineered to enhance complement activation on one or both of the two Fab-arms of the molecule.

In another embodiment, each of the Fab-arms present in the bispecific molecule is derived from a different IgG subclass.

In another embodiment, each of the Fab-arms present in the bispecific molecule carries different allotypic mutations (Jefferis & Lefranc, 2009, *MABs* 1:332-8).

In another embodiment, another category of asymmetric immunotherapeutic molecules is generated by replacement of the Fab of one of the Fab-arms of the bispecific molecule by an immune-active, -stimulating or -inhibiting cytokine. Non-limiting examples of such cytokines are IL-2, IFN-α, IFN-β, IFN-γ, TNF-α, G-CSF, GM-CSF, IL-10, IL-4, IL-6, IL-13. Alternatively, a (growth) factor or hormone stimulating or inhibition agent is included in the molecules.

In another embodiment, a Fab of one of the Fab-arms is replaced by a lytic peptide, i. e. peptides that are able to lyse tumor cells, bacteria, fungi etc, including but not limited to antimicrobial peptides like magainin, mellitin, cecropin, KLAKKLAK and variants thereof (Schweizer et al. Eur. J. Pharmacology 2009; 625: 190-194, Javadpour, *J. Med. Chem.*, 1996, 39: 3107-3113, Marks et al, *Cancer Res* 2005; 65:2373-2377, Rege et al, *Cancer Res.* 2007; 67:6368-6375) or cationic lytic peptides (CLYP technology, US2009/0269341).

In another embodiment, one or both of the Fabs on the Fab-arms is replaced by receptors for cytokines and/or growth factors, creating socalled decoy receptors, of which Enbrel® (etanercept) targeting TNF-α, and VEGF-trap, targeting VEGF, are well-known examples. Combining these two decoy receptors into one molecule showed superior activity over the single decoy receptors (Jung, *J. Biol. Chem.* 2011; 286:14410-14418).

In another embodiment, another category of asymmetric immunotherapeutic molecules is generated by fusion of immuno-active, -stimulating or -inhibiting cytokines to the N-terminus or C-terminus of one, or both, of the Fab-arms present in the bispecific molecules. This may positively impact anti-tumor activity of the bispecific molecule. Examples of such molecules, however not limited to the list below, are IL-2 (Fournier et al., 2011, Int. J. Oncology, doi: 10.3892/ijo.2011.976), IFN-α, IFN-β or IFN-γ (Huan et al., 2007; *J. Immunol.* 179:6881-6888, Rossie et al., 2009; *Blood* 114: 3864-3871), TNF-α. Alternatively, N-terminal or C-terminal fusion of cytokines, such as for example G-CSF, GM-CSF, IL-10, IL-4, IL-6, or IL-13 may positively impact the bispecific antibody molecule effector function. Alternatively a growth factor or hormone stimulating or inhibition agent is included in the molecules on the N-terminus or C-terminus.

In another embodiment, N-terminal or C-terminal fusion of a lytic peptide, such as for example antimicrobial peptides like magainin, mellitin, cecropin, KLAKKLAK and variants thereof (Schweizer et al. Eur. J. Pharmacology 2009; 625: 190-194, Javadpour, *J. Med. Chem.*, 1996, 39: 3107-3113, Marks et al, *Cancer Res* 2005; 65:2373-2377, Rege et al, *Cancer Res.* 2007; 67:6368-6375) or cationic lytic peptides (CLYP technology, US2009/0269341) on one or both of the Fab-ams may enhance the activity of the molecule.

In another embodiment, another category of asymmetric immunotherapeutic molecules is monovalent antibodies, molecules which interact with one Fab-arm to the target of choice. In such molecule, one of the Fab-arms present in the bispecific molecule is directed against the target molecule of choice, the second Fab-arm of the molecule does not carry a Fab or has a non-binding/non-functional Fab such as described for MetMab (Genentech; WO 96/38557). Alternatively, monomeric Fc-fusion proteins such as those described for Factor VIII and IX (Peters et al., *Blood* 2010; 115: 2057-2064) may be generated.

Alternatively, combinations of any of the above mentioned asymmetrical molecules may be generated by the method of the invention.

A heterodimeric protein produced by the method of the present invention may comprise a first polypeptide comprising a first Fc region of an immunoglobulin, said first Fc region comprising a first CH3 region, and a second polypeptide comprising a second Fc region of an immunoglobulin, said second Fc region comprising a second CH3 region, wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407 and/or wherein the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 when assayed as described in Example 21.

In one embodiment, said first CH3 region has an amino acid other than Lys, Leu or Met at position 409 and said second CH3 region has an amino acid other than Phe at position 405
and/or
the sequences of said first and second CH3 regions are such that the dissociation constants of homodimeric interactions of each of the CH3 regions are between 0.01 and 10 micromolar, such as between 0.05 and 10 micromolar, more preferably between 0.01 and 5, such as between 0.05 and 5 micromolar, even more preferably between 0.01 and 1 micromolar, such as between 0.05 and 1 micromolar, between 0.01 and 0.5 or between 0.01 and 0.1 micromolar, when assayed as described in Example 21.

In a further embodiment of the heterodimeric protein
said first CH3 region has an amino acid other than Lys, Leu or Met at position 409 and said second CH3 region has an amino acid other than Phe at position 405, such as other than Phe, Arg or Gly, at position 405
or
said first CH3 region has an amino acid other than Lys, Leu or Met at position 409 and said second CH3 region has an amino acid other than Tyr, Asp, Glu, Phe, Lys, Gln, Arg, Ser or Thr at position 407.

In further embodiments, the heterodimeric protein according to the invention comprises any of the further features described above for the methods of production.

Thus, in a further embodiment of the heterodimeric protein of the invention, said first polypeptide is a full-length heavy chain of an antibody, preferably a human antibody.

In another embodiment of the heterodimeric protein of the invention, said second polypeptide is a full-length heavy chain of an antibody, preferably a human antibody.

In a further embodiment of the heterodimeric protein of the invention, said first and second polypeptides are both full-length heavy chains of two antibodies, preferably both human antibodies that bind different epitopes, and thus the resulting heterodimeric protein is a bispecific antibody. This bispecific antibody can be a heavy-chain antibody, or an antibody which in addition to the heavy chains comprises two full-length light chains, which may be identical or different.

In a further embodiment of the heterodimeric protein of the invention, the Fc region of the first polypeptide is similar or identical to an Fc region derived from of an isotype selected from the group consisting of IgG1, IgG2, IgG3 and IgG4 (except for the specified mutations) and the Fc region of the second polypeptide is of an isotype selected from the group consisting of IgG1, IgG2, IgG3 and IgG4 (except for the specified mutations).

In a further embodiment of the heterodimeric protein of the invention, said first CH3 region comprises a Phe at position 405 and an amino acid other than Lys, Leu or Met at position 409 and said second CH3 region comprises an amino acid other than Phe at position 405 and a Lys at position 409.

In a further embodiment of the heterodimeric protein of the invention, said first CH3 region comprises a Phe at position 405 and an amino acid other than Lys, Leu or Met at position 409 and said second CH3 region comprises a Leu at position 405 and a Lys at position 409.

In a further embodiment of the heterodimeric protein of the invention, said first CH3 region comprises Phe at position 405 and an Arg at position 409 and said second CH3 region comprises a Leu at position 405 and a Lys at position 409.

In a further embodiment of the heterodimeric protein of the invention, said first CH3 region comprises an amino acid other than Lys, Leu or Met at position 409 and said second CH3 region comprises a Lys at position 409 and: a) an Ile at position 350 and a Leu at position 405, or b) a Thr at position 370 and a Leu at position 405.

In a further embodiment of the heterodimeric protein of the invention, said first CH3 region comprises an Arg at position 409 and said second CH3 region comprises a Lys at position 409 and: a) an Ile at position 350 and a Leu at position 405, or b) a Thr at position 370 and a Leu at position 405.

In a further embodiment of the heterodimeric protein of the invention, said first CH3 region comprises a Thr at position 350, a Lys at position 370, a Phe at position 405 and an Arg at position 409 and said second CH3 region comprises a Lys at position 409 and: a) an Ile at position 350 and a Leu at position 405, or b) a Thr at position 370 and a Leu at position 405.

In a further embodiment of the heterodimeric protein of the invention, said first CH3 region comprises a Thr at position 350, a Lys at position 370, a Phe at position 405 and an Arg at position 409 and said second CH3 region comprises an Ilie at position 350, a Thr at position 370, a Leu at position 405 and a Lys at position 409.

In a further embodiment of the heterodimeric protein of the invention, neither said first nor said second polypeptide comprises a Cys-Pro-Ser-Cys sequence in the hinge region.

In a further embodiment of the heterodimeric protein of the invention, both said first and said second polypeptide comprise a Cys-Pro-Pro-Cys sequence in the hinge region.

In a further embodiment of the heterodimeric protein of the invention, said first and/or said second polypeptide comprises a mutation removing the acceptor site for Asn-linked glycosylation.

Target Antigens

As explained above, in an important embodiment of the invention, the heterodimeric protein is a bispecific antibody comprising two variable regions that differ in binding specificity, i.e. bind different epitopes.

In principle, any combination of specificities is possible. As mentioned above, bispecific antibodies can potentially be used to further increase the potency and efficacy of monoclonal antibody therapies. One possible limitation of a monospecific antibody is a lack of specificity for the desired target cells due to expression of the target antigen on other cell types towards which no antibody binding is desired. For example, a target antigen overexpressed on tumor cells may also be expressed in healthy tissues which could result in undesired side-effects upon treatment with an antibody directed against that antigen. A bispecific antibody having a further specificity against a protein which is exclusively expressed on the target cell type could potentially improve specific binding to tumor cells.

Hence in one embodiment the homodimeric proteins are both antibodies, wherein the first antibody and the second antibody binds to different epitopes on the same tumor cell.

In another embodiment the homodimeric proteins are both antibodies, wherein the first antibody binds to an epitope on a tumor cell, and the other antibody is an irrelevant or inactive antibody without any relevant in vivo binding activity for the application intended.

Thus, in one embodiment of the invention, said first and second epitopes are located on the same cell, e.g. a tumor cell. Suitable targets on tumor cells include, but are not limited to, the following: erbB1 (EGFR), erbB2 (HER2), erbB3, erbB4, MUC-1, CD19, CD20, CD4, CD38, CD138, CXCR5, c-Met, HERV-envelop protein, periostin, Bigh3, SPARC, BCR, CD79, CD37, EGFRvIII, L1-CAM, AXL, tissue factor (TF), CD74, EpCAM and MRP3. Possible combinations of tumor cell targets include, but are not limited to: erbB1+erbB2, erbB2+erbB3, erbB1+erbB3, CD19+CD20, CD38+CD34, CD4+CXCR5, CD38+RANKL, CD38+CXCR4, CD20+CXCR4, CD20+CCR7, CD20+CXCR5, CD20+RANKL, erbB2+AXL, erbB1+cMet, erbB2+c-Met, erbB2+EpCAM, c-Met+AXL, c-Met+TF, CD38+CD20, CD38+CD138.

In a further embodiment, said first and second epitopes may be located on the same target antigen, wherein the location of the two epitopes on the target antigen is such that binding of an antibody to one epitope does not interfere with antibody binding to the other epitope. In a further embodiment hereof, said first and second homodimeric proteins are antibodies that bind to two different epitopes located on the same target antigen, but have a different mode-of-action for killing the target cell, e.g. a tumor cell. For example, in one embodiment, the target antigen is erbB2 (HER2) and the bispecific antibody combines the pertuzumab and trastuzumab antigen-binding sites. In another embodiment, the target antigen is erbB1 (EGFr) and the bispecific antibody combines the zalutumumab and nimotuzumab antigen-binding sites.

Bispecific antibodies can also be used as mediators to retarget effector mechanisms to disease-associated tissues, e.g. tumors. Thus, in a further embodiment, said first or said second epitope is located on a tumor cell, such as a tumor cell protein or tumor cell carbohydrate, and the other epitope is located on an effector cell.

In one embodiment, the effector cell is a T cell.

Possible targets on effector cells include the following: FcγRI (CD64): expressed on monocytes and macrophages and activated neutrophils; FcγRIII (CD16): expressed on natural killer and macrophages; CD3: expressed on circulating T cells; CD89: expressed on PMN (polymorphonuclear neutrophils), eosinophils, monocytes and macrophages; CD32a: expressed on macrophages, neutrophils, eosinophils; FcεRI expressed on basophils and mast cells. In one embodiment the epitope is located on CD3 expressed on T cells.

In another embodiment, the first antibody has binding specificity for a pathogenic microorganism and the second antibody has binding specificity for an effector cell protein, such as CD3, CD4, CD8, CD40, CD25, CD28, CD16, CD89, CD32, CD64, FcεRI or CD1.

Furthermore, bispecific antibodies can be used to target a chemotherapeutic agent more specifically to the cells on which the agent should act. Thus, in one embodiment, one of the homodimeric proteins is an antibody which recognizes a small molecule or peptide, or is able to form a covalent bond with such a molecule, e.g. according to the principle described in Rader et al, (2003) PNAS 100:5396. In a further embodiment of the method of the invention, the first antibody has binding specificity for (i.e. binds to an epitope on) a tumor cell or tumor cell surface protein, such as erbB1, erbB2, erbB3, erbB4, EGFR3vIII, CEA, MUC-1, CD19, CD20, CD4, CD38, EpCAM, c-Met, AXL, L1-CAM, tissue factor, CD74 or CXCR5 and the second antibody has a binding specificity for a chemotherapeutic agent, such as a toxin (including a radiolabelled peptide), a radioisotope, a drug or a prodrug which may optionally be coupled or linked to a peptide or hapten.

Bispecific antibodies may also be used to target a vesicle, e.g. an electron dense vesicles, or minicell containing a toxin, drug or prodrug to a tumor. See e.g. MacDiarmid et al. (2009) Nature Biotech 27:643. Minicells are achromosomal cells that are products of aberrant cell division which do not contain chromosomal DNA. Thus, in another embodiment, said first or said second epitope is located on a tumor cell, such as a tumor cell protein or tumor cell carbohydrate, and the other epitope is located on an electron-dense vesicle or minicell.

Furthermore, serum half-life of an antibody may be altered by including in a bispecific antibody a binding specificity for a serum protein. For instance, serum half-life may be prolonged by including in a bispecific antibody, a binding specificity for serum albumin. Thus, in a further embodiment of the method of the invention, the first antibody has binding specificity for a tumor cell or tumor cell protein, such as erbB1 (EGFR), erbB2 (HER2), erbB3, erbB4, MUC-1, CD19, CD20, CD4, CD38, CD138, CXCR5, c-Met, HERV-envelope protein, periostin, Bigh3, SPARC, BCR, CD79, CD37, EGFRvIII, Li-CAM, AXL, tissue factor (TF), CD74, EpCAM or MRP3, CEA, and the second antibody has a binding specificity for a blood protein, such as serum albumin. A second binding specificity can also be used to target an antibody to a specific tissue, such as the central nervous system or brain (across the blood brain barrier). Thus, in a further embodiment of the method of the invention, the first antibody has binding specificity for a brain-specific target, such as amyloid-beta (e.g. for treatment of Alzheimer's disease), Her-2 (e.g. for treatment of breast cancer metastases in brain), EGFR (e.g. for treatment of primary brain cancer), Nogo A (e.g. for treatment of brain injury), TRAIL (e.g. for treatment of HIV), alpha-synuclein (e.g. for treatment of Parkinson), Htt (e.g. for treatment of Huntington), a prion (e.g. for treatment of mad cow disease), a West Nile virus protein, and the second antibody has a binding specificity for a blood brain barrier protein, such as transferrin receptor (TfR), insulin receptor, melanotransferrin receptor (MTfR), lactoferrin receptor (LfR), Apolipoprotein E receptor 2 (ApoER2), LDL-receptor-related protein 1 and 2 (LRP1 and LRP2), receptor for advanced glycosylation end-products (RAGE), diphtheria toxin-receptor=heparin-binding epidermal growth factor-like growth factor (DTR=HB-EGF), gp190 (Abbott et al, Neurobiology of Disease 37 (2010) 13-25).

A binding specificity for a blood brain barrier protein can also be used to target another, non-antibody, molecule, to a specific tissue, such as the central nervous system or brain (across the blood brain barrier). Thus, in a further embodiment, one of the homodimeric proteins is a full-length antibody having a binding specificity for a blood brain barrier protein (such as TfR, insulin receptor, MTfR, LfR, ApoER2, LRP1, LRP2, RAGE, DTR (=HB-EGF) or gp190) and the other homodimeric protein is an Fc region linked at the N- or C-terminus to another protein, such as a cytokine, a soluble receptor or other protein, e.g. VIP (vasoactive intestinal peptide), BDNF (brain-derived neurotrophic factor), FGF (fibroblast growth factor), multiple FGFs, EGF (epidermal growth factor), PNA (peptide nucleic acid), NGF (Nerve growth factor), Neurotrophin (NT)-3, NT-4/5, glial derived neurotrophic factor, ciliary neurotrophic factor, neurturin, neuregulins, interleukins, transforming growth factor (TGF)-alpha, TGF-beta, erythropoietin, hepatocyte growth factor, platelet derived growth factor, artemin, persephin, netrins, cardiotrophin-1, stem cell factor, midkine, pleiotrophin, bone morphogenic proteins, saposins, semaphorins, leukocyte inhibitory factor, alpha-L-iduronidase, iduronate-2-sulfatase, N-acetyl-galactosamine-6-sulfatase, arylsulphatase B, acid alpha-glucosidase, or sphingomyelinase (Pardridge, Biopharmaceutical drug targeting to the brain, Journal of Drug Targeting 2010, 1-11; Pardridge, Re-engineering Biopharmaceuticals for delivery to brain with molecular Trojan horses. Bioconjugate Chemistry 2008, 19: 1327-1338).

In a further embodiment of the method of the invention, the first antibody has binding specificity for a tumor cell or tumor cell protein, such as erbB1, erbB2, erbB3, erbB4, MUC-1, CD19, CD20, CD4 or CXCR5 and the second antibody has a binding specificity for a protein involved in blood clotting, such as tissue factor.

Further particularly interesting binding specificity combinations include: CD3+HER2, CD3+CD20, IL-12+IL18, IL-1a+IL-1b, VEGF+EGFR, EpCAM+CD3, GD2+CD3, GD3+CD3, HER2+CD64, EGFR+CD64, CD30+CD16, NG2+CD28, HER2+HER3, CD20+CD28, HER2+CD16, Bcl2+CD3, CD19+CD3, CEA+CD3, EGFR+CD3, IgE+CD3, EphA2+CD3, CD33+CD3, MCSP+CD3, PSMA+CD3, TF+CD3, CD19+CD16, CD19+CD16a, CD30+CD16a, CEA+HSG, CD20+HSG, MUC1+HSG, CD20+CD22, HLA-DR+CD79, PDGFR+VEGF, IL17a+IL23, CD32b+CD25, CD20+CD38, HER2+AXL, CD89+HLA class II, CD38+CD138, TF+c-Met, Her2+EpCAM, HER2+HER2, EGFR+EGFR, EGFR+c-Met, c-Met+non-binding arm and combinations of G-protein coupled receptors.

In a further embodiment, the bispecific antibodies according to the invention may be used to clear pathogens, pathogenic autoantibodies or harmful compounds such as venoms and toxins from the circulation by targeting to erythrocytes, essentially as described in Taylor et al. J. Immunol. 158: 842-850 (1997) and Taylor and Ferguson, J. Hematother. 4:357-362, 1995. Said first epitope is located on an erythrocyte (red blood cell) protein, including, but not limited to, the erythrocyte complement receptor 1 and said second epitope is located on the compound or organism to be targeted for clearance.

In a further embodiment, the second Fab-arm comprises a fusion protein representing an autoantigen or a conjugation site to attach an autoantigen such as dsDNA. Targeting of pathogens, autoantibodies or harmful compounds by the bispecific antibodies of the invention followed by erythrocyte-mediated clearance may thus have therapeutic utility in the treatment of various diseases and syndromes.

Conjugation

In further embodiments of the invention, the first and/or second homodimeric protein is linked to a compound selected from the group consisting of: a toxin (including a radioisotope) a prodrug or a drug. Such compound may make killing of target cells more effective, e.g. in cancer therapy. The resulting heterodimeric protein is thus an immunoconjugate. The compound may alternatively be coupled to the resulting heterodimeric protein, i.e. after the Fab-arm exchange has taken place.

Hence in a further embodiment the method of the present invention further comprises a step of linking or conjugating the first and/or second homodimeric protein to another compound; e.g. a toxin, prodrug or drug.

Alternatively, the method of the present invention further comprises a step of linking or conjugating the heterodimeric protein to another compound; e.g. a toxin, prodrug or drug.

As described elsewhere herein, the first and second homodimeric protein may be conjugated to different compounds, thereby resulting in production of a heterodimeric protein being conjugated to two different compounds; e.g. toxin, prodrug and/or drug. This may be particularly useful if the method for conjugation of the first compound is not compatible with the method for conjugation of the second compound. The different compounds may for example be two different toxins, or two different prodrugs, or two different drugs, or one compound may be a toxin while the other is a prodrug or a drug, or one compound may be prodrug while the other is a drug. Any suitable combination may be used.

Alternatively, the method of the present invention comprises combining the formation of the heterodimeric protein with conjugation of the toxin using reduction-oxidation.

Suitable compounds for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydro-testosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include ribonuclease (RNase), DNase I, Staphylococcal enterotoxin-A, pokeweed antiviral protein, diphtherin toxin, *Pseudomonas* endotoxin, Maytansinoids, Auristatins (MMAE, MMAF), Calicheamicins and Duocarmycin analogs (Ducry and Stump, Bioconjugate Chem. 2010, 21: 5-13), Dolostatin-10, Dolostatin-15, Irinotecan or its active metabolite SN38, pyrrolobenzodiazepines (PBD's).

In a further embodiment of the invention, the first and/or second homodimeric protein is linked to an alpha emitter, including but not limited to Thorium-227, Radium-223, Bismuth-212, and Actinium-225.

In a further embodiment of the invention, the first and/or second homodimeric protein is linked to a beta emitting radionuclide, including but not limited to Imodium-313, Yttrium-90, Fluorine-18, Rhenium-186, Gallium-68, Technetium-99, Indium-111, and Lutetium-177.

In another embodiment, the compound to be conjugated comprises a nucleic acid or nucleic acid-associated molecule. In one such facet of the present invention, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule).

Any method known in the art for conjugating may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Conjugates may be produced by chemically conjugating the other moiety to the N-terminal side or C-terminal side of the protein (see, e.g., Antibody Engineering Handbook, edited by Osamu Kanemitsu, published by Chijin Shokan (1994)). Such conjugated antibody derivatives may also be generated by conjugation at internal residues or sugars, where appropriate. The agents may be coupled either directly or indirectly to a protein of the present invention. One example of indirect coupling of a second agent is coupling by a spacer moiety. Linking technologies for drug-conjugates have recently been summarized by Ducry and Stump (2010) Bioconjugate Chem. 21: 5.

Compositions and Uses

The heterodimeric proteins produced by a method of the present invention may be used in a pharmaceutical composition with a pharmaceutically-acceptable carrier.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate-buffered saline, ethanol, dextrose, polyols (such as glycerol, propylene glycol, polyethylene glycol). Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intra-arterial, intrathecal, intracapsular, intra-orbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

In one embodiment, the pharmaceutical composition is administered by intravenous or subcutaneous injection or infusion.

In a main aspect, the invention relates to a heterodimeric protein according to the invention, such as a bispecific antibody according to the invention, for use as a medicament. The heterodimeric protein of the invention may be used for a number of purposes. In particular, as explained above the heterodimeric proteins of the invention may be used for the treatment of various forms of cancer, including metastatic cancer and refractory cancer.

Thus, in one aspect, the invention relates to a method for inhibiting growth and/or proliferation of and/or for killing of a tumor cell comprising administration of a heterodimeric protein according to the invention as described herein to an individual in need thereof.

In another embodiment the heterodimeric proteins of the invention are used for the treatment of immune and autoimmune diseases, inflammatory diseases, infectious diseases, cardiovascular diseases, CNS and musculo-skeletal diseases.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

The efficient dosages and the dosage regimens for the heterodimeric proteins depend on the disease or condition to be treated and may be determined by the persons skilled in the art. An exemplary, non-limiting range for a therapeutically effective amount of a bispecific antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the heterodimeric protein employed in the pharmaceutical composition at levels lower than that required to achieve the desired therapeutic effect and gradually increase the dosage until the desired effect is achieved. In general, a suitable dose of a composition of the present invention will be that amount of the compound which is the lowest dose effective to produce a therapeutic effect. Administration may e.g. be parenteral, such as intravenous, intramuscular or subcutaneous.

A heterodimeric protein of the invention may also be administered prophylactically in order to reduce the risk of developing disease, such as cancer, delay the onset of the occurrence of an event in disease progression, and/or reduce the risk of recurrence when a disease, such as cancer is in remission.

Heterodimeric proteins, such as bispecific antibodies, of the present invention may also be administered in combination therapy, i.e., combined with other therapeutic agents relevant for the disease or condition to be treated. Accordingly, in one embodiment, the heterodimeric protein-containing medicament is for combination with one or more further therapeutic agents, such as a cytotoxic, chemotherapeutic or anti-angiogenic agents. Such combined administration may be simultaneous, separate or sequential. In a further embodiment, the present invention provides a method for treating disease, such as cancer, which method comprises administration to a subject in need thereof of a therapeutically effective amount of a heterodimeric protein, such as a bispecific antibody of the present invention, in combination with radiotherapy and/or surgery.

Heterodimeric proteins, such as bispecific antibodies, of the present invention may also be used for diagnostic purposes.

EXAMPLES

Example 1: Expression Vectors for the Expression of Human IgG1-2F8 and IgG1-7D8

The VH and VL coding regions of HuMab 2F8 (WO 02/100348) and HuMab 7D8 (WO 04/035607) were cloned in the expression vector pConG1f (containing the genomic sequence of the human IgG1m(f) allotype constant region (Lonza Biologics)) for the production of the human IgG1 heavy chain and pConKappa (containing the human kappa light chain constant region, Lonza Biologics) for the production of the kappa light chain. For IgG4 antibodies the VH regions were inserted in the pTomG4 vector (containing the genomic sequence of the human IgG4 constant region in the pEE12.4 vector (Lonza Biologics)). Alternatively, in follow-up constructs, vectors were used containing the fully codon-optimized coding regions of the heavy chain (IgG1 or IgG4) in the pEE12.4 vector or the human kappa light chain of HuMab 2F8 or HuMab 7D8 in the pEE6.4 vector (Lonza Biologics). Additionally, the codon-optimized VH coding region of HuMab-2F8 together with the codon-optimized sequence of the human IgG1m(za) allotype constant region containing the F405L mutation, were cloned in the pcDNA3.3 vector (Invitrogen), yielding expression vector p33G1za-2F8-F405L.

Example 2: Expression Vectors for the Expression Hinge-Deleted-IgG1-2F8, and Human IgG1 and IgG4 CH2-CH3 Fragments Containing Specific Mutations To introduce mutations in the hinge and CH3 regions of the antibody heavy chains, Quickchange site-directed mutagenesis kit (Stratagene, La Jolla, Calif.) was used according to the manufacturer's recommendations. Alternatively the constructs were fully synthesized or VH regions were cloned in a vector already containing the specific amino acid encoding substitutions.

Constructs encoding the CH2 and CH3 fragments were constructed either by PCR or synthesized fully codon optimized. These constructs had an N-terminal signal peptide and a 6 amino acid His tag and contained amino acids 341-447 of the human IgG1/4 constant region. The constructs were cloned in pEE12.4.

To construct hinge-deleted-IgG1 (Uni-G1) molecules, a synthetic DNA construct were was made encoding the Uni-G1 format for human IgG1 isotypes with EGFR specificity. In this construct the natural hinge region (as defined by the hinge exon) was deleted. An extra Ser to Cys mutation at position 158 was made in the IgG1 construct to salvage the Cys bond between the HC and LC chains in this isotype. The protein sequence is shown below (SEQ ID NO:4). The construct was inserted in the pEE6.4 vector and named pHG1-2F8.

```
QVQLVESGGGVVQPGRSLRLSCAASGFTFSTYGMHWVRQAPGKGLEWVAV

IWDDGSYKYYGDSVKGRFTISRDNSKNTLYLQMNSLRAEDTAVYYCARDG

ITMVRGVMKDYFDYWGQGTLVTVSSASTKGPSVFPLAPCSKSTSGGTAAL

GCLVKDYFPEPVTVSWNSGALTSGVHTFPAVLQSSGLYSLSSVVTVPSSS

LGTQTYICNVNHKPSNTKVDKRVAPELLGGPSVFLFPPKPKDTLMISRTP

EVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLY

SKLTVDKSRWQQGNVFSCSVMHEALHNHYTQKSLSLSPGK
```

Example 3: Expression Vectors for the Expression of Rhesus IgG4-2F8 and IgG4-7D8

Vectors containing the coding regions for the IgG4 heavy and kappa light chains of Chinese Rhesus monkey and the VH and VL regions of Humab 2F8 and 7D8 were synthesized, fully codon-optimized and inserted in pEE12.4 (heavy chain) and pEE6.4 (light chain). The heavy chain constant region sequence as used (based on the sequences described by Scinicariello et al., Immunology 111: 66-74, 2004) was the following (aligned to the human sequence):

```
Human IgG4
ASTKGPSVFPLAPCSRSTSESTAALGCLVKDYFPEPVTVSWNSGALTSGVH

Rhesus (Ch) IgG4
-STKGPSVFPLASCSRSTSESTAALGCLVKDYFPEPVTVSWNSGALTSGVH

Human IgG4
TFPAVLQSSGLYS-
LSSVVTVPSSSLGTKTYTCNVDHKPSNTKVDKRVESKYG

Rhesus (Ch) IgG4
TFPAVLQSSGLYSLSSVVTVPSSSLGTQTYVCNVVHEP-
SNTKVDKRVEFT--

Human IgG4
PPCPSCPAPEFLGGPSVFLEPPKPKDTLMISRTPEVTCVVVDVSQEDPEV

Rhesus (Ch) IgG4
PPCPACPAPELLGGPSVFLFPPKPKDTLMISRTPEVTCVVVDVSQEDPEV

Human IgG4
QFNWYVDGVEVHNAKTKPREEQFNSTYRVVSVLTVLHQDWLNGKEYKCKV

Rhesus (Ch) IgG4
QFNWYVDGAEVHHAQTKPRERQFNSTYRVVSVLTVTHQDWLNGKEYTCKV

Human IgG4
SNKGLPSSIEKTISKAKGQPREPQVYTLPPSQEEMTKNQVSLTCLVKGFY

Rhesus (Ch) IgG4
SNKGLPAPIEKTISKAKGQPREPQVYILPPPQEELTKNQVSLTCLVTGFY

Human IgG4
PSDIAVEWESNGQPENNYKTTPPVLDSDGSFFLYSRLTVDKSRWQEGNVF

Rhesus (Ch) IgG4
PSDIAVEWESNGQPENTYKTTPPVLDSDGSYLLYSKLTVNKSRWQPGNIF

Human IgG4
                                         (SEQ ID NO: 5)
SCSVMHEALHNHYTQKSLSLSLGK Rhesus (Ch) IgG4
                                         (SEQ ID NO: 6)
TCSVMHEALHNHYTQKSLSVSPGK
```

The Rhesus light chain constant region (CL) sequence used was:

```
                                         (SEQ ID NO: 7)
AVAAPSVFIFPPSEDQVKSGTVSVVCLLNNFYPREASVKWKVDGVLKTGN

SQESVTEQDSKDNTYSLSSTLTLSSTDYQSHNVYACEVTHQGLSSPVTKS

FNRGEC
```

Example 4: Antibody Production by Transient Expression in HEK-293F Cells

Antibodies were produced, under serum-free conditions, by cotransfecting relevant heavy and light chain expression vectors in HEK-293F cells (Invitrogen), using 293fectin (Invitrogen), according to the manufacturer's instructions.

Example 5: Purification of IgG1 and IgG4 Antibodies

IgG1 and IgG4 antibodies were purified by protein A affinity chromatography. The cell culture supernatants were filtered over a 0.20 μM dead-end filter, followed by loading on a 5 mL Protein A column (rProtein A FF, GE Healthcare, Uppsala, Sweden) and elution of the IgG with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis, samples were sterile filtered over a 0.20 μM dead-end filter. Concentration of the purified IgGs was determined by nephelometry and absorbance at 280 nm. Purified proteins were analyzed by SDS-PAGE, IEF, mass spectrometry and glycoanalysis.

Example 6: Purification of CH2-CH3 Fragments

The His-tagged CH2-CH3 proteins were purified by immobilized metal ion ($Ni^{2+}$) affinity chromatography (Macherey-Nagel GmbH, Düren, Germany), desalted using PD-10 columns (GE Healthcare) equilibrated with PBS and filtered-sterilized over 0.2 μM dead-end filters. The concentration of the purified proteins was determined by absorbance at 280 nm. The quality of the purified proteins was analyzed by SDS-PAGE.

Example 7: Generation of Bispecific Antibodies by GSH-Induced Fab-Arm Exchange Between Human and Rhesus IgG4 Antibodies To test for Fab-arm exchange between human and rhesus IgG4 antibodies, human IgG4-2F8 (anti-EGFR), human IgG4-7D8 (anti-CD20), rhesus IgG4-2F8 and rhesus IgG4-7D8 were used to make all possible combinations of two antibodies. For the in vitro Fab-arm exchange, the antibody mixtures, containing each antibody at a final concentration of 4 μg/mL in 0.5 mL PBS with 0.5 mM reduced glutathione (GSH), were incubated at 37° C. for 24 h. To stop the reduction reaction, 0.5 mL PBS/0.05% Tween 20 (PBST) was added to the reaction mixture.

The presence of bispecific antibodies was tested by determination of bispecific binding using a sandwich enzyme-linked immunosorbent assay (ELISA). ELISA plates (Greiner bio-one, Frickenhausen, Germany) were coated overnight with 2 μg/mL (100 μL/well) of recombinant extracellular domain of EGFR in PBS at 4° C. The plates were washed once with PBST. Dilution series of the antibody samples (0-1 μg/mL in 3-fold dilutions) in PBST/0.2% BSA (PBSTB) were transferred to the coated ELISA plates (100 μL/well) and incubated on a plate shaker (300 rpm) for 60 min at room temperature (RT). Samples were discarded and the plates were washed once with PBS/0.05% Tween 20 (PBST). Next, the plates were incubated on a plate shaker (300 rpm) with 2 μg/mL mouse anti-idiotypic monoclonal antibody 2F2 SAB1.1 (directed against 7D8; Genmab) in PBSTB (100 μL/well) for 60 min. The plates were washed once with PBS/0.05% Tween 20 (PBST). Next, the plates were incubated on a plate shaker (300 rpm) with an HRP-conjugated goat anti-mouse IgG (15G; Jackson ImmunoResearch Laboratories, Westgrove, Pa., USA; 1:5.000) in PBSTB (100 μL/well) for 60 min at RT. The plates were washed once with PBS/0.05% Tween 20 (PBST). ABTS (50 mg/mL in PBS; Roche Diagnostics GmbH, Mannheim, Germany) was added (100 μL/well) and incubated protected from light for 30 min at RT. The reaction was stopped with 2% oxalic acid (100 μL/well; Riedel de Haen Seelze, Germany). After 10 min at RT, absorbance at 405 nm was measured in an ELISA plate reader.

Figure 1:
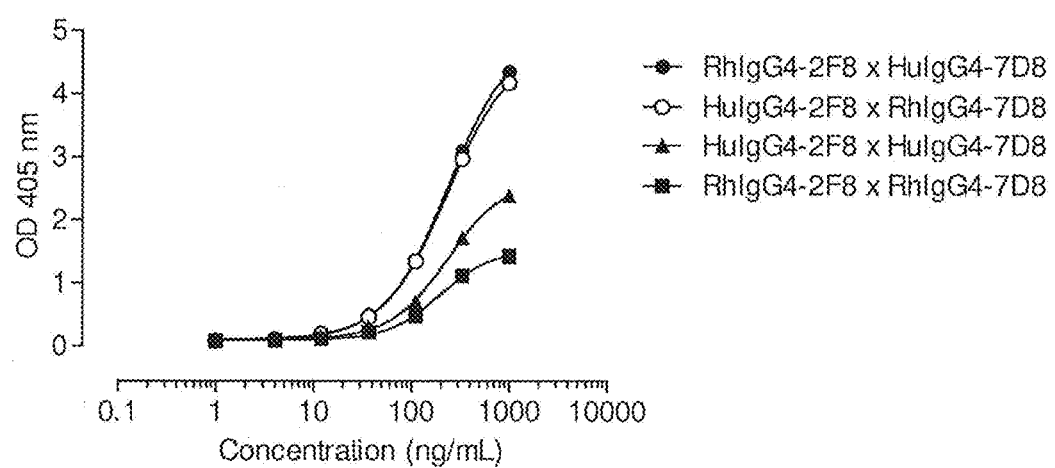
FIG. 1: Generation of bispecific antibodies by interspecies Fab-arm exchange. The generation of bispecific antibodies after GSH-induced in vitro Fab-arm exchange between the indicated anti-EGFR (2F8) and CD20 (7D8) IgG4 antibodies was determined by an ELISA. A concentration series (total antibody) of 0-1 μg/mL was analyzed in the ELISA. Bispecific binding was higher after Fab-arm exchange between rhesus (Rh) and human (Hu) IgG4 antibodies than between two antibodies of the same species.

FIG. 1 shows that a combination of human and rhesus IgG4 resulted in more bispecific binding (a higher OD 405 nm) compared with each of the combinations of IgG4 molecules of the same species. These data show that Fab-arm exchange occurs between human IgG4 and rhesus IgG4. Moreover, the higher bispecific binding suggests that human IgG4 half molecules show preferential dimerisation to rhesus IgG4 half molecules (heterodimerization), resulting in an equilibrium of the Fab-arm exchange reaction that is shifted towards the bispecific heterodimer instead of a stochastic exchange with 50% heterodimer and 50% homodimers.

Example 8: Sequence Analysis of Human and Rhesus IgG4

In an attempt to elucidate the increased Fab-arm exchange between human and rhesus IgG4 compared to the Fab-arm exchange between IgG4 molecules of the same species, the core hinge and CH3-CH3 interface amino acids of human and rhesus antibodies were analyzed (see e.g. Dall'Acqua, et al (1998) Biochemistry 37:9266 for an overview of the residues of the human CH3-CH3 interface). FIG. 2 shows that the core hinge sequence in Chinese rhesus IgG4 is 226-CPAC-229 and that the CH3 domain contains a Lysine (K) at position 409. In addition, sequence alignment showed that rhesus IgG4 is characterized by three more amino acid substitutions in the CH3-CH3 interface as compared to human IgG4: isoleucine (I) at position 350 in rhesus versus threonine (T) in human; threonine (T) at position 370 in rhesus versus lysine (K) in human; and leucine (L) at position 405 in rhesus versus phenylalanine (F) in human.

Example 9: Generation of Bispecific Antibodies Using GSH-Induced Fab-Arm Exchange Between Human IgG4 and Human IgG1 Containing Rhesus IgG4 CH3 Sequences Based on the Fab-arm exchange between human and rhesus IgG4 described in Example 7, it was analyzed whether the Chinese rhesus IgG4 CH3 sequence could engage human IgG1 for Fab-arm exchange. Therefore, the triple mutation T350I-K370T-F405L (referred to as ITL hereafter) was introduced in human IgG1-2F8 in addition to the P228S mutation that results in the hinge sequence CPSC. The human IgG1-2F8 mutants were combined with human IgG4-7D8 for in vitro GSH-induced Fab-arm exchange. The antibody mixtures, containing each antibody at a final concentration of 4 µg/mL in 0.5 mL PBS with 0.5 mM GSH, were incubated at 37° C. for 0-3-6-24 h. To stop the reduction reaction, 0.5 mL PBS/0.05% Tween 20 (PBST) was added to the reaction mixture. Measurements of bispecific binding in an ELISA were performed as described in Example 7.

Figure 3:
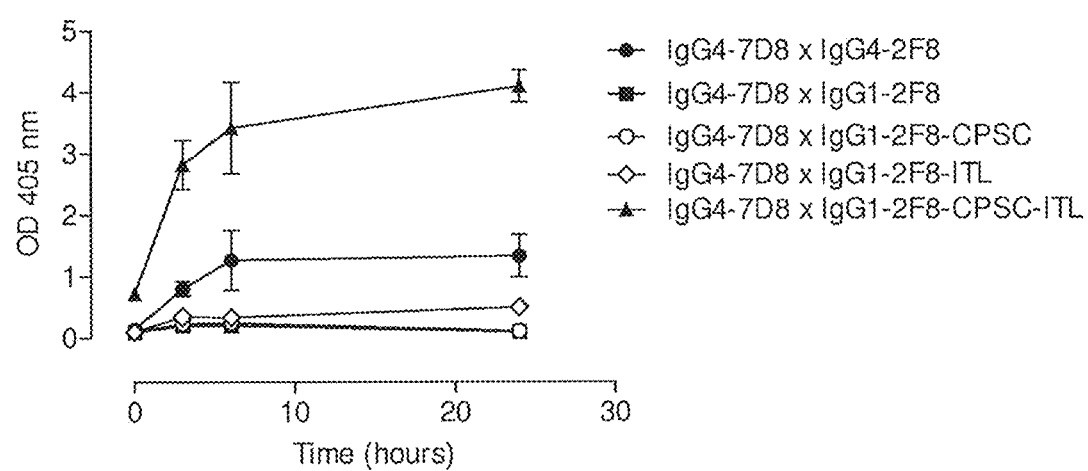
FIG. 3: Generation of bispecific antibodies using mutant human IgG1 engaged for Fab-arm exchange. The generation of bispecific antibodies by GSH-induced in vitro Fab-arm exchange between human CD20 (7D8) IgG4 antibody and the indicated human EGFR (2F8) IgG1 antibodies was determined by an ELISA. The presented graph shows average numbers of three independent Fab-arm exchange experiments, in which a total antibody concentration of 1 μg/mL was used for ELISA. Bispecific binding was higher after Fab-arm exchange between IgG1-2F8-CPSC-ITL and IgG4-7D8 than between two IgG4 antibodies. Combining IgG4-7D8 with IgG1-2F8, IgG1-2F8-CPSC or IgG1-2F8-ITL did not result in bispecific antibodies under the conditions used.

FIG. 3 confirms that introduction of a CPSC hinge alone does not engage human IgG1-2F8 for GSH-induced Fab-arm exchange when combined with human IgG4-7D8. Also the introduction of the rhesus IgG4-specific CH3 interface amino acids (ITL) into human IgG1-2F8, while preserving the wild type IgG1 hinge, did not result in engagement for Fab-arm exchange when combined with human IgG4-7D8 under these conditions. In contrast, a variant human IgG1-2F8 backbone sequence that harbors both a CPSC sequence in the hinge and the rhesus IgG4-specific CH3 interface amino acids (ITL) showed increased bispecific binding after GSH-induced Fab-arm exchange with human IgG4-7D8 compared to two human IgG4 antibodies. These data show that a CPSC-containing hinge in combination with a CH3 domain containing I, T and L at positions 350, 370 and 405, respectively, is sufficient to engage human IgG1 for GSH-induced Fab-arm exchange and that the equilibrium of the exchange reaction is shifted towards the exchanged bispecific product when combined with human IgG4.

Example 10: Generation of Bispecific Antibodies by In Vivo Fab-Arm Exchange Between Human IgG4 and IgG1 or IgG4 Mutants To further identify the required characteristics for Fab-arm exchange engagement, human IgG4 and IgG1 variants were analyzed in vivo. Four female SCID mice (Charles River, Maastricht, The Netherlands) per group were i.v. injected with antibody mixtures, containing 600 µg antibody (500 µg 7D8+100 µg 2F8) in a total volume of 300 µL. Blood samples were drawn from the saphenal vein at 3, 24, 48 and 72 hours after injection. Blood was collected in heparin-containing vials and centrifuged at 10,000 g for 5 min to separate plasma from cells. The generation of bispecific antibodies was followed by assessing CD20 and EGFR bispecific reactivity in an ELISA using serial diluted plasma samples in PBSTB as described in Example 7. Bispecific antibodies in plasma samples were quantified by non-linear regression curve-fitting (GraphPad Software, San Diego, Calif.) using an in vitro exchanged antibody mixture as reference.

Figure 4:
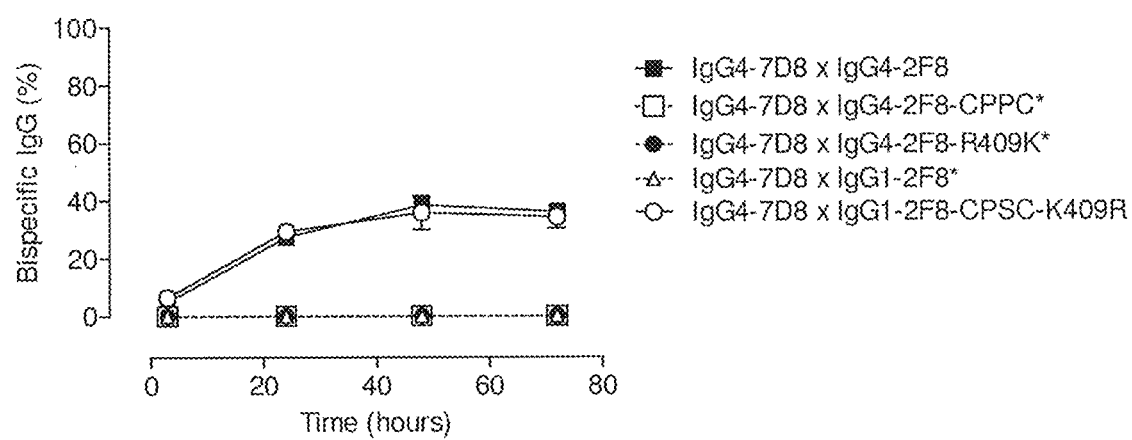
FIG. 4: Generation of bispecific antibodies by in vivo Fab-arm exchange of human IgG4 and mutant IgG1 antibodies. The generation of bispecific antibodies by in vivo Fab-arm exchange in immunodeficient mice between human CD20 (7D8) IgG4 and the indicated human EGFR (2F8) IgG1 and IgG4 mutant antibodies was determined by an ELISA. The presented graph shows average numbers (n=4). Bispecific reactivity is presented as the concentration bispecific antibodies relative to the total IgG concentration (percentage). Human IgG4 with a stabilized hinge (CPPC) or R409K mutation in the CH3 domain is not able to participate in Fab-arm exchange. IgG1 with both a CPSC sequence in the hinge and a K409R mutation in the CH3 domain is engaged for Fab-arm exchange. (*) Bispecific binding for the mixtures containing either IgG1-2F8, IgG4-2F8-CPPC or IgG4-2F8-R409K was below the detection limit and therefore arbitrarily set to zero.

FIG. 4 shows that human IgG4-2F8, in which either the hinge or the CH3 sequence is converted to the corresponding human IgG1 sequence (CPPC or R409K, respectively), does not engage in Fab-arm exchange in vivo anymore. Vice versa, human IgG1, in which both the hinge region and the CH3 interface sequences are converted to the corresponding human IgG4 sequences (CPSC and K409R), is able to participate in Fab-arm exchange in vivo. These data show that a CPSC-containing hinge (S at position 228) in combination with a CH3 domain containing an arginine (R) at position 409 is enough to enable Fab-arm exchange between human IgG1 and human IgG4 in vivo.

Example 11: Generation of Bispecific Antibodies by 2-MEA-Induced Fab-Arm Exchange: Bypass/Disruption of a Stabilized Hinge 2-Mercaptoethylamine.HCl (2-MEA) is a mild reducing agent that has been described to selectively cleave disulphide bonds in the hinge region of antibodies, while preserving the disulphide bonds between the heavy and light chains. A concentration series of 2-MEA was tested for its ability to induce the generation of bispecific antibodies by Fab-arm exchange between two antibodies containing CPSC or CPPC hinge regions. The antibody mixtures, containing each antibody at a final concentration of 0.5 mg/mL, were incubated with a concentration series of 2-MEA (0, 0.5, 1.0, 2.0, 5.0, 7.0, 10.0, 15.0, 25.0 and 40.0 mM) in a total volume of 100 µL Tris-EDTA (TE) at 37° C. for 90 min. To stop the reduction reaction, the reducing agent 2-MEA was removed by desalting the samples using spin columns (Microcon centrifugal filters, 30 k, Millipore) according to the manufacturer's recommendations. Bispecific binding was measured in an ELISA as described in Example 7.

Figure 5:
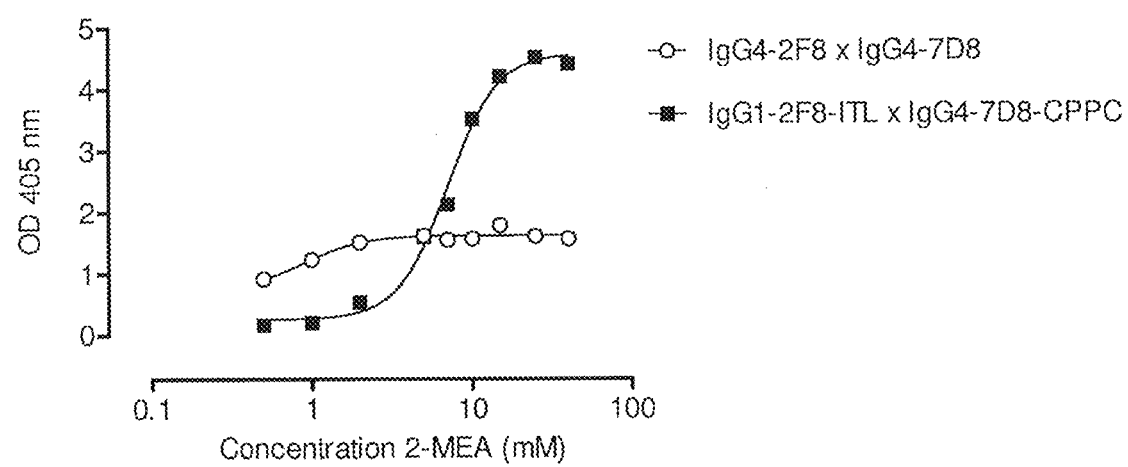
FIG. 5: Generation of bispecific antibodies using 2-mercapto-ethylamine.HCl-(2-MEA-) induced Fab-arm exchange between human IgG1 and IgG4 antibodies. The generation of bispecific antibodies after 2-MEA-induced in vitro Fab-arm exchange between the indicated human EGFR (2F8) and CD20 (7D8) antibodies was determined by an ELISA. A concentration series of 0-40 mM 2-MEA was tested. The presented graph shows the result of the ELISA in which a total antibody concentration of 20 μg/mL was used. 2-MEA efficiently induced Fab-arm exchange, also between antibodies containing a stabilized hinge (CPPC). Concerning the CH3 domains, a combination of human IgG4×human IgG1 with the triple mutation T350I-K370T-F405L, resulted in higher levels of bispecific reactivity compared to two wild type IgG4 antibodies.

2-MEA-induced Fab-arm exchange was tested for the combination IgG4-2F8×IgG4-7D8, containing CPSC hinge regions and known to participate in GSH-induced Fab-arm exchange, and for the combination IgG1-2F8-ITL×IgG4-7D8-CPPC, not participating in GSH-induced Fab-arm exchange due to the stabilized hinge regions (described in Example 9, FIG. 3). Surprisingly, 2-MEA was found to induce separation of light chains from heavy chains as determined by non-reducing SDS-PAGE (data not shown). Nonetheless, functional bispecific antibodies were generated as shown in FIG. 5. The maximal level of bispecific binding after Fab-arm exchange between wild type human IgG4-2F8 and IgG4-7D8 was reached at a concentration of 2.0 mM 2-MEA and was comparable to the level reached with 0.5 mM GSH as described in Example 9 (FIG. 3). However, 2-MEA was able to induce Fab-arm exchange between the human antibodies IgG1-2F8-ITL and IgG4-7D8-CPPC (with stabilized hinge regions) in a dose-dependent manner. While little or no bispecific antibodies were formed at low 2-MEA concentrations, probably due to the presence of a CPPC sequence in the hinge region of both antibodies, the generation of bispecific antibodies was very efficient at higher concentrations of 2-MEA. Maximal bispecific binding was reached at 25 mM 2-MEA and exceeded maximal binding after Fab-arm exchange between the two wild type IgG4 antibodies. These maximal binding levels were comparable to what is described in Example 9 (FIG. 3) for GSH treatment of the corresponding antibody with a CPSC hinge (IgG1-2F8-CPSC-ITL). As IgG1-2F8-ITL and IgG4-7D8-CPPC both contain a CPPC hinge, these data indicate that 2-MEA could bypass the requirement of a CPSC hinge for in vitro Fab-arm exchange.

Figure 6A:
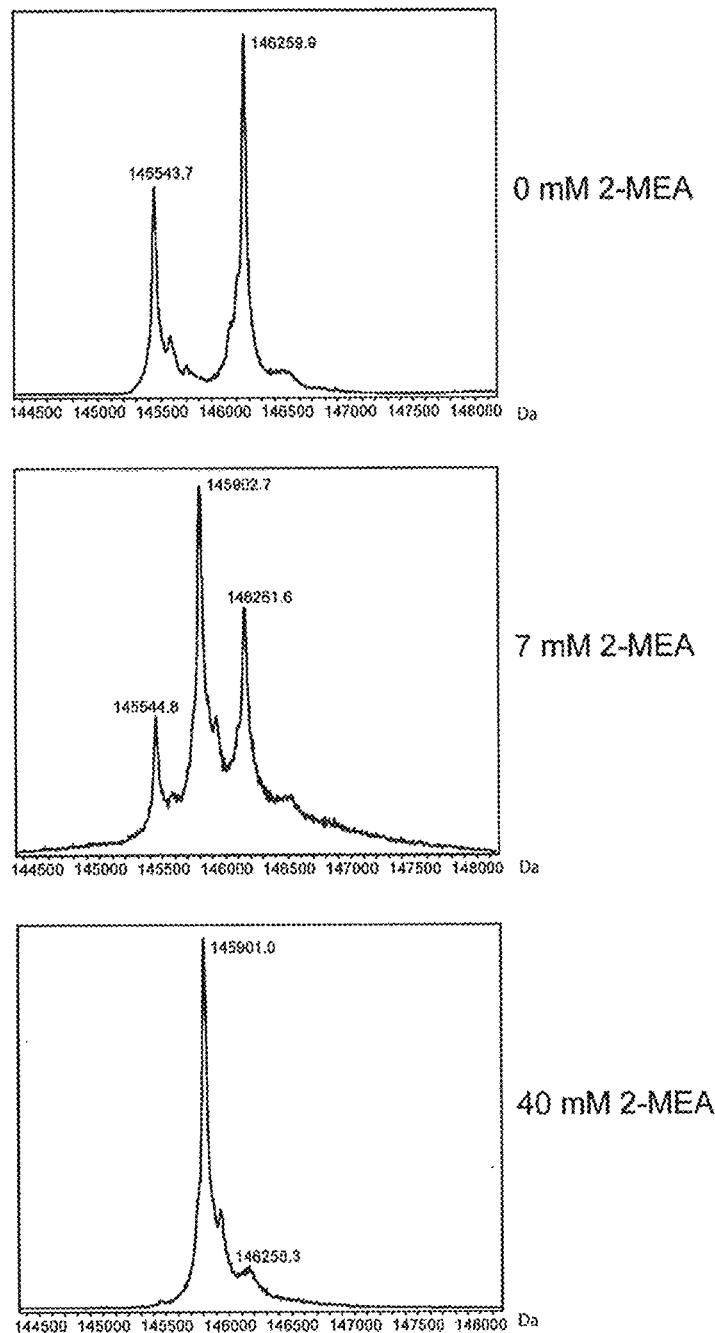
FIGS. 6A and 6B: Generation of bispecific antibodies using 2-MEA-induced Fab-arm exchange between human IgG1 and IgG4 antibodies.
Figure 6B:
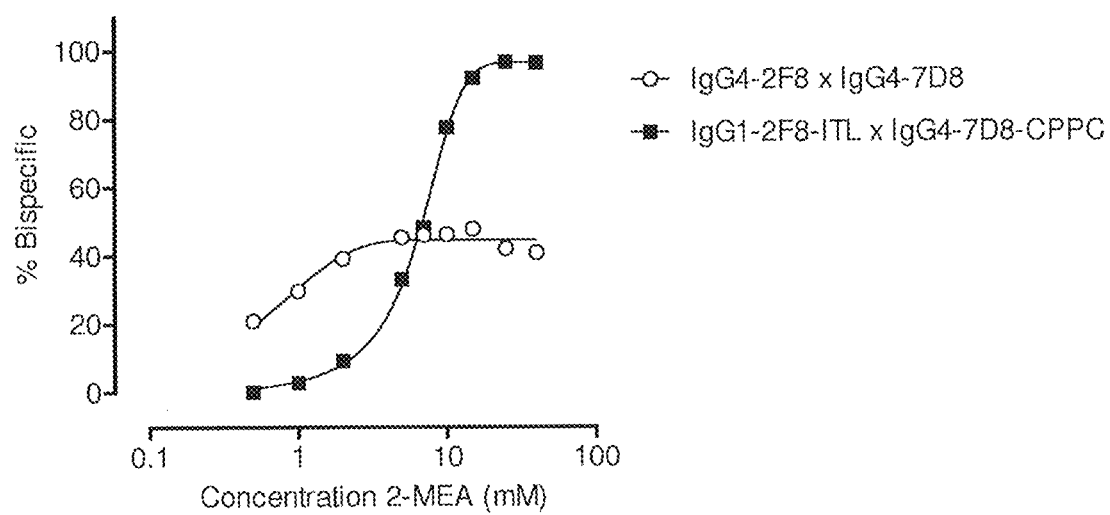

Example 12: Mass Spectrometry to Follow the Generation of Bispecific Antibodies by 2-MEA-Induced Fab-Arm Exchange The generation of bispecific antibodies by 2-MEA-induced Fab-arm exchange is described in Example 11, where bispecific binding was shown by an ELISA (FIG. 5). To confirm that bispecific antibodies are formed, the samples were analyzed by electrospray ionization mass spectrometry (ESI-MS) to determine the molecular weights. First, samples were deglycosylated by incubating 200 µg antibody overnight at 37° C. with 0.005 U N-Glycanase (cat. no. GKE-5006D; Prozyme) in 180 µL PBS. Samples were desalted on an Aquity UPLC™ (Waters, Milford, USA) with a BEH300 C18, 1.7 µm, 2.1×50 mm column at 60° C. and eluted with a gradient of a mixture of MQ water (Eluens A) and LC-MS grade acetonitrile (eluens B) (Biosolve, Valkenswaard, The Netherlands) containing 0.05% formic acid (Fluka Riedel-de Haën, Buchs, Germany). Time-of-flight electrospray ionization mass spectra were recorded on-line on a micrOTOF™ mass spectrometer (Bruker, Bremen, Germany) operating in the positive ion mode. Prior to analysis, a 500-4000 m/z scale was calibrated with ES tuning mix (Agilent Technologies, Santa Clara, USA). Mass spectra were deconvoluted by using Maximal Entropy that is provided with the DataAnalysis™ software v. 3.4 (Bruker, Bremen, Germany). Based on the molecular mass of the antibodies used for Fab-arm exchange in this experiment, the bispecific antibodies could be discriminated from the original antibodies (also described in Example 15, FIG. 9C for IgG1-2F8-ITL×IgG4-7D8-CPPC). For the peak of bispecific antibody, the area under the curve was determined and divided by the total area under the curves to calculate the percentage bispecific antibody in each sample. FIG. 6A shows three representative mass spectrometry profiles of the Fab-arm exchange reaction between IgG1-2F8-ITL and IgG4-7D8-CPPC with 0 mM 2-MEA (two peaks corresponding to the parental antibodies), 7 mM 2-MEA (three peaks corresponding to the parental and the bispecific antibodies), and 40 mM 2-MEA (one peak corresponding to the bispecific antibody). The homogenous peak of the bispecific product indicates that no light chain mispairing occurred, which would have resulted in subdivided peaks. The quantified data are presented in FIG. 6B and show that Fab-arm exchange between IgG1-2F8-ITL and IgG4-7D8-CPPC resulted in nearly 100% bispecific antibody. In contrast, Fab-arm exchange between wild type IgG4 antibodies resulted in less than 50% bispecific product. These data confirm the results from the bispecific binding ELISA described in Example 11 (FIG. 5).

Example 13: Stability of Bispecific Antibodies Generated by 2-MEA-Induced Fab-Arm Exchange The stability of bispecific antibodies generated by 2-MEA-induced in vitro Fab-arm exchange was tested. Therefore, 2 µg of a bispecific sample generated from IgG1-2F8-ITL and IgG4-7D8-CPPC with 7.0 mM 2-MEA (as described in Example 11, FIG. 5) was used in a GSH-induced Fab-arm exchange reaction in the presence of a concentration series (0, 2, 20, 100 µg) irrelevant IgG4 (IgG4-MG against acetylcholine receptor), representing a 0, 1, 10, 50× excess of IgG4-MG compared to the 2 µg bispecific test sample. Fab-arm exchange in this reaction would result in loss of bispecific EGFR/CD20 binding. The conditions for the GSH reduction reaction were the same as described in Example 7 (24 h at 37° C. in 0.5 mL PBS/0.5 mM GSH). To stop the reduction reaction, 0.5 mL PBSTB was added to the reaction mixture. Bispecific binding was measured in an ELISA as described in Example 7. Bispecific binding after the GSH reduction reaction is presented relative to the bispecific binding measured in the starting material (control), which was set to 100%.

Figure 7A:
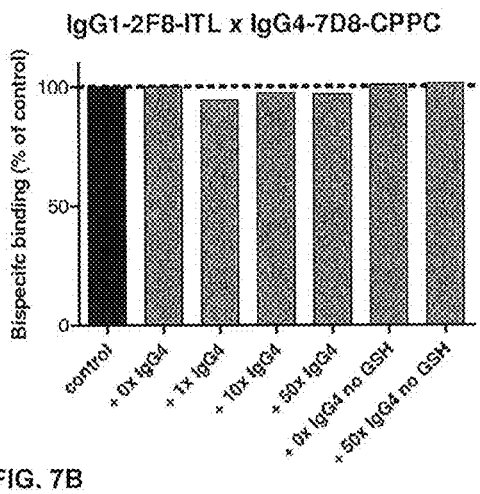
FIGS. 7A and 7B: Stability analysis of heterodimeric bispecific antibodies obtained by 2-MEA-induced Fab-arm exchange. The stability of bispecific samples generated by 2-MEA-induced Fab-arm exchange by combining either IgG1-2F8-ITL×IgG4-7D8-CPPC (FIG. 7A), or IgG4-2F8×IgG4-7D8 (FIG. 7B) was tested by measuring EGFR/CD20 bispecific binding in an ELISA after a GSH-induced Fab-arm exchange reaction in the presence of the indicated concentrations irrelevant IgG4. Bispecific binding is presented relative to the bispecific binding of the starting material (control), which was set to 100%.
Figure 7B:
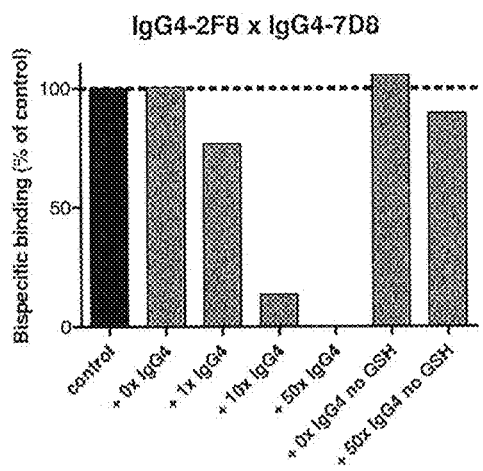

FIG. 7A shows that for the IgG1-2F8-ITL×IgG4-7D8-CPPC derived bispecific sample, EGFR/CD20 bispecific binding is not significantly changed after GSH-induced Fab-arm exchange in the presence of irrelevant IgG4. This indicates that the bispecific product is stable, i.e. does not participate in GSH-induced Fab-arm exchange. As a control, FIG. 7B shows that an IgG4-2F8×IgG4-7D8 derived sample shows diminished EGFR/CD20 bispecific binding after GSH-induced Fab-arm exchange in the presence of irrelevant IgG4, indicating that this product is not stable. These data show that the heterodimer consisting of a human IgG1 heavy chain containing the triple mutation T350I-K370T-F405L in the CH3 domain, and a human IgG4 heavy chain containing the S228P substitution resulting in a stabilized hinge (CPPC), is stable.

Example 14: In Vivo Analysis of the Pharmacokinetics and Stability of Bispecific Antibodies Generated by 2-MEA-Induced Fab-Arm Exchange The bispecific antibody generated by in vitro 2-MEA-induced Fab-arm exchange between IgG1-2F8-ITL and IgG4-7D8-CPPC (example 11, FIG. 5, 7 mM 2-MEA) was injected in SCID mice to analyze its stability (in vivo Fab-arm exchange) and pharmacokinetic properties (plasma clearance rate) in comparison to the parental antibodies IgG1-2F8-ITL and IgG4-7D8-CPPC. Three groups of mice (3 mice per group) were injected intravenously in the tail vein with 200 µL purified antibody: (1) 100 µg bispecific antibody; (2) 100 µg bispecific antibody+1,000 µg irrelevant IgG4 (natalizumab, anti-α4-integrin); (3) 50 µg IgG1-2F8-ITL+50 µg IgG4-7D8-CPPC. Blood samples (50-100 µL) were collected by cheek puncture at predetermined time intervals after antibody administration (10 min, 3 h, 1, 2, 7, 14, 21 days). Blood was collected into heparin containing vials and centrifuged for 10 min at 14,000 g. Plasma was stored at −20° C. before further analysis.

Total IgG concentrations in the plasma samples were assayed by ELISA. The assay conditions of the succeeding steps were the same as for the ELISA described in Example 7. Specific compounds used for total IgG measurement were the following: coat with 2 μg/mL mouse anti-human IgG (clone MH16-1; CLB; cat. no. M1268); serum samples dilutions (1:500 and 1:2,500 for groups 1 and 3) and (1:2,500 and 1:10,000 for group 2); conjugate: HRP-conjugated goat anti-human IgG (clone 11H; Jackson; cat. no. 109-035-098; 1:10,000). The presence of bispecific antibodies in the plasma samples was assayed and quantified by CD20 and EGFR bispecific reactivity in an ELISA as described in Example 10.

Figure 8A:
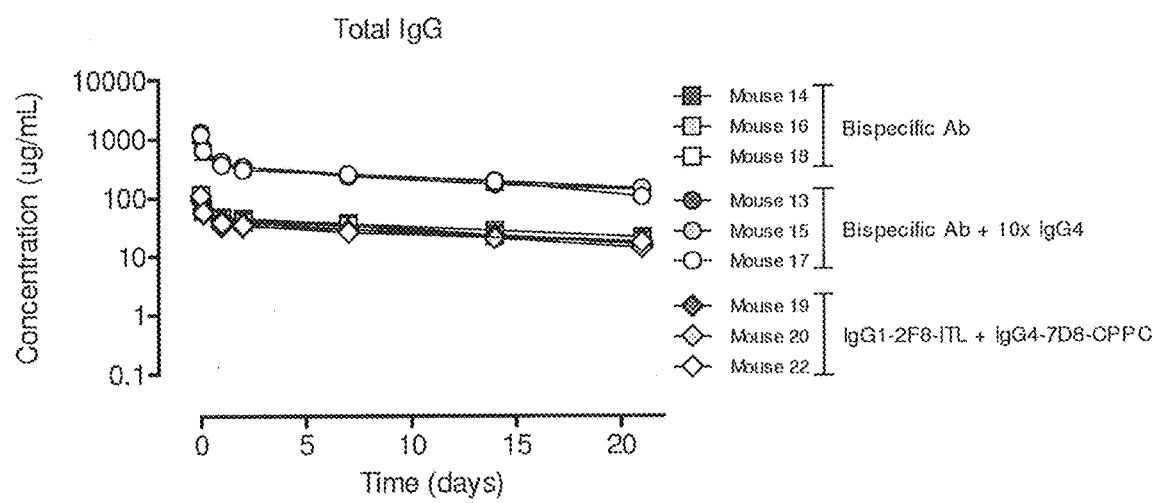
FIGS. 8A and 8B: Plasma clearance rate of a heterodimeric bispecific antibody generated by 2-MEA-induced Fab-arm exchange. Three groups of mice (3 mice per group) were injected with the indicated antibodies: (1) 100 μg bispecific antibody, generated by in vitro 2-MEA-induced Fab-arm exchange between IgG1-2F8-ITL×IgG4-7D8-CPPC; (2) 100 μg bispecific antibody+1,000 μg irrelevant IgG4; (3) 50 μg IgG1-2F8-ITL+50 μg IgG4-7D8-CPPC.
Figure 8B:
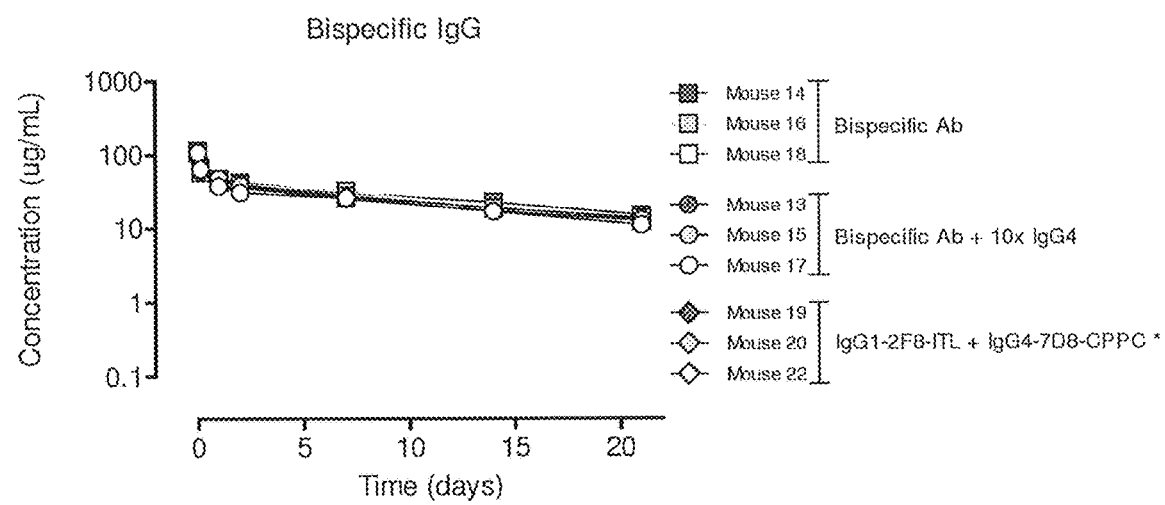

FIG. 8A shows total antibody plasma concentrations. The shape of the plasma clearance curves was identical in all groups, indicating that the plasma clearance of the bispecific antibody was the same as for the parental antibodies IgG1-2F8-ITL and IgG4-7D8-CPPC over the analyzed time interval. FIG. 8B shows the plasma concentrations of bispecific antibodies over time. The addition of a 10-fold excess irrelevant IgG4 to the bispecific antibody did not affect bispecific antibody concentrations, indicating that no Fab-arm exchange occurred in vivo. After injection of the parental antibodies (IgG1-2F8-ITL+IgG4-7D8-CPPC), no bispecific antibodies were detectable in the plasma, confirming that these antibodies do not participate in Fab-arm exchange in vivo. These data indicate that the bispecific antibody product, generated by in vitro 2-MEA-induced Fab-arm exchange between IgG1-2F8-ITL×IgG4-7D8-CPPC, was stable in vivo (no Fab-arm exchange) and showed comparable pharmacokinetic properties (plasma clearance rate) as the parental monovalent antibodies.

Example 15: Purity of the Bispecific Antibody Generated by 2-MEA-Induced Fab-Arm Exchange Between Two Antibodies A batch of bispecific antibody, generated by 2-MEA-induced Fab-arm exchange between human IgG1-2F8-ITL× IgG4-7D8-CPPC, was purified on a PD-10 desalting column (cat. no. 17-0851-01; GE Healthcare). Next, the purity of the bispecific product was analyzed by sodium dodecyl sulfate polyacrylamide gelelectrophoresis (SDS-PAGE), high performance size exclusion chromatography (HP-SEC) and mass spectrometry. The functionality of the generated bispecific antibody was confirmed by bispecific binding in an ELISA (data not shown).

Figure 9A:
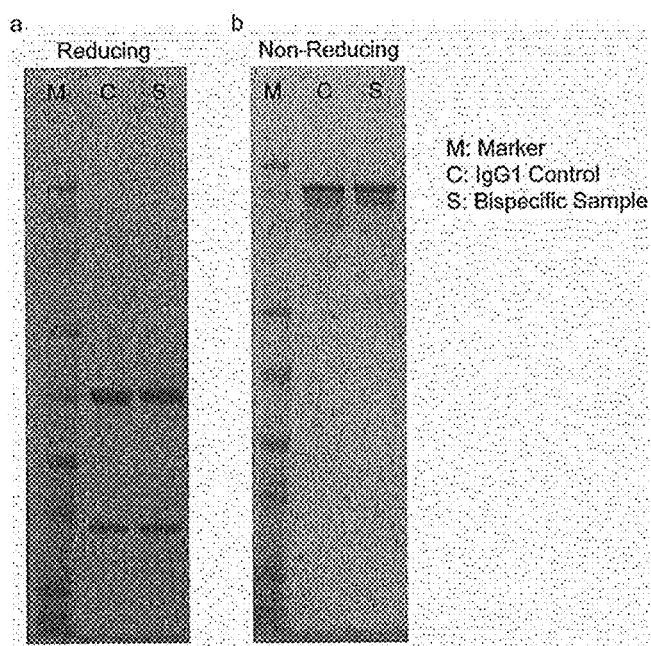
FIGS. 9A-9C: Purity of bispecific antibody generated by Fab-arm exchange between human IgG1-2F8 and IgG4-7D8-CPPC.
Figure 9B:
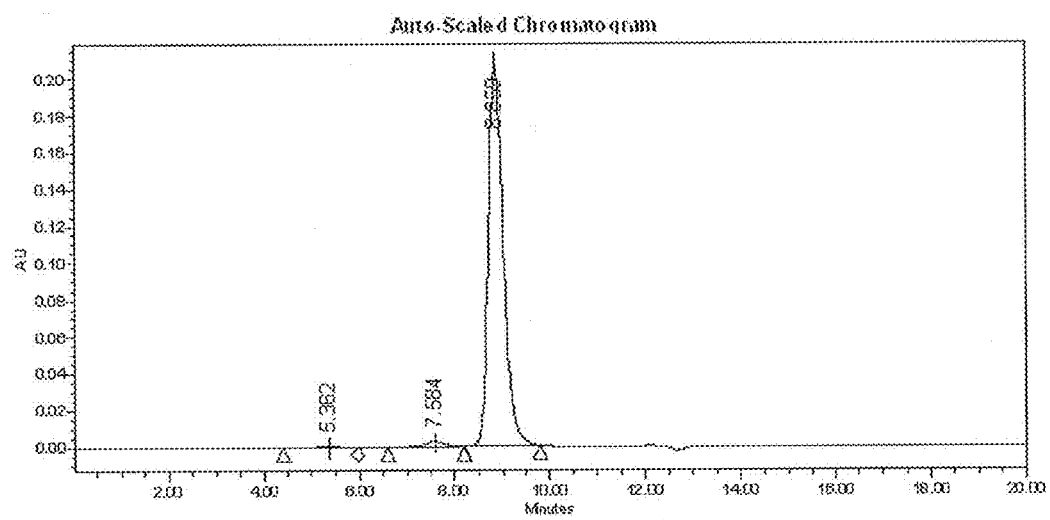

SDS-PAGE was performed under reducing and non-reducing conditions on 4-12% NuPAGE Bis-Tris gels (Invitrogen, Breda, The Netherlands) using a modified Laemmli method (Laemmli 1970 Nature 227(5259): 680-5), where the samples were run at neutral pH. The SDS-PAGE gels were stained with Coomassie and digitally imaged using the GeneGenius (Synoptics, Cambridge, UK). FIG. 9A shows that the antibody sample after Fab-arm exchange consists of intact IgG, with a trace of half molecules (H1L1) detectable on the non-reduced gel (FIG. 9A-b).

HP-SEC fractionation was performed using a Waters Alliance 2695 separation unit (Waters, Etten-Leur, The Netherlands) connected to a TSK HP-SEC column (G3000SW$_{xl}$; Toso Biosciences, via Omnilabo, Breda, The Netherlands) and a Waters 2487 dual λ absorbance detector (Waters). The samples were run at 1 mL/min. Results were processed using Empower software version 2002 and expressed per peak as percentage of total peak height. FIG. 9B shows that >98% of the sample consists of intact IgG, with practically no aggregates formed.

Figure 9C:
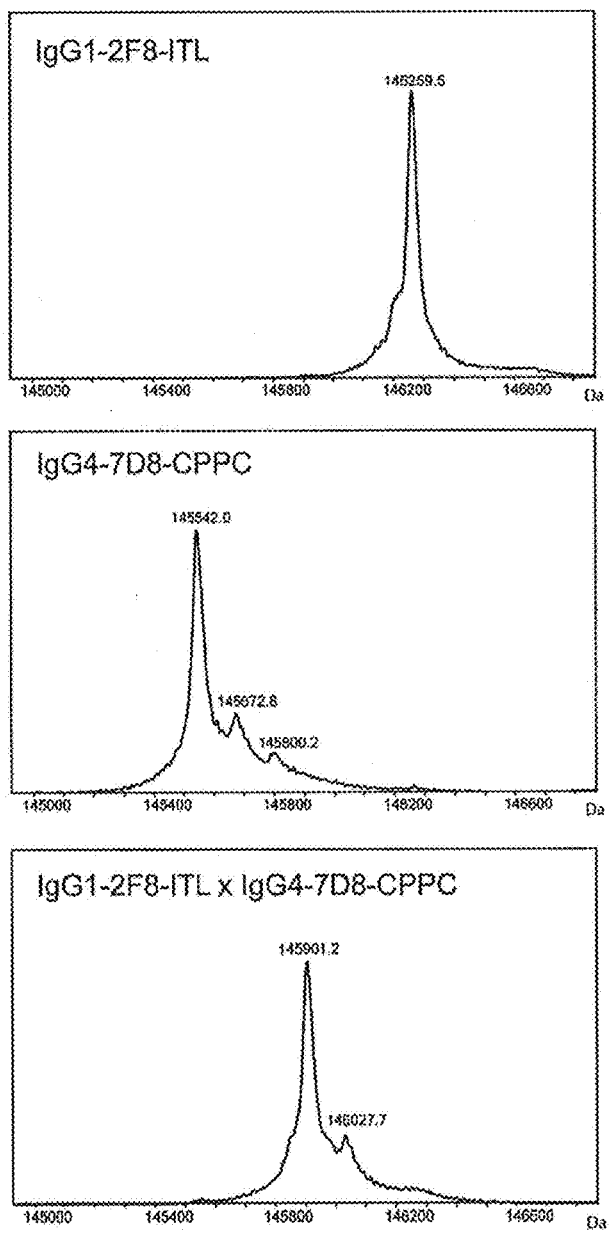

Mass spectrometry was performed as described in Example 12. FIG. 9C shows the mass spectrometry profiles of the starting materials IgG1-2F8-ITL and IgG4-7D8-CPPC and the bispecific product generated by Fab-arm exchange between IgG1-2F8-ITL×IgG4-7D8-CPPC. The product in the Fab-arm exchanged sample is 145,901 kDa, which perfectly matches with the bispecific product derived from IgG1-2F8-ITL (146,259.5/2=73,130)+IgG4-7D8-CPPC (145,542.0/2=72,771). Moreover, the bispecific antibody product showed a homogenous peak, indicating that no light chain mispairing occurred, which would have resulted in subdivided peaks. These data show that Fab-arm exchange resulted in 100% bispecific antibody. The small peaks detected in addition to the main peak (K0) of the IgG4-7D8-CPPC and bispecific sample can be attributed to the presence of one (K1) or two (K2) C-terminal lysines in the heavy chain of the antibody.

These data show that a ~100% functional bispecific antibody sample was generated by 2-MEA-induced Fab-arm exchange between IgG1-2F8-ITL×IgG4-7D8-CPPC.

Example 16: Unraveling the Requirement of the T350I, K370T and F405L Substitutions for Fab-Arm Exchange Engagement of Human IgG1

To further identify the determinants in the IgG1 CH3 domain that are required for IgG1 to be engaged in Fab-arm exchange, IgG1 containing the triple mutation T350I-K370T-F405L (ITL) was compared to the double mutants T350I-K370T (IT), T350I-F405L (IL) and K370T-F405L (TL). Also the single mutant F405L (L) was tested. 2-MEA was used as a reductant to induce in vitro Fab-arm exchange (50 μg of each antibody in 100 μL PBS/25 mM 2-MEA for 90 min at 37° C.). For the single mutant F405L antibody, unpurified antibody from supernatant of a transient transfection was used after buffer-exchange to PBS using Amicon Ultra centrifugal devices (30 k, Millipore, cat. no. UFC803096). To stop the reduction reaction, the reducing agent 2-MEA was removed by desalting the samples using spin columns as described in Example 11. The generation of bispecific antibodies was determined by bispecific binding measured in an ELISA as described in Example 7.

Figure 10A:
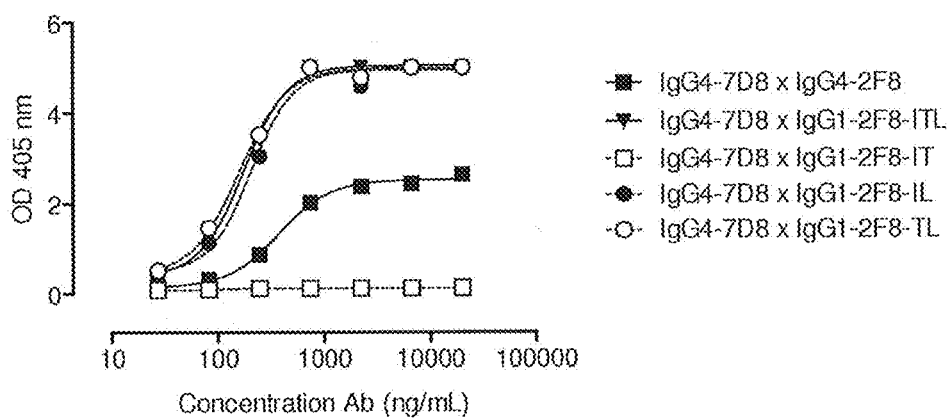
FIGS. 10A-10C: Comparison between triple mutant (ITL), double mutants (IT, IL, TL) and single mutant (L) human IgG1-2F8 in the generation of bispecific antibodies by Fab-arm exchange with human IgG4-7D8. The generation of bispecific antibodies after 2-MEA-induced in vitro Fab-arm exchange between the human IgG1-2F8 triple and double mutants and wild type IgG4-7D8 with a CPSC hinge (FIG. 10A) or mutant IgG4-7D8-CPPC with a stabilized hinge (FIG. 10B), or the single mutant IgG1-2F8-F405L and IgG4-7D8 with a wild type CPSC or stabilized CPPC hinge (FIG. 10C), was determined by an ELISA. A concentration series (total antibody) of 0-20 µg/mL or 0-10 µg/mL was analyzed in the ELISA for the experiments including the double and single mutants, respectively. Combinations of IgG4 with the double mutants IgG1-2F8-IL and -TL result in bispecific EGFR/CD20 binding similar as the triple mutant IgG1-ITL. Combinations with the IgG1-2F8-IT do not result in a bispecific product. Combinations of both IgG4 wild type and IgG4 with a stabilized hinge with the single mutant IgG1-2F8-F405L result in bispecific EGFR/CD20 binding.
Figure 10B:
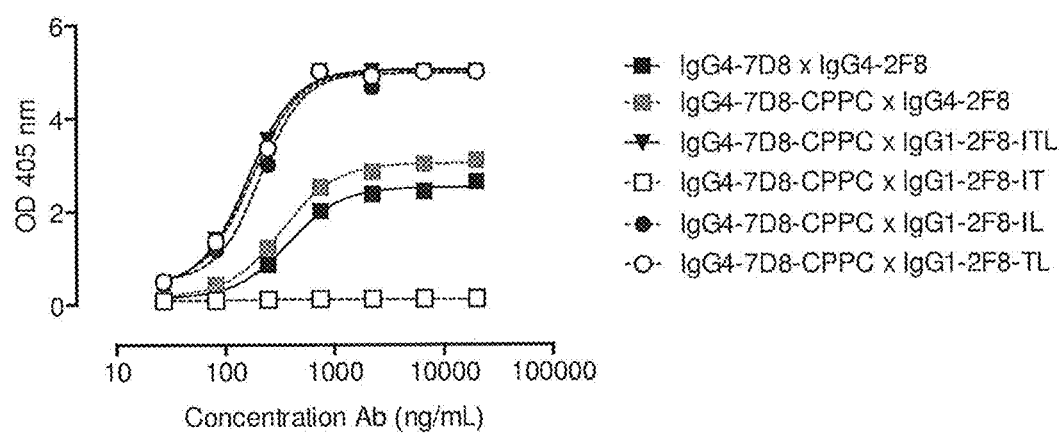
Figure 10C:
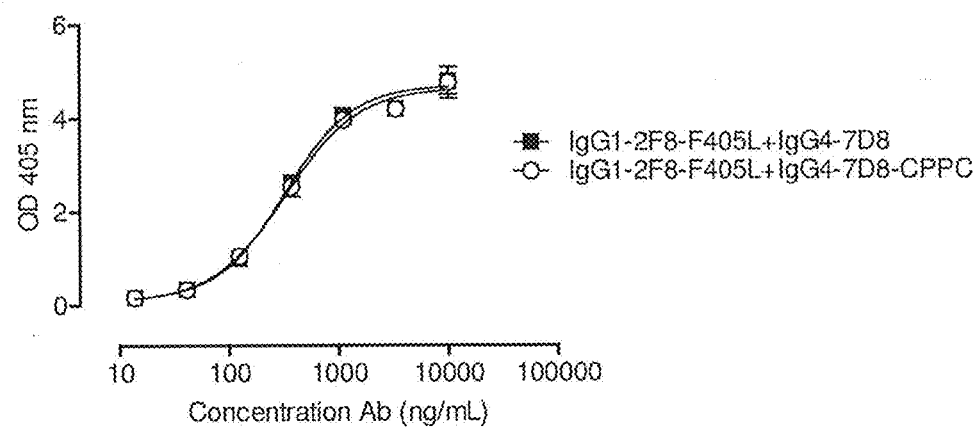

The triple (ITL), double mutations (IT, IL and TL) and single mutation (L) were introduced in IgG1-2F8. These mutants were combined with IgG4-7D8, containing a CPSC hinge (wild type) or a stabilized hinge (IgG4-7D8-CPPC), for Fab-arm exchange using 25 mM 2-MEA for 90 min at 37° C. FIG. 10A-B shows that the IgG1-2F8-IL and -TL mutants showed Fab-arm exchange to the same level as the triple mutant ITL, irrespective of the combined IgG4-7D8 (CPSC or CPPC hinge). In contrast, no bispecific binding was found for the combination with the IgG1-2F8-IT mutant. FIG. 10C shows that also the IgG1-2F8-F405L mutant showed Fab-arm exchange, irrespective of the combined IgG4-7D8 (CPSC or CPPC hinge). These data indicate that the F405L mutation is sufficient to engage human IgG1 for Fab-arm exchange under the conditions mentioned above.

Example 17: Generation of Bispecific Antibodies by 2-MEA-Induced Fab-Arm Exchange at Different Temperatures The ability of 2-MEA to induce the generation of bispecific antibodies by Fab-arm exchange between two different antibodies, was tested at different temperatures. The Fab-arm exchange reactions were started by incubating 160 μg human IgG1-2F8-ITL with 160 μg IgG4-7D8-CPPC in 320 μl PBS/25 mM 2-MEA (final concentration of 0.5 mg/mL for each antibody) at either 0° C., 20° C. (RT) or 37° C.

From these reactions, 20 µL samples were taken at different time points (0, 2.5, 5, 10, 15, 30, 45, 60, 75, 90, 120, 150, 180 and 240 min). 20 µL PBS was added to each sample before the reducing agent 2-MEA was removed by desalting the samples using a Zeba 96-well spin desalting plate (7 k, cat #89808 Thermo Fisher Scientific), according to the manufacturer's recommendations. The total antibody concentrations were determined by measuring absorbance at 280 nm wavelength using a Nanodrop ND-1000 spectrophotometer (Isogen Life Science, Maarssen, The Netherlands). Dilution series of the antibody samples (total antibody concentration 0-20 µg/mL in 25-fold dilutions) were used in an ELISA to measure bispecific binding as described in Example 7.

Figure 11:
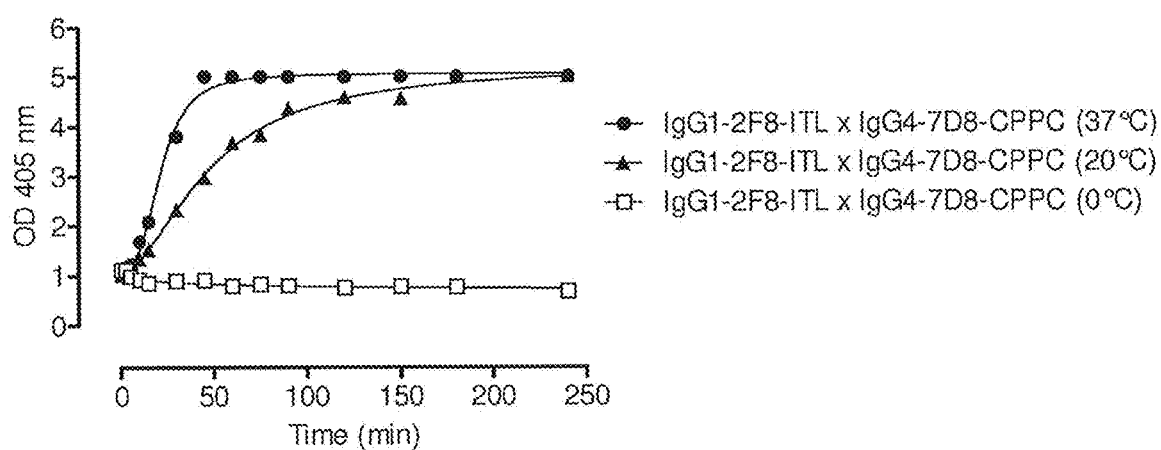
FIG. 11: Generation of bispecific antibodies using 2-MEA-induced Fab-arm exchange at different temperatures. The generation of bispecific antibodies by combining the indicated human EGFR (2F8) and CD20 (7D8) antibodies in 2-MEA-induced in vitro Fab-arm exchange reactions at 0° C., 20° C. and 37° C. was followed in time by an ELISA. Induction of bispecific binding was most efficient at 37° C., and slower at 20° C. At 0° C., no generation of bispecific binding was measured.

FIG. 11 shows that the generation of bispecific antibodies by 2-MEA-induced Fab-arm exchange between human IgG1-2F8-ITL and IgG4-7D8-CPPC was found to be most efficient at 37° C., with maximal bispecific binding reached after 45 min. At room temperature, the generation of bispecific antibodies was slower, reaching maximal bispecific binding after 240 min. At 0° C., no generation of bispecific binding was observed during the analyzed time course.

Example 18: Analysis of Different Reducing Agents for their Ability to Induce the Generation of Bispecific Antibodies by In Vitro Fab-Arm Exchange It has been shown above that 0.5 mM GSH can induce in vitro Fab-arm exchange between human IgG4 and IgG1-CPSC-ITL, but not between human IgG4 and IgG1-ITL containing a stable hinge (FIG. 3). In addition, 2-MEA was found to be able to induce Fab-arm exchange between antibodies with stabilized hinge regions, such as IgG1-ITL× IgG4-CPPC (FIG. 5). To test whether other concentrations of GSH or 2-MEA or other reducing agents are capable of inducing in vitro Fab-arm exchange between two different antibodies, concentration series of 2-MEA, GSH and DTT (dithiothreitol) were tested. Therefore, combinations of 10 µg human IgG1-2F8-ITL and 10 µg IgG4-7D8-CPPC in 20 µl PBS (final concentration of 0.5 mg/mL for each antibody) were incubated at 37° C. with concentration series of the different reducing agents (0.0, 0.04, 0.1, 0.2, 0.5, 1.0, 2.5, 5.0, 12.5, 25.0 and 50.0 mM). After 90 min, 20 µL PBS was added to each sample and the reducing agent was removed by desalting the samples using spin desalting plate as described in Example 17. Total antibody concentrations were determined as described in Example 17. Dilution series of the antibody samples (total antibody concentration 0-20 µg/mL in 3-fold dilutions) were used in an ELISA to measure bispecific binding as described in Example 7.

Figure 12:
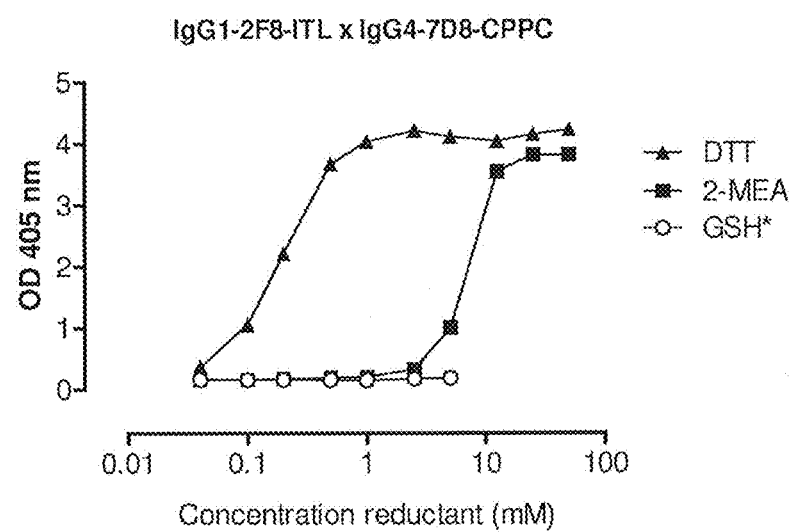
FIG. 12: Generation of bispecific antibodies by in vitro Fab-arm exchange induced by different reducing agents. An ELISA was used to measure the generation of bispecific antibodies by combining human IgG1-2F8-ITL and IgG4-7D8-CPPC in a reduction reaction with concentration series of the indicated reducing agents. Bispecific binding was measured after the reactions with DTT (maximum obtained at 2.5 mM DTT) and 2-MEA (maximum obtained at 25 mM 2-MEA), but not with GSH. (*) Data for GSH concentrations >10 mM were excluded due to the formation of antibody aggregates.

FIG. 12 confirms that 2-MEA induces maximal bispecific binding at a concentration of 25 mM 2-MEA. DTT was found to be very effective in the generation of bispecific antibodies with maximal bispecific binding reached at 2.5 mM DTT. GSH concentrations in the range 0-5 mM were not able to induce the generation of bispecific antibodies by Fab-arm exchange between the IgG1-ITL and IgG4-CPPC antibodies, both containing stabilized hinge regions. Higher GSH concentrations (12.5-50 mM) resulted in the formation of antibody aggregates, as was determined by non-reducing SDS-PAGE (data not shown). Therefore, these samples were excluded from the analysis. These data show that the generation of bispecific antibodies by Fab-arm exchange between two different antibodies can be induced by different reducing agents.

Example 19: Determinants at the IgG1 409 Position for Engagement in 2-MEA-Induced Fab-Arm Exchange in Combination with IgG1-ITL 2-MEA can induce Fab-arm exchange between human IgG1-ITL and IgG4-CPPC, as described in Example 11 (FIG. 5). The CH3 interface residues of human IgG1 and IgG4 differ at position 409 only: lysine (K) in IgG1 and arginine (R) in IgG4 (described in Example 8, FIG. 2). Therefore, it was tested whether substitution of lysine at position 409 by arginine or any other amino acid (K409X) could enable IgG1 to engage in 2-MEA-induced Fab-arm exchange with IgG1-ITL. Combinations of 10 µg human IgG1-2F8-ITL and 10 µg IgG1-7D8-K409X in 20 µl PBS/25 mM 2-MEA (final concentration of 0.5 mg/mL for each antibody) were incubated for 90 min at 37° C. Unpurified antibodies from supernatants of transient transfections were used after buffer-exchange to PBS using Amicon Ultra centrifugal devices (30 k, Millipore, cat. no. UFC803096). After the Fab-arm exchange reaction, 20 µL PBS was added to each sample and the reducing agent was removed by desalting the samples using spin desalting plate as described in Example 17. Dilution series of the antibody samples (total antibody concentration 0-20 µg/mL in 3-fold dilutions) were used in an ELISA to measure bispecific binding as described in Example 7.

Figure 13A:
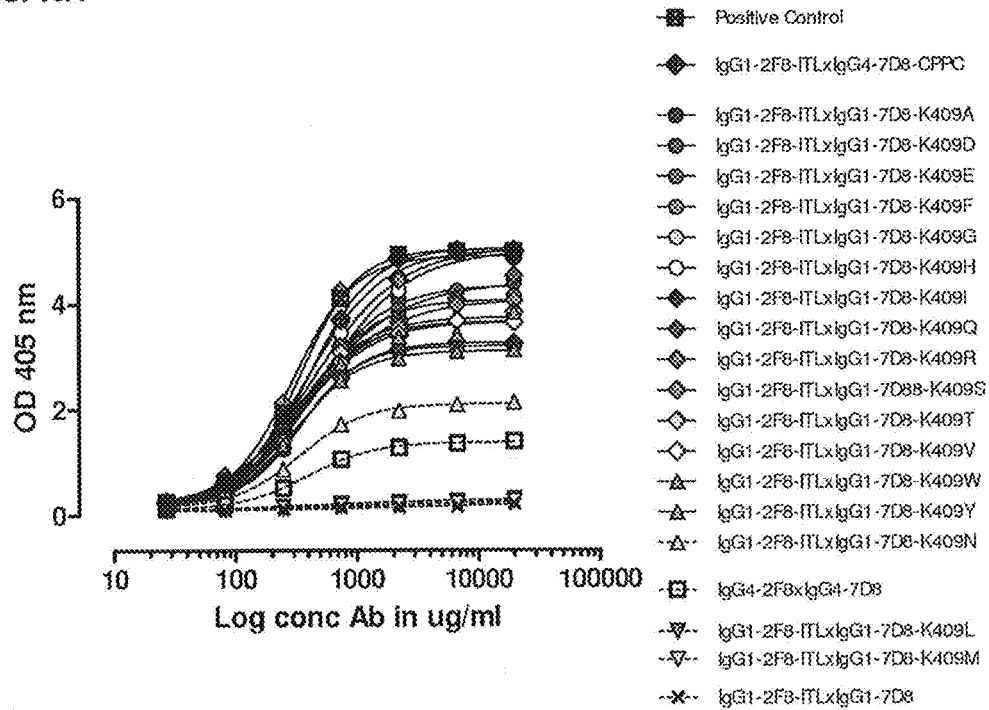
FIGS. 13A and 13B: 2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and the indicated IgG1-7D8-K409X mutants was determined by an ELISA.
Figure 13B:
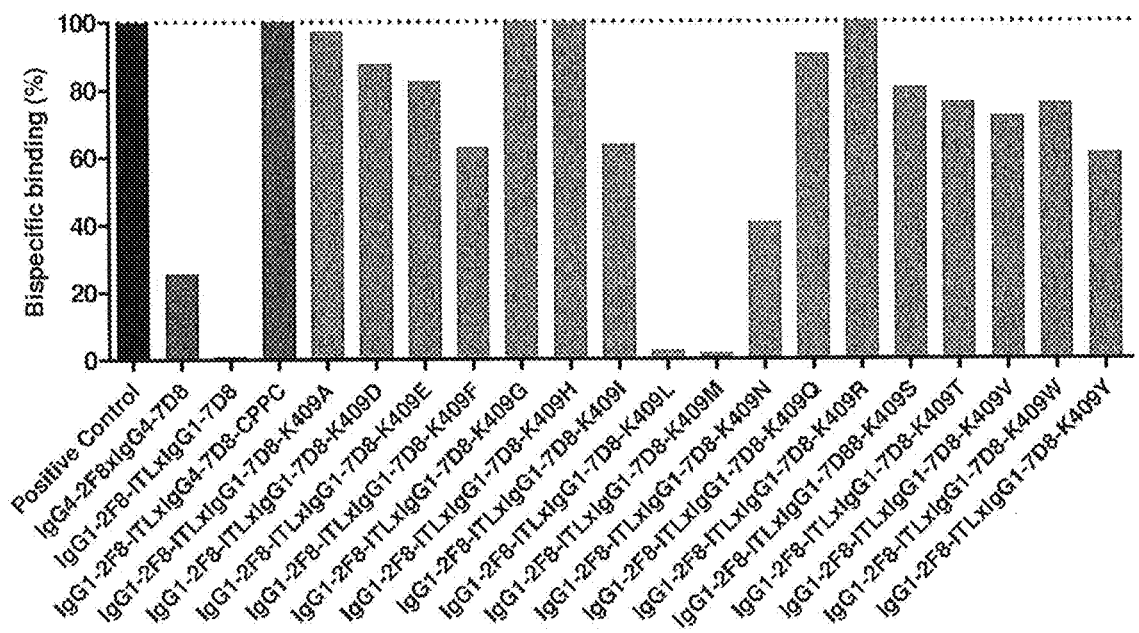

FIG. 13A shows the results of bispecific binding upon 2-MEA induced Fab-arm exchange between IgG1-2F8-ITL×IgG1-7D8-K409X. In FIG. 13B, the exchange is presented as bispecific binding relative to a purified batch of bispecific antibody derived from a 2-MEA-induced Fab-arm-exchange between IgG1-2F8-ITL and IgG4-7D8-CPPC, which was set to 100%. These data were also scored as (−) no Fab-arm exchange, (+/−) low, (+) intermediate or (++) high Fab-arm exchange, as presented in Table 1. No Fab-arm exchange (−) was found when the 409 position in IgG1-7D8 was K (=wild type IgG1), L or M. Fab-arm exchange was found to be intermediate (+) when the 409 position in IgG1-7D8 was F, I, N or Y and high (++) when the 409 position in IgG1-7D8 was A, D, E, G, H, Q, R, S, T, V or W.

TABLE 1

2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and IgG1-7D8-K409X mutants was determined by a sandwich ELISA. (−) no, (+/−) low, (+) intermediate, (++) high Fab-arm exchange.

| IgG1-7D8-K409X | Fab-arm exchange X IgG1-2F8-ITL |
| --- | --- |
| A | ++ |
| D | ++ |
| E | ++ |
| F | + |
| G | ++ |
| H | ++ |
| I | + |
| K | − |
| L | − |
| M | − |
| N | + |
| Q | ++ |
| R | ++ |
| S | ++ |

TABLE 1-continued

2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and IgG1-7D8-K409X mutants was determined by a sandwich ELISA. (−) no, (+/−) low, (+) intermediate, (++) high Fab-arm exchange.

| IgG1-7D8-K409X | Fab-arm exchange<br>X IgG1-2F8-ITL |
|---|---|
| T | ++ |
| V | ++ |
| W | ++ |
| Y | + |

Example 20: Antibody Deglycosylation does not Influence the Generation of Bispecific Antibodies by 2-MEA-Induced Fab-Arm Exchange IgG4-7D8 and IgG4-7D8-CPPC samples were deglycosylated by incubating 200 μg antibody overnight at 37° C. with 0.005 U N-Glycanase (cat. no. GKE-5006D; Prozyme) in 180 μL PBS. These samples were used directly in a Fab-arm exchange reaction. Fab-arm exchange was performed by incubating 50 μg of each antibody in 100 μl PBS/25 mM 2-MEA (final concentration of 0.5 mg/mL for each antibody) for 90 min at 37° C. The reducing agent 2-MEA was removed by desalting the samples using spin columns as described in Example 11. Dilution series of the antibody samples (total antibody concentration 0-20 μg/mL in 3-fold dilutions) were used in a sandwich ELISA to measure bispecific binding as described in Example 7.

Figure 14:
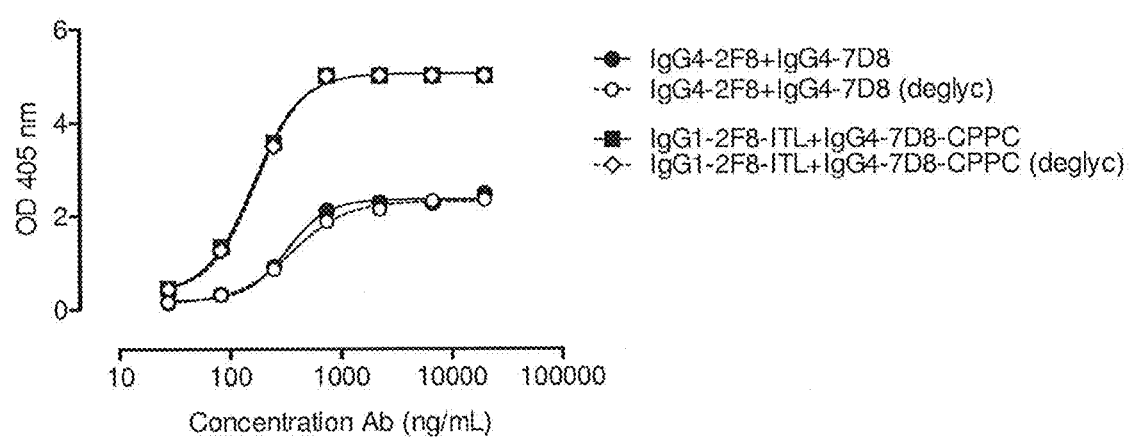
FIG. 14: Antibody deglycosylation does not affect the generation of bispecific antibodies by 2-MEA-induced Fab-arm exchange. The generation of bispecific antibodies after 2-MEA-induced in vitro Fab-arm exchange between the indicated EGFR (2F8) and CD20 (7D8) antibodies was determined by an ELISA. Exchange with the 7D8 antibodies was compared with their enzymatically deglycosylated variants. A concentration series (total antibody) of 0-20 µg/mL was analyzed in the ELISA. Fab-arm exchange reactions involving deglycosylated (deglyc) antibodies showed identical bispecific binding curves as the glycosylated variants from which they were derived.

Mass spectrometry analysis showed that the deglycosylation reaction resulted in 100% deglycosylated antibody product (data not shown). FIG. 14 shows that Fab-arm exchange involving deglycosylated antibodies did not differ from Fab-arm exchange with the corresponding glycosylated antibodies (IgG4-2F8×IgG4-7D8-deglycosylated versus IgG4-2F8×IgG4-7D8 and IgG1-2F8-ITL×IgG4-7D8-CPPC-deglycosylated versus IgG1-2F8-ITL×IgG4-7D8-CPPC). These data indicate that deglycosylation did not affect the generation of bispecific antibodies by 2-MEA-induced Fab-arm exchange.

Example 21: Quantification of the Non-Covalent CH3-CH3 Interaction

The strength of the interactions at the CH3 interface should be such that it is possible that both heavy chains in the parental antibodies dissociate in the Fab-arm exchange reaction and that they subsequently associate in the heterodimerization reaction. Therefore, the correlation between the ability to participate in Fab-arm exchange and the strength of the non-covalent CH3-CH3 interaction (dissociation constant, $K_D$) was analyzed. GSH-induced Fab-arm exchange was performed as described in Example 9 (0.5 mM GSH at 37° C.) for the following combinations of human antibodies:

IgG1-2F8×IgG1-7D8
IgG1-2F8-CPSC×IgG1-7D8-CPSC
IgG1-2F8-CPSC-T350I×IgG1-CPSC-7D8-T350I
IgG1-2F8-CPSC-K370T×IgG1-7D8-CPSC-K370T
IgG1-2F8-CPSC-ITL×IgG1-7D8-CPSC-ITL
IgG1-2F8-CPSC-K409R×IgG1-7D8-CPSC-K409R
IgG4-2F8×IgG4-7D8
IgG4-2F8-R409K×IgG4-7D8-R409K
IgG4-2F8-R409A×IgG4-7D8-R409A
IgG4-2F8-R409L×IgG4-7D8-R409L
IgG4-2F8-R409M×IgG4-7D8-R409M
IgG4-2F8-R409T×IgG4-7D8-R409T
IgG4-2F8-R409W×IgG4-7D8-R409W
IgG4-2F8-F405A×IgG4-7D8-F405A
IgG4-2F8-F405L×IgG4-7D8-F405L
IgG4-2F8-Y349D×IgG4-7D8-Y349D
IgG4-2F8-L351K×IgG4-7D8-L351K
IgG4-2F8-E357T×IgG4-7D8-E357T
IgG4-2F8-S364D×IgG4-7D8-S364D
IgG4-2F8-K370Q×IgG4-7D8-K370Q
IgG4-2F8-K370E×IgG4-7D8-K370E

Figure 15A:
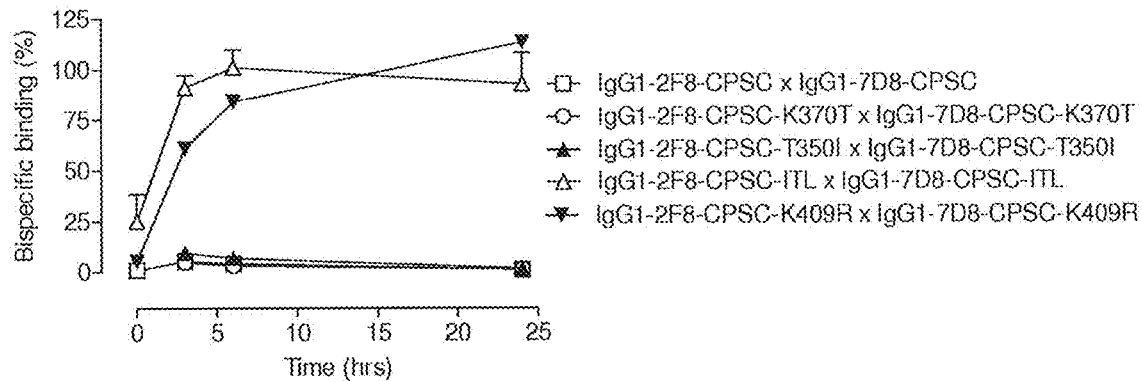
FIGS. 15A-15E: The ability to engage in Fab-arm exchange is correlated to the CH3-CH3 interaction strength.
Figure 15B:
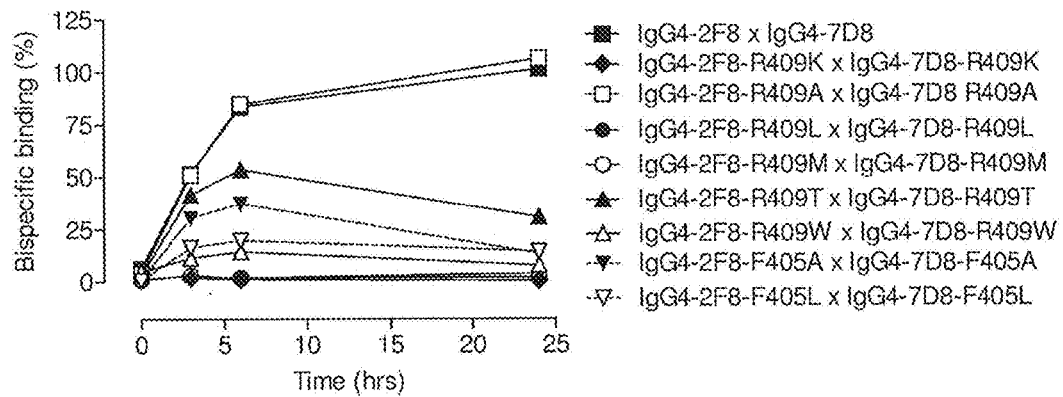
Figure 15C:
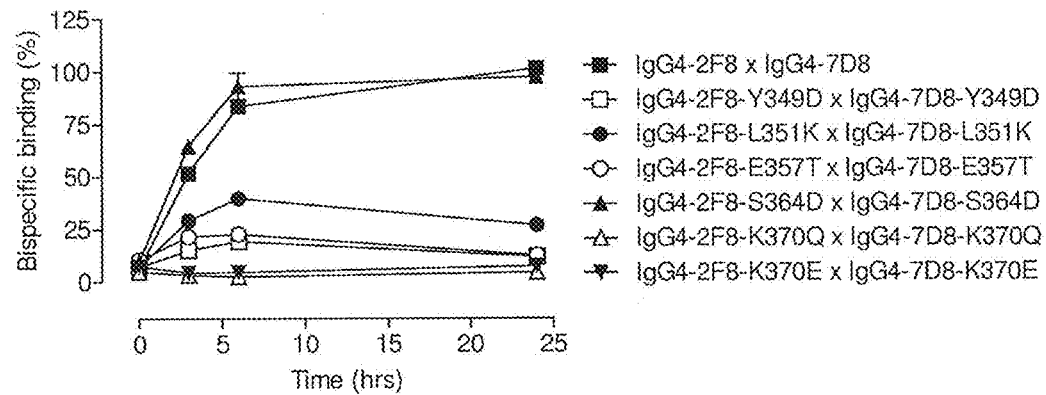

The generation of bispecific antibodies was measured by determination of bispecific binding in a sandwich ELISA as described in Example 7. FIGS. 15A/B/C show the results of the bispecific binding after the Fab-arm exchange reaction.

To measure the effect of the above mentioned CH3 mutations on the strength of the CH3-CH3 interaction, fragments composed of only the CH2-CH3 domains were made. The lack of a hinge region in these fragments prevented covalent inter-heavy chain disulfide bonds. The fragments were analyzed by native mass spectrometry. Samples were buffer-exchanged to 100 mM ammonium acetate pH 7, using 10 kDa MWCO spin-filter columns. Aliquots (~1 μL) of serial diluted samples (20 μM-25 nM; monomer equivalent) were loaded into gold-plated borosilicate capillaries for analysis on a LCT mass spectrometer (Waters). The monomer signal, $M_s$, was defined as the area of the monomer peaks as a fraction of the area of all peaks in the spectrum ($M_s/(M_s+D_s)$ where $D_s$=the dimer signal). The concentration of monomer at equilibrium, $[M]_{eq}$, was defined as $M_s \cdot [M]_0$ where $[M]_0$ is the overall protein concentration in terms of monomer. The dimer concentration at equilibrium, $[D]_{eq}$, was defined as $([M]_0-[M]_{eq})/2$. The $K_D$, was then extracted from the gradient of a plot of $[D]_{eq}$ versus $[M]_{eq}^2$. The $K_D$ of the non-covalent CH3-CH3 interactions is presented in Table 2.

Figure 15D:
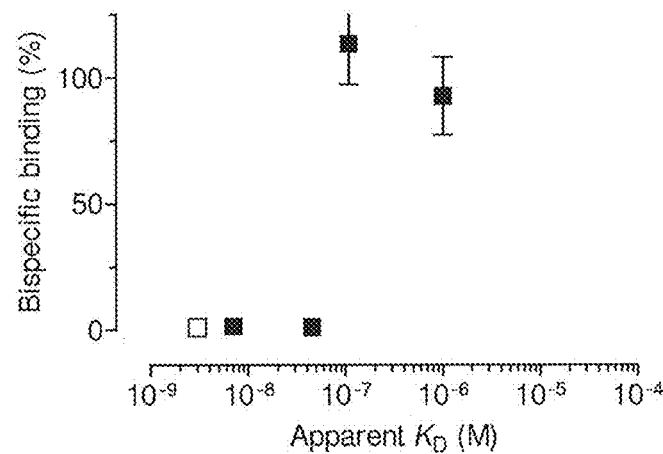
Figure 15E:
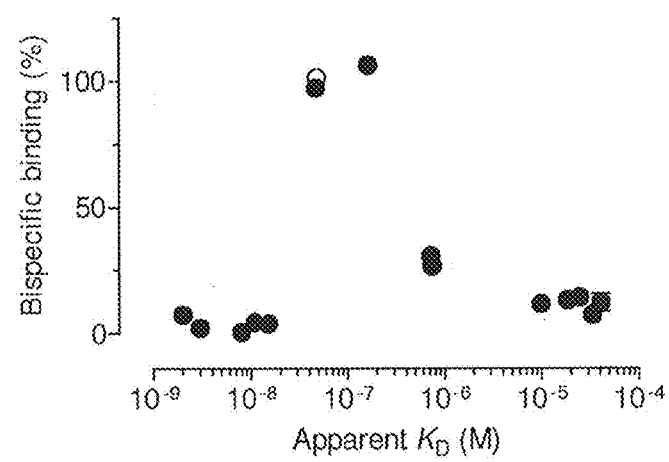

The correlation between the ability to engage in Fab-arm exchange and the strength of the non-covalent CH3-CH3 interactions was analyzed. FIGS. 15D/E show the percentage bispecific binding after Fab-arm exchange plotted against the measured $K_D$ of the corresponding CH2-CH3 fragment (FIG. 15D for IgG1; FIG. 15E for IgG4). These data suggest that under the tested conditions there is a specific range of apparent $K_D$ values of the CH3-CH3 interaction that allows efficient Fab-arm exchange.

TABLE 2

The $K_D$ of the non-covalent CH3—CH3 interactions

| CH2—CH3 construct | $K_D$ (M) | fold-difference* |
|---|---|---|
| G1 | $3.0 \times 10^{-9}$ | 1.0000 |
| G1-T350I | $7.0 \times 10^{-9}$ | 0.4000 |
| G1-K370T | $4.5 \times 10^{-8}$ | 0.0700 |
| G1-ITL | $1.0 \times 10^{-6}$ | 0.0030 |
| G1-K409R | $1.1 \times 10^{-7}$ | 0.0300 |
| G4 | $4.8 \times 10^{-8}$ | 1.0000 |
| G4-R409K | $8.0 \times 10^{-9}$ | 6.0000 |
| G4-R409A | $1.6 \times 10^{-7}$ | 0.3000 |
| G4-R409L | $1.5 \times 10^{-8}$ | 3.2000 |
| G4-R409M | $3.0 \times 10^{-9}$ | 16.0000 |
| G4-R409T | $7.2 \times 10^{-7}$ | 0.0700 |
| G4-R409W | $3.4 \times 10^{-5}$ | 0.0014 |
| G4-F405A | $1.9 \times 10^{-5}$ | 0.0025 |
| G4-F405L | $2.5 \times 10^{-5}$ | 0.0019 |
| G4-L351K | $7.4 \times 10^{-7}$ | 0.0600 |
| G4-E357T | $4.1 \times 10^{-5}$ | 0.0012 |
| G4-S364D | $4.7 \times 10^{-8}$ | 1.0200 |

TABLE 2-continued

| The $K_D$ of the non-covalent CH3—CH3 interactions | | |
|---|---|---|
| CH2—CH3 construct | $K_D$ (M) | fold-difference* |
| G4-K370Q | $1.1 \times 10^{-8}$ | 4.3000 |
| G4-K370E | $2.0 \times 10^{-9}$ | 24.0000 |

*Compared to the corresponding CH2—CH3 fragments of wild type IgG1 or IgG4

Example 22: Analysis of Different Reductantia for their Ability to Induce the Generation of Bispecific Antibodies by In Vitro Fab-Arm-Exchange Between IgG1-2F8-F405L and IgG1-7D8-K409R 2-MEA and DTT were found to induce in vitro Fab-arm-exchange between human IgG1-ITL and IgG4-CPPC (FIG. 12). It was tested whether these reductantia can also induce in vitro Fab-arm-exchange between human IgG1-2F8-F405L and IgG1-7D8-K409R. Concentration series of 2-MEA, DTT, GSH and TCEP (tris(2-carboxyethyl)phosphine) were tested. Fab-arm-exchange was performed as described in Example 18. The tested concentration series of the different reducing agents were as follows: 0.0, 0.04, 0.1, 0.2, 0.5, 1.0, 5.0, 25.0, 50.0 mM 2-MEA, GSH, DTT or TCEP.

Figure 17:
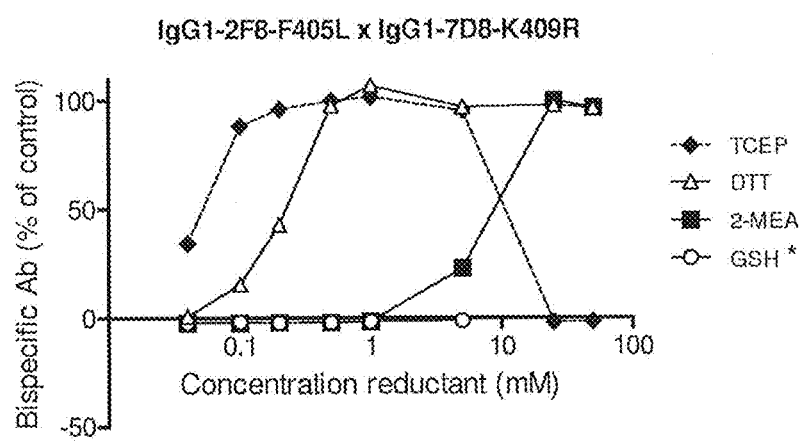
FIG. 17: Generation of bispecific antibodies by in vitro Fab-arm exchange induced by different reducing agents. An ELISA was used to measure the generation of bispecific antibodies by combining human IgG1-2F8-F405L and IgG1-7D8-K409R in a reduction reaction with concentration series of the indicated reducing agents. Measured OD values were normalized to the signal of a bispecific control sample derived from 2-MEA-induced Fab-arm exchange between IgG1-2F8-ITL×IgG4-7D8-CPPC, which was set to 100%. Maximal bispecific binding was measured after the reactions with DTT in the concentration range 0.5-50 mM, 2-MEA in the concentration range 25-50 mM and tris(2-carboxyethyl) phosphine (TCEP) in the concentration range 0.5-5.0 mM, but not with GSH. (*) Data for GSH concentration ≥25 mM were excluded due to the formation of antibody aggregates.

FIG. 17 confirms that 2-MEA induces maximal Fab-arm-exchange at a concentration of 25 mM 2-MEA, which persisted at the higher concentration of 50.0 mM 2-MEA. DTT was found to be very effective in the generation of bispecific antibodies with maximal Fab-arm-exchange reached at 0.5 mM DDT, which also persisted over higher concentrations of DTT (1.0-50.0 mM). Also TCEP was found to be very effective in the generation of bispecific antibodies with maximal Fab-arm-exchange reached at 0.5 mM. At a concentration ≥25.0 mM, Fab-arm-exchange by TCEP was disturbed. GSH concentrations in the range 0.0-5.0 mM were not able to induce the generation of bispecific antibodies by Fab-arm-exchange. Higher GSH concentrations (25.0-50.0 mM) resulted in the formation of antibody aggregates (data not shown). Therefore, these samples were excluded from the analysis. These data show that the generation of bispecific antibodies by Fab-arm-exchange between two different antibodies can be induced by different reducing agents.

Example 23: Generation of Bispecific Antibodies by 2-MEA-Induced Fab-Arm-Exchange Between IgG1-2F8-F405L and IgG1-7D8-K409R To confirm the formation of bispecific antibodies by 2-MEA-induced Fab-arm exchange between human IgG1-2F8-F405L and IgG1-7D8-K409R, the molecular weights of samples from the Fab-arm-exchange reactions with a concentration series of 2-MEA were determined by ESI-MS. The tested concentration series was as follows: 0.0, 0.5, 1.0, 2.0, 5.0, 7.0, 10.0, 15.0, 25.0 and 40.0 mM 2-MEA. Fab-arm-exchange (in PBS) and sandwich ELISA were performed as described in Example 11. ESI-MS was performed as described in Example 12.

Figure 18A:
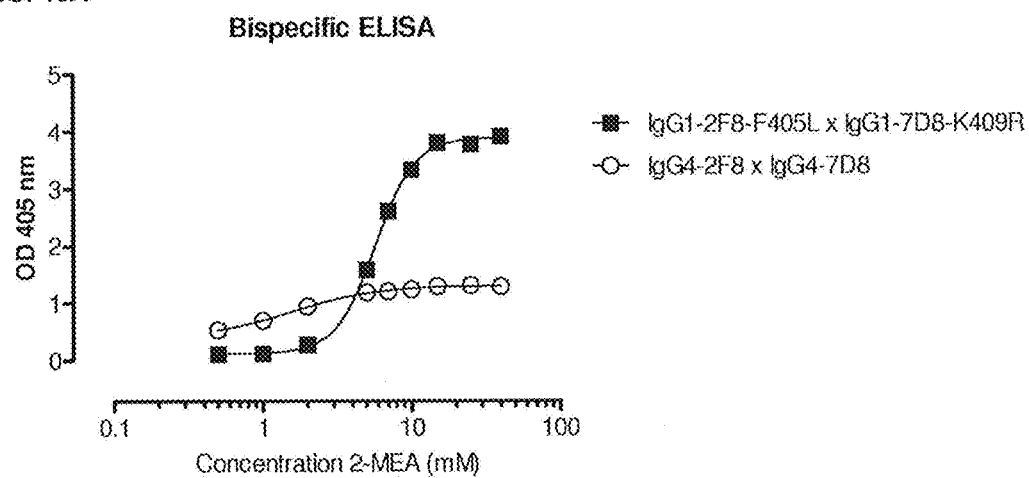
FIGS. 18A and 18B: Generation of bispecific antibodies using 2-MEA-induced Fab-arm exchange between human IgG1-2F8-F405L and IgG1-7D8-K409R.
Figure 18B:
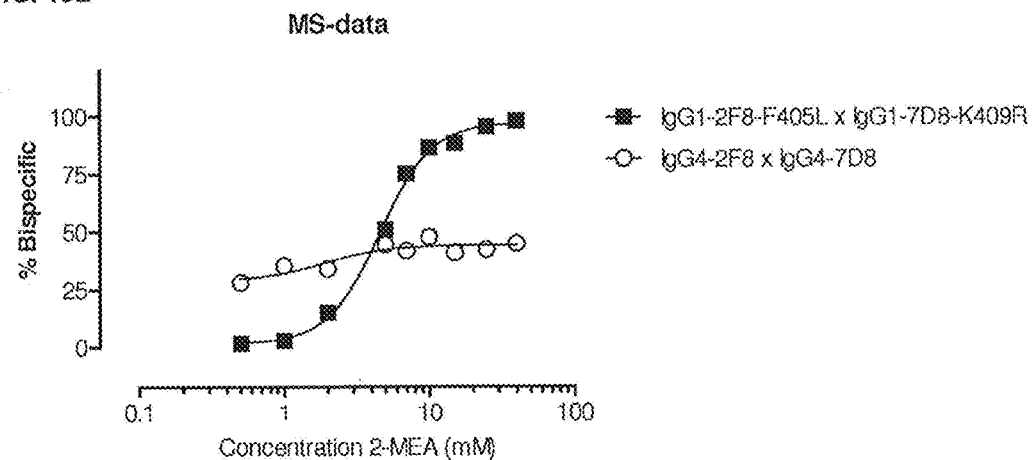

FIG. 18A shows that 2-MEA induced Fab-arm-exchange between IgG1-2F8-F405L and IgG1-7D8-K409R in a dose-dependent manner, efficiently leading to the generation of bispecific antibodies with a maximal level of bispecific binding at a concentration of 15.0 mM 2-MEA. The quantified ESI-MS data are presented in FIG. 18B and show that Fab-arm-exchange between IgG1-2F8-F405L and IgG1-7D8-K409R resulted in nearly 100% bispecific antibody, confirming the results from the bispecific-binding ELISA.

Example 24: Purity of the Bispecific Antibody Generated by 2-MEA-Induced Fab-Arm-Exchange Between Human IgG1-2F8-F405L×IgG1-7D8-K409R A batch of bispecific antibody, generated by 2-MEA-induced Fab-arm-exchange between human IgG1-2F8-F405L×IgG1-7D8-K409R, was purified using a PD-10 desalting column (cat. no. 17-0851-01; GE Healthcare). Next, the purity of the bispecific product was analyzed by mass spectrometry as described in Example 12.

FIG. 19 shows the mass spectrometry profiles of the starting materials IgG1-2F8-F405L and IgG1-7D8-K409R and the bispecific product generated by Fab-arm-exchange between IgG1-2F8-F405L×IgG1-7D8-K409R. The product in the Fab-arm-exchanged sample is 146,160.7 kDa, which matches with the bispecific product derived from IgG1-2F8-F405L (146,606.8/2=73,303.3)×IgG1-7D8-K409R (146,312.2/2=73,156.1)=146,459.4 kDa. Moreover, the bispecific antibody product showed a homogenous peak, indicating that no light chain mispairing occurred, which would have resulted in subdivided peaks. These data show that Fab-arm-exchange resulted in approximately 100% bispecific antibody.

Example 25: In Vivo Analysis of the Stability and Pharmacokinetics of Bispecific Antibodies Generated from IgG1-2F8-F405L×IgG1-7D8-K409R by 2-MEA-Induced Fab-Arm-Exchange The bispecific antibody generated by in vitro 2-MEA-induced Fab-arm-exchange between IgG1-2F8-F405L×IgG1-7D8-K409R was injected in SCID mice to analyze its stability (in vivo Fab-arm-exchange) and pharmacokinetic properties as described in Example 14. Two groups of mice (3 mice per group) were analyzed: (1) 100 µg bispecific antibody; (2) 100 µg bispecific antibody+1,000 µg irrelevant IgG4 (IgG4-637, described in WO2007068255). Total IgG concentrations in the plasma samples were assayed by ELISA as described in Example 14, with the exception that in this example, HRP-conjugated goat anti-human IgG (Jackson, cat. no. 109-035-098, 1/10,000) was used as a conjugate for detection. The presence of bispecific antibodies in the plasma samples was assayed and quantified by CD20 and EGFR bispecific reactivity in a sandwich ELISA as described in Example 14.

Figure 20A:
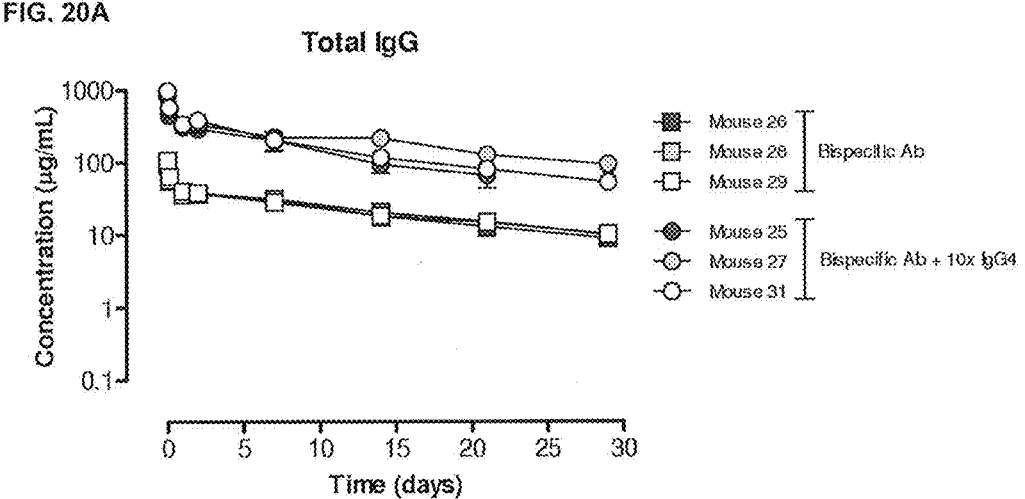
FIGS. 20A and 20B: Plasma clearance of a bispecific antibody generated by 2-MEA-induced Fab-arm exchange. Two groups of mice (3 mice per group) were injected with the indicated antibodies: (1) 100 µg bispecific antibody, generated by in vitro 2-MEA-induced Fab-arm-exchange between IgG1-2F8-F405L×IgG1-7D8-K409R; (2) 100 µg bispecific antibody+1,000 µg irrelevant IgG4 (10×IgG4).
Figure 20B:
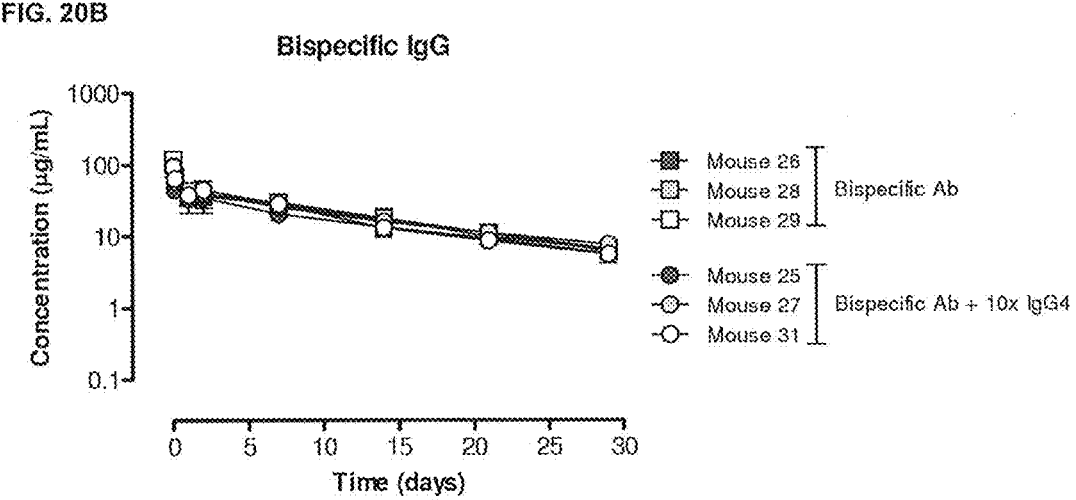

FIG. 20A shows total antibody plasma concentrations over time. The shape of the plasma clearance curves was identical in both groups. FIG. 20B shows the plasma concentrations of bispecific antibody over time. The addition of a 10-fold excess irrelevant IgG4 to the bispecific antibody did not affect bispecific antibody concentrations, indicating that no Fab-arm-exchange occurred in vivo. These data indicate that the bispecific antibody product, generated by in vitro 2-MEA-induced Fab-arm-exchange between IgG1-2F8-F405L×IgG1-7D8-K409R, was stable in vivo (no Fab-arm-exchange).

Example 26: CDC-Mediated Cell Kill by Bispecific Antibody Generated by 2-MEA-Induced Fab-Arm-Exchange Between Human IgG1-2F8-F405L×IgG1-7D8-K409R The CD20 antibody IgG1-7D8 can efficiently kill CD20-expressing cells by complement-dependent cytotoxicity (CDC). In contrast, the EGFR antibody IgG1-2F8 does not mediate CDC on target cells expressing EGFR. It was tested whether the mutant IgG1-7D8-K409R and the bispecific antibody generated by 2-MEA-induced Fab-arm-exchange between IgG1-2F8-F405L×IgG1-7D8-K409R were still able to induce CDC on CD20-expressing cells. $10^5$ Daudi or Raji cells were pre-incubated for 15 min with a concentration series of antibody in 80 µL RPMI medium supplemented with 0.1% BSA in a shaker at room temperature. 20 µL normal human serum (NHS) was added as a source of complement (20% NHS final concentration) and incubated for 45 min at 37° C. 30 µL ice cold RPMI medium supplemented with 0.1% BSA was added to stop the CDC reaction. Dead and viable cells were discriminated by adding 10 µL 10 µg/mL propidium iodide (PI) (1 µg/mL final concentration) and FACS analysis.

Figure 21A:
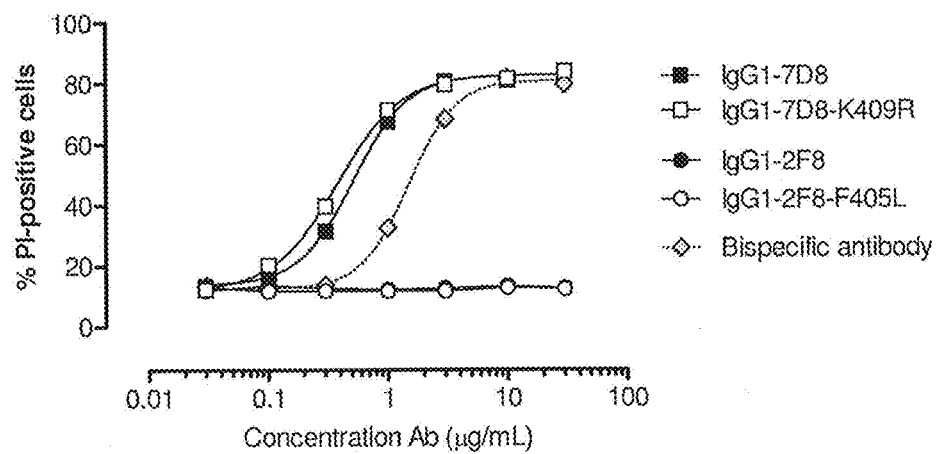
FIGS. 21A and 21B: CDC-mediated cell kill of CD20-expressing cells by a bispecific antibody generated by 2-MEA-induced Fab-arm exchange between IgG1-2F8-F405L×IgG1-7D8-K409R. Concentration series of the indicated antibodies were used to test their capacity to mediate CDC on Daudi (FIG. 21A) and Raji (FIG. 215) cells. Both cell lines express CD20, but not EGFR. Introduction of the K409R in IgG1-7D8 did not influence its capacity to induce CDC. The bispecific antibody derived from 2-MEA-induced Fab-arm exchange between IgG1-2F8-F405L×IgG1-7D8-K409R was still capable to induce CDC.
Figure 21B:
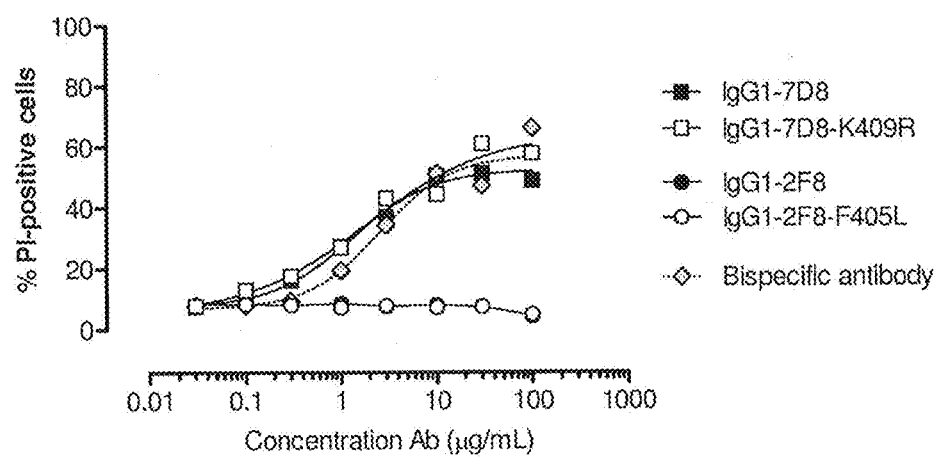

FIG. 21 shows that CDC-mediated cell kill of CD20-expressing Daudi (FIG. 21A) and Raji (FIG. 21B) cells by IgG1-7D8 was not influenced by the introduction of the K409R mutation. Both Daudi and Raji cells do not express EGFR, resulting in monovalent binding of the bispecific antibody generated by 2-MEA-induced Fab-arm-exchange between IgG1-2F8-F405L×IgG1-7D8-K409R. Nonetheless, the bispecific antibody still induced CDC-mediated cell kill of the CD20-expressing cells. These data indicate that CDC capacity of a parental antibody was retained in the bispecific format.

Example 27: ADCC-Mediated Cell Kill by the Bispecific Antibody Generated by 2-MEA-Induced Fab-Arm-Exchange Between Human IgG1-2F8-F405L×IgG1-7D8-K409R The EGFR antibody IgG1-2F8 can kill EGFR-expressing cells, such as A431, by antibody-dependent cellular cytotoxicity (ADCC). A431 cells do not express CD20 and therefore the CD20 antibody IgG1-7D8 does not induce ADCC on these cells. It was tested whether the mutant IgG1-2F8-F405L and the bispecific antibody generated by 2-MEA-induced Fab-arm-exchange between IgG1-2F8-F405L×IgG1-7D8-K409R were still able to induce ADCC on A431 cells. For effector cell isolation, peripheral blood mononuclear cells (PBMCs) were isolated from whole blood of a healthy donor using Leucosep® tubes (Greiner Bio-one, cat. #227290) according to the manufacturer's recommendations. Target cells were labelled by adding 100 pCi $^{51}$Cr to $5\times10^6$ A431 cells in 1 mL RPMI medium supplemented with 0.1% BSA and incubating for 60 min in a 37° C. shaking water bath. Labelled cells were washed and resuspended in RPMI supplemented with 0.1% BSA. $5\times10^4$ labelled target cells in RPMI supplemented with 0.1% BSA were preincubated in 100 µL for 15 min with the antibody concentrations series (range 0-10 µg/mL final concentration in ADCC assay in 3-fold dilutions) at room temperature. The ADCC assay was started by adding 50 µL effector cells ($5\times10^6$ cells) in an E:T ratio 100:1. After 4 hours at 37° C., $^{51}$Cr release from triplicate experiments was measured in a scintillation counter as counts per min (cpm). The percentage of cellular toxicity was calculated using the following formula: percentage of specific lysis=(experimental cpm−basal cpm)/(maximal cpm−basal cpm)×100. Maximal $^{51}$Cr release was determined by adding 50 µL 5% Triton X-100 to 50 µL target cells ($5\times10^4$ cells), and basal release was measured in the absence of sensitizing antibody and effector cells.

Figure 22:
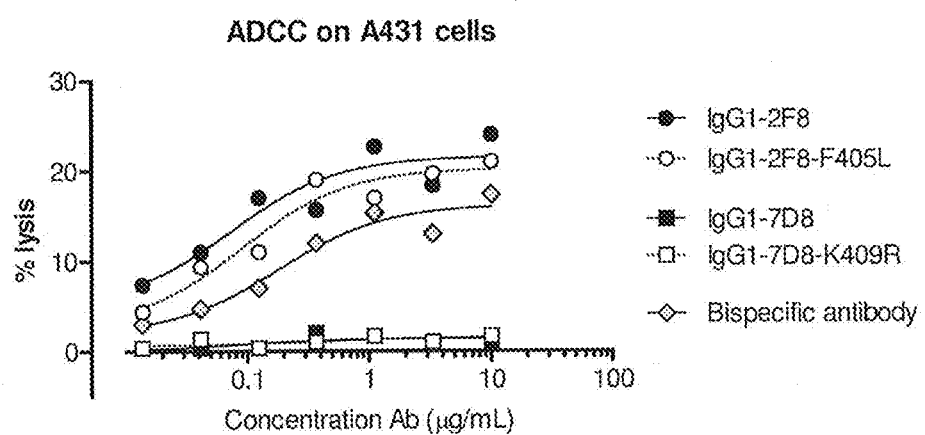
FIG. 22: ADCC-mediated cell kill of EGFR-expressing cells by a bispecific antibody generated by 2-MEA-induced Fab-arm exchange between IgG1-2F8-F405L×IgG1-7D8-K409R. Concentration series of the indicated antibodies were used to test their capacity to mediate ADCC on A431 cells. IgG1-7D8 can not bind the CD20-negative A431 cells and consequently did not induce ADCC. ADCC was induced by the EGFR antibody IgG1-2F8, also after introduction of the F405L mutations in the CH3 domain. The ADCC effector function of IgG1-2F8-F405L was retained in the bispecific format obtained by Fab-arm exchange between IgG1-2F8-F405L×IgG1-7D8-K409R.

FIG. 22 shows that the CD20-specific antibody IgG1-7D8 did not induce ADCC on the CD20-negative A431 cells.

Both IgG1-2F8 and the mutant IgG1-2F8-F405L were able to induce ADCC on A431 cells, indicating that introduction of the F405L mutation in IgG1-2F8 did not affect its ADCC effector function. Also the bispecific antibody derived from IgG1-2F8-F405L×IgG1-7D8-K409R induced ADCC on A431 cells in a dose-dependent manner, indicating that the ADCC effector function was retained in the bispecific format.

Example 28: Determinants at the IgG1 405 Position for Engagement in 2-MEA-Induced Fab-Arm-Exchange in Combination with IgG1-K409R In Example 16 it is described that the F405L mutation is sufficient to enable human IgG1 to engage in Fab-arm-exchange when combined with IgG4-7D8. To further test the determinants at the IgG1 405 position for engagement in 2-MEA-induced Fab-arm-exchange in combination with human IgG1-K409R, all possible IgG1-2F8-F405X mutants (with the exception of C and P) were combined with IgG1-7D8-K409R. The procedure was performed with purified antibodies as described in Example 19.

Figure 23A:
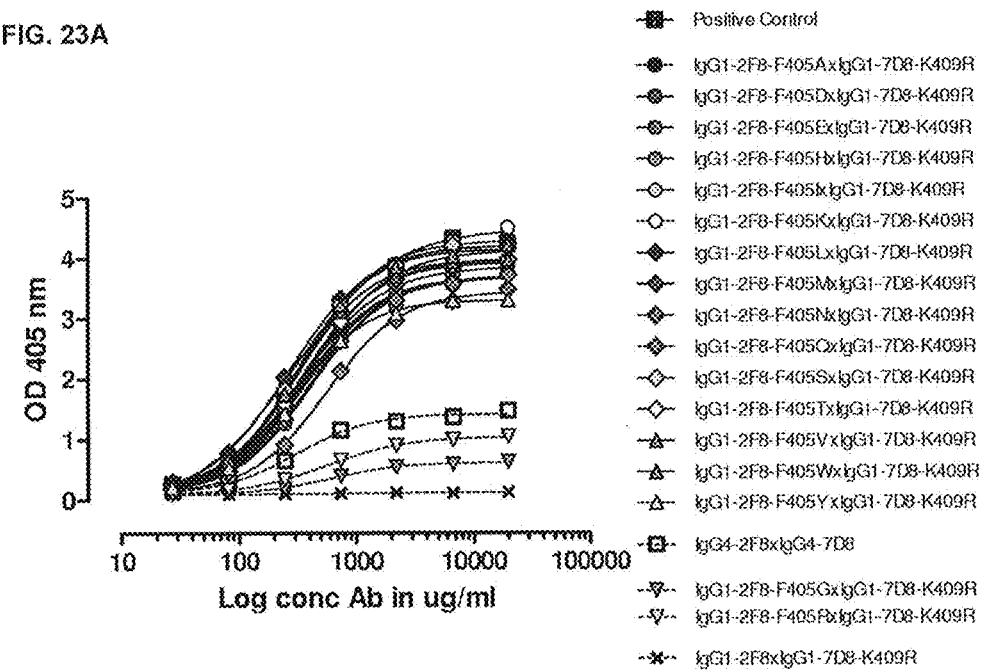
FIGS. 23A and 23B: 2-MEA-induced Fab-arm exchange between IgG1-2F8-F405X mutants and IgG1-7D8-K409R. The generation of bispecific antibodies after 2-MEA-induced in vitro Fab-arm exchange between the indicated IgG1-2F8-F405X mutants and IgG1-7D8-K409R was determined by an ELISA.
Figure 23B:
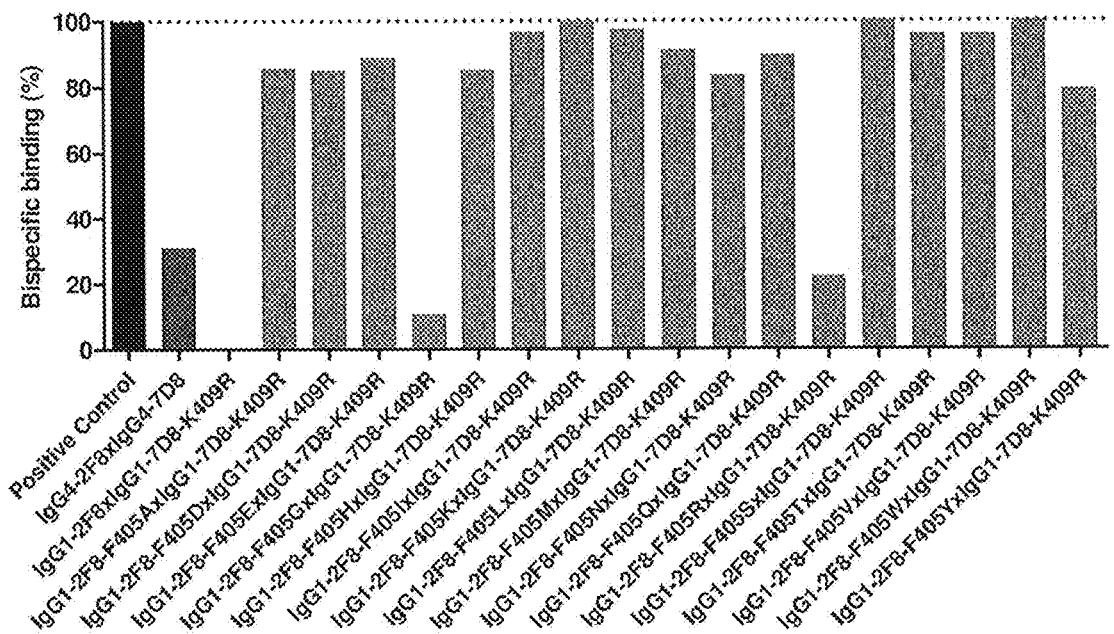

FIG. 23 shows the results of bispecific binding upon 2-MEA-induced Fab-arm-exchange between IgG1-2F8-F405X and IgG1-7D8-K409R. These data were also scored as (−) no Fab-arm exchange, (+/−) low, (+) intermediate or (++) high Fab-arm exchange, as presented in Table 3. No Fab-arm exchange (−) was found when the 405 position in IgG1-2F8 was F (=wild type IgG1). Fab-arm exchange was found to be low (+/−) when the 405 position in IgG1-2F8 was G or R. Fab-arm exchange was found to be high (++) when the 405 position in IgG1-2F8 was A, D, E, H, I, K, L, M, N, Q, S, T, V, W or Y. These data indicate that particular mutations at the IgG1 405 position allow IgG1 to engage in 2-MEA-induced Fab-arm-exchange when combined with IgG1-K409R.

TABLE 3

2-MEA-induced Fab-arm-exchange between IgG1-2F8-F405X mutants and IgG1-7D8-K409R.
The generation of bispecific antibodies after 2-MEA-induced in vitro Fab-arm-exchange between IgG1-2F8-F405X mutants and IgG1-7D8-K409R was determined by a sandwich ELISA. (−) no, (+/−) low, (+) intermediate, (++) high Fab-arm-exchange.

| IgG1-2F8-F405X | Fab-arm-exchange X IgG1-7D8-K409R |
| --- | --- |
| A | ++ |
| D | ++ |
| E | ++ |
| F | − |
| G | +/− |
| H | ++ |
| I | ++ |
| K | ++ |
| L | ++ |
| M | ++ |
| N | ++ |
| Q | ++ |
| R | +/− |
| S | ++ |
| T | ++ |
| V | ++ |
| W | ++ |
| Y | ++ |

Example 29: Determinants at the IgG1 407 Position for Engagement in 2-MEA-Induced Fab-Arm-Exchange in Combination with IgG1-K409R In Example 28, it is described that certain single mutations at position F405 are sufficient to enable human IgG1 to engage in Fab-arm-exchange when combined with IgG1-K409R. To test whether other determinants implicated in the Fc:Fc interface positions in the CH3 domain could also mediate the Fab-arm-exchange mechanism, mutagenesis of the IgG1 407 position was performed and the mutants were tested for engagement in 2-MEA-induced Fab-arm-exchange in combination with human IgG1-K409R. All possible IgG1-2F8-Y407X mutants (with the exception of C and P) were combined with IgG1-7D8-K409R. The procedure was performed with purified antibodies as described in Example 19.

Figure 24A:
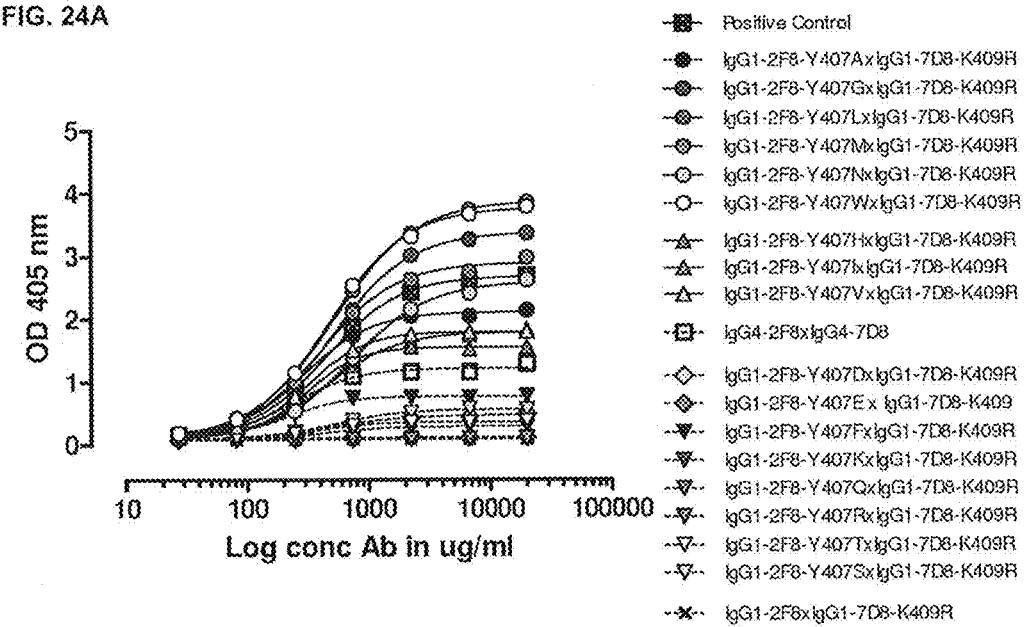
FIGS. 24A and 24B: 2-MEA-induced Fab-arm exchange between IgG1-2F8-Y407X mutants and IgG1-7D8-K409R. The generation of bispecific antibodies after 2-MEA-induced in vitro Fab-arm exchange between the indicated IgG1-2F8-Y407X mutants and IgG1-7D8-K409R was determined by an ELISA.
Figure 24B:
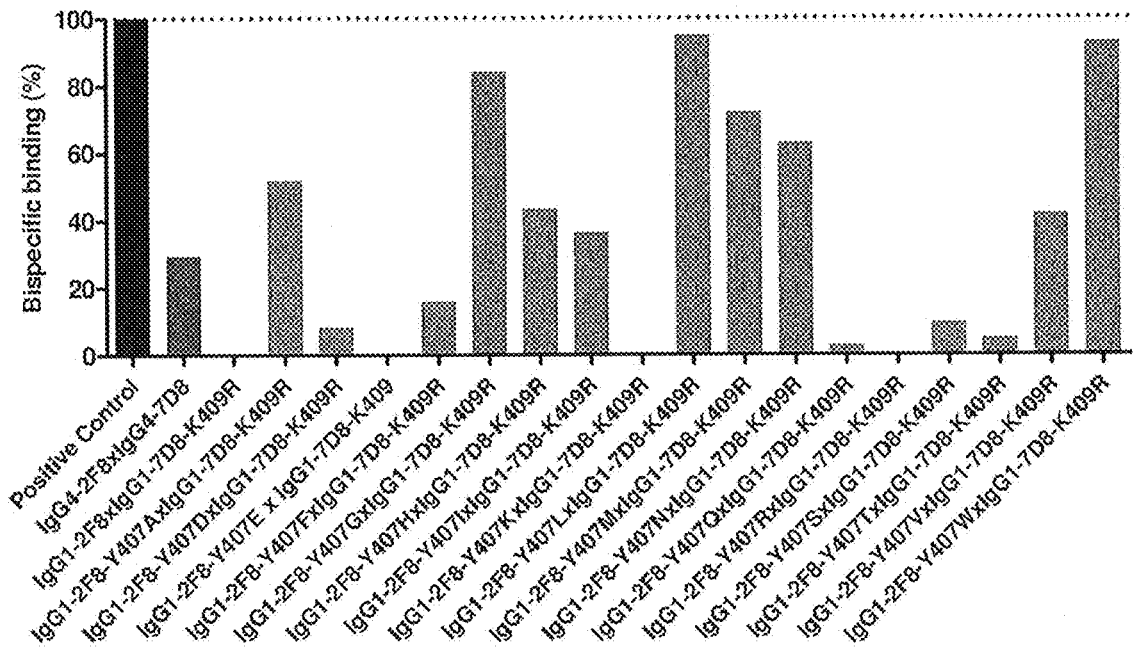

FIG. 24 shows the results of bispecific binding upon 2-MEA-induced Fab-arm-exchange between IgG1-2F8-Y407X×IgG1-7D8-K409R. These data were also scored as (−) no Fab-arm exchange, (+/−) low, (+) intermediate or (++) high Fab-arm exchange, as presented in Table 4. No Fab-arm exchange (−) was found when the 407 position in IgG1-2F8 was Y (=wild type IgG1), E, K, Q, or R. Fab-arm exchange was found to be low (+/−) when the 407 position in IgG1-2F8 was D, F, I, S or T and intermediate (+) when the 407 position in IgG1-2F8 was A, H, N or V, and high (++) when the 407 position in IgG1-2F8 was G, L, M or W. These data indicate that particular single mutations at the IgG1 407 position allow IgG1 to engage in 2-MEA-induced Fab-arm-exchange when combined with IgG1-K409R.

TABLE 4

2-MEA-induced Fab-arm-exchange between IgG1-2F8-Y407X mutants and IgG1-7D8-K409R
The generation of bispecific antibodies after 2-MEA-induced in vitro Fab-arm exchange between IgG1-2F8-Y407X mutants and IgG1-7D8-K409R was determined by a sandwich ELISA. (−) no, (+/−) low, (+) intermediate, (++) high Fab-arm-exchange.

| IgG1-2F8-Y407X | Fab-arm-exchange X IgG1-7D8-K409R |
|---|---|
| A | + |
| D | +/− |
| E | − |
| F | +/− |
| G | ++ |
| H | + |
| I | +/− |
| K | − |
| L | ++ |
| M | ++ |
| N | + |
| Q | − |
| R | − |
| S | +/− |
| T | +/− |
| V | + |
| W | ++ |
| Y | − |

Example 30: Quantification of the Non-Covalent CH3-CH3 Interaction in IgG1 Heterodimers It is described in Example 21 that there is a specific range in the strength of the interaction of the CH3-CH3 homodimers that allows efficient Fab-arm-exchange. The strength of the interactions at the CH3 interface should be such that it is possible that both heavy chains in the parental antibodies (homodimers) dissociate in the Fab-arm-exchange reaction and that they subsequently associate in the heterodimerization reaction. To generate a stable heterodimer, the strength of the heterodimer interaction should be greater than the strength of the homodimer interaction, such that it favors heterodimerization over homodimerization. To confirm this, the strength of the CH3-CH3 interaction in the heterodimers was measured and compared to the strength in the homodimers. The $K_D$ of the CH2-CH3 fragments derived from IgG1-K409R, IgG1-F405L and IgG1-ITL homodimers were measured as described in Example 21. For the determination of the $K_D$ in heterodimers, CH2-CH3 domain fragments (G1-F405L and G1-ITL) were mixed with the IgG1Δhinge fragment of IgG1-7D8-K409R, which contain all antibody domains except the hinge. The lack of hinge regions in both fragments prevented covalent inter-heavy chain disulfide bonds. The fragments were mixed and analyzed after 24 hours by native mass spectrometry as described in Example 21. The $K_D$ values of the non-covalent CH3-CH3 interactions in the indicated CH2-CH3 fragments or mixtures of CH2-CH3 fragments with IgG1Δhinge are presented in Table 5. These data suggest that under the tested conditions, the strength of the heterodimer interaction is greater (lower $K_D$) than the corresponding homodimer interactions.

TABLE 5

| CH2—CH3 construct/ (IgG1Δhinge) | Interaction | $K_D$ (M) |
|---|---|---|
| G1-F405L/G1-K409R | Heterodimer | $1.2 \times 10^{-8}$ |
| G1-ITL/G1-K409R | Heterodimer | $1.7 \times 10^{-8}$ |
| G1-K409R | Homodimer | $1.1 \times 10^{-7}$ |
| G1-F405L | Homodimer | $8.5 \times 10^{-7}$ |
| G1-ITL | Homodimer | $1.2 \times 10^{-6}$ |

Example 31: Biochemical Analysis of a Bispecific Antibody Generated by 2-MEA-Induced Fab-Arm Exchange A batch of bispecific antibody, generated by 2-MEA-induced Fab-arm exchange between human IgG1-2F8-F405L×IgG1-7D8-K409R, was purified on a PD-10 desalting column (cat. no. 17-0851-01; GE Healthcare). Next, the purity of the bispecific product was analyzed by sodium dodecyl sulfate polyacrylamide gelelectrophoresis (SDS-PAGE), High Performance Size Exclusion Chromatography (HP-SEC), mass spectrometry, HPLC cation exchange chromatography (HPLC-CIEX), capillary isoelectrofocussing (cIEF).

Figure 25A:
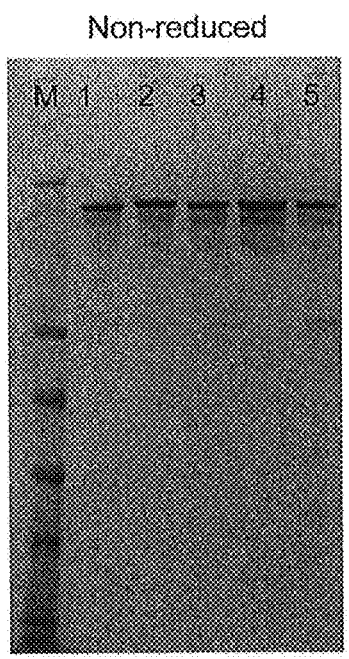
FIGS. 25A and 25B: Analysis of bispecific antibody generated by 2-MEA-induced Fab-arm exchange by SDS-PAGE under non-reducing (FIG. 25A) and reducing (FIG. 25B) conditions.
Figure 25B:
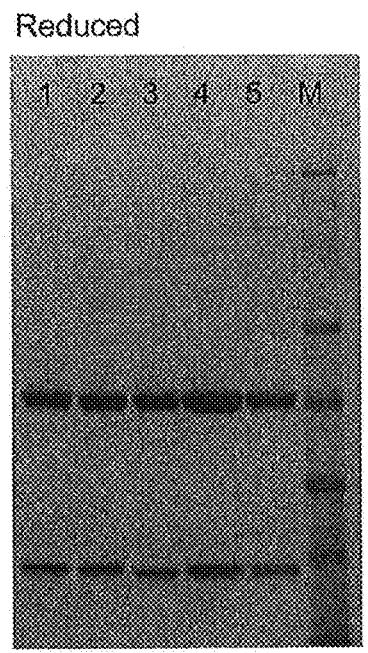

SDS-PAGE was performed under non-reducing (FIG. 25A) and reducing (FIG. 25B) conditions as described in Example 15. FIG. 25A show that the antibody sample after 2-MEA induced Fab-arm exchange consists of intact IgG, with a trace of half molecules (H1L1) detectable on the non-reduced gel.

Figure 26A:
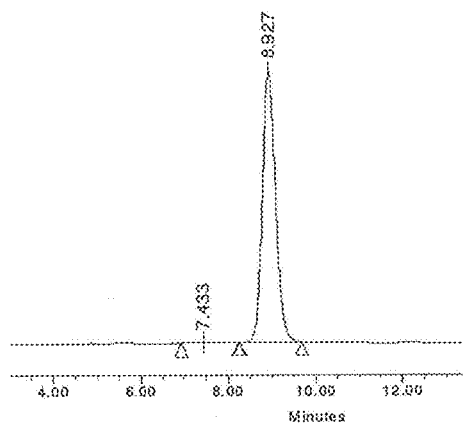
FIGS. 26A-26D: HP-SEC profiles of the homodimer starting material IgG1-2F8-F405L (FIG. 26B), the homodimer starting material IgG1-7D8-K409R (FIG. 26A), the mixture (1:1) of both homodimers (FIG. 26C), and the bispecific product generated by 2-MEA-induced Fab-arm exchange between IgG1-2F8-F405L×IgG1-7D8-K409R (FIG. 26D).
Figure 26B:
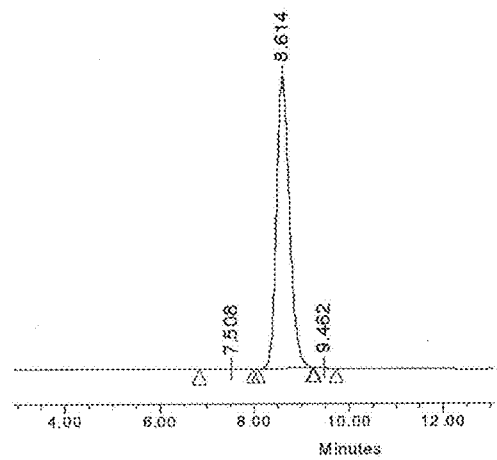
Figure 26C:
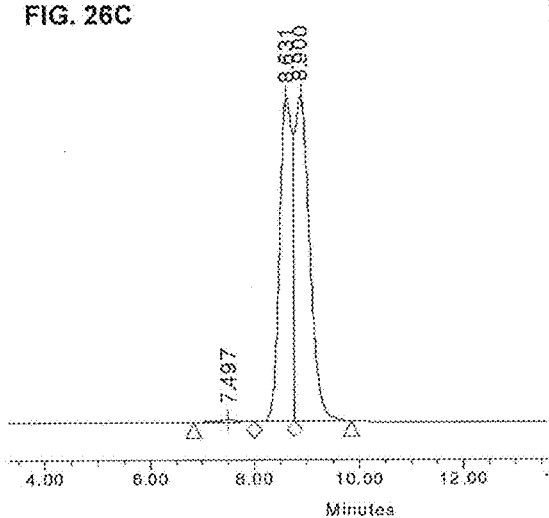
Figure 26D:
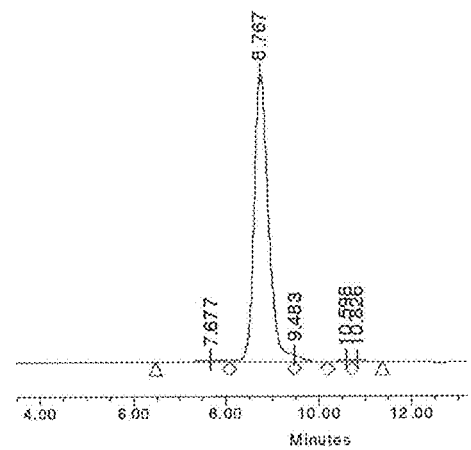

HP-SEC was performed as described in Example 15. FIG. 26(B) and FIG. 26(A) show the HP-SEC profiles of the starting materials IgG1-2F8-F405L and IgG1-7D8-K409R, respectively. The mixture (1:1) of both antibodies and the bispecific product generated by 2-MEA induced Fab-arm exchange between IgG1-2F8-F405L×IgG1-7D8-K409R are shown in FIG. 26C and FIG. 26D, respectively. In addition, FIG. 26D shows that >99% of the sample consists of intact IgG with practically no aggregates formed.

Figure 27A:
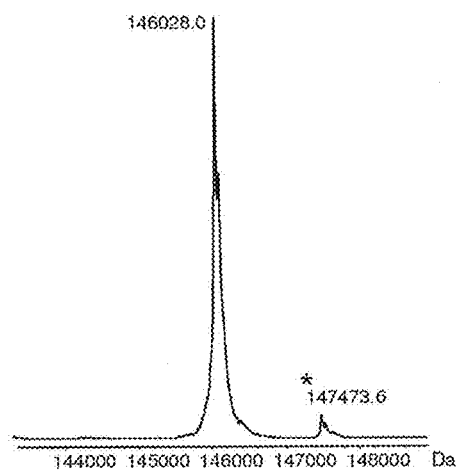
FIGS. 27A-27D: Mass spectrometry (ESI-MS) of the homodimer starting material IgG1-2F8-F405L (FIG. 27B), the homodimer starting material IgG1-7D8-K409R (FIG. 27A), the mixture (1:1) of both homodimers (FIG. 27C), and the bispecific product generated by 2-MEA-induced Fab-arm exchange between IgG1-2F8-F405L×IgG1-7D8-K409R (FIG. 27D).
Figure 27B:
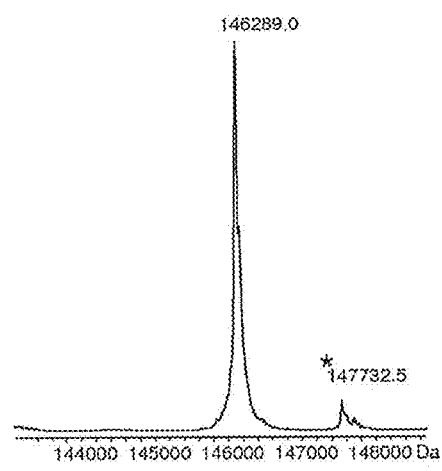
Figure 27C:
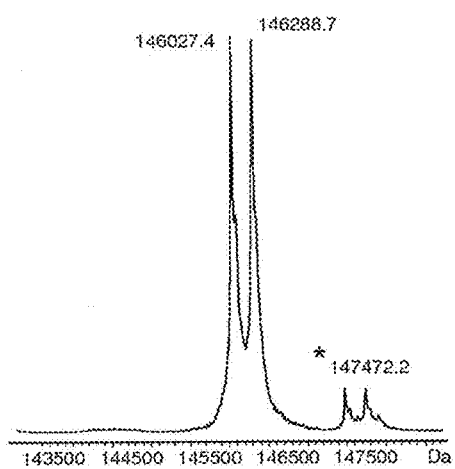
Figure 27D:
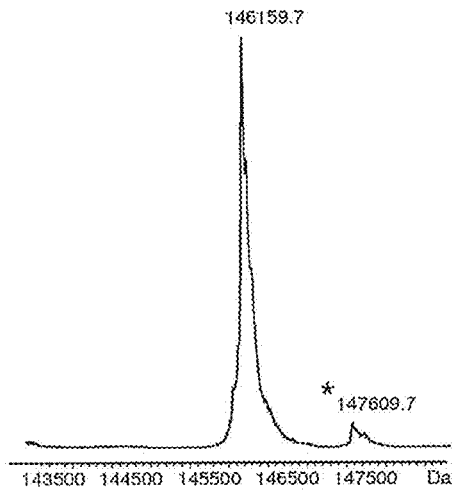

Mass spectrometry (ESI-MS) was performed as described in Example 12. FIG. 27(B) and FIG. 27(A) show the mass spectrometry profiles of the starting materials IgG1-2F8-F405L and IgG1-7D8-K409R, respectively. The mixture (1:1) of both antibodies and the bispecific product generated by 2-MEA induced Fab-arm exchange between IgG1-2F8-F405L×IgG1-7D8-K409R are shown in FIG. 27C and FIG. 27D, respectively. The product in the 2-MEA induced Fab-arm exchanged sample is 146,159.7 kDa, which perfectly matches with the bispecific product derived from IgG1-2F8-F405L (146,289.0/2=73,145)×IgG1-7D8-K409R (146,028.0/2=73,014). Moreover, the bispecific antibody product showed a homogenous peak, indicating that no light chain mispairing occurred, which would have resulted in subdivided peaks. These data show that 2-MEA induced Fab-arm exchange resulted in bispecific IgG. The small peaks indicated by (*) resulted from incomplete deglycosylation prior to analysis. These data show that a bispecific antibody sample was generated by 2-MEA-induced Fab-arm exchange between IgG1-2F8-F405L×IgG1-7D8-K409R.

Figure 28A:
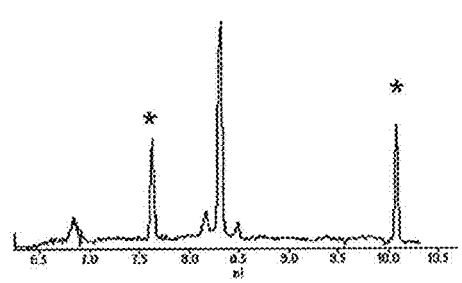
FIGS. 28A-28D: Capillary isoelectrofocussing (cIEF) profiles of the homodimer starting material IgG1-2F8-F405L (FIG. 28A), the homodimer starting material IgG1-7D8-K409R (FIG. 28B), the mixture (1:1) of both homodimers (FIG. 28C), and the bispecific product generated by 2-MEA-induced Fab-arm exchange between IgG1-2F8-F405L×IgG1-7D8-K409R (FIG. 28D).
Figure 28B:
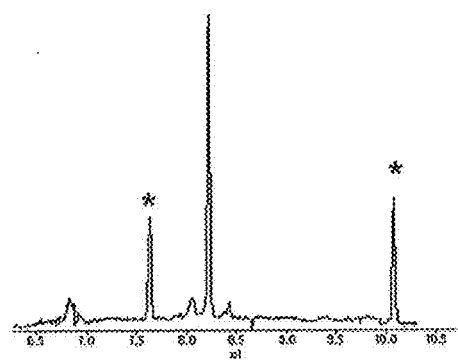
Figure 28C:
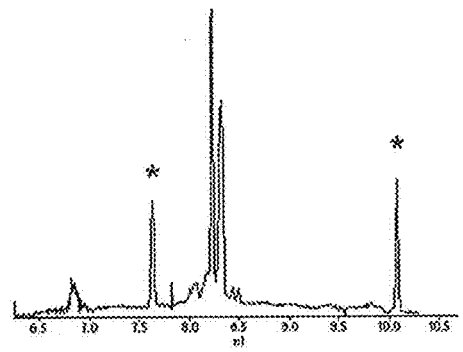
Figure 28D:
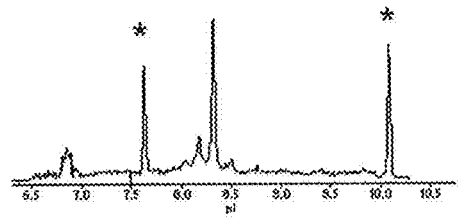

Capillary isoelectrofocussing (cIEF) was performed using an iCE280 Analyzer (Convergent Biosciences). FIG. 28A and FIG. 28B shows cIEF profiles of the starting materials IgG1-2F8-F405L and IgG1-7D8-K409R, respectively. The mixture (1:1) of both antibodies and the bispecific product generated by Fab-arm exchange between IgG1-2F8-F405L× IgG1-7D8-K409R are shown in FIG. 28C and FIG. 28D, respectively. All samples were desalted before use. Final concentrations in the assay mix were 0.3 mg/mL IgG (0.35% Methyl Cellulose; 2% Carrier Ampholytes 3-10; 6% Carrier Ampholytes 8-10.5; 0.5% pI marker 7.65 and 0.5% pI marker 10.10). Focusing was performed for 7 min at 3000 V and the whole-capillary absorption image was captured by a charge-coupled device camera. After calibration of the peak profiles, the data were analyzed by the EZChrom software. pI markers are indicated by (*). These data show that a bispecific antibody sample was generated by 2-MEA-induced Fab-arm exchange between IgG1-2F8-F405L×IgG1-7D8-K409R.

Figure 29A:
FIGS. 29A-29D: HPLC-CIEX profiles of the homodimer starting material IgG1-2F8-F405L (FIG. 29A), the homodimer starting material IgG1-7D8-K409R (FIG. 29B), the mixture (1:1) of both homodimers (FIG. 29C), and the bispecific product generated by 2-MEA-induced Fab-arm exchange between IgG1-2F8-F405L×IgG1-7D8-K409R (FIG. 29D).
Figure 29B:
Figure 29C:
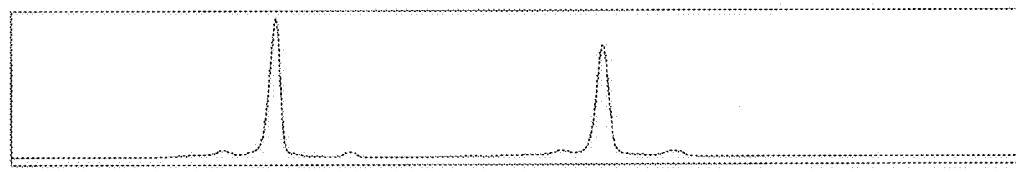
Figure 29D:
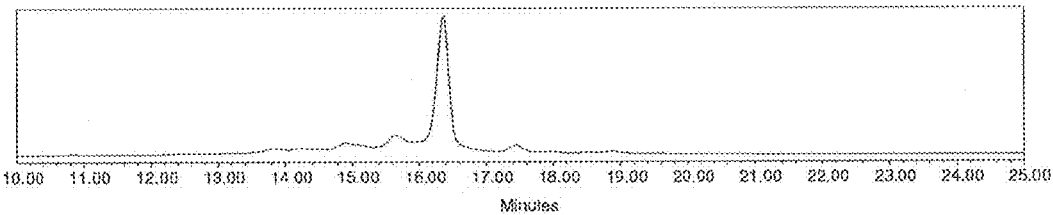

Another technique to study the charged isoforms of monoclonal antibodies is High Pressure Liquid Chromatography Cation Exchange (HPLC-CIEX). FIG. 29A and FIG. 29B show HPLC-CIEX profiles of the starting materials IgG1-2F8-F405L and IgG1-7D8-K409R, respectively. The mixture (1:1) of both antibodies and the bispecific product generated by 2-MEA induced Fab-arm exchange between IgG1-2F8-F405L×IgG1-7D8-K409R are shown in FIG. 29C and FIG. 29D, respectively. Samples were diluted to 1 mg/mL in mobile Phase A (10 mM NaPO4, pH 7.0) for injection onto the HPLC. The differently charged IgG molecules were separated by using a ProPac® WCX-10, 4 mm×250 mm, analytical column with a flow rate of 1 mL/min. Elution was performed with a gradient of Mobile Phase A to Mobile Phase B (10 mM NaPO$_4$, pH 7.0, 0.25 M NaCl) and detection occurred at 280 nm. These data show that a bispecific antibody sample was generated by 2-MEA-induced Fab-arm exchange between IgG1-2F8-F405L× IgG1-7D8-K409R. It also shows that cation exchange is a powerful tool to separate residual homodimers from the heterodimer. Another application of cation exchange chromatography is therefore the polishing of a bispecific heterodimer, i.e. to purify away any residual homodimers after exchange.

Example 32: Monitoring the Kinetics of 2-MEA-Induced Fab-Arm Exchange and Quantifying Residual Homodimers after Exchange by Using HPLC-CIEX The generation of bispecific antibodies by 2-MEA-induced Fab-arm exchange is described in Example 11. In this example the exchange reaction was monitored by conducting High Pressure Liquid Chromatography Cation Exchange (HPLC-CIEX; as described in Example 31) at various time points during the exchange reaction.

Figure 31A:
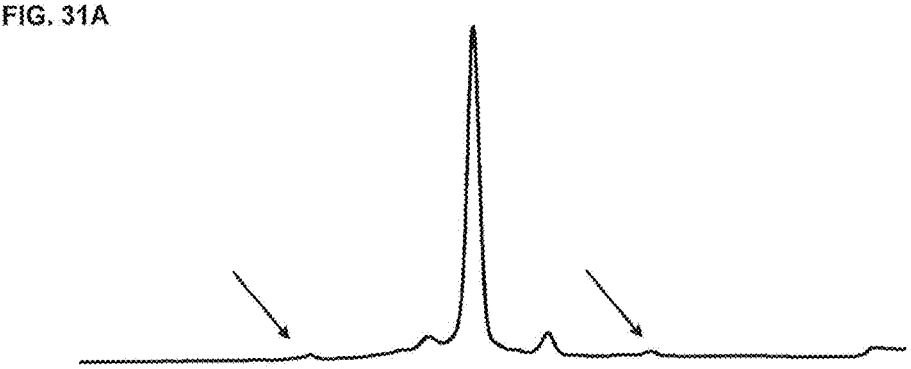
FIGS. 31A and 31B: Residual homodimers after the exchange reaction as detected with the CIEX method (indicated by arrows).
Figure 31B:
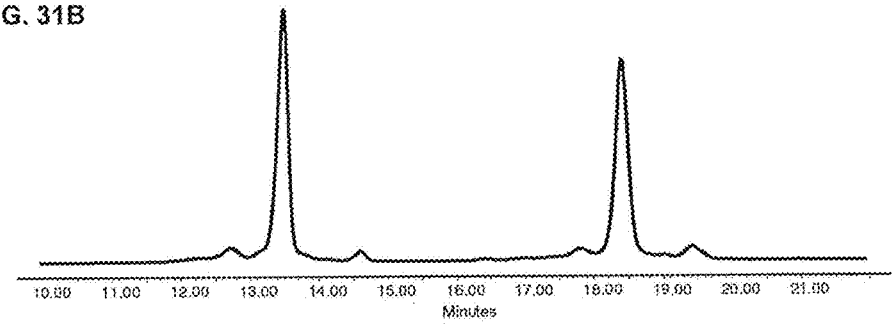
Figure 32A:
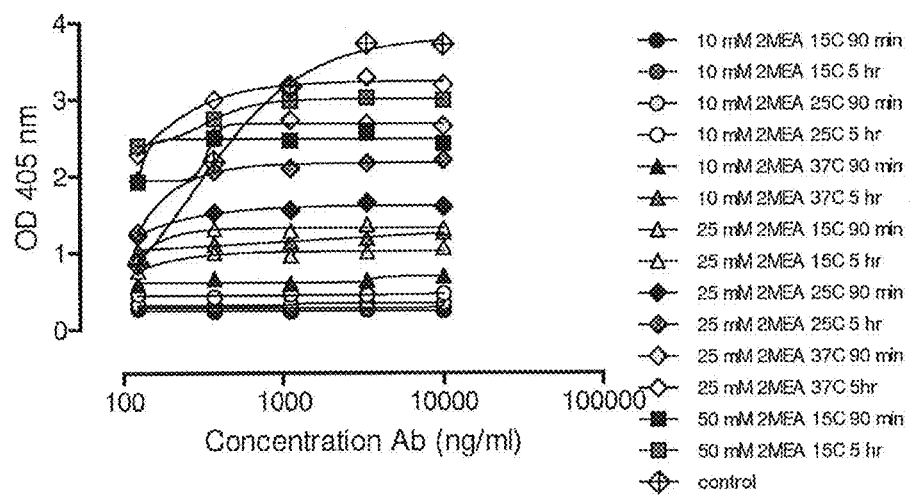
FIGS. 32A-32F: Influence of IgG concentrations, 2-MEA concentrations, incubation temperatures and incubation times on generation of bispecific antibodies, as determined by an ELISA.
Figure 32B:
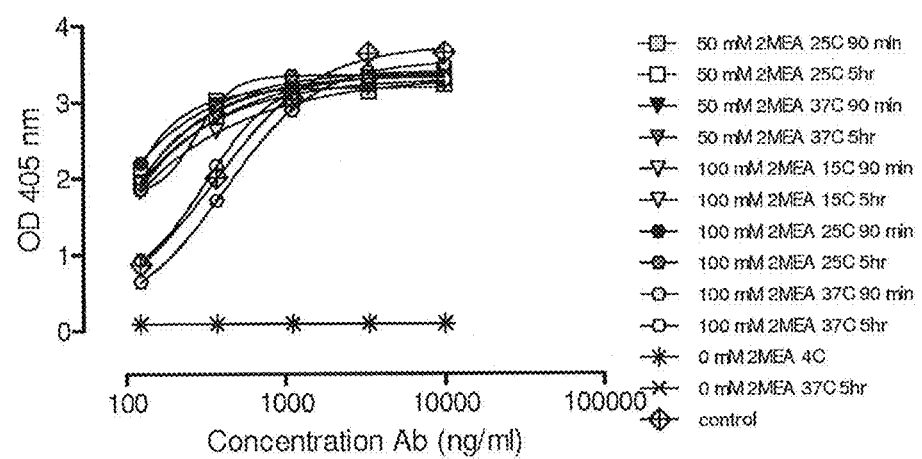
Figure 32C:
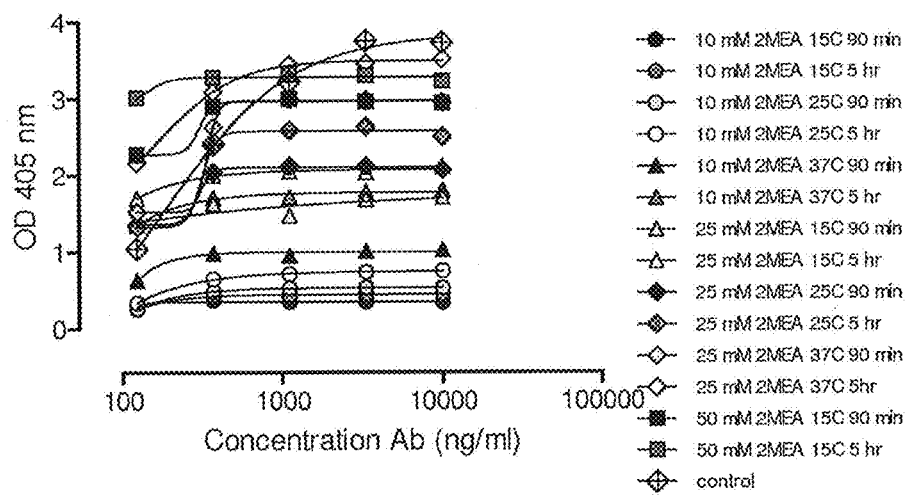
Figure 32D:
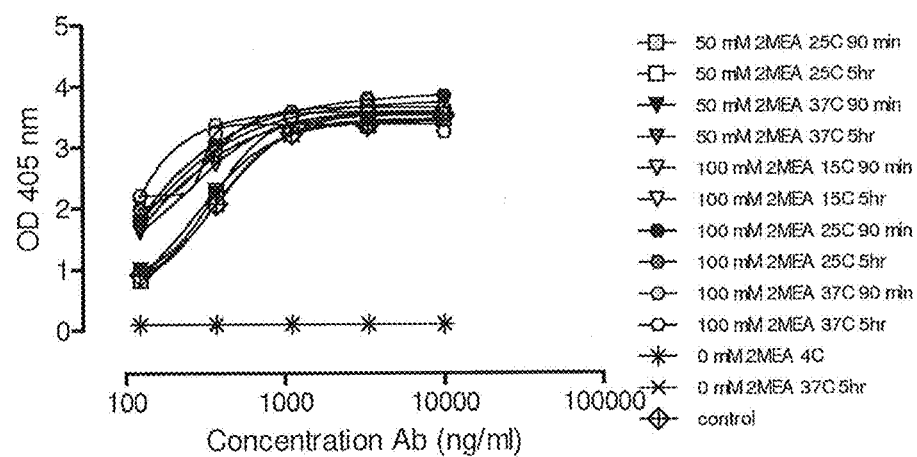
Figure 32E:
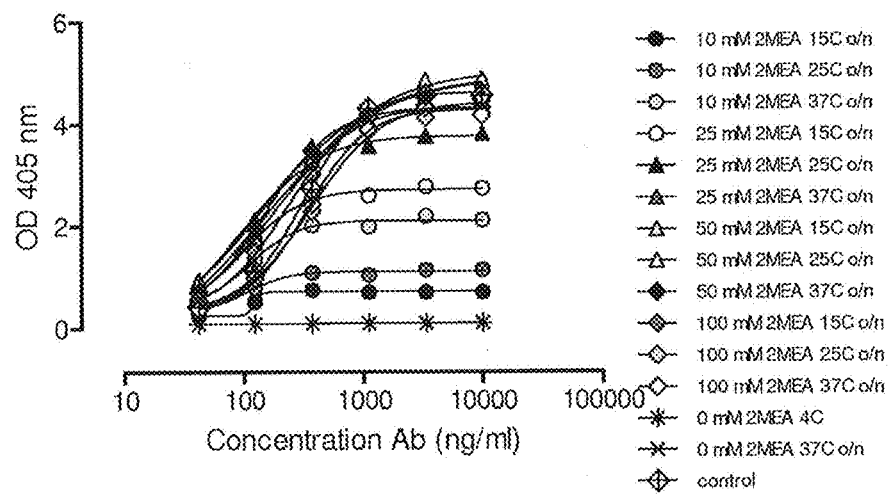
Figure 32F:
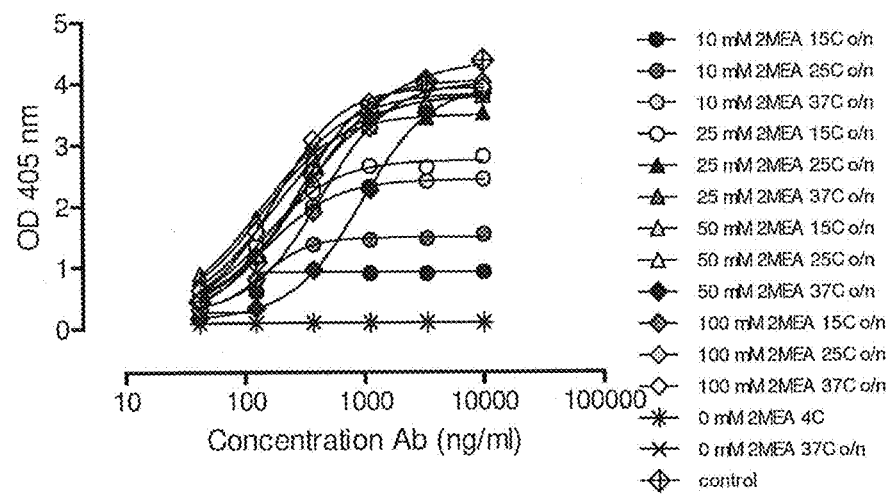
Figure 33A:
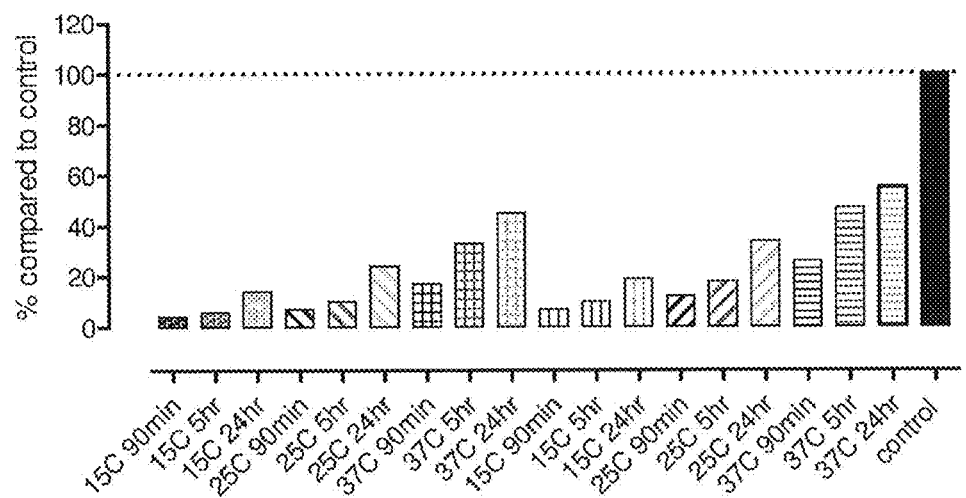
FIGS. 33A-33D: Generation of bispecific antibodies at various IgG concentrations, 2-MEA concentrations, incubation temperatures and times as determined by an ELISA and compared to control which was arbitrarily set to 100%.
Figure 33B:
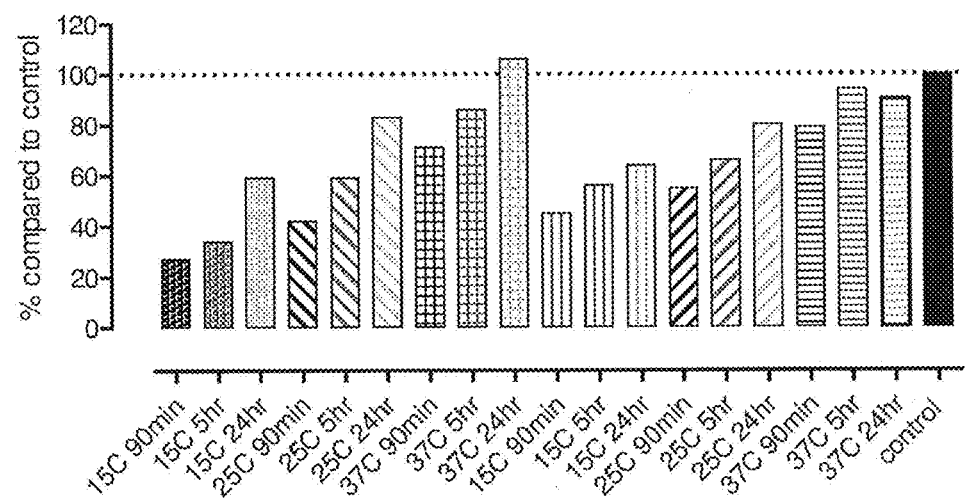
Figure 33C:
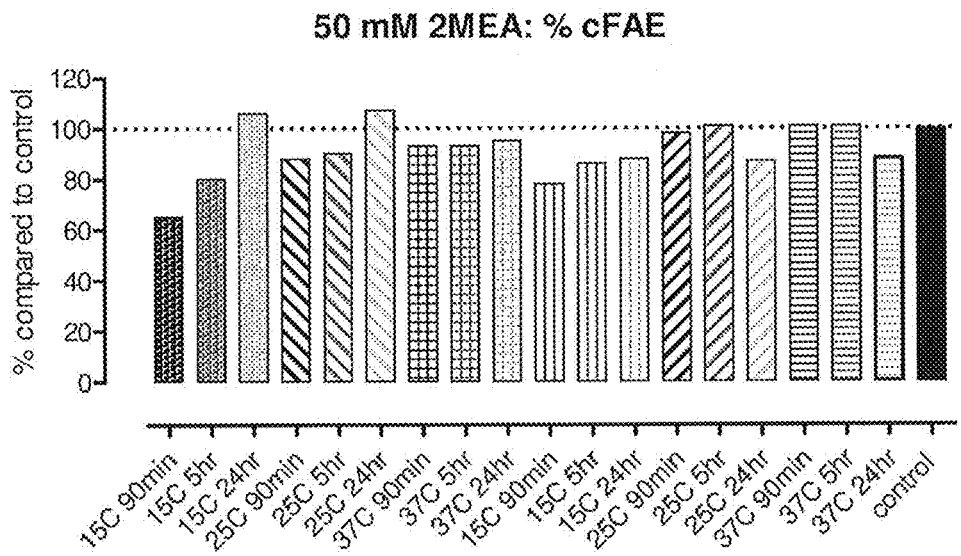
Figure 33D:
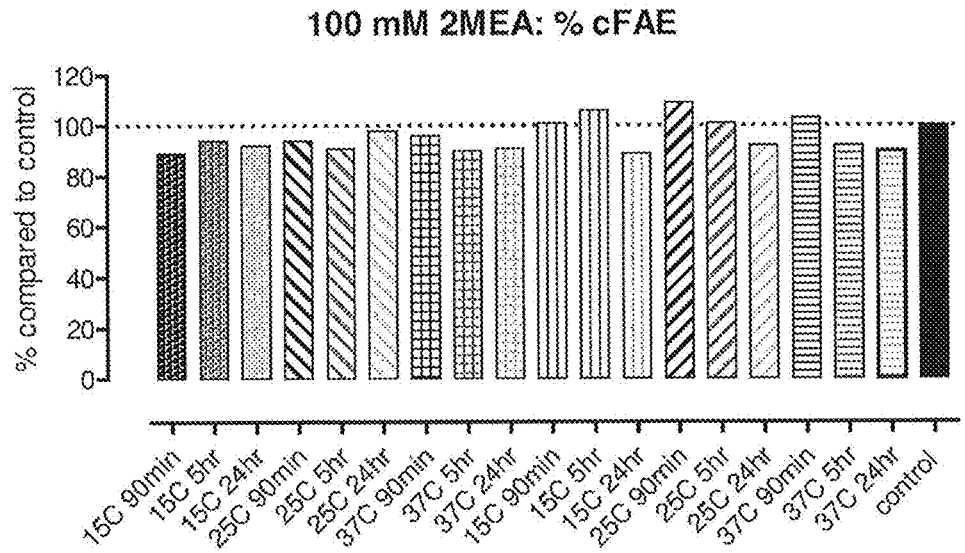
Figure 34A:
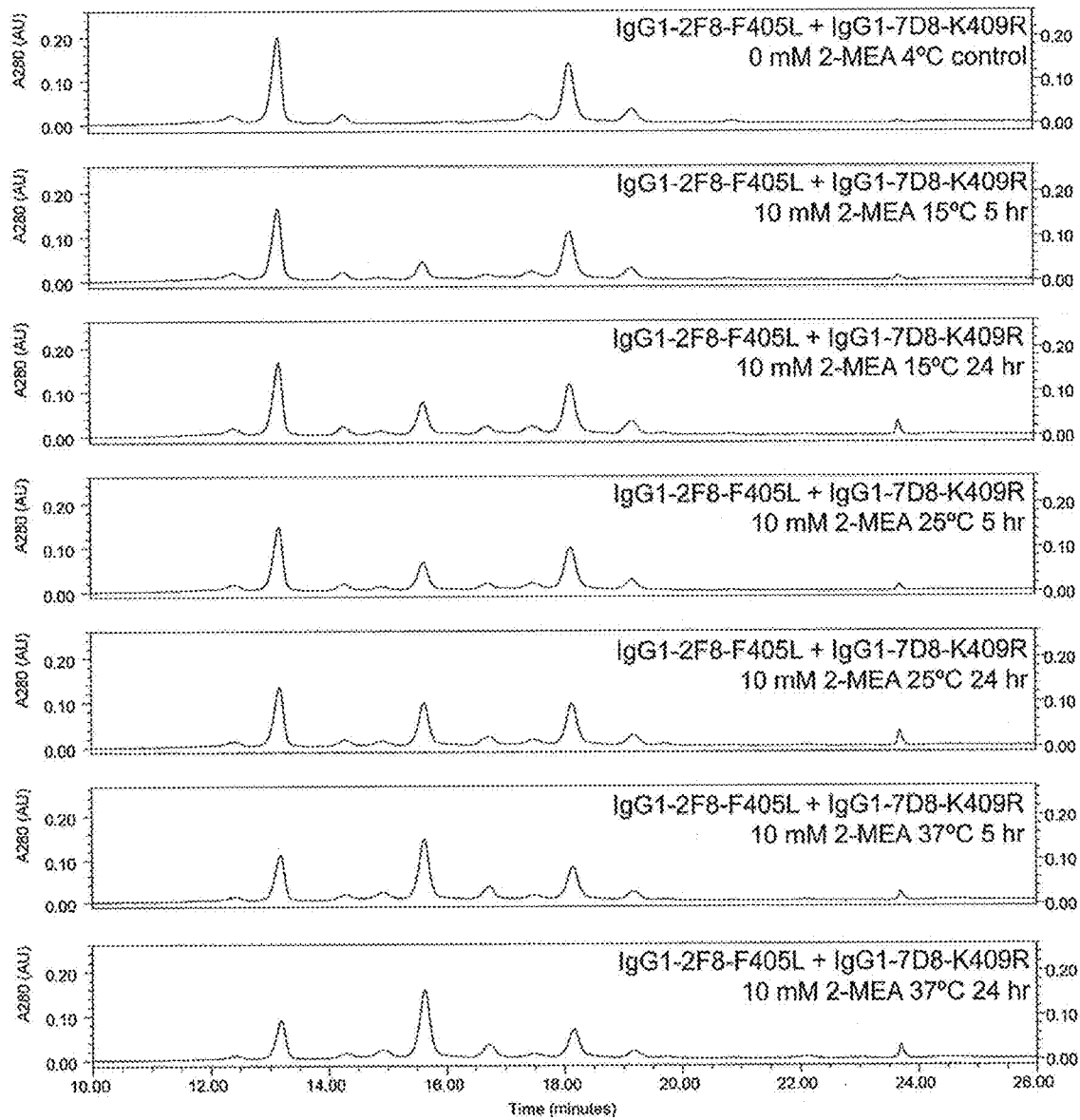
FIGS. 34A-34D: Generation of bispecific antibodies at various IgG concentrations, 2-MEA concentrations, incubation temperatures and times as analysed by HPLC-CIEX.
Figure 34B:
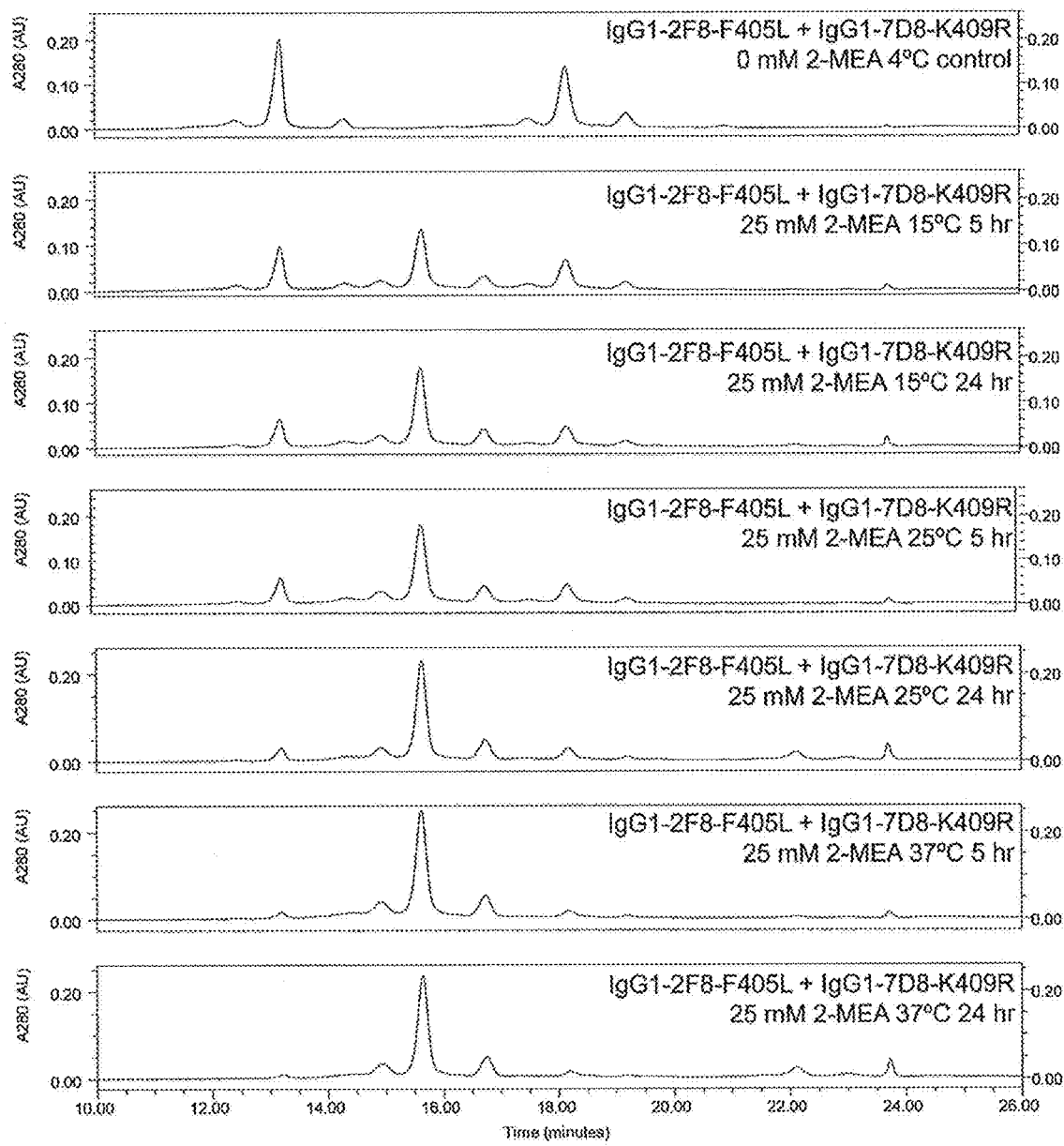
Figure 34C:
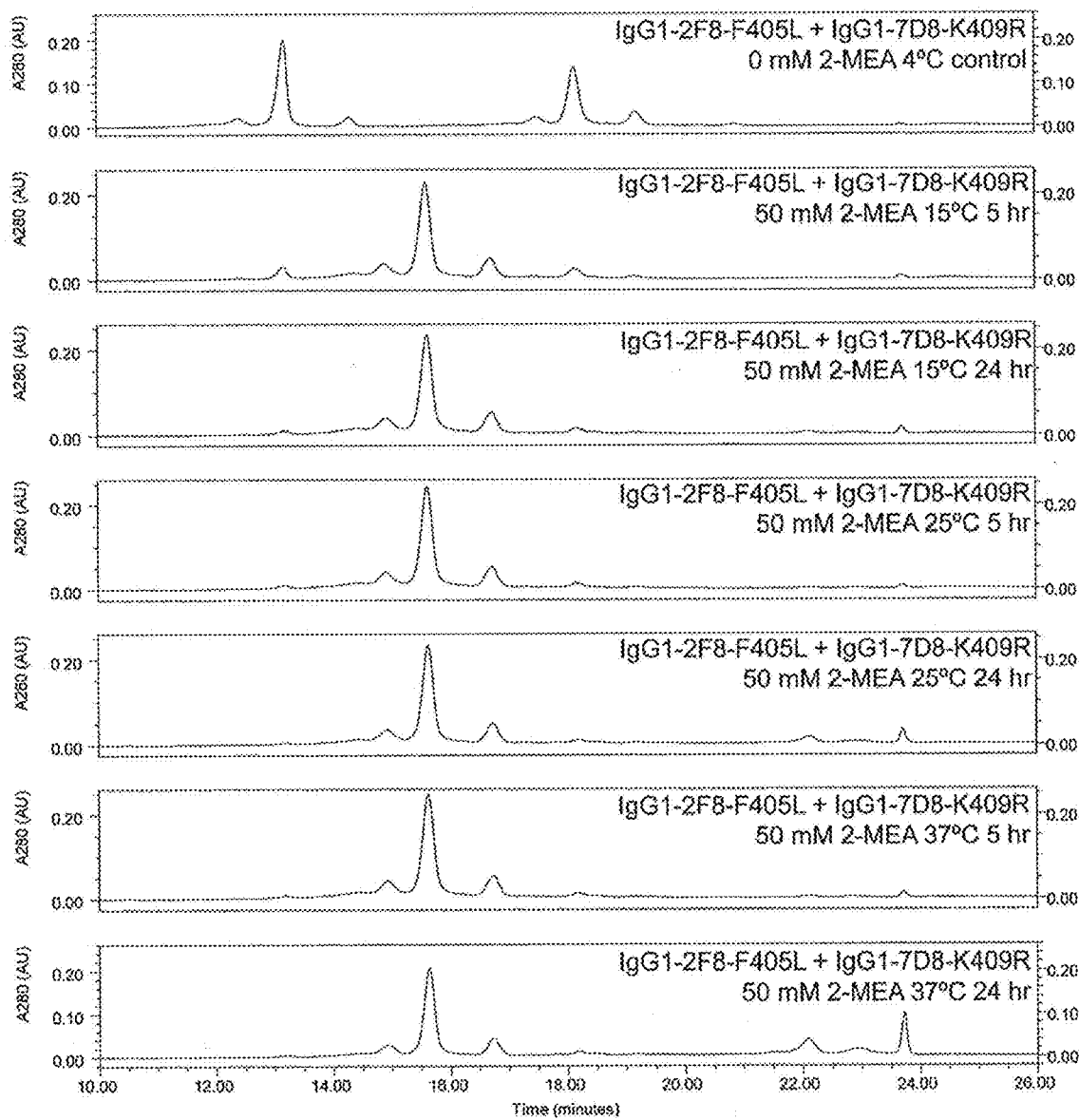
Figure 34D:
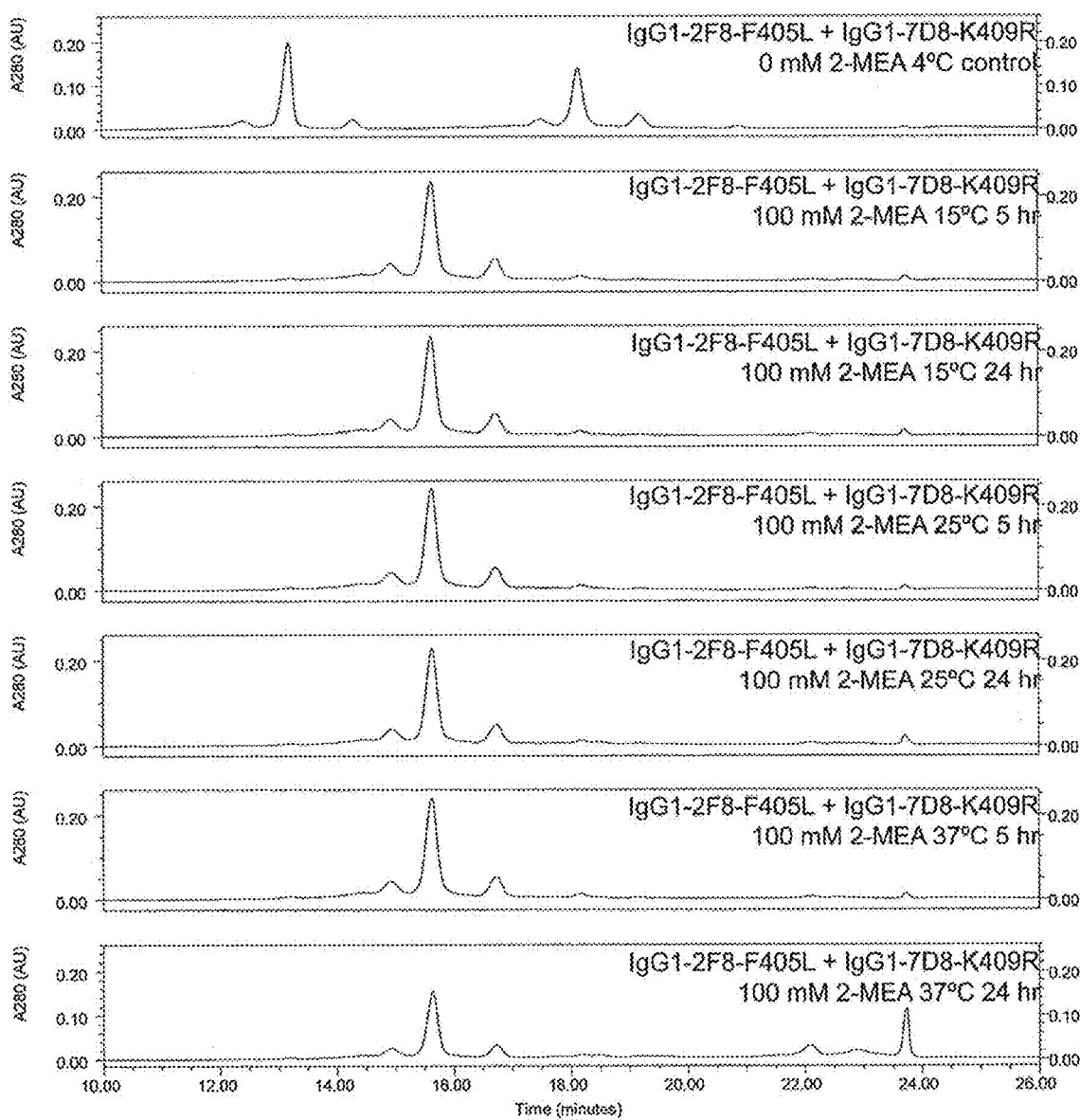

Homodimers IgG1-2F8-F405L and IgG1-7D8-K409R were mixed in the molar ratio 1:1 at a concentration of 1 mg/mL each. After the addition of 25 mM 2-MEA, the sample was placed in the autosampler of the HPLC, pre-warmed at 25° C. FIG. 30A to 30H shows eight consecutive injections at different time intervals obtained by HPLC-CIEX ranging from t=0 min to t=450 min, respectively, after the addition of 2-MEA. The data show that bispecific IgG was formed rather quickly and most of the homodimer was exchanged after 135 min. The heterogeneous heterodimer peaks appearing after 45 min resolved into more homogeneous peaks after approximately 180 min, suggesting that exchange occurs in different phases. Furthermore, FIG. 31A shows that approximately 3% of residual homodimers was detected with the CIEX method (indicated by arrows). As shown this method is suitable for quantitating the remaining homodimer content (elution of the homodimers is shown in FIG. 31B) when exchange reaction was almost complete).

Example 33: Generation of Bispecific Antibodies by 2-MEA-Induced Fab-Arm Exchange at High Antibody Concentrations at Various 2-MEA Concentrations, Temperatures and Incubation Times 2-MEA induced Fab-arm exchange was performed at high IgG concentrations. The influence of 2-MEA concentration, incubation temperature and time on the amount of exchange was studied.

The exchange process was performed using the combination of IgG1-7D8-K409R×IgG1-2F8-F405L. Both materials were purified with affinity chromatography using protein A. After concentration of the material to >20 mg/mL, a successive anion exchange step was performed (in flow through mode) using HiPrep Q FF 16/10 (GE Health Care, #28-9365-43). The final purified material was buffer-exchanged to PBS.

The bispecific exchange was studied at final IgG concentrations of 20 mg/mL (each homodimer at a final concentration of 10 mg/mL) and 10 mg/mL (each homodimer at a final concentration of 5 mg/mL) in PBS. Separate mixtures were prepared for both IgG concentrations including 2-MEA at final concentrations of 10, 25, 50 and 100 mM. The mixtures were divided into 100 µL aliquots in eppendorf tubes and stored at 15, 25 and 37° C. Separate tubes were used for different incubation times of 90 min, 5 hours and 24 hours at each temperature.

The mixture was also prepared without 2-MEA for both IgG concentrations and stored at 4° C. as an untreated control. After the appropriate incubation times, the 90 min and 5 hours samples were collected for desalting to remove the 2-MEA (the 90 min samples were initially put on ice to stop the exchange reaction). The samples were desalted using a Zeba 96-well desalting plate (7 k, cat #89808, Thermo Fisher Scientific). The 24 hours samples were desalted separately after 24 hours incubation.

Serial dilutions of the antibody samples (total antibody concentration 10-0.123 µg/mL in 3-fold dilutions for the 90 min and 5 hours samples; 10-0.041 µg/mL in 3-fold dilutions for the 24 hours samples) were used in a sandwich ELISA to measure bispecific binding as described in Example 7. For each plate, a control was included of a purified batch of bispecific antibody derived from a 2-MEA-induced Fab-arm exchange between IgG1-2F8-ITL and IgG4-7D8-CPPC (as described in Example 15). FIG. 32(A)-(F) shows the results of the bispecific binding as measured in the individual ELISA plates. The top OD405 values (as determined for the 10 µg/mL concentrations in the ELISA) were used to calculate the bispecific binding in comparison to the control, which was arbitrarily set at 100%. This resulted in the percentage of controlled Fab-arm exchange (% cFAE) compared to the control as is shown in FIG. 33(A)-(D) for each 2-MEA concentration.

The data show that maximal level of bispecific binding (89-109% with respect to control) was reached at a concentration of 100 mM 2-MEA for both IgG concentrations at all temperature-time conditions. At 50 mM 2-MEA, maximal binding (88-107%) was achieved at 25° C. and 37° C. and also at 15° C. after 24 hours incubation. For the lower concentrations of 25 mM and 10 mM 2-MEA, the exchange was more efficient at higher temperatures and increased with prolonged incubation time, leading to maximal exchange at 37° C. upon 24 hours incubation at 25 mM 2-MEA. None of the conditions tested at 10 mM 2-MEA generated 100% bispecific product. The exchange process was slightly faster at IgG concentrations of 10 mg/mL compared to 20 mg/mL total IgG.

To confirm that bispecific antibodies were formed and to study the bispecific products in more detail, samples were analyzed with Cation Exchange (HPLC-CIEX) analysis. The HPLC-CIEX analysis was performed, as described in Example 31, for the samples with IgG concentrations of 20 mg/mL after 5 hours and 24 hours incubation and all 2-MEA concentrations.

The CIEX chromatograms in FIG. 34(A)-(D) show that the highest yield of bispecific product was obtained at 50 and 100 mM 2-MEA confirming the results of the bispecific ELISA. However, minor amounts of residual homodimer were still detected at 50 and 100 mM 2-MEA (2-3.5% of each homodimer for samples incubated at 25° C. and 37° C.). Exchange at higher temperature, longer (24 hours) incubation time and increasing 2-MEA concentration result in the appearance of additional peaks at 22-24 min in the CIEX profile.

Minimal amounts of additional peaks were obtained when exchange was concluded within 5 hours. To identify the nature of these peaks, SDS-PAGE analysis and HP-SEC analysis was performed. HP-SEC showed that the amount of aggregates was below 1% for all conditions, suggesting that the additional peaks do not represent aggregates. However, non-reduced SDS-PAGE indicated that the extra peaks may represent heterodimer lacking one or two light chains. Minor amounts of half-molecules were detected as well.

The experiment shows that the exchange reaction takes place at high homodimer concentrations, which makes the process attractive for commercial scale, and that the yield of bispecific antibody depends on 2-MEA concentration, temperature and incubation time.

Example 34: Determinants at the IgG1 368 Position for Engagement in 2-MEA-Induced Fab-Arm Exchange in Combination with IgG1-K409R Example 28 and 29 show that certain single mutations at position F405 and Y407 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect, mutagenesis of the IgG1 368 position was performed and the mutants were tested for engagement in 2-MEA-induced Fab-arm-exchange in combination with human IgG1-K409R. All possible IgG1-2F8-L368X mutants (with the exception of C and P) were combined with IgG1-7D8-K409R. The procedure was performed with purified antibodies as described in Example 19.

Figure 35A:
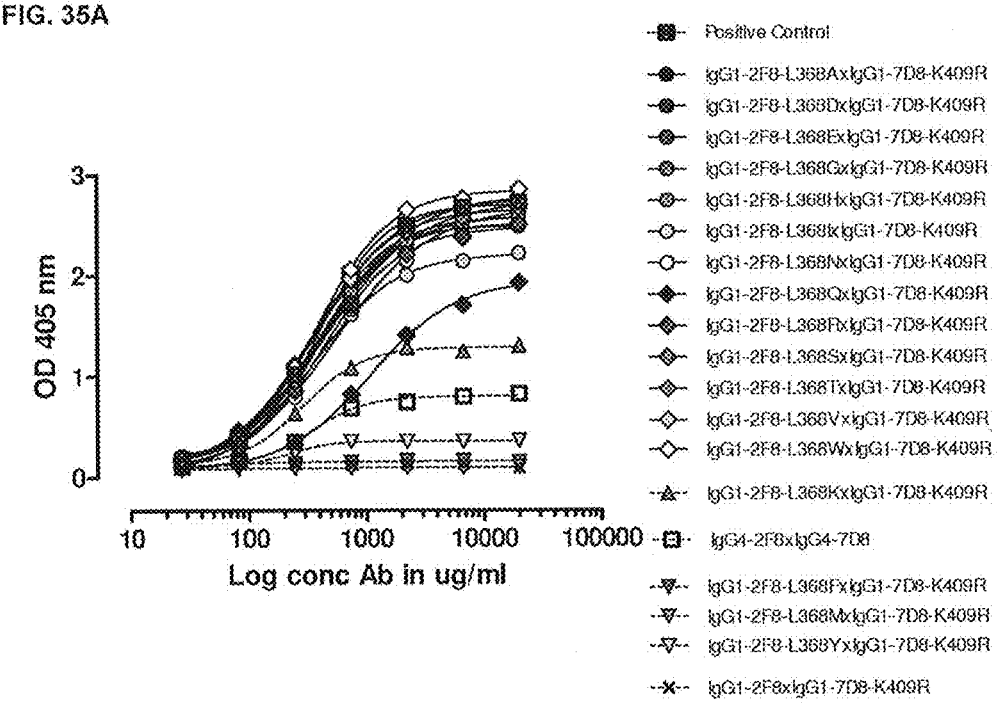
FIGS. 35A and 35B: Generation of bispecific antibodies after 2-MEA-induced in vitro Fab-arm exchange between the indicated IgG1-2F8-L368X mutants and IgG1-7D8-K409R was determined by an ELISA using a concentration series (total antibody) of 0-20 μg/mL (FIG. 35A). The positive control is a purified batch of bispecific antibody, derived from IgG1-2F8-F405L×IgG1-7D8-K409R.
Figure 35B:
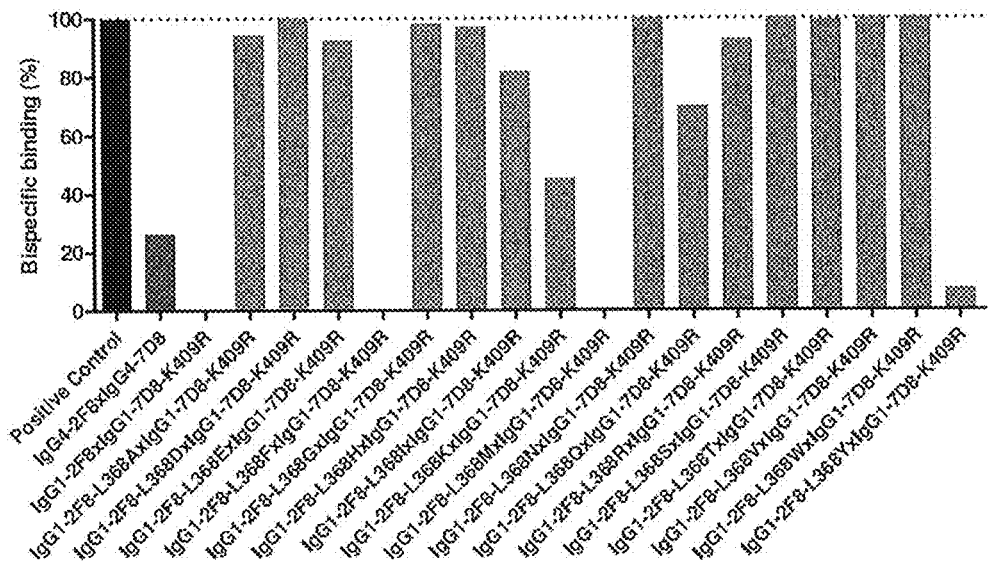

FIG. 35 shows the results of bispecific binding upon 2-MEA-induced Fab-arm exchange between IgG1-2F8-L368X×IgG1-7D8-K409R. These data were also scored as (−) no Fab-arm exchange, (+/−) low, (+) intermediate or (++) high Fab-arm exchange, as presented in Table 6. No Fab-arm exchange (−) was found when the 368 position in IgG1-2F8 was L (=wild type IgG1), F or M. Fab-arm exchange was found to be low (+/−) when the 368 position in IgG1-2F8 was Y. Fab-arm exchange was found to be intermediate (+) when the 368 position in IgG1-2F8 was K and high (++) when the 368 position in IgG1-2F8 was A, D, E, G, H, I, N, Q, R, S, T, V, or W. These data indicate that particular mutations at the IgG1 368 position allow IgG1 to engage in 2-MEA-induced Fab-arm exchange when combined with IgG1-K409R.

TABLE 6

2-MEA-induced Fab-arm exchange between IgG1-2F8-L368X mutants and IgG1-7D8-K409R
The generation of bispecific antibodies after 2-MEA-induced in vitro Fab-arm exchange between IgG1-2F8-L368X mutants and IgG1-7D8-K409R was determined by a sandwich ELISA. (−) no, (+/−) low, (+) intermediate or (++) high Fab-arm exchange.

| IgG1-2F8-L368X | Fab-arm exchange X IgG1-7D8-K409R |
|---|---|
| A | ++ |
| D | ++ |
| E | ++ |
| F | − |
| G | ++ |
| H | ++ |
| I | ++ |
| K | + |
| L | − |
| M | − |
| N | ++ |
| Q | ++ |
| R | ++ |
| S | ++ |
| T | ++ |
| V | ++ |
| W | ++ |

Example 35: Determinants at the IgG1 370 Position for Engagement in 2-MEA-Induced Fab-Arm Exchange in Combination with IgG1-K409R Examples 28, 29 and 34 show that certain single mutations at positions F405, Y407 or L368 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 370 position was performed and the mutants were tested for engagement in 2-MEA-induced Fab-arm-exchange in combination with human IgG1-K409R. All possible IgG1-2F8-K370X mutants (with the exception of C and P) were combined with IgG1-7D8-K409R. The procedure was performed with purified antibodies as described in Example 19.

Figure 36A:
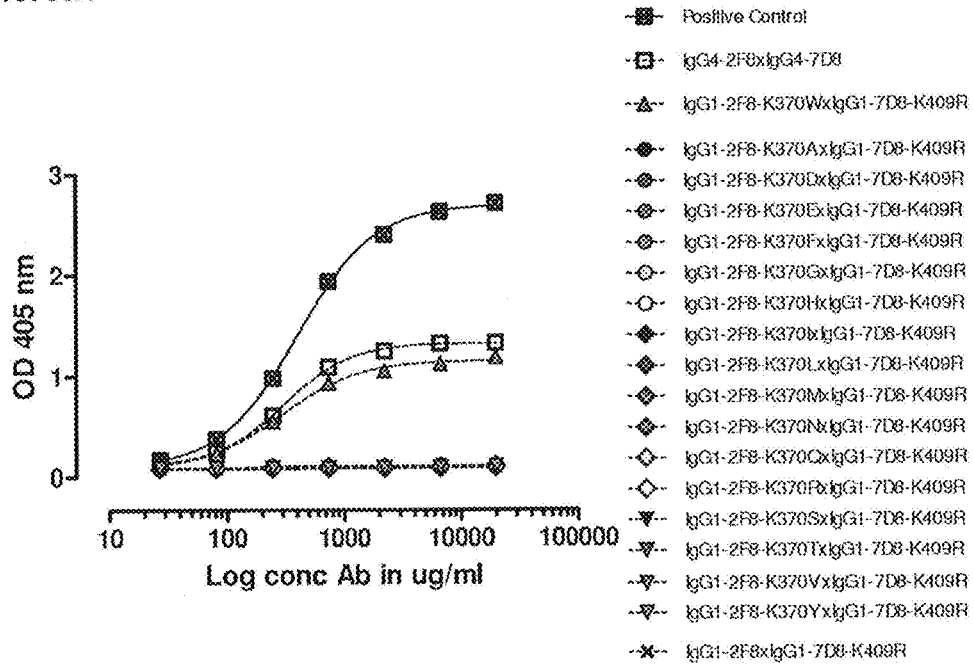
FIGS. 36A and 36B: Generation of bispecific antibodies after 2-MEA-induced in vitro Fab-arm exchange between the indicated IgG1-2F8-K370X mutants and IgG1-7D8-K409R was determined by an ELISA using a concentration series (total antibody) of 0-20 μg/mL (FIG. 36A). The positive control is a purified batch of bispecific antibody, derived from IgG1-2F8-F405L×IgG1-7D8-K409R.
Figure 36B:
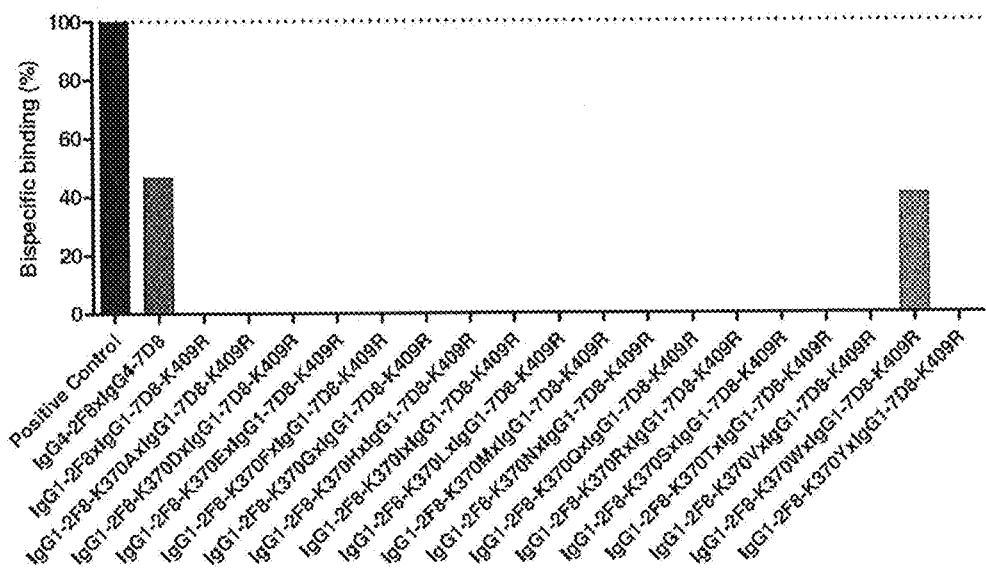

FIG. 36 shows the results of bispecific binding upon 2-MEA-induced Fab-arm exchange between IgG1-2F8-K370X×IgG1-7D8-K409R. These data were also scored as (−) no Fab-arm exchange, (+/−) low, (+) intermediate or (++) high Fab-arm exchange, as presented in Table 7. No Fab-arm exchange (−) was found when the 370 position in IgG1-2F8 was K (=wild type IgG1), A, D, E, F, G, H, I, L, M, N, Q, R, S, T, V or Y. Only substitution of K370 with W resulted in intermediate Fab-arm exchange (+). These data indicate that only one mutation at the IgG1 370 position (K370W) allows IgG1 to engage in 2-MEA-induced Fab-arm exchange when combined with IgG1-K409R.

TABLE 7

2-MEA-induced Fab-arm exchange between IgG1-2F8-K370X mutants and IgG1-7D8-K409R
The generation of bispecific antibodies after 2-MEA-induced in vitro Fab-arm exchange between IgG1-2F8-K370X mutants and IgG1-7D8-K409R was determined by a sandwich ELISA. (−) no, (+/−) low, (+) intermediate or (++) high Fab-arm exchange.

| IgG1-2F8-K370X | Fab-arm exchange X IgG1-7D8-K409R |
|---|---|
| A | − |
| D | − |
| E | − |
| F | − |
| G | − |
| H | − |
| I | − |
| K | − |
| L | − |
| M | − |
| N | − |
| Q | − |
| R | − |
| S | − |
| T | − |
| V | − |
| W | + |
| Y | − |

Example 36: Determinants at the IgG1 399 Position for Engagement in 2-MEA-Induced Fab-Arm Exchange in Combination with IgG1-K409R Examples 28, 29, 34 and 35 show that certain single mutations at positions F405, Y407, L368 or K370 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 399 position was performed and the mutants were tested for engagement in 2-MEA-induced Fab-arm-exchange in combination with human IgG1-K409R. All possible IgG1-2F8-D399X mutants (with the exception of C and P) were combined with IgG1-7D8-K409R. The procedure was performed with purified antibodies as described in Example 19.

Figure 37A:
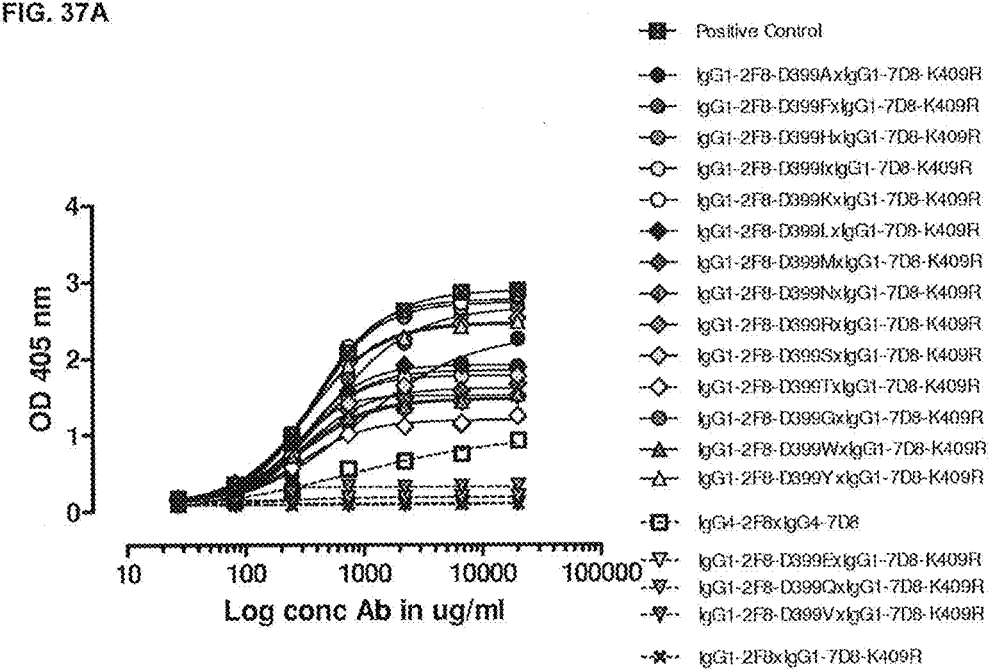
FIGS. 37A and 37B: Generation of bispecific antibodies after 2-MEA-induced in vitro Fab-arm exchange between the indicated IgG1-2F8-D399X mutants and IgG1-7D8-K409R was determined by an ELISA using a concentration series (total antibody) of 0-20 μg/mL (FIG. 37A).
Figure 37B:
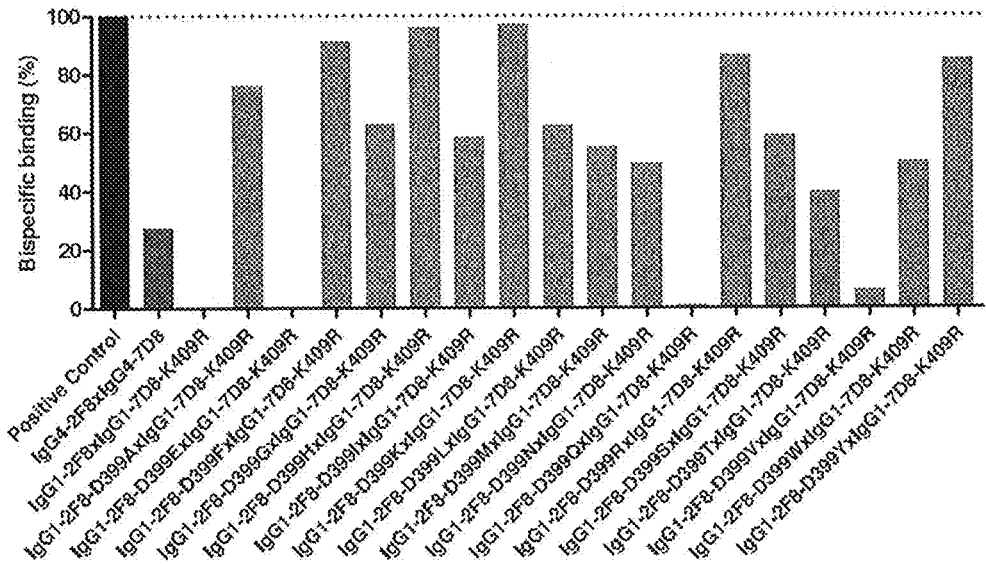

FIG. 37 shows the results of bispecific binding upon 2-MEA-induced Fab-arm exchange between IgG1-2F8-D399X×IgG1-7D8-K409R. These data were also scored as (−) no, (+/−) low, (+) intermediate or (++) high Fab-arm exchange, as presented in Table 8. No Fab-arm exchange (−) was found when the 399 position in IgG1-2F8 was D (=wild type IgG1), E and Q. Fab-arm exchange was found to be low (+/−) when the 399 position in IgG1-2F8 was V, intermediate (+) when the 399 position in IgG1-2F8 was G, I, L, M, N, S, T or W. Fab-arm exchange was found to be high (++) when the 399 position in IgG1-2F8 was A, F, H, K, R or Y. These data indicate that particular mutations at the IgG1 399 position allow IgG1 to engage in 2-MEA-induced Fab-arm exchange when combined with IgG1-K409R.

TABLE 8

2-MEA-induced Fab-arm exchange between IgG1-2F8-D399X mutants and IgG1-7D8-K409R
The generation of bispecific antibodies after 2-MEA-induced in vitro Fab-arm exchange between IgG1-2F8-D399X mutants and IgG1-7D8-K409R was determined by a sandwich ELISA. (−) no, (+/−) low, (+) intermediate or (++) high Fab-arm exchange.

| IgG1-2F8-D399X | Fab-arm exchange X IgG1-7D8-K409R |
|---|---|
| A | ++ |
| D | − |
| E | − |
| F | ++ |
| G | + |
| H | ++ |
| I | + |
| K | ++ |
| L | + |
| M | + |
| N | + |
| Q | − |
| R | ++ |
| S | + |
| T | + |
| V | +/− |
| W | + |
| Y | ++ |

Example 37: Determinants at the IgG1 366 Position for Engagement in 2-MEA-Induced Fab-Arm Exchange in Combination with IgG1-K409R Examples 28, 29, 34, 35 and 36 show that certain single mutations at positions F405, Y407, L368, K370 or D399 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect, mutagenesis of the IgG1 366 position was performed and the mutants were tested for engagement in 2-MEA-induced Fab-arm-exchange in combination with human IgG1-K409R. All possible IgG1-2F8-T366X mutants (with the exception of C and P) were combined with IgG1-7D8-K409R. The procedure was performed with purified antibodies as described in Example 19.

Figure 38A:
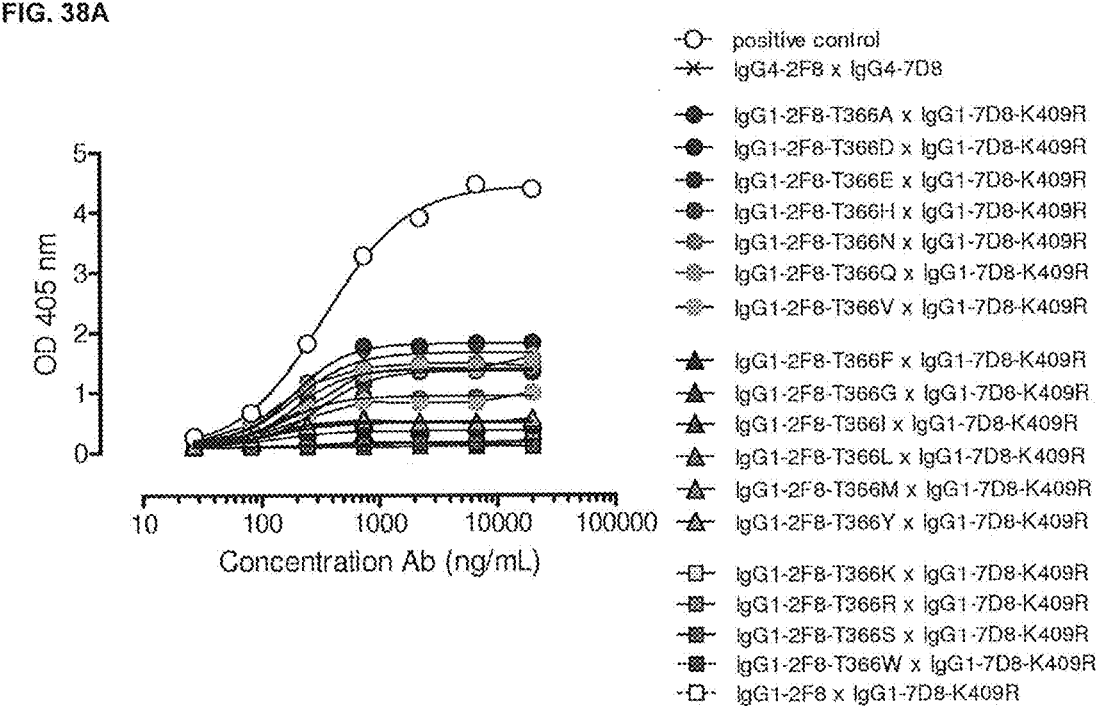
FIGS. 38A and 38B: Generation of bispecific antibodies after 2-MEA-induced in vitro Fab-arm exchange between the indicated IgG1-2F8-T366X mutants and IgG1-7D8-K409R was determined by an ELISA using a concentration series (total antibody) of 0-20 μg/mL (FIG. 38A).
Figure 38B:
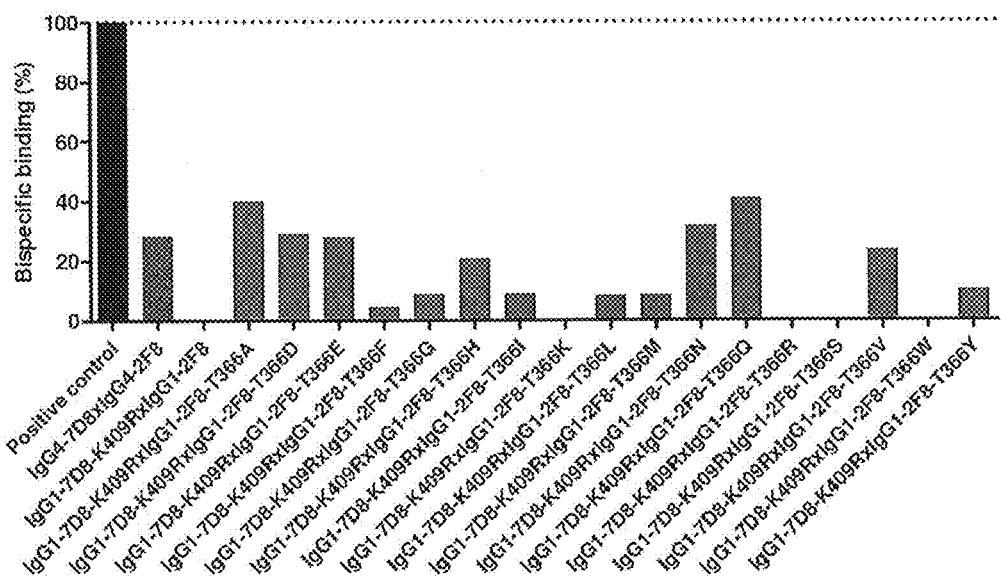

FIG. 38 shows the results of bispecific binding upon 2-MEA-induced Fab-arm exchange between IgG1-2F8-T366X and IgG1-7D8-K409R. These data were also scored as (−) no, (+/−) low, (+) intermediate or (++) high Fab-arm exchange, as presented in Table X. No Fab-arm exchange (−) was found when the 366 position in IgG1-2F8 was T (=wild type IgG1), K, R, S or W. Fab-arm exchange was found to be low (+/−) when the 366 position in IgG1-2F8 was F, G, I, L, M or Y, intermediate (+) when the 366 position in IgG1-2F8 was A, D, E, H, N, V or Q. These data indicate that particular mutations at the IgG1 366 position allow IgG1 to engage in 2-MEA-induced Fab-arm exchange when combined with IgG1-K409R.

TABLE 9

2-MEA-induced Fab-arm exchange between IgG1-2F8-T366X mutants and IgG1-7D8-K409R
The generation of bispecific antibodies after 2-MEA-induced in vitro Fab-arm exchange between IgG1-2F8-T366X mutants and IgG1-7D8-K409R was determined by a sandwich ELISA. (−) no, (+/−) low, (+) intermediate or (++) high Fab-arm exchange.

| IgG1-2F8-T366X | Fab-arm exchange x IgG1-7D8-K409R |
|---|---|
| A | + |
| D | + |
| E | + |
| F | +/− |
| G | +/− |
| H | + |
| I | +/− |
| K | − |
| L | +/− |
| M | +/− |
| N | + |
| Q | + |
| R | − |
| S | − |
| T | − |
| V | + |
| W | − |
| Y | +/− |

Example 38: Determination of the Condition Range in which 2-MEA-Induced Fab-Arm Exchange Occurs Suboptimally to Discriminate Between Highly Efficient IgG1 Mutants The process of 2-MEA-induced Fab-arm exchange occurs efficiently at 37° C. when 25 mM 2-MEA is used. Under these conditions, the majority of permissive IgG1 mutants (IgG1 with certain single mutations at positions 366, 368, 370, 399, 405 and 407 and/or 409 as described in Examples 19, 28, 29, and 34-37) show high levels of 2-MEA-induced Fab-arm exchange (80%-100%). To identify experimental conditions that would allow discrimination between the IgG1 mutants with the highest efficiency, 2-MEA-induced Fab-arm for four different mutant combinations (IgG1-2F8-F405S×IgG1-7D8-K409A, IgG1-2F8-D399R×IgG1-7D8-K409G, IgG1-2F8-L368R×IgG1-7D8-K409H and IgG1-2F8-F405L×IgG1-7D8-K409R) was studied over time at 15° C. and 20° C., respectively. Apart from changes in temperature, time period and antibody dilution (20, 2, 0.2 and 0.02 µg/mL) the procedure was performed as described in Example 19.

At 20° C., 2-MEA-induced Fab-arm exchange of the four mutant combinations occurred at different rates compared to the maximal exchange (positive control). After 105 min incubation, IgG1-2F8-L368R×IgG1-7D8-K409H reached the maximal level of exchange, whereas IgG1-2F8-F405S×IgG1-7D8-K409A, IgG1-2F8-D399R×IgG1-7D8-K409G and IgG1-2F8-F405L×IgG1-7D8-K409R reached a maximum of 90%, 85% and 85%, respectively, after 200 min.

Figure 39:
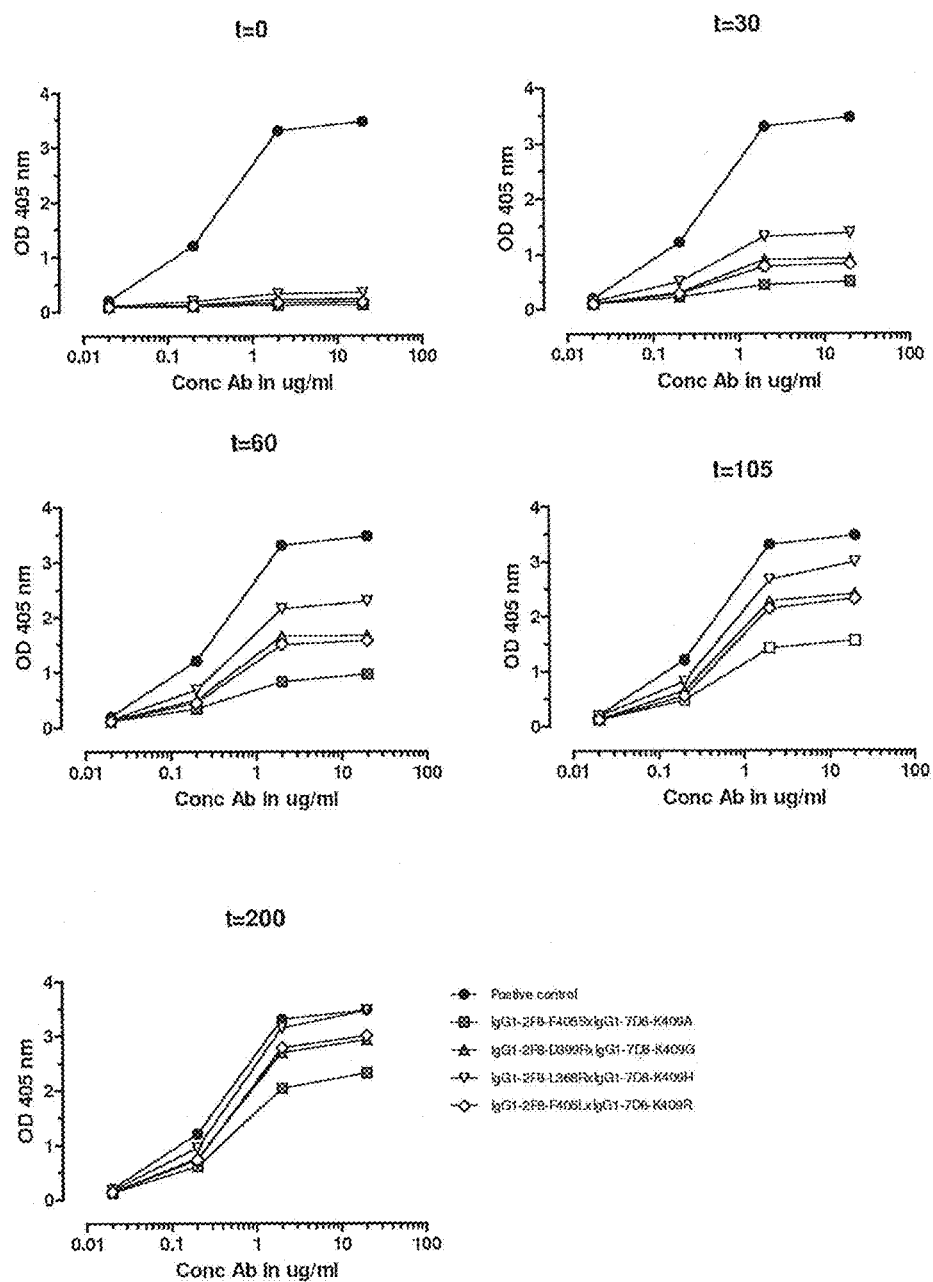
FIG. 39: 2-MEA-induced Fab-arm exchange between four different IgG1 mutant combinations (as indicated) at 15° C. after 0, 30, 60, 105 and 200 min incubations as determined by sandwich ELISA.

Incubation of the different IgG1 mutant combinations at 15° C. showed most prominent differences in exchange rates (shown in FIG. 39). After 60 and 105 min incubations, 2-MEA-induced Fab-arm exchange, the differences between the four mutant combinations were most extreme. Fab-arm exchange after 200 min incubation showed efficiencies of 100% (IgG1-2F8-L368R×IgG1-7D8-K409H), 85% (IgG1-2F8-F405L×IgG1-7D8-K409R and IgG1-2F8-D399R×IgG1-7D8-K409G) or 65% (IgG1-2F8-F405S×IgG1-7D8-K409A) compared to the positive control.

Example 39: Analyzing 2-MEA-Induced Fab-Arm Exchange Efficiencies of Mutants at Suboptimal Conditions The process of 2-MEA-induced Fab-arm exchange occurs efficiently at 37° C. when 25 mM 2-MEA is used. Under these conditions, the majority of permissive IgG1 mutants (IgG1 with certain single mutations at positions 366, 368, 370, 399, 405 and 407 and/or 409 as described in Examples 19, 28, 29, and 34-37) show high levels of 2-MEA-induced Fab-arm exchange (80-100%). In Example 38 it is described that differences in 2-MEA-induced Fab-arm exchange efficiencies are most pronounced after incubation at so called suboptimal conditions, namely at 15° C. for 60 to 105 min. In total 24 IgG1-2F8 mutants at the L368, D399, F405 and Y407 (see Table 11) that show >90% 2-MEA-induced Fab-arm exchange with IgG1-7D8-K409R (Example 28, 29, and 34-37) were selected and subjected to Fab-arm exchange analysis with IgG1-7D8-K409A, G, H or R (based on results shown in Example 19). To categorize these mutant combinations upon their efficiencies to generate bispecific antibodies, 2-MEA-induced Fab-arm exchange was performed at 15° C. for 90 min (suboptimal conditions). Two IgG1-2F8 mutants (Y407Q) and (D399Q) that showed weak 2-MEA-induced Fab-arm exchange after incubation with IgG1-7D-K409R (Example 29 and 36) were taken along as additional negative controls and used to study whether incubation with another amino acid at the K409 position (G, H, or W) leads to a different result. Apart from a change in temperature and changes in antibody dilution (20, 2, 0.2 and 0.02 ug/mL), the procedure was performed as described in Example 19.

Incubation of all different IgG1 mutant combinations (shown in Table 10) at 15° C. for 90 min showed a range of different 2-MEA-induced Fab-arm exchange efficiencies. The result of bispecific binding at an antibody concentration of 20 µg/mL, is shown in Table 10. Results were categorized in 4 classes; no (−), low (+/−) intermediate (+) and high (++) bispecific binding efficiency as is specified in the legend below for Table 10. From these results it becomes clear that under suboptimal conditions some combinations of amino acid mutations in IgG1 molecules will be favorable for 2-MEA-induced Fab-arm exchange.

TABLE 10

Bispecific binding (% relative to positive control) between permissive IgG1 mutants (20 µg/mL) at 15° C. for 90 min

| Fab-arm exchange | IgG1-7D8-K409A | IgG1-7D8-K409G | IgG1-7D8-K409R | IgG1-7D8-K409H |
|---|---|---|---|---|
| IgG1-2F8-L368A | 33 | 33 | 25 | 37 |
| IgG1-2F8-L368D | 49 | 50 | 41 | 54 |
| IgG1-2F8-L368E | 32 | 38 | 37 | 42 |
| IgG1-2F8-L368G | 46 | 53 | 44 | 53 |
| IgG1-2F8-L368H | 26 | 25 | 21 | 29 |
| IgG1-2F8-L368N | 47 | 52 | 43 | 54 |
| IgG1-2F8-L368R | 55 | 64 | 52 | 91 |
| IgG1-2F8-L368S | 39 | 45 | 37 | 53 |
| IgG1-2F8-L368T | 42 | 51 | 39 | 56 |
| IgG1-2F8-L368V | 42 | 49 | 33 | 51 |
| IgG1-2F8-L368W | 56 | 56 | 41 | 60 |
| IgG1-2F8-D399F | 13 | 15 | 14 | 15 |
| IgG1-2F8-D399H | 12 | 14 | 10 | 19 |
| IgG1-2F8-D399K | 40 | 43 | 34 | 46 |
| IgG1-2F8-D399R | 47 | 45 | 38 | 52 |
| IgG1-2F8-D399Q | 0 | 0 | 0 | 0 |
| IgG1-2F8-F405I | 32 | 49 | 39 | 60 |
| IgG1-2F8-F405K | 29 | 48 | 47 | 40 |
| IgG1-2F8-F405L | 31 | 44 | 39 | 46 |

TABLE 10-continued

Bispecific binding (% relative to positive control) between permissive IgG1 mutants (20 µg/mL) at 15° C. for 90 min

| Fab-arm exchange | IgG1-7D8-K409A | IgG1-7D8-K409G | IgG1-7D8-K409R | IgG1-7D8-K409H |
|---|---|---|---|---|
| IgG1-2F8-F405S | 34 | 51 | 45 | 39 |
| IgG1-2F8-F405T | 35 | 47 | 42 | 46 |
| IgG1-2F8-F405V | 36 | 46 | 37 | 43 |
| IgG1-2F8-F405W | 17 | 20 | 16 | 18 |
| IgG1-2F8-Y407L | 44 | 41 | 49 | 49 |
| IgG1-2F8-Y407W | 48 | 53 | 47 | 62 |
| IgG1-2F8-Y407Q | 4 | 9 | 1 | 44 |

Legend for Table 10
No (0-3%) bispecific binding (−)
Low (4-39%) bispecific binding (+/−)
Intermediate (40-69%) bispecific binding (+)
High (70-100%) bispecific binding (++)

Figure 40:
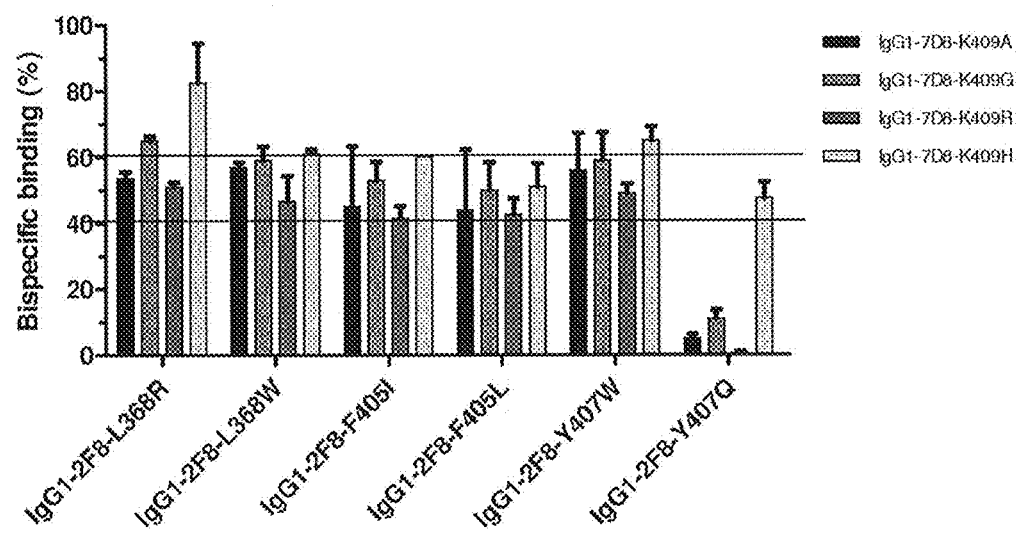
FIG. 40: 2-MEA-induced Fab-arm exchange between different IgG1 mutant combinations after antibody incubation at 15° C. for 90 min as determined by sandwich ELISA.

From the mutated IgG1-2F8 molecules tested (Table 10), six were selected for a second analysis to confirm the results obtained before (Table 10). Several mutants were selected for their high (IgG1-2F8-L368R) and intermediate (IgG1-2F8-L368W, IgG1-2F8-F405I, IgG1-2F8-F405L and IgG1-2F8-Y407W) 2-MEA-induced Fab-arm exchange efficiency. Also IgG1-2F8-Y407Q was analyzed for a second time since it showed an unexpected positive 2-MEA-induced Fab-arm exchange reaction with IgG1-7D8-K409H. In general, these results, presented in FIG. 40, confirmed the primary analysis (Table 10) and show that 2-MEA-induced Fab-arm exchange reactions of mutated IgG1-2F8 molecules with IgG1-7D8-K409H showed highest efficiency. Furthermore, 2-MEA-induced Fab-arm exchange reactions between mutated IgG1-2F8 molecules with IgG1-7D8-K409R that are reported in Examples 28, 29, and 34-37 as negative are still of interest as potentially promoting the IgG1 2-MEA-induced Fab-arm exchange.

Example 40: Generation of CHO Cells Expressing Homodimeric Proteins

Stable CHO-K1SV cell lines expressing IgG1-2F8-F405L and IgG1-7D8-K409R were generated by transfecting CHO-K1SV host cells (Lonza Biologics, Slough, UK) with the Glutamine Synthase (GS) expression vector system (Lonza Biologics, Slough, UK) encoding the IgG heavy and light chain sequences. Cells were transfected using nucleofection (Lonza Biologics, Slough, UK) in protein-free chemically defined medium (CD-CHO; cat. no. 10743-029; Invitrogen, Life Sciences, Breda, The Netherlands). Cells were were plated at 0.1 cell/well in glutamine-deficient CD-CHO medium. After selection of clonal cell lines resistant to growth in glutamine-deficient medium, cells were adapted to suspension growth in CD-CHO and secured in frozen vials. Cells were not subjected to gene-amplification. To produce IgG, cells were inoculated in a p-24 Micro-Reactor at a concentration of $4.0 \times 10^5$ cells/mL in CD-CHO supplemented with 0.7 g/L L-Tyrosine disodium salt (cat. no. T1145-500; Sigma-Aldrich, Zwijndrecht, The Netherlands) and 0.15 g/L L-Cysteine (cat. no. C7352; Sigma-Aldrich), and incubated at 37° C. for 15 days, pH 7.00, initial agitation rate at 70 rpm, a gas flow rate at 20 slpm, a maximum oxygen flow rate at 85% and a DO at 30%. Feeding started at day 3 and continued until day 14. Feeding consisted of CHO-efficient feed with chemical defined media, yielding production levels at harvest of ~1.3-3.4 and 0.1-3.5 g/L for the CHO-K1SV cell lines expressing IgG-2F8-F405L and IgG1-7D8-K409R, respectively. The best producing cell lines were subsequently used to run 2-L Bioreactors using a similar fed-batch process. IgG was purified using Protein A chromatography. After purification, IgGs were formulated in PBS.

Example 41: Formation of Bispecific Antibodies, Generated by 2-MEA-Induced Fab-Arm Exchange Between Human IgG1-2F8-F405L and IgG1-7D8-K409R A 40-mL batch of bispecific antibodies, generated by 2-MEA-induced Fab-arm exchange between human IgG1-2F8-F405L and IgG1-7D8-K409R, was produced. The antibody mixture, containing each antibody at a final concentration of 10 mg/mL (i.e. 20 mg/mL total), was incubated in PBS in the presence of 50 mM 2-MEA at 25° C. for 5 hours. The antibody mixture was stored on ice, O/N. The batch was buffer-exchanged by desalting using HiPrep 26/10 desalting column (cat. no. 17-5087-01, GE Health Care) and analyzed by SDS-PAGE after the purification, or after an additional storage at 4° C. for six days. SDS-PAGE analysis was performed under reducing and non-reducing conditions as described supra. FIG. 42 shows that only partial re-oxidation was observed immediately after buffer-exchange (A, lane 3), as illustrated by the presence of a band representing half molecules (HL) and bands representing other combinations, in addition to the complete IgG band (LHHL). Analysis after six days storage at 4° C. showed that re-oxidation was complete (C, lane 4). Reduced gels (B, D) show single heavy and light chains.

This indicates that re-oxidation occurred quite slow in a large volume and was not complete after O/N incubation.

Example 42: Role of Trace-Metals in the Re-Oxidation Process

To investigate the role of trace-metals in the re-oxidation process, anti-CD38 antibodies were incubated (15 mg/mL; 1 mL) in the presence of 50 mM 2-MEA at 25° C. for 5 h. Samples were desalted using a PD-10 column (GE Healthcare), and buffer was exchanged to PBS containing 0.5 mg/L $Cu^{2+}$ ($CuSO_4$; cat. no. 451657-10G, Sigma Aldrich) or to PBS containing 2 mM EDTA. Samples were taken after incubation at RT for different time periods, quenched with 3 µL of 1 M 2-odoacetamide (IAA; cat. no. I-1149, Sigma Aldrich) and stored in the dark at RT for 30 minutes. Subsequently, samples were stored at 5° C. until further analysis.

SDS-PAGE analysis was performed under non-reducing and reducing conditions as described supra.

Figure 62:
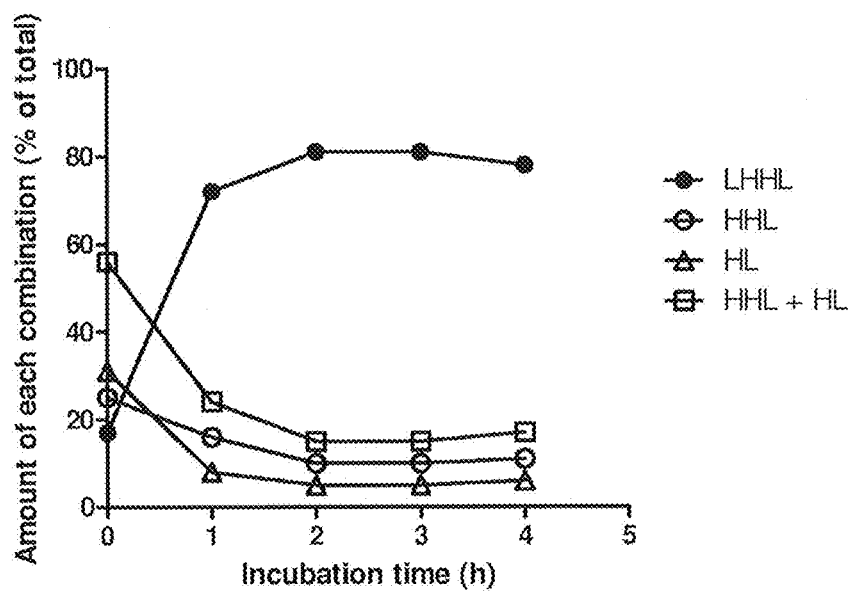
FIG. 62: Relative amount of heavy chain-light chain combinations after different incubation times in the presence of $Cu^{2+}$. Individual molecular species were quantified by densitometry from the SDS-PAGE gels. The total intensity of all scanned bands was set to 100%.

FIG. 61A shows that buffer exchange into PBS containing EDTA prevented re-oxidation. In the presence of EDTA (lane 2 till 7), free light chains (L) and heavy chains (H) were present at all time points. In addition, other incompletely re-oxidized species were present such as antibody half molecules (HL) and antibodies missing one light chain (HHL) or two light chains (HH). Buffer exchange into PBS containing $Cu^{2+}$ induced re-oxidation (FIG. 61B lane 2 till 7, and FIG. 62). Although complete re-oxidation was not reached, significant re-oxidation of the antibody and the complete absence of free light and heavy chains were observed at all time points. Reduced gels (B, D) show single heavy and light chains.

Example 43: Formation of Bispecific Antibodies, Generated by 2-MEA-Induced Fab-Arm Exchange Between Human IgG1-2F8-F405L and IgG1-7D8-K409R, Under Different Buffer Conditions Batches of bispecific antibody were generated by 2-MEA-induced Fab-arm exchange between human IgG1-2F8-

Figure 41:
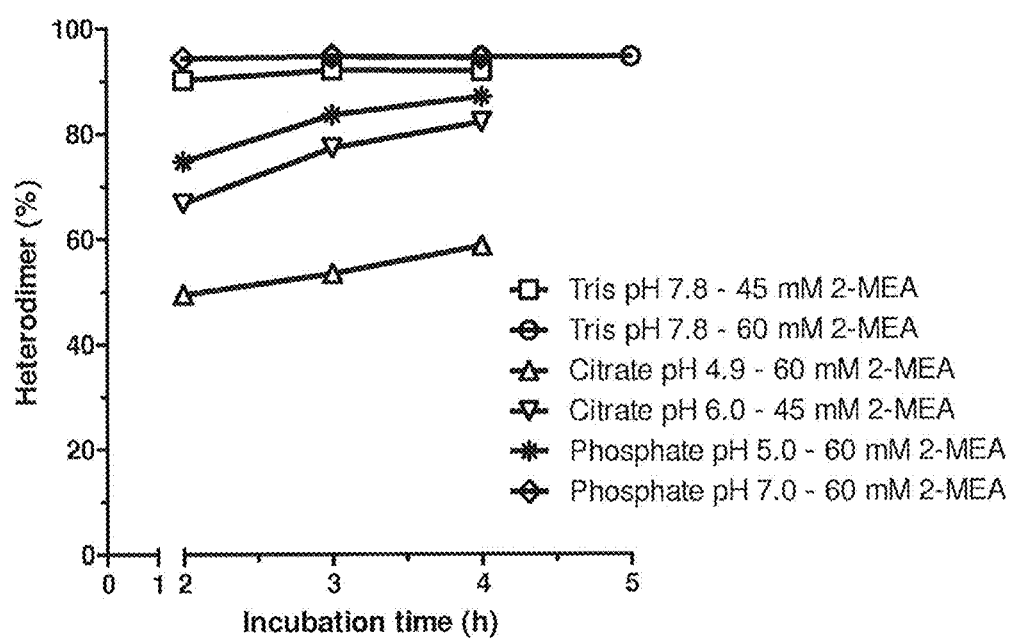
FIG. 41: Bispecific antibodies were analyzed by analytical CIEX and the percentage of heterodimers formed over time in the different buffers (as indicated in the legend) was calculated as follows: Heterodimer (%)=100%−[peak area % IgG1-2F8-F405L+peak area % IgG1-7D8-K409R].
Figure 42A:
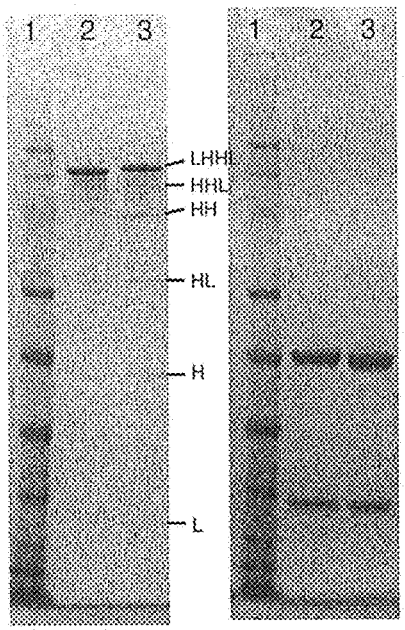
FIGS. 42A-42D: The 40 mL batch of bispecific antibodies produced with a mixture containing 10 mg/mL of each antibody, was analyzed by SDS-PAGE under non-reducing (FIG. 42A, FIG. 42C) and reducing (FIG. 42B, FIG. 42D) conditions, after storage at 0° C., O/N (FIG. 42A, FIG. 42B) or at 4° C. for six days (FIG. 42C, FIG. 42D). Lane 1 of each gel contains the MW marker, lane 2 contains the IgG1 internal assay control. A, B: lane 3: 40 mL batch of bispecifics produced with a mixture containing 10 mg/mL of each antibody; C, D: lane 4: 40 mL batch produced with a mixture containing 10 mg/mL of each antibody. For non-reducing conditions, different combinations of heavy chain (H) and light chain (L) are indicated: 148 kDa (LHHL), 125 kDa (HHL), 99 kDa (HH), 67 kDa (HL), 51 kDa (H) and 25 kDa (L).
Figure 42B:
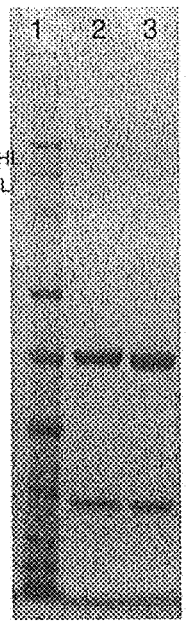
Figure 42C:
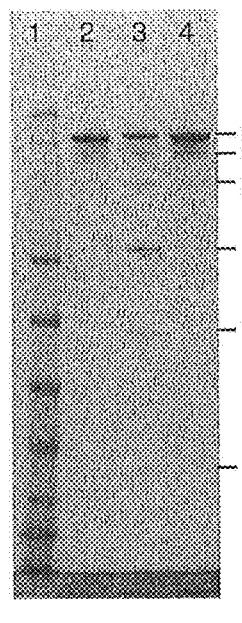
Figure 42D:
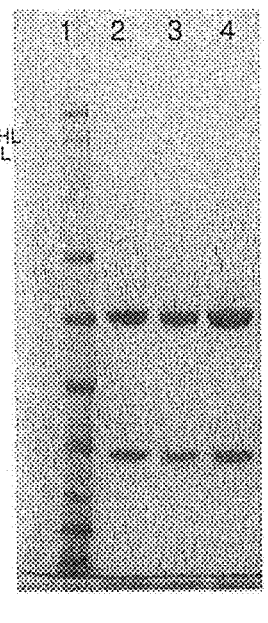

F405L and IgG1-7D8-K409R under different buffer conditions at 0.5 mL scale. The antibodies were diluted to a concentration of 5 mg/mL in the following buffers: 1) 1× Dulbecco's phosphate-buffered saline (DPBS): 8.1 mM sodium phosphate ($Na_2HPO_4$-$7H_2O$), 1.5 mM potassium phosphate ($KH_2PO_4$), 138 mM sodium chloride (NaCl), 2.7 mM potassium chloride (KCl) pH 5.0 (diluted from 10×DPBS, cat. no. 14200, Invitrogen); 2) 1×DPBS pH 7.0 3) 20 mM sodium citrate (cat. no. 0119-01, JT Baker), pH 4.9; 4) 20 mM sodium citrate, pH 6.0; and 5) 20 mM Tris-HCl (cat. no. T6666 and T6791, Sigma), 20 mM NaCl (cat. no. 3624-01, JT Baker), pH 7.8. Subsequently, the antibodies, each at a final concentration of 2 mg/mL (i. e. a total antibody concentration of 4 mg/mL), were incubated in the presence of 45 or 60 mM 2-MEA at 25° C. for 2-5 hours. 2-MEA was added from a 300 mM stock solution prepared using the same buffer as the antibodies. At various time points, samples were taken and desalted using illustrate microspin G-25 columns (cat. no. 27-5325-01, GE Healthcare) to 10 mM sodium phosphate (sodium phosphate dibasic, cat. no. 3828-01 and sodium phosphate monobasic, cat. no. 3818-01, both JT Baker), pH 7.0, according to the manufacturer's instructions. Next, samples were analyzed by analytical CIEX, as described supra, to determine the percentage of heterodimerization. FIG. 41 shows that the final heterodimer levels were comparable in Tris and phosphate buffer, but that the kinetics of heterodimer formation were clearly impacted by the type of buffer and the pH. The kinetics appeared slower in citrate buffer, pH 4.9 than in phosphate buffer, pH 5.0 and in citrate buffer, pH 6.0. Kinetics were slower in 1×DPBS pH 5.0 compared to 1×DPBS pH 7.0.

Figure 43:
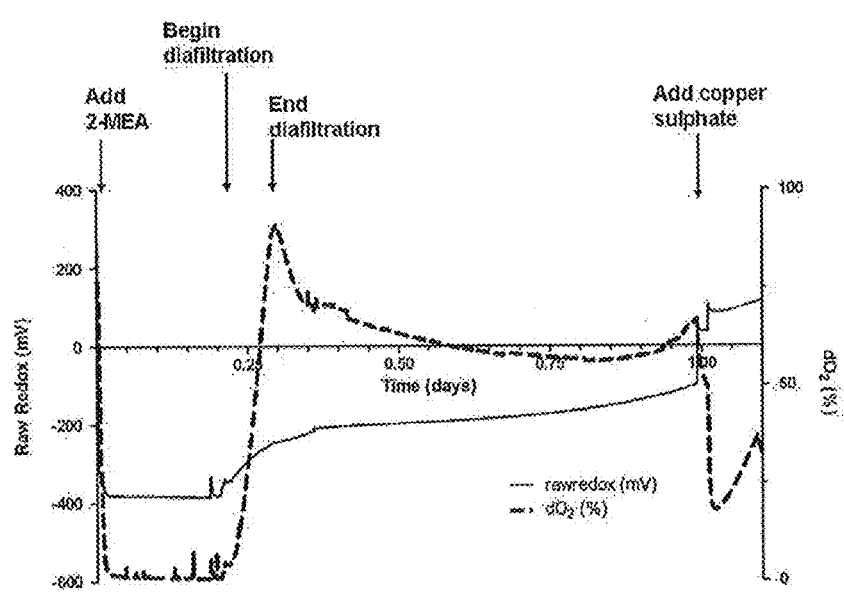
FIG. 43: Redox potential and oxygen saturation during reduction and oxidation of IgG1 anti-CD38 antibody. Redox potential and oxygen saturation during reduction and oxidation phase were followed using a redox probe and a dissolved oxygen (DO) probe. The left y-axis and the solid line show redox potential; the right y-axis and the dashed line show oxygen saturation as measured in the solution during the different phases of the process, as indicated by the arrows.
Figure 44:
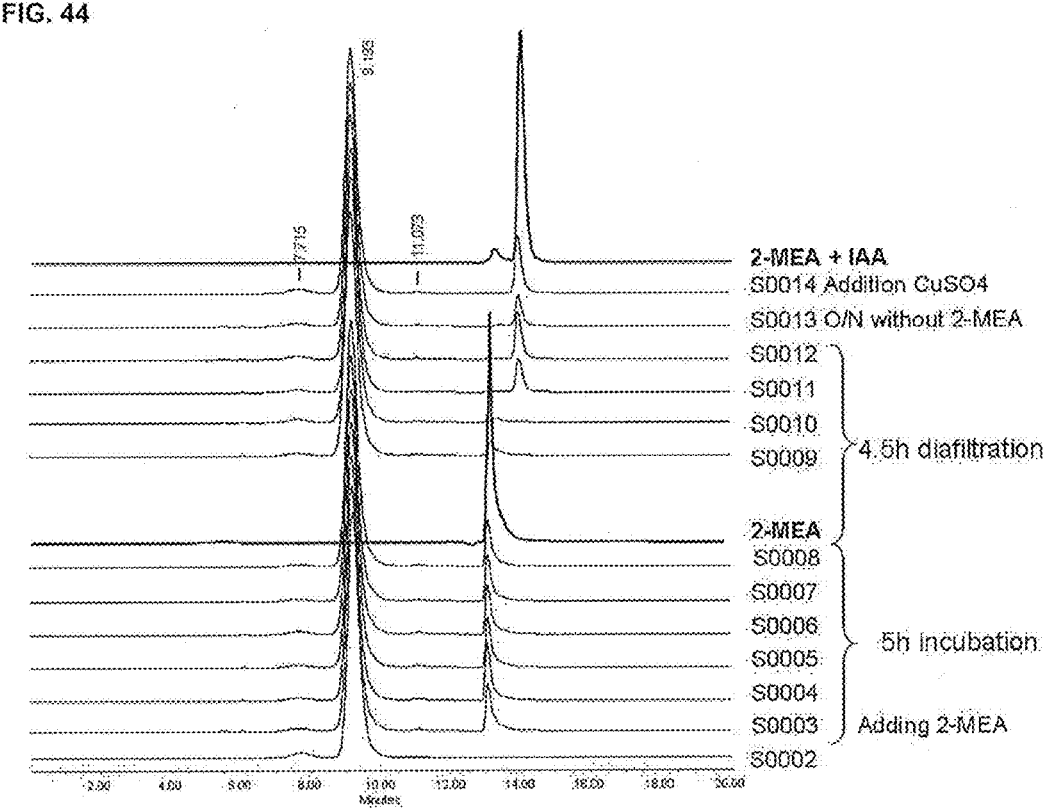
FIG. 44: HP-SEC analysis during reduction and oxidation of anti-CD38 antibody. Samples taken during the reduction and oxidation of anti-CD38 antibody were analyzed by HP-SEC. Sample 2 (S0002): anti-CD38 antibody after buffer exchange from formulation buffer to PBS; sample 3 to 8: anti-CD38 antibody during reduction phase (incubation times: 1, 2, 3, 4, 4½, 5 h); sample 9 to 12: anti-CD38 antibody during the diafiltration process (samples at 1, 2, 3, 4 h); sample 13: anti-CD38 antibody after O/N incubation; sample 14: anti-CD38 antibody after addition of CuSO$_4$ to the solution. For comparison, HP-SEC profiles of 2-MEA alone and 2-MEA with 2-iodoacetamide (IAA) are shown in bold lines. The peaks at 7.715 and 9.193 represent dimeric and monomeric IgG1. The nature of the peak at 11.073 is not known.
Figure 45:
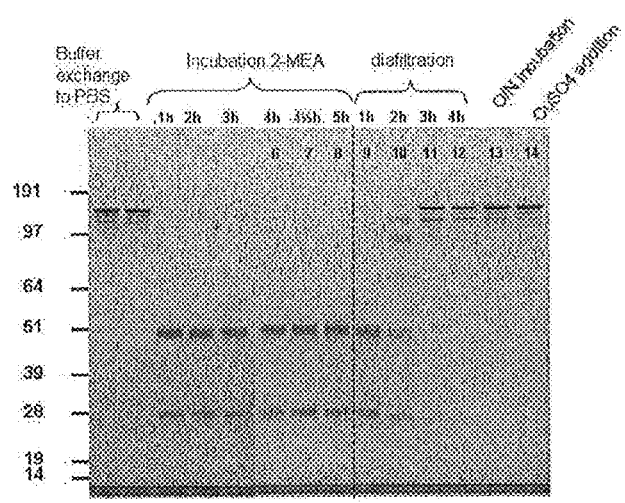
FIG. 45: SDS-PAGE analysis during reduction and oxidation of anti-CD38 antibody. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange to PBS; lane 3 till 8: anti-CD38 antibody during reduction phase (incubation times indicated above the figure); lane 9 till 12: anti-CD38 antibody during the diafiltration process; lane 13: anti-CD38 antibody after O/N incubation; lane 14: anti-CD38 antibody after addition of CuSO$_4$ to the solution.
Figure 46:
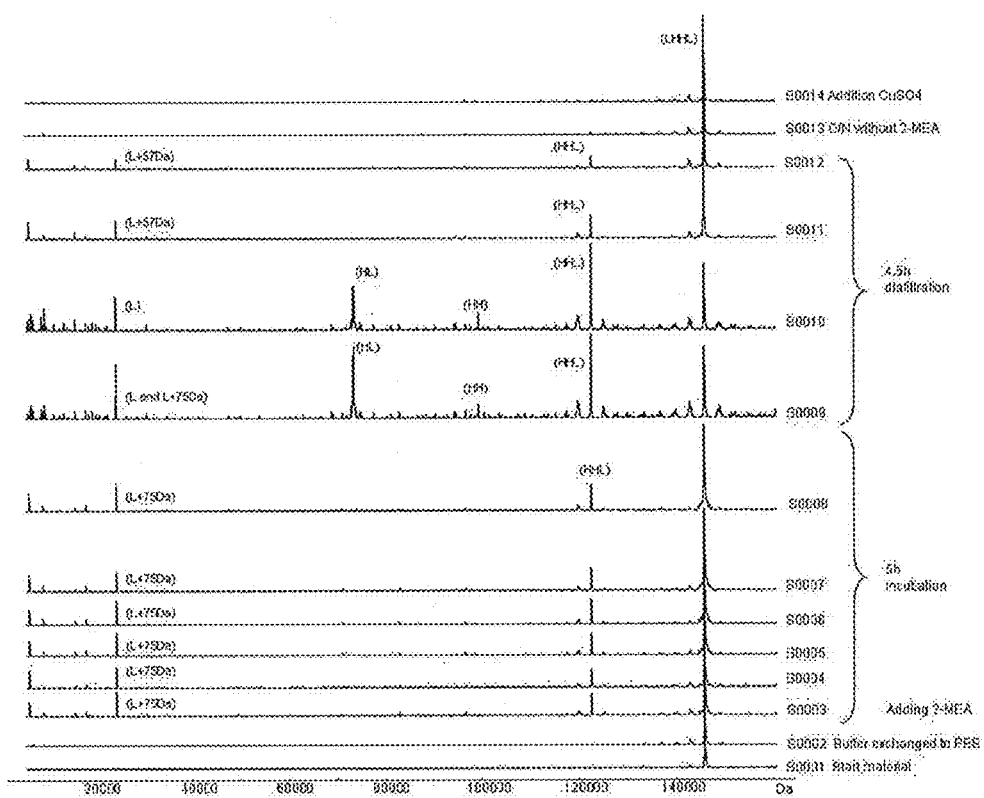
FIG. 46: ESI-MS analysis during reduction and oxidation of anti-CD38 antibody. Samples taken during reduction and re-oxidation of anti-CD38 antibody were quenched and analyzed by ESI-MS analysis. Sample 1 (S0001): anti-CD38 antibody in formulation buffer; sample 2: anti-CD38 antibody after buffer exchange to PBS; sample 3 till 8: anti-CD38 antibody during reduction phase (incubation times: 1, 2, 3, 4, 4½, 5 h); sample 9 till 12: anti-CD38 antibody during the diafiltration process (samples at 1, 2, 3, 4 h); sample 13: anti-CD38 antibody after O/N incubation; sample 14: anti-CD38 antibody after addition of CuSO$_4$ to the solution. It should be noted that LC-MS facilitates the re-oxidation process by either reductant removal in the LC system or during the electrospray process were the sample is exposed to air, i.e. oxygen. Samples may lose covalently attached reductant molecules which have not been capped by IAA during the quench step. Hence, covalently intact re-oxidized IgG is therefore over-estimated by ESI-MS compared to SDS-PAGE. Different combinations of heavy chain (H) and light chain (L) are indicated: LHHL, HHL, HH, HL, H and L. Mass details are only given for the light chain (L) in the figure; +2-MEA=+75 Da; +2-iodoacetamide=+57 Da.

Example 44: Redox Potential, Oxygen Saturation and Formation of Intermediates During Reduction and Oxidation of Human IgG1 Anti-CD38 Antibody Human IgG1 anti-CD38 antibody (005, described in WO 2006099875 (Genmab) was used to develop a model system for evaluating the reduction and re-oxidation processes. Anti-CD38 antibody (20 g/L) was diafiltered with a hollow fiber cartridge, 30 kDa molecular weight cut-off (MWCO), 0.1 m² (cat. no. P-N1-030E-200-01N, J & M Separations, Tilburg, The Netherlands) from formulation buffer (25 mM sodium acetate, 60 mM sodium chloride [cat. no. 3624-01, JT Baker], 140 mM mannitol, 0.006% polysorbate 20, pH 5.5) into PBS (cat. no. 3623140, B. Braun, Oss, The Netherlands), pH 7.4, and concentrated to 24 g/L in 833 mL total volume in a 2-L reactor. Temperature was controlled at 25° C. and agitation at 100 rpm. To follow the reaction, the solution was monitored using a redox probe (Applicon Biotech, Schiedam, The Netherlands) and a dissolved oxygen (DO) probe (Applicon Biotech). At the start of the experiment, the solution redox was 259.6 mV and the DO was 100% (air saturation of oxygen). At time 0, reductant 2-MEA (2-mercaptoethylamine-HCl, cysteamine) was added to the reactor at a final concentration of 300 mM, resulting in an initial solution of 20 g/L anti-CD38 antibody and 300 mM 2-MEA. Upon addition of 2-MEA, the redox potential immediately dropped to ~–400 mV (FIG. 43). The DO also dropped at this time to 2.6% of the original 100% air saturation of oxygen, indicating that 2-MEA was auto-oxidizing to the dimeric form cystamine. Five hours later, excess 2-MEA (and cystamine) was removed via diafiltration with PBS, pH 7.4. To accomplish this, the reactor contents were circulated through a 30 kDa modified polyethersulfone (mPES) hollow fiber cartridge (cat. no. P-N1-030E-200-01N, J & M Separations, Tilburg, The Netherlands) 30 kDa molecular weight cut-off (MWCO), 0.1 m². The cartridge inlet pressure was controlled at 25 PSI (170 kPa), resulting in a permeate flow of 25 mL/min. Diafiltration buffer, e.g. PBS, was added to the system at the same rate as permeate left the system. Diafiltration proceeded until seven times the original volume (seven diavolumes; ~7 L) had passed through the system, which took 4% hours. After that point, the system was incubated with active temperature and agitation control, O/N. The next day, the DO and redox values remained substantially below starting levels, suggesting that the reaction had not completed. To evaluate this hypothesis, copper sulphate was added to a final concentration of 0.5 mg/L ($CuSO_4$; cat. no. 451657-10G, Sigma Aldrich). Divalent metal ions such as $Cu^{2+}$ are a catalyst for sulfhydryl oxidation. Upon addition of copper sulphate, an immediate further drop in DO occurred, suggesting immediate consumption of oxygen e.g. (re-)oxidation. Throughout the experiment, 14 samples were taken from the reactor and immediately quenched with 2-iodoacetamide (IAA, cat. no. I-1149, Sigma) (20 μL of 1 M 2-iodoacetamide was added to 1 mL of reactor sample). 2-iodoacetamide binds covalently to the thiol group of cysteine, thus blocking the ability of any reduced cysteine to reform an inter-chain disulfide bond. In this manner, the kinetics of reduction by 2-MEA and re-oxidation of the antibody by oxygen can be tracked. Samples were analyzed by HP-SEC (FIG. 44), non-reduced SDS-PAGE (FIG. 45) and liquid chromatography electrospray ionization mass spectrometry (LC-ESI-MS) (FIG. 46). Samples 1 and 2 are controls showing anti-CD38 antibody before and after transfer from formulation buffer into PBS. Samples 3 till 8 show the product during the 5-hour reduction phase. By HP-SEC (monitoring at 280 nm), the antibody eluted as an intact product; a later eluting product is cystamine (2-MEA does not strongly absorb at 280 nm). On SDS-PAGE, the product ran as two independent bands of heavy and light chain under the denaturing conditions of a non-reduced gel. Taken together, these data show that the product was fully reduced within one hour (SDS-PAGE), but that the heavy and light chains remained associated by non-covalent interactions under native conditions (HP-SEC). Samples 9-12 were taken during the diafiltration process. By HP-SEC, the product remained intact under native conditions; the late eluting cystamine peak gradually disappeared followed by the appearance of a peak corresponding to 2-iodoacetamide that reacted with 2-MEA. These results suggest that there is still excess 2-MEA in solution that reacts with 2-iodoacetamide or that 2-MEA was bound to the protein and released O/N or upon addition of 2-iodoacetamide. By SDS-PAGE, there was a transition from a single heavy chain and single light chain band to multiple bands of unknown composition; however, by the end of diafiltration (sample 13), the product was fully re-oxidized to the native form, even prior to the addition of copper sulfate (sample 14).

To monitor the process of reduction and re-oxidation of the antibodies, samples were analyzed by ESI-MS to determine the molecular weights. Different peaks in the profile represent intermediates, such as half molecules, formed during the process. Samples were desalted on an Aquity UPLC™ (Waters, Milford, USA) with a BEH300 C18, 1.7 μm, 2.1×50 mm column at 60° C. and eluted with a gradient of a mixture of MQ water (eluens A) and LC-MS grade acetonitrile (eluens B) (Biosolve, Valkenswaard, The Netherlands) containing 0.05% formic acid (Fluka Riedel-de Haën, Buchs, Germany). Time-of-flight electrospray ionization mass spectra were recorded on-line on a micrOTOF™ mass spectrometer (Bruker, Bremen, Germany) operating in the positive ion mode. Prior to analysis, a 500-4000 m/z scale was calibrated with ES tuning mix (Agilent Technologies, Santa Clara, USA). Mass spectra were deconvoluted using Maximal Entropy that is provided with the DataAnalysis™ software v. 3.4 (Bruker, Bremen, Germany).

FIG. 46 shows mass spectrometry profiles during reduction and re-oxidation of anti-CD38 antibody. Samples taken during the reduction phase (sample 3-8) showed that 2-MEA was covalently bound to the reduced light chain (mass difference of 75 Da), likely explaining the multiple light chain bands on non-reduced SDS-PAGE (FIG. 45). Apparently, re-oxidation into full length IgG was induced by the mass spectrometry procedure, as full length IgG, detected by ESI-MS samples taken during the reduction phase, was not detected by non-reduced SDS-PAGE (FIG. 45). Upon start of the diafiltration, re-oxidation into full length antibody occurred, with HL (mass around 75 kDa) and HHL fragments (mass around 120 kDa) as intermediates. These data show also that during reductant (e.g. 2-MEA) removal by diafiltration, the antibody was re-oxidized by reforming its natural covalent cysteine bridges.

Figure 47:
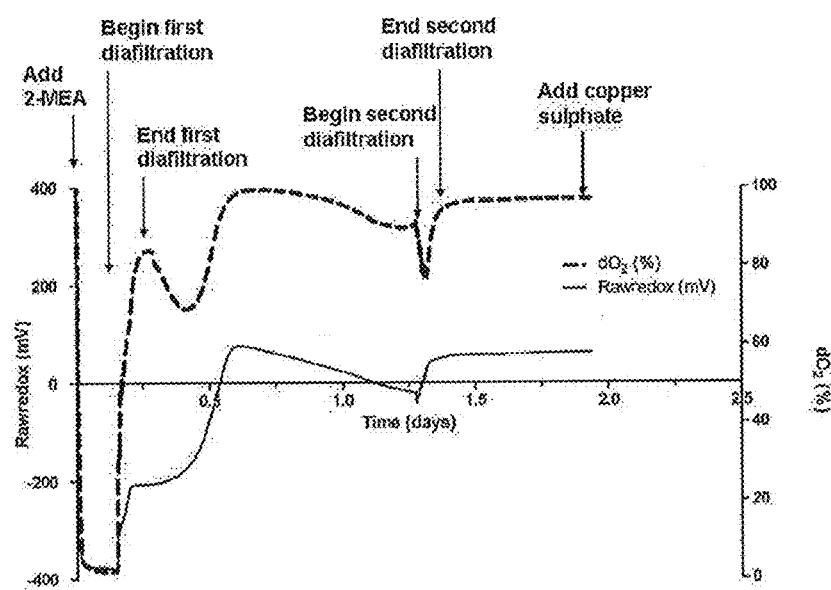
FIG. 47: Redox potential and oxygen saturation during reduction and oxidation of IgG1 anti-CD38 antibody—faster diafiltration and second diafiltration step. Redox potential and oxygen saturation during reduction and oxidation phase were followed using a redox probe and a dissolved oxygen (DO) probe. The left y axis and the solid line show redox potential; the right y axis and the dashed line show oxygen saturation as measured in the solution during the different phases of the process, as indicated by the arrows.
Figure 48:
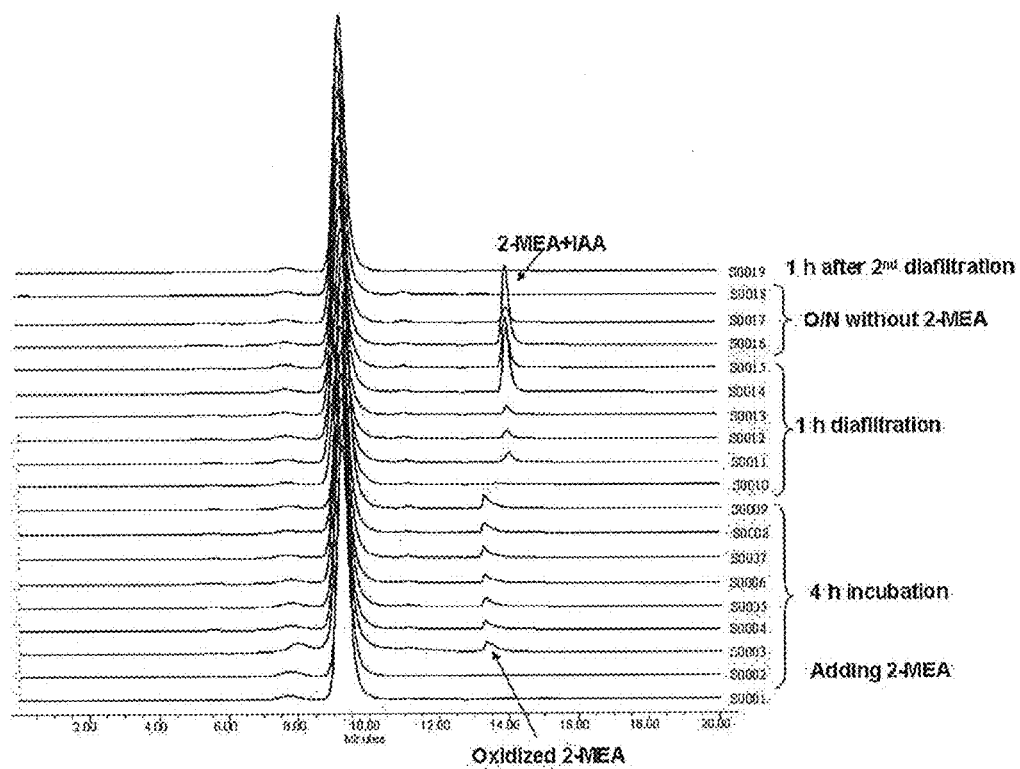
FIG. 48: HP-SEC analysis during reduction and oxidation of anti-CD38 antibody—faster diafiltration and second diafiltration step. Samples taken during the reduction and oxidation of anti-CD38 antibody were analyzed by HP-SEC. Sample 1 (S0001): anti-CD38 antibody in formulation buffer, sample 2: anti-CD38 antibody after buffer exchange from formulation buffer to PBS; sample 3 till 9: anti CD38 antibody during reduction phase (incubation times 5, 10, 15, 30 and 60 min and 2 and 3 h); sample 10 till 15: anti-CD38 antibody during the diafiltration process (samples after 10, 20, 30, 40, 50 and 60 min); sample 16 till 18: anti-CD38 antibody 1, 2 and 25 hours after diafiltration; sample 19: anti-CD38 antibody 1 hour after second diafiltration.
Figure 49:
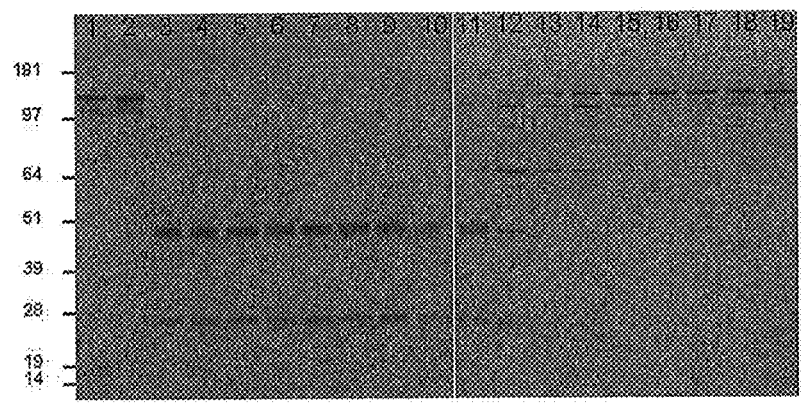
FIG. 49: SDS-PAGE analysis during reduction and oxidation of anti-CD38 antibody—faster diafiltration and second diafiltration step. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange to PBS; lane 3 till 9: anti-CD38 antibody during reduction phase (incubation times 5, 10, 15, 30 and 60 min and 2 and 3 h); lane 10 till 15: anti-CD38 antibody during the diafiltration process (samples after 10, 20, 30, 40, 50 and 60 min); lane 16 till 18: anti-CD38 antibody 1, 2 and 25 hours after diafiltration; lane 19: anti-CD38 antibody 1 hour after second diafiltration.

Example 45: Influence of Faster Diafiltration and Second Diafiltration on the Re-Oxidation Process The experiment in Example 44 was repeated with the following differences. First, the reduction step was reduced from 5 to 4 hours, since it was observed that reduction was already complete within 4 hours. Second, to accelerate the process, the diafiltration time was reduced to 1 hour by using a larger hollow fiber cartridge 30 kDa, 0.4 m$^2$. The permeate flow per cm$^2$ was the same as in example 44, resulting in a four times faster diafiltration step. Third, following the O/N oxidation period, a second diafiltration was performed using an additional seven diavolumes, since the first experiment demonstrated the appearance of 2-MEA after O/N incubation. The trend in redox and DO traces (FIG. 47) as well as the HP-SEC (FIG. 48) and SDS-PAGE (FIG. 49) results of 2-iodoacetamide-treated samples were consistent with the results in Example 44 up to the point of the second diafiltration (note that the time scale for the redox potential and oxygen saturation in example 44 and the present example are different). Just prior to the second diafiltration, the product appeared to be slightly more reduced compared to the end of diafiltration on the previous day (FIG. 49, lane 18 versus lane 15). After the second diafiltration (lane 19), the product reverted back to that from the original state and the 2-MEA-2-iodoacetamide peak disappeared from the HP-SEC profile. In addition, after the second diafiltration, the redox and DO probe values (FIG. 47) were similar to those from the start of the experiment, suggesting that the reaction was complete and that traces of 2-MEA and cystamine were more fully removed from the system than in the experiment described in example 44. Furthermore, the addition of copper sulfate after the second diafiltration did not result in a change in redox or DO, demonstrating the absence of appreciable levels of oxidizable sulfhydryls. These results indicate that a second diafiltration was useful to remove any excess of 2-MEA that was either left in solution or liberated from the protein after O/N incubation.

Figure 50:
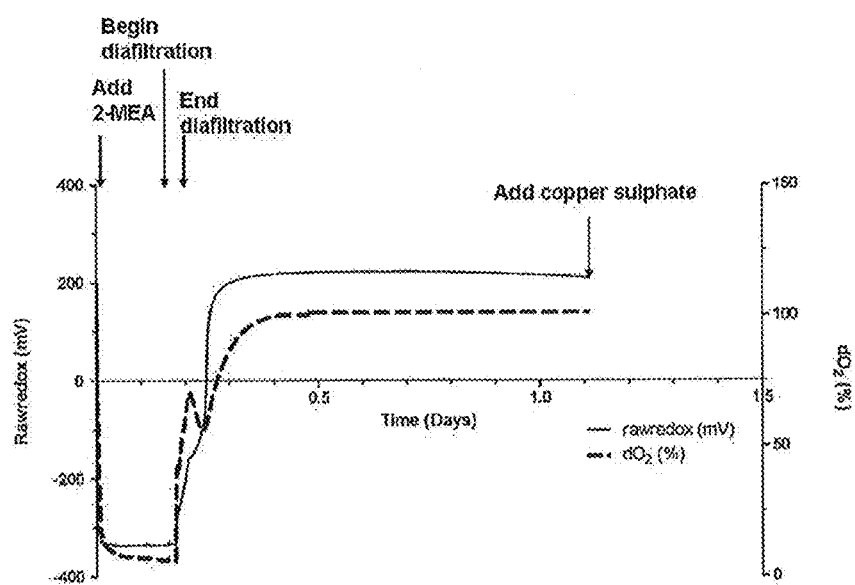
FIG. 50: Redox potential and oxygen saturation during reduction and oxidation of IgG1 anti-CD38 antibody—faster diafiltration and lower 2-MEA concentration. Redox potential and oxygen saturation during reduction and oxidation phase were followed using a redox probe and a dissolved oxygen (DO) probe. The left y axis and the solid line show redox potential; the right y axis and the dashed line show oxygen saturation as measured in the solution during the different phases of the process, as indicated by the arrows.
Figure 51:
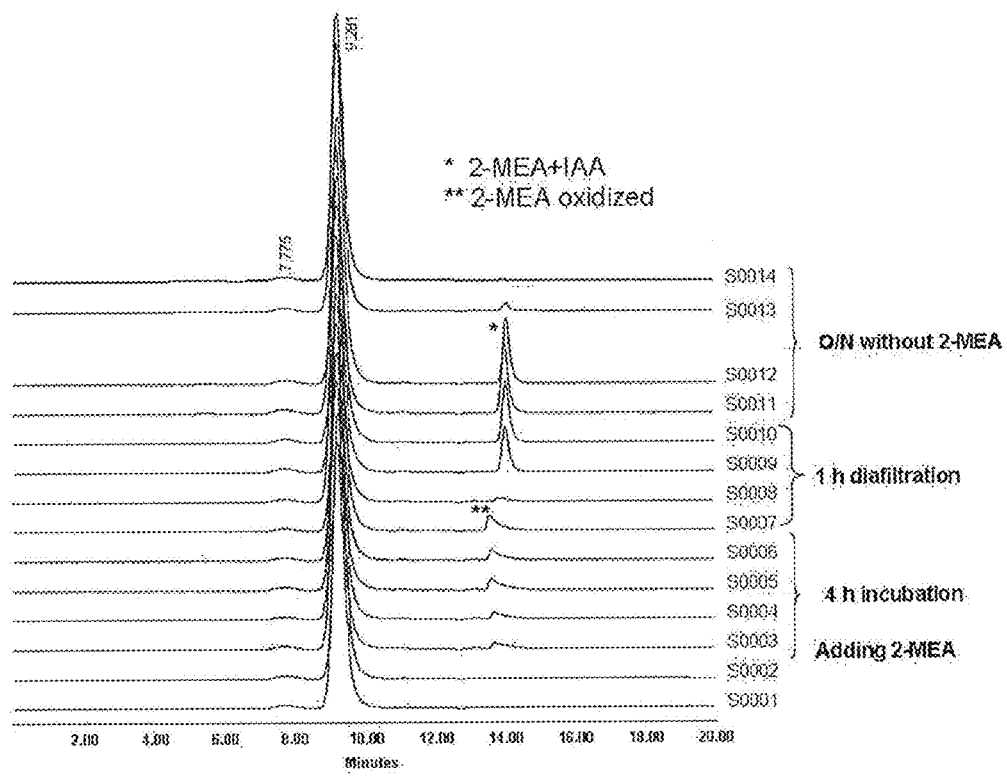
FIG. 51: HP-SEC analysis during reduction and oxidation of anti-CD38 antibody—faster diafiltration and lower 2-MEA concentration. Samples taken during the reduction and oxidation of anti-CD38 antibody were analyzed by HP-SEC. Sample 1 (S0001): anti-CD38 antibody in formulation buffer; sample 2: anti-CD38 antibody after buffer exchange from formulation buffer to PBS; sample 3 till 6: anti-CD38 antibody during reduction phase (incubation times: 20 and 60 min and 3 and 4 hours); sample 7 till 10: anti-CD38 antibody during the diafiltration process (samples after 10, 20, 40 and 60 min); sample 11 till 14: anti-CD38 antibody 1, 2, 3 and 24 hours after diafiltration stop.
Figure 52:
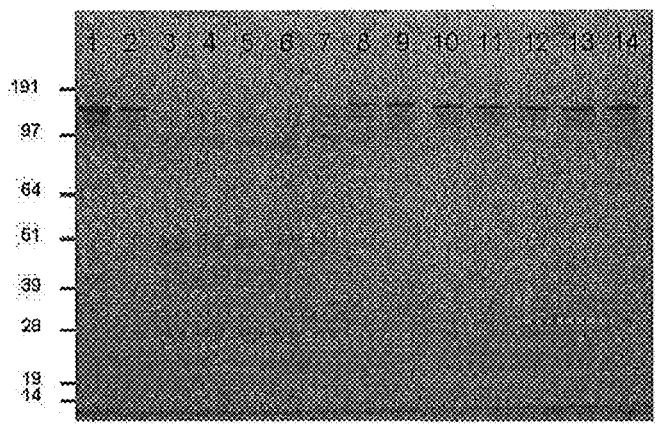
FIG. 52: SDS-PAGE analysis during reduction and oxidation of anti-CD38 antibody—faster diafiltration and lower 2-MEA concentration. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange from formulation buffer to PBS; lane 3 till 6: anti-CD38 antibody during reduction phase (incubation times: 20 and 60 min and 3 and 4 hours); lane 7 till 10: anti-CD38 antibody during the diafiltration process (samples after 10, 20, 40 and 60 min); lane 11 till 14: anti-CD38 antibody 1, 2, 3 and 24 hours after diafiltration stop.

Example 46: Influence of Faster Diafiltration Combined with Lower 2-MEA Concentration The residual 2-MEA observed after O/N incubation in Example 44 suggested that the 2-MEA concentration was too high. Therefore, the experiment in Example 44 was repeated with the exception that the 2-MEA concentration was reduced from 300 mM to 50 mM and, as in Example 45, the the reduction step was reduced to 4 hours and the diafiltration time was accelerated to 1 hour. Following reduction and diafiltration, the DO and redox probes returned to the original values, suggesting that the reaction was complete (FIG. 50). Addition of copper had no effect, further suggesting that the reaction was complete. As observed in examples 44 and 45, the product remained intact under native conditions in HP-SEC analysis (FIG. 51); furthermore, the late eluting cystamine peak gradually disappeared, followed by the appearance of a peak corresponding to 2-iodoacetamide bound to 2-MEA. However, in this case, all later eluting peaks were gone after O/N incubation. The SDS-PAGE results (FIG. 52) demonstrated the absence of intact antibody during the reduction phase (lane 3 till 6), although in this case, the molecule was not fully reduced into separate heavy and light chains. Upon diafiltration (lane 7 till 10), it was apparent by SDS-PAGE that the antibody reformed to the original banding pattern and remained that way through O/N incubation (lane 11 till 14).

Figure 53A:
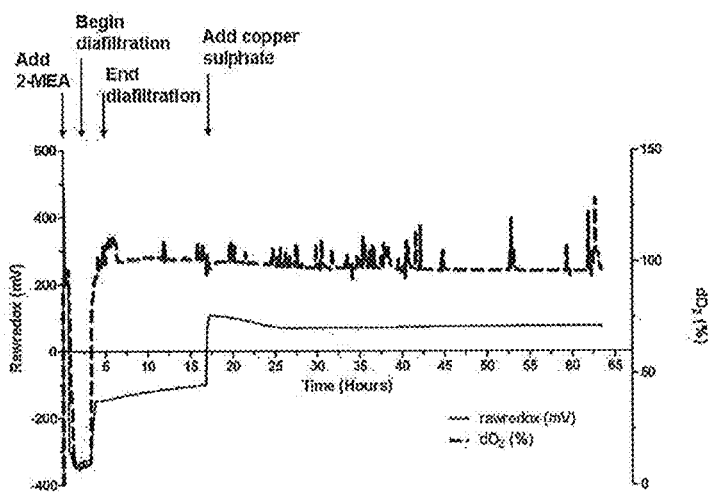
FIGS. 53A and 53B: Redox potential and oxygen saturation during reduction and oxidation of IgG1 anti-CD38 antibody—faster diafiltration and presence of EDTA during reduction phase.
Figure 53B:
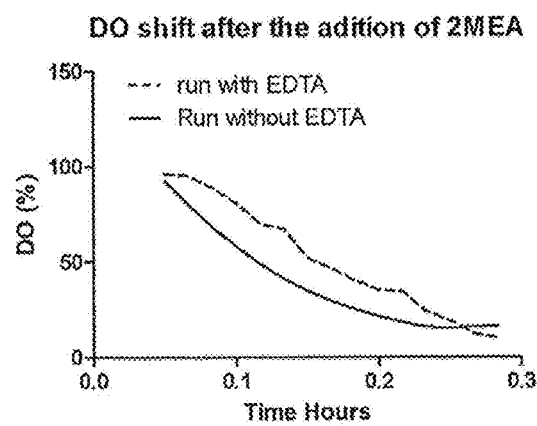

Example 47: Influence of Faster Diafiltration and the Presence of EDTA During the Reduction Phase The experiment of example 46 was repeated with the exception that the anti-CD38 antibody was exchanged from formulation buffer into PBS containing 2 mM EDTA. The goal of the addition of EDTA was to inhibit auto-oxidation of 2-MEA during the reduction phase and potentially to limit binding of 2-MEA to free protein sulfhydryls. Upon addition of 2-MEA, the redox potential dropped immediately (FIG. 53), as was shown in Example 46 (FIG. 50). However, the rate of DO drop was much lower than that observed in Example 46 (see FIG. 53 B). The drop in oxidation rate upon addition of the metal-chelating agent EDTA, suggests that trace-metal impurities in the buffer reagents were catalyzing the auto-oxidation of 2-MEA during the reduction phase. However, EDTA was not able to fully inhibit auto-oxidation of 2-MEA, since the DO finally dropped close to zero, suggesting that under the experimental conditions, oxygen transfer was eventually rate limiting in the auto-oxidation of 2-MEA. After diafiltration to PBS without EDTA, the DO almost returned to the starting point of 100%, suggesting a low rate of oxygen consumption, while the redox potential was still substantially below the starting point. Upon addition of 0.5 mg/L copper sulfate, a small amount of precipitate formed, likely due to the binding of copper ions by the residual EDTA. In addition, the DO dropped almost 10%, indicating increased oxidation upon addition of copper ions.

Figure 54:
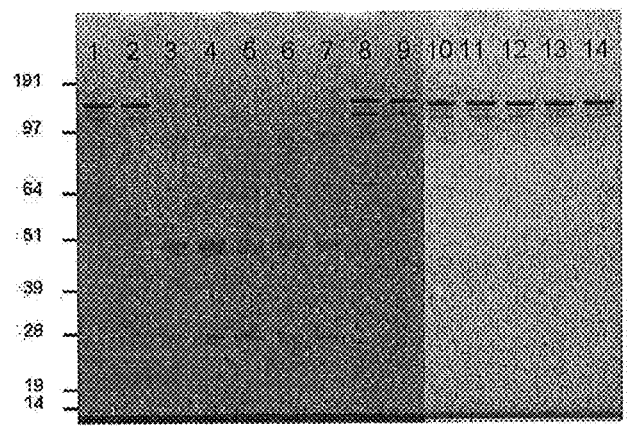
FIG. 54: SDS-PAGE analysis during reduction and oxidation of anti-CD38 antibody—faster diafiltration and presence of EDTA during reduction phase. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange from formulation buffer to PBS; lane 3 till 7: anti-CD38 antibody during reduction phase (incubation times: 10 min and 1, 2, 3 and 4 hours); lane 8 till 11: anti-CD38 antibody during the diafiltration process (samples at 10, 30, 40 and 60 min after start diafiltration); lane 12 till 14: anti-CD38 antibody 1 and 24 hours and 6 days after stop diafiltration.

The SDS-PAGE results (FIG. 54) were comparable to those observed in example 46 and demonstrated that the addition of EDTA during reduction did not have a clear effect on the overall reduction of the antibody (lane 3 till 7). Furthermore, re-oxidation after diafiltration was not affected (lane 12 till 14).

Example 48: Influence of Faster Diafiltration and the Presence of $N_2$ after the Reduction Phase The experiment of example 46 was repeated with some changes. During the first diafiltration, head space of the vessel was aerated with nitrogen. This resulted in a dissolved oxygen concentration of 20%. During reduction, a continuous flow of 50 mL/min nitrogen was sent through the vessel. After reduction, the second diafiltration was done into PBS that was 100% saturated with nitrogen, to prevent any addition of extra oxygen to the system.

Figure 55:
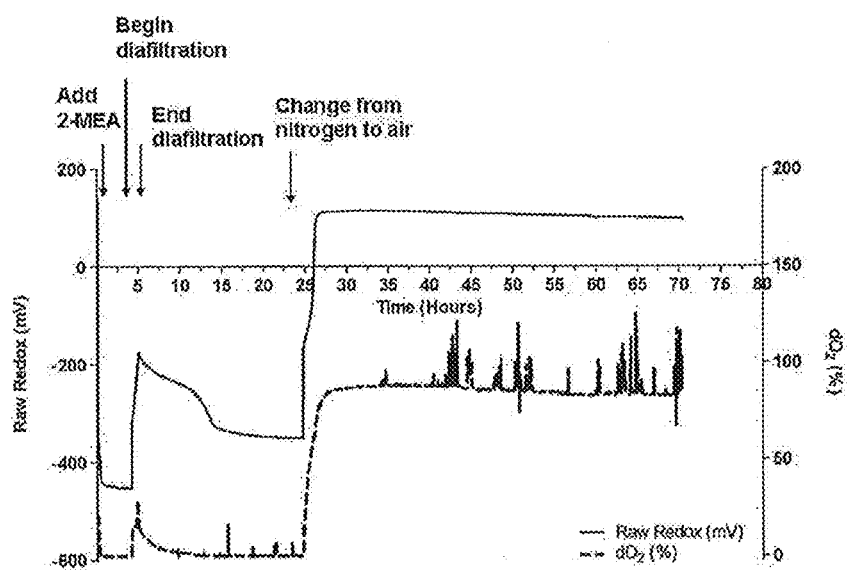
FIG. 55: Redox potential and oxygen saturation during reduction and oxidation of IgG1 anti-CD38 antibody—faster diafiltration and presence of N2 after reduction phase. Redox potential and oxygen saturation during reduction and oxidation phase were followed using a redox probe and a dissolved oxygen (DO) probe. The left y axis and the solid line show redox potential; the right y axis and the dashed line show oxygen saturation as measured in the solution during the different phases of the process, as indicated by the arrows.

DO concentration was 20% at the time 2-MEA was added. All oxygen was immediately consumed by the 2-MEA (FIG. 55). The redox potential immediately dropped to −440 mV upon addition of 2-MEA. The redox potential after diafiltration was lower (−250 mV) than the start value (+200 mV), indicating that re-oxidation was not complete.

After nitrogen was replaced by air aeration, the redox potential climbed, indicating that the re-oxidation had started again. The redox potential climbed back to the start value, indicating re-oxidation was complete.

Figure 56:
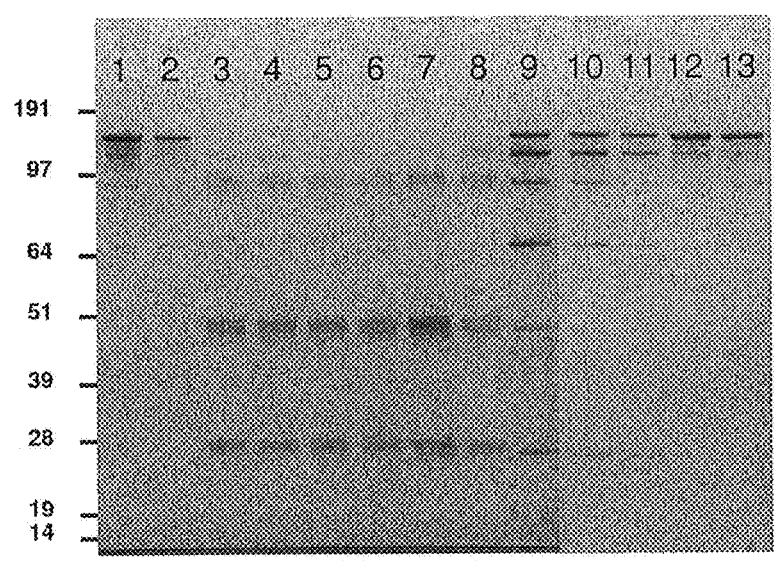
FIG. 56: SDS-PAGE analysis during reduction and oxidation of anti-CD38 antibody—faster diafiltration and presence of $N_2$ after reduction phase. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange from formulation buffer to PBS; lane 3 till 7: anti-CD38 antibody during reduction phase (incubation times: 10 min and 1, 2, 3 and 4 hours); lane 8 till 10: anti-CD38 antibody during the diafiltration process (samples at 10, 30, and 60 min after start diafiltration); lane 11: anti-CD38 antibody 24 hours after stop diafiltration; lane 12 and 13: anti-CD38 antibody 1 and 24 hours after aeration with nitrogen was stopped and aeration with oxygen was started.

The SDS-PAGE results (FIG. 56) were comparable to those observed in example 46 up to the reduction phase (lane 3 till 7). However, the lack of oxygen clearly inhibited the re-oxidation process (lane 8 till 11). Only after replacement of nitrogen by an air flow, re-oxidation occurred (lane 12, 13).

Example 49: Influence of Faster Diafiltration and the Presence of EDTA after the Reduction Phase The experiment of example 46 was repeated with the exception that 2-MEA was removed by diafiltration with PBS containing 2 mM EDTA, instead of PBS alone.

Figure 57:
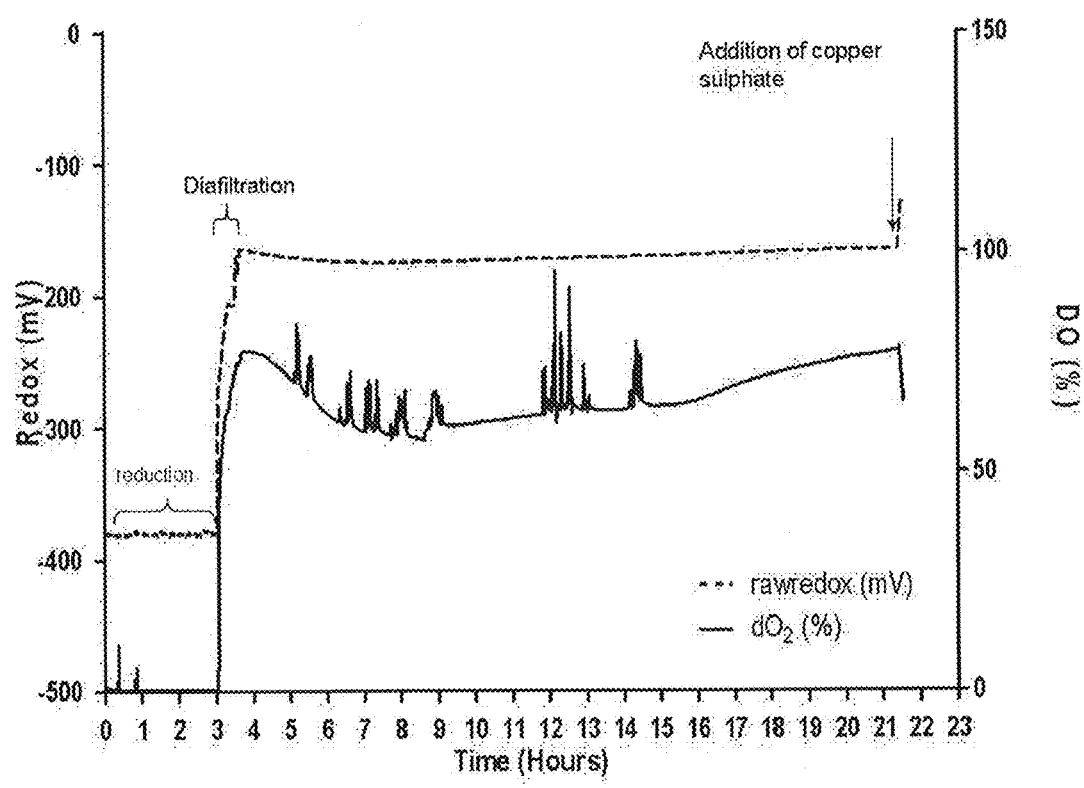
FIG. 57: Redox potential and oxygen saturation during reduction and oxidation of IgG1 anti-CD38 antibody—faster diafiltration and presence of EDTA after reduction phase. Redox potential and oxygen saturation during reduction and oxidation phase were followed using a redox probe and a dissolved oxygen (DO) probe. The left y axis and the solid line show redox potential; the right y axis and the dashed line show oxygen saturation as measured in the solution during the different phases of the process, as indicated by the arrows.
Figure 58:
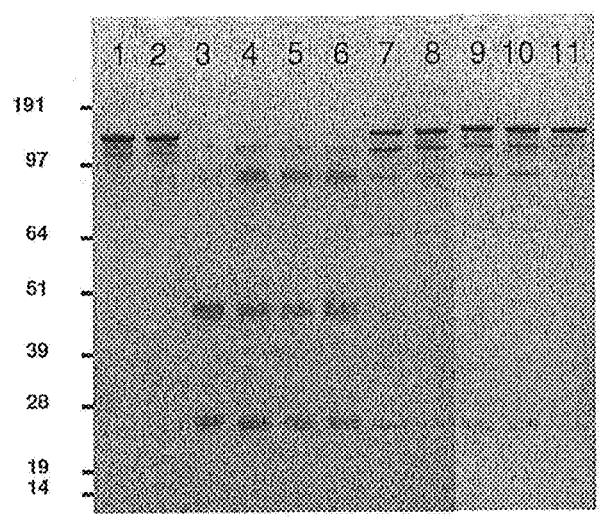
FIG. 58: SDS-PAGE analysis during reduction and oxidation of anti-CD38 antibody—faster diafiltration and presence of EDTA after reduction phase. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange from formulation buffer to PBS; lane 3 till 6: anti-CD38 antibody during reduction phase (incubation times: 10 min and 2, 3 and 4 hours); lane 7 till 9: anti-CD38 antibody during the diafiltration process (samples at 10, 30 and 60 min after start diafiltration); lane 10: anti-CD38 antibody 24 hours after stop diafiltration; lane 11: anti-CD38 antibody 30 min after addition of copper sulphate.

During diafiltration, the redox potential increased. This was mainly due to the increase in oxygen that affected the redox potential (FIG. 57). The SDS-PAGE (FIG. 58) of samples taken during the reduction phase was comparable to those observed in example 46 (lane 3 till 6). Presence of EDTA clearly affected the re-oxidation by capturing trace-elements leading to a slower re-oxidation rate (lane 7 till 10). Even 24 hours after diafiltration, not all antibodies had re-oxidized yet (lane 10). Addition of copper sulphate induced an immediate increase in redox potential and a decrease in DO. SDS-PAGE results confirmed that re-oxidation was complete only after addition of copper sulphate (lane 11) and not before (lane 10).

Example 50: Influence of Faster Diafiltration and the Presence of Copper Sulfate after the Reduction Phase The experiment of example 46 was repeated with the exception that 2-MEA was removed by diafiltration with PBS containing 0.5 mg/L copper sulfate, instead of PBS.

Figure 59:
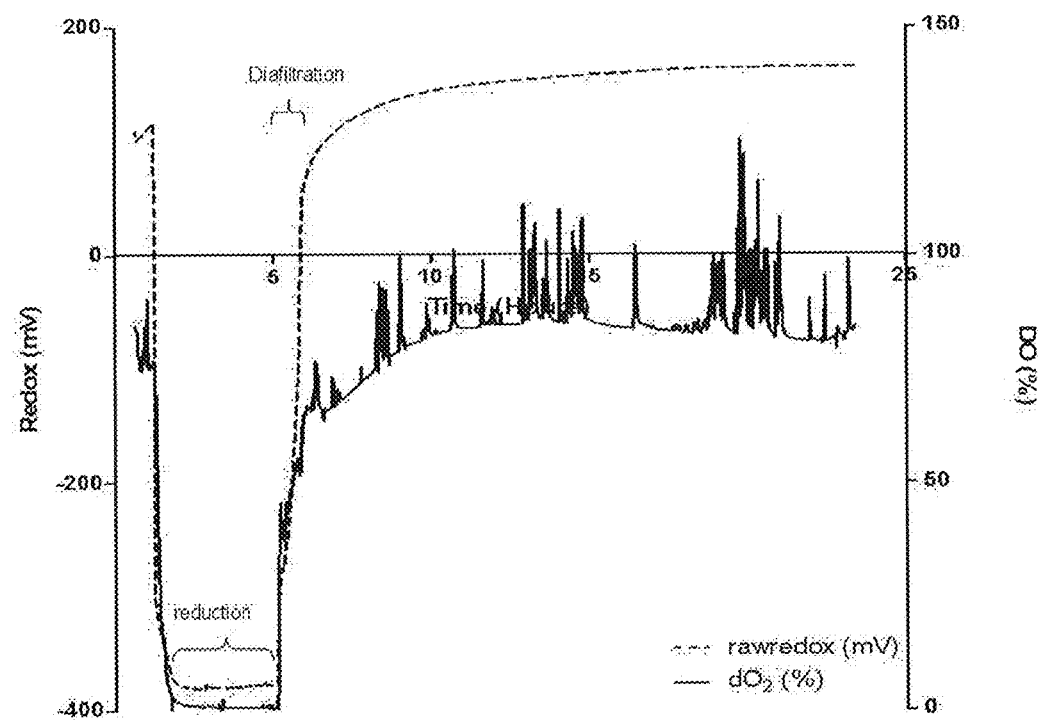
FIG. 59: Redox potential and oxygen saturation during reduction and oxidation of IgG1 anti-CD38 antibody—faster diafiltration and presence of copper sulfate after reduction phase. Redox potential and oxygen saturation during reduction and oxidation phase were followed using a redox probe and a dissolved oxygen (DO) probe. The left y axis and the solid line show redox potential; the right y axis and the dashed line show oxygen saturation as measured in the solution during the different phases of the process, as indicated by the arrows.

The DO and redox profiles showed that re-oxidation was faster than that observed in all examples described supra. After diafiltration the redox potential was at its start value, indicating that re-oxidation was complete (FIG. 59).

Figure 60:
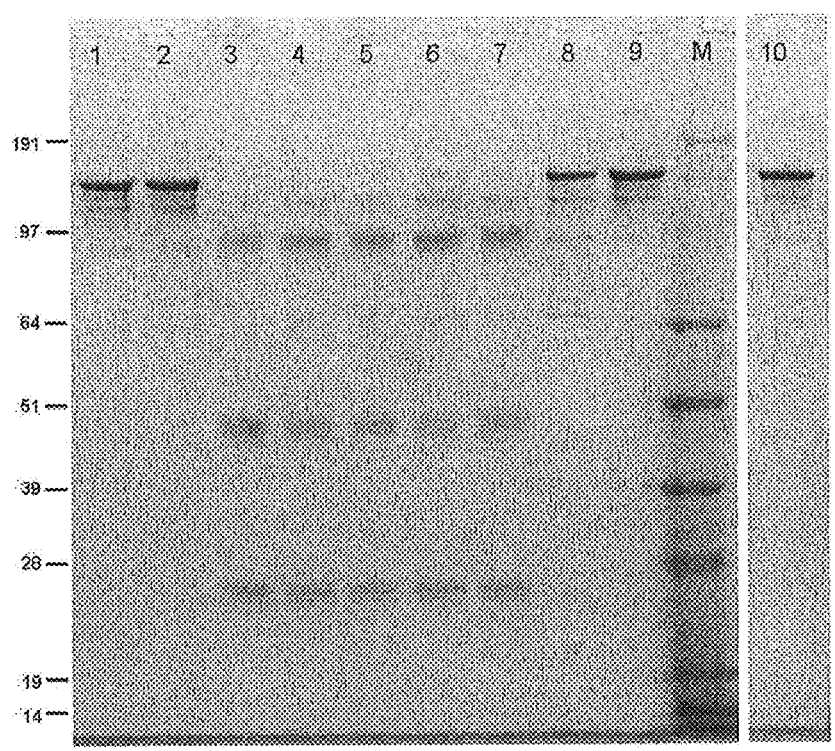
FIG. 60: SDS-PAGE analysis during reduction and oxidation of anti-CD38 antibody—faster diafiltration and presence of copper sulfate after reduction phase. Samples taken during reduction and oxidation of anti-CD38 antibody were analyzed by non-reduced SDS-PAGE analysis. Lane 1: anti-CD38 antibody in formulation buffer; lane 2: anti-CD38 antibody after buffer exchange from formulation buffer to PBS; lane 3 till 7: anti-CD38 antibody during reduction phase (incubation times: 10 min and 1, 2, 3 and 4 hours); lane 8 and 9: anti-CD38 antibody during the diafiltration process (samples at 10 and 60 min after start diafiltration); lane 10: anti-CD38 antibody 24 hours after stop diafiltration; lane M: MW marker.

This was confirmed on SDS-page. SDS-PAGE results (FIG. 60) were comparable to those described in example 46 until the diafiltration steps. SDS-PAGE results of samples during re-oxidation phase clearly showed that presence of copper sulphate increased the re-oxidation rate of the antibody. Re-oxidation was almost complete already after 60 min of diafiltration (lane 9).

Example 51: Production of Bispecific Antibodies Lacking c-Terminal Lysines

Mammalian expression vectors for the expression of monospecific antibodies completely lacking c-terminal lysines (by deleting the c-terminal lysine; delK) in the heavy chain, in addition to the F405L or K409R mutation, will be created by standard molecular biologic techniques known in the art. This will yield expression vectors pIgG1f-F405L-delK and pIgG1f-K409R-delK. Relevant VH sequences corresponding to the two antibodies of interest, will be inserted into the two heavy chain vectors. Additionally, expression vectors for the light chains will be created by standard molecular biologic techniques known in the art. Relevant VL sequences corresponding to the two antibodies of interest, will be inserted into these light chain vectors.

Both antibody mutants will be produced under serum-free conditions, using Freestyle medium (Invitrogen, Carlsbad, Calif.), by transiently co-transfecting relevant heavy and light chain expression vectors in HEK293F cells (Invitrogen) using 293fectin (Invitrogen) according to the manufacturer's instructions. Antibodies will be purified by Protein A affinity chromatography (MabSelect SuRe, GE Healthcare, Uppsala, Sweden), dialyzed O/N to PBS and filter-sterilized over 0.2 µM dead-end filters. Concentrations of purified IgG1 variants will be determined by absorbance at 280 nm. The purified antibodies will used to make bispecific antibodies according to a method described herein. These bispecific antibodies will completely lack both c-terminal lysines.

Example 52: Homodimer Production at 1000-L Scale and Scale Up of Heterodimeric Protein Production from 60 mg- to 0.5 kg-Scale One batch of each of two homodimers was produced and purified at 1000-L scale using a standard process (not specifically optimized for the cell lines or for the designated antibodies). The cell lines used for this process are described in Example 40. Cells were thawed and scaled up in 17 days for inoculation into a 1000-L reactor through five passage steps, including a 500-mL shake flask (thaw), a 1-L shake flask, a 3-L shake flask (all flasks form Corning), a wave bag (Wave Biotech), a 100-L seed bioreactor, and finally into a 1000-L production bioreactor. The shake flasks and wave bags were in incubators controlled at 5% $CO_2$ and 37° C. The seed bioreactor and production bioreactor were controlled at pH 7.0 ($CO_2$ and carbonate), at DO 30% (air/$O_2$ and agitation), and at a temperature of 37° C. (water jacket). The production bioreactor was inoculated at 500 L, with daily feed additions starting on day 3 until the end of the run. The IgG1-7D8-K409R cell line produced as expected and the run was stopped on day 11 with sufficient material (i.e. 1.85 g/L). The IgG1-2F8-F405L cell line lost productivity from original banking to scale-up and the run was stopped on day 15 at 0.6 g/L. Subsequently, in each case, the bioreactor was chilled to 12° C., the pH was reduced to 4.5, using 2 M citric acid, and the product was harvested by centrifugation. Next, depth filtration (Millipore) was applied and 0.2 µm filtration (Sartorius) was performed to remove the cells, and the pH was neutralized using 2 M Tris. Harvest recovery was 93% for IgG1-7D8-K409R and 80% for IgG1-2F8-F405L.

The cell-free harvests were loaded onto a MabSelect SuRe protein A (GE Healthcare) chromatography column. Bound antibody was released from the resin using a step change in the pH of the mobile phase. Following this initial purification step, viral inactivation was performed by incubation at low pH for 60 min at ambient temperature. Subsequently, the pH was increased by titration to pH 7.8 for the subsequent anion exchange step. Homodimers were then loaded onto a flow through (non-binding) Anion Exchange (AEX) chromatography column packed with Q Sepharose Fast Flow (GE Healthcare). Each purified homodimer was then buffer-exchanged into a phosphate buffered saline solution (1.92 mM $NaH_2PO_4$*$H_2O$, 8.66 mM $Na_2HPO_4$*$7H_2O$, 140.31 mM NaCl; pH 7.4) using a 30 kDa cut-off Pall Omega membrane in a tangential flow mode and stored at 5° C. in a disposable Flexboy bag (Sartorius Stedim). Material was finally passed through a 0.2 µm sterilizing grade filter into 1-L PETG bottles (Nalgene) and stored at 5° C. The final concentration of IgG1-7D8-K409R was 26.0 g/L and of IgG1-2F8-F405L 28.2 g/L. The overall downstream yield was 86% for IgG1-7D8-K409R and 92% for IgG1-2F8-F405L. The monomer levels, as analyzed by HP-SEC, were 100% and 99.9%, respectively. IgG1-7D8-K409R material had a residual level of leached protein A that was below the detection limit of 0.078 ng/mL with a residual CHO host cell protein level measured by ELISA (Cygnus) of 0.57 ppm (the other material was not evaluated).

Figure 63:
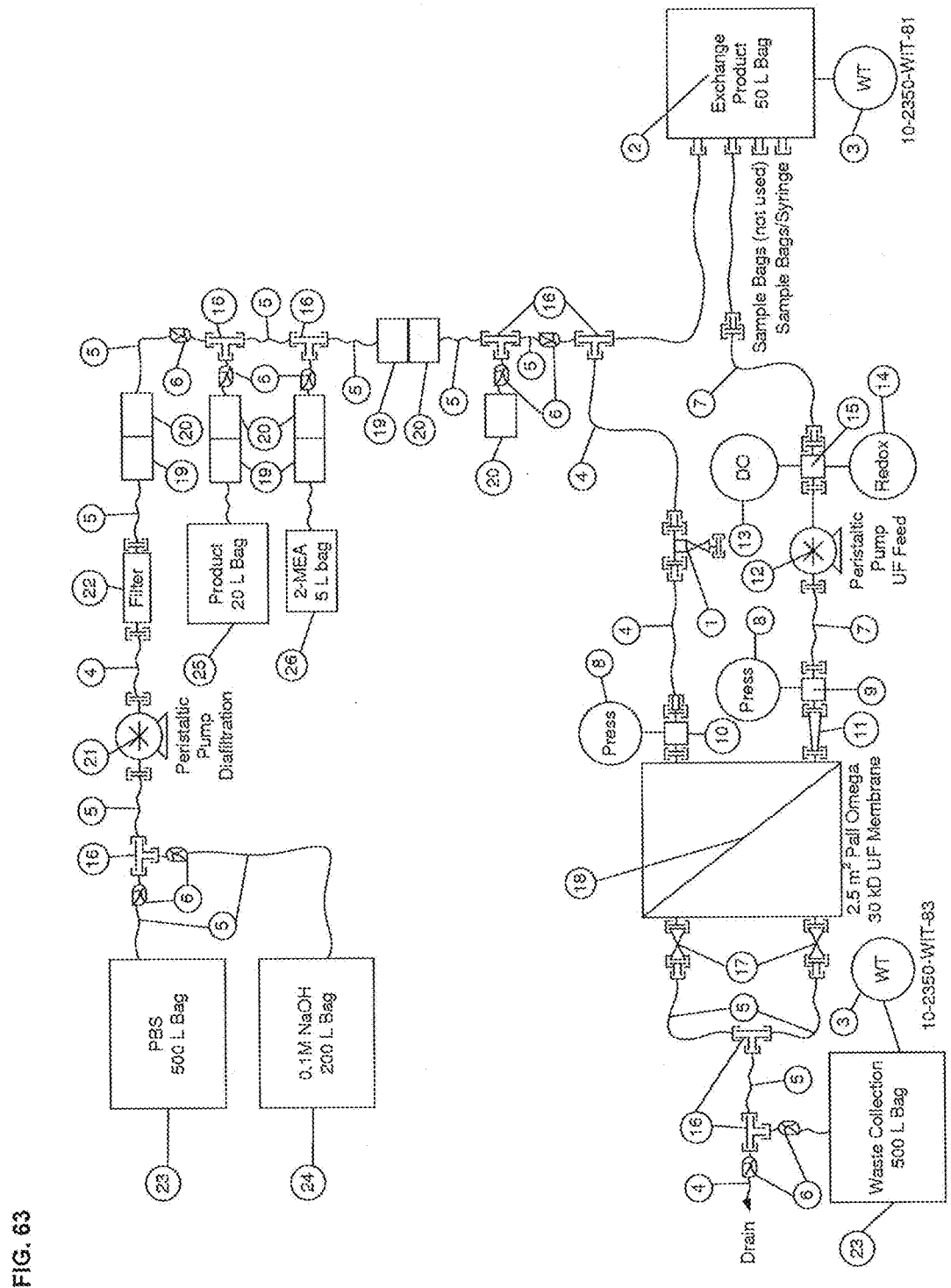
FIG. 63: Reactor flow path, bill of materials and process. The flow path was sanitized using 0.2 N NaOH and rinsed with WFI. The morning of the exchange reaction, the appropriate amount of PBS was added to the system from the buffer bag. Homodimers were added by gravity feed and the system circulated at 7 LPM to mix the contents. The reaction was initiated by gravity addition of the 2-MEA stock solution. The permeate valves were closed and the feed pump was set at 30 RPM (7 LPM) for the reduction process. After five hours, the permeate valves were opened and the pump speed was increased to meet a target feed pressure of 70 kPa for diafiltration. For the 1 g/L condition, the pump was set at 165 RPM (31 LPM). For the 20 g/L condition, the pump was set at 140 RPM (26 LPM). The PBS addition path was opened and the diafiltration pump speed was controlled to keep a constant weight in the reactor bag. This procedure resulted in a diafiltration rate of 250 L/h for the 1 g/L condition and 125 L/h for the 20 g/L condition. Once the target diafiltration volume was collected in the 500-L waste bag, the permeate valves were closed and the diafiltration pump was stopped. The feed pump was returned to 30 RPM (7 LPM) circulation during the oxidation time. After O/N incubation, a second diafiltration was performed (three diavolumes for the 1 g/L condition and 4 diavolumes for the 20 g/L condition). All processes were carried out at ambient temperature (22-25° C.). Samples were removed either directly from the bag or from valve 1 (FIG. 1).

Bispecific antibody was produced from the homodimers under three conditions (Table 11). The first condition was a standard bench-scale condition of 10 g/L of each homodimer in a polypropylene tube containing 50 mM 2-MEA at ambient temperature (22-25° C.) for 5 hours. Next, 2-MEA was removed using a desalting column and the solution was incubated at ambient temperature, O/N. This exchange was performed in a total volume of 3 mL for production of 60 mg bispecific antibody. The second condition was a scale-up to 25 L with 0.5 g/L of each homodimer for production of 25 g bispecific antibody. As in the bench-scale process, the reduction phase was performed in 50 mM 2-MEA at ambient temperature for 5 hours. However, in this case, the reaction was carried out it in a bag on a rocker plate and 2-MEA was removed via diafiltration using PBS pH 7.4 (FIG. 63). The material was kept O/N at ambient temperature and diafiltered once more using PBS pH 7.4. The extra diafiltration was used to remove potential residual 2-MEA. The third condition was similar to the second condition, except that 10 g/L of each homodimer was used in 25 L, to produce a 0.5 kg batch of bispecific antibody.

CIEX analysis of the final product from the three runs demonstrated similar profiles (FIG. 64). The homodimers had exchanged into the bispecific antibody in high yield (Table 12). The process did not induce significant aggregation or degradation, as determined by HP-SEC, and the final concentrations recovered from the system were near the expected results (Table 12). In addition, SDS-PAGE results demonstrated a fully re-oxidized, intact product (FIG. 65).

TABLE 11

Summary of bispecific production scale-up conditions.

| Procedure | 20 g/L Bench | 1 g/L Mfg* | 20 g/L Mfg* |
|---|---|---|---|
| Total Volume | 3000 µL | 25 L | 25 L |
| IgG1-2F8-F405L | 10 g/L (1064 µL) | 0.5 g/L (0.43 L) | 10 g/L (8.87 L) |
| IgG1-7D8-K409R | 10 g/L (1154 µL) | 0.5 g/L (0.48 L) | 10 g/L (9.61 L) |
| PBS | 282 µL | 19.91 L | 2.35 L |
| 300 mM 2-MEA | 50 mM (500 µL) | 50 mM (4.17 L) | 50 mM (4.17 L) |
| Temperature | Ambient | Ambient | Ambient |
| Reduction Time | 5 h | 5 h | 5 h |
| 2-MEA Removal | Desalting | Diafiltration | Diafiltration |
| Oxidation Time | Overnight | Overnight | Overnight |
| Second DF | No | Yes | Yes |
| 0.2 µm filtered | No | Yes | Yes |
| Duobody Produced | 60 mg | 25 g | 500 g |

*Mfg refers to manufacturing

TABLE 12

Quality results for the final product obtained under different conditions.

| | % by CIEX | | | | % by HP-SEC | | |
|---|---|---|---|---|---|---|---|
| Condition | IgG1-2F8-F405L | Bispec. | IgG1-7D8-K409R | Conc. (g/L) | Mono. | Aggr. | Degr. |
| 20 g/L; 3 mL | 3.3 | 94.6 | 2.1 | ND | ND | ND | ND |
| 1 g/L; 25 L | 4.3 | 94.9 | 0.8 | 0.92 | 99.1 | 0.9 | 0 |
| 20 g/L; 25 L | 2.8 | 96.3 | 0.9 | 20.0 | 99.4 | 0.6 | 0 |

ND: not determined
Degr.: degradation product
Aggr.: aggregation
Bispec.: bispecific antibody
Mono.: Monomer Example 53: Generation of Bispecific Antibody (Heterodimeric Protein) at 1-L Scale The experiment of Example 46 was essentially repeated with the following changes: first, two different homodimers were used instead of one (the anti-CD38 antibody); second, the reduction time was shortened from four hours to three hours; third, a different diafiltration cartridge was used; last, IAA was only added to samples for SDS-PAGE analysis.

Human IgG1-7D8-K409R (10 g) and IgG1-2F8-F405L (10 g) were placed in a 2-L working volume bioreactor (Applikon) in 990 mL PBS, pH 7.4. The PBS was a mixture of an in-house prepared solution used to formulate the homodimers (1.92 mM $NaH_2PO_4*H_2O$, 8.66 mM $Na_2HPO_4*7H_2O$, 140.31 mM NaCl, pH 7.4) and the B. Braun formulation; these two formulations are essentially equivalent. Temperature was controlled at 25° C., agitation rate at 100 RPM, and headspace gassing at 15 mL/min air. The reactor was additionally equipped with a DO, pH and redox probe. The exchange reaction was initiated by adding 2-MEA to a final concentration of 50 mM (10 mL of a freshly prepared 5 M solution of cysteamine hydrochloride was added to the 990 mL PBS containing the homodimers). After three hours, 2-MEA was removed via diafiltration (DF) against 7 L of PBS, pH 7.4 (B. Braun). DF was carried out using a 0.16 $m^2$, 30 kDa modified polyethersulfone (mPES) hollow fiber cartridge (cat. no. PN-S04-E030-05-N, J & M Separations, Tilburg, The Netherlands). The first 300 mL of the PBS was used to increase the volume of the system to 1300 mL to carry out the diafiltration. The cartridge inlet pressure was controlled at 25 PSI (170 kPa). This was achieved by using a peristaltic pump at maximum pump speed, 1750 mL/min, and a valve placed on the retentate flow of the system, resulting in a permeate flow of approximately 52.5 mL/min. The bispecific product was kept O/N at 25° C., 100 RPM agitation, and 15 mL/min headspace gassing. Samples (approximately 5 mL) were taken just prior to 2-MEA addition at 0.5, 1, 2, and 3 hours post 2-MEA addition, at 1, 2, 3, 5, and 7 L of diafiltrated buffer, at 1 hour post completion of diafiltration and finally the next day. At each sampling point, a 0.4 mL portion of the sample was added to 8 µL of a 1 M stock solution of IAA. All samples were snap frozen immediately, using liquid nitrogen, and stored at −80° C. until analysis. The freeze/thaw procedures did not impact sample integrity (data not shown). Samples without IAA were analyzed by CIEX to determine the extent of exchange and by HP-SEC to determine product aggregation. Samples with IAA were analyzed by non-reducing SDS-PAGE to determine the extent of inter-chain disulfide bond formation.

The addition of 2-MEA resulted in an immediate drop in redox potential from 155 mV to −290 mV, due to the low redox potential of 2-MEA. The redox dropped more gradually to −410 mV over the first hour, likely due to the decrease of DO from 100% to 0% over this time (FIG. 66). The decrease in DO was due to oxygen consumption by auto-oxidation of 2-MEA. The pH dropped from 7.4 to 6.7 due to the acidity of 2-MEA hydrochloride (FIG. 67). Redox and DO were relatively stable during the reduction period, while there was a gradual rise in pH, possibly due to a decrease in acidity, caused by auto-oxidation of 2-MEA to cystamine. Following diafiltration, DO returned to 100% within a few hours, while redox increased to −20 mV and gradually increased to 109 mV, O/N. During diafiltration, pH increased and was stable close to the starting value of 7.4; the slight offset between initial and final pH was due to the use of different lots of PBS. The most likely interpretation of the data is that not all 2-MEA was removed after diafiltration and the slow rise in redox O/N indicates a final approach to complete auto-oxidation of 2-MEA to cystamine. During this time, the rate of oxygen consumption by 2-MEA auto-oxidation was slow enough, compared to oxygen transfer through the surface, so that the DO remained near the saturation value. In later experiments, it was discovered that the cleaning procedure was not sufficient to unblock all pores in the cartridge, likely leading to lower than expected 2-MEA removal during this run. The original cleaning procedure was to rinse three times with water, then incubate for six hours at ambient temperature with 0.2 M NaOH and then rinse three times with water. This cleaning procedure was used prior to Example 53 and prior to Example 54. As a result, these two examples had the same issue. Prior to example 55, the cleaning procedure was modified to rinsing three times with water, then incubating in 0.5 M NaOH and 250 ppm sodium hypochlorite at ambient temperature for 60 min, and finally rinsing three times with water. The stronger cleaning procedure was used there (from example 55 onwards), which resolved the issue (as shown by redox potential returning to normal values after diafiltration).

The rate and extent of 2-MEA auto-oxidation was estimated by determining the oxygen consumption rate during the reduction phase, assuming that one mole of $O_2$ oxidized two moles of 2-MEA. Oxygen consumption (OC) (over one minute intervals) was calculated with Equation 3. It was assumed that the air saturation of oxygen in the solution was 0.2 mM. It was determined previously that kla at these conditions was 0.76/h, using the dynamic outgassing method.

$$OC = kla \times \ln(DO^* - DO) \times s \times (t_2 - t_1) + (DO_1 - DO_2) \times s \quad \text{Equation 3:}$$

OC=oxygen consumption over one minute period (mM)
kla=oxygen transfer coefficient (1/hour)
$DO^*$=equilibrium DO concentration (100%)
DO=average DO concentration between time 1 and time 2(%)
$DO_1$=initial DO concentration
$DO_2$=final DO concentration
s=oxygen solubility (0.2 mM/100%)
$t_2-t_1$=elapsed time (hour)
Total oxygen consumption was determined by adding up the oxygen consumed during each one minute interval.

The oxygen consumption rate (OCR [mM/h]) at each one minute interval was then calculated with Equation 4:

$$OCR = \frac{(OC_2 - OC_1)}{(t_2 - t_1)}$$

Upon addition of 2-MEA, the oxygen consumption rate increased rapidly to approximately 1.4 mM/h (FIG. 68). However, this rate dropped rapidly to near 0.15 mM/h as the DO dropped to 0%. These results demonstrate that 2-MEA auto-oxidation was limited by transfer of oxygen to the vessel, since all oxygen transferred was immediately consumed by the process. The total amount of oxygen consumed over the three-hour reduction period was 0.64 mM/L. Therefore, it was estimated that 1.28 mM 2-MEA, or 2.6% of the 2-MEA present, was auto-oxidized during the reduction phase.

SDS-PAGE analysis (FIG. 69) demonstrated complete reduction of the inter-chain disulfide bonds within 30 min. Upon diafiltration, the molecule started re-oxidizing as soon as one diavolume, at which time the redox potential was −275 mV. During diafiltration, bands were apparent corresponding to the expected migration of all possible combinations of heavy and light chain (L, H, HL, HHL, LHHL). The molecule was completely re-oxidized within seven diavolumes, at which time the redox potential was −45 mV. These data suggest that complete re-oxidation of the inter-chain disulfide bonds does not require return to the initial redox.

CIEX analysis demonstrated efficient exchange of the homodimers into the heterodimer product (FIG. 70); substantial exchange had already occurred within 30 min of reduction. The final product was 93.6% bispecific, 5.8% 7D8 homodimer, and 0.4% 2F8 homodimer. Determination of the concentration of the beginning and final samples by OD280 measurement demonstrated almost complete recovery (98%). HP-SEC analysis of the final sample demonstrated that the process did not induce product aggregation (>99% monomer) (FIG. 71).

Example 54: Impact of EDTA and Copper Ions on Generation of Bispecific Antibody at 1-L Scale The experiment of example 53 was repeated, with the following changes. 2 mM EDTA (Fluka, cat. no 03677; disodium dihydrate) was added to both the reduction and diafiltration buffer with pH readjusted to 7.4 using 2 M NaOH. EDTA binds metals which can inhibit metal-catalyzed auto-oxidation of 2-MEA during the reduction period and re-oxidation of the heterodimer during the diafiltration/re-oxidation phase.

As observed in example 53 (without EDTA), the addition of 2-MEA resulted in an immediate drop in redox potential from 162 mV to −290 MV and then to −416 mV over the first hour as the DO dropped. In contrast to example 53 (without EDTA), where DO dropped to 0% within an hour, in the presence of 2 mM EDTA the DO dropped initially to 10% and then gradually to 3% by the end of the three-hour reduction period. This finding of less consumption of oxygen is consistent with the premise that trace metal ions accelerate the auto-oxidation of 2-MEA. The presence of EDTA did not impact the pH profile of the run (FIG. 73, compared to FIG. 67).

Following diafiltration, DO returned to 100% within a few hours, while redox increased to only −115 mV. As in example 53 (without EDTA), the fact that the redox did not return to the starting value was due to the use of an ineffective cleaning procedure prior to use resulting in suboptimal 2-MEA removal. However, without EDTA (example 53), there was a gradual rise in redox O/N, whereas in the presence of EDTA, the redox remained essentially unchanged (FIG. 72), indicating inhibition of oxidation. In this case, following O/N oxidation, 0.5 mg/mL $CuSO_4$ (final concentration; Sigma, cat. no 451657) was added to the reactor. This resulted in an immediate drop in DO, coupled with a rise in redox. This finding is consistent with the premise that there was residual oxidizable substance in the reactor and that trace metal ions accelerate the reoxidation process.

The rate and extent of 2-MEA auto-oxidation during the reduction phase was determined as described in example 53. Although EDTA inhibited auto-oxidation, the amount of oxygen consumed in the presence of EDTA was 0.60 mM, which is just slightly less than that without EDTA (example 53) of 0.64 mM. The most likely explanation is that, under the conditions of the example, the oxygen consumption is limited by the rate of oxygen transfer from the headspace into the solution, since in either case the DO was less than 10%.

As in example 53, SDS-PAGE analysis (FIG. 74) demonstrated complete reduction of the inter-chain disulfide bonds within 30 min. However, re-oxidation during diafiltration was delayed, compared to the condition without EDTA (FIG. 69, Example 53). Upon diafiltration, a slight amount of re-oxidation of the heavy chain inter-chain bonds was observed after one diavolume, where the redox potential was −326 mV. All expected forms of the antibody (L, H, HL, HH, HHL, LHHL) were observed after 2 L diafiltered buffer, where the redox potential was −282 mV. Complete re-oxidation was not observed within one hour of completion of diafiltration (redox −115 mV) or after O/N incubation (redox −110 mV), in contrast to the condition without EDTA (FIG. 69). After addition of $CuSO_4$, complete re-oxidation was observed. These results demonstrate that the addition of a sufficient amount of metal ions can overcome the impact of EDTA.

CIEX analysis demonstrated efficient exchange of the homodimers into the heterodimer product (FIG. 75); substantial exchange had already occurred within 30 minutes of reduction. The final product was 92.7% bispecific antibody, 4.7% 7D8 homodimer, and 2.6% 2F8 homodimer. Determination of the concentration of these same samples by OD280 measurement, demonstrated almost complete recovery of 98%. HP-SEC analysis of the final sample demonstrated that the process did not induce product aggregation or degradation; the sample was >99% intact monomer (data not shown).

Example 55: Impact of Increased Agitation on Generation of Bispecific Antibody at 1-L Scale The experiment of example 53 was repeated, except that the DO control set-point was set to 50% DO, to determine the impact of increased oxygen concentration and increased oxygen transfer rate. The control strategy was to maintain a minimum agitation of 100 RPM and, subsequently, increase agitation automatically upon 2-MEA addition to maintain the 50% DO set-point in case the DO dropped below 50%. Initially, the maximum agitation rate was set to 500 RPM.

Upon addition of 2-MEA, the DO dropped and the agitation immediately increased to 500 RPM (FIGS. 76-77). However, due to the observation of foaming, the maximum agitation rate was lowered to 400 RPM and remained there over the entire reduction time. At this rate, the DO could not be maintained at 50%; instead, it dropped to near 3%. Some entrainment of air through the surface was still observed at 400 RPM.

Under conditions at 100 RPM (example 53), addition of 2-MEA resulted in an immediate drop in redox potential from 151 mV to −297 mV, and a further drop to −416 mV within one hour; however, under conditions of increased oxygen transfer, the redox only dropped to −366 mV within an hour. The pH dropped from 7.4 to 6.9 and increased slightly during the reduction phase (FIG. 78).

During diafiltration, the DO increased upon removal of 2-MEA and due to introduction of more oxygen through the diafiltration buffer. The increased DO resulted in reduced agitation rate. By the end of diafiltration, the pH had returned to the start value. The DO and redox values became close to the initial start values directly after diafiltration and gradually reached the start values by the end of the O/N incubation.

The rate and extent of 2-MEA auto-oxidation during the reduction phase was determined as described in example 53. At the increased agitation rate of 400 RPM, the kla value was 4.0/h, resulting in the consumption of 2.31 mM of oxygen during the reduction phase. This corresponds to auto-oxidation of 4.62 mM 2-MEA, or 9.2% of the reductant, compared to 2.6% of the reductant at 100 RPM.

In contrast to the condition at 100 RPM, the condition at 400 RPM resulted in incomplete reduction of the inter-chain heavy chain bonds, as assessed by SDS-PAGE analysis (FIG. 79). This is likely due to the elevated redox potential under these conditions, (near −360 mV, compared to −411 under conditions of 100 RPM). After 1 L diafiltered buffer, the redox was −282 mV, and all expected forms of the antibody were observed (L, H, HL, HH, HHL, LHHL). The extent of oxidation was complete after 5 L diafiltered buffer, at which time the redox potential was −53 mV.

Similar to the example at 100 RPM (example 53), CIEX analysis for the present run demonstrated that substantial exchange already had occurred within 30 min of reduction (FIG. 80). However, in contrast to the 100 RPM conditions (FIG. 70), during the present run the homodimer peaks increased during diafiltration. As a result, the O/N sample contained only 79.8% heterodimer with 9.2% residual homodimer IgG1-7D8K409R and 11.0% residual homodimer IgG1-2F8-F405L. Determination of the concentration of these same samples by OD280 measurement demonstrated 100% recovery. HP-SEC of the final sample demonstrated that the process did not induce product aggregation or degradation; the sample was >99% intact monomer (data not shown).

The finding of incomplete inter-chain disulfide bonding during reduction (SDS-PAGE) and the low percentage of exchange (CIEX) for the final sample in this example could be due to increased shear and/or increased oxygen transfer during the reduction phase.

Example 56: Impact of Increased Agitation and Sparging on Generation of Bispecific Antibody at 1-L Scale The experiment of example 53 was repeated, except that the DO control set-point was set to 50% DO to determine the impact of increased oxygen concentration and increased oxygen transfer rate. The control strategy was to maintain a minimum airflow of 0 mL/min and agitation of 100 RPM, and if the DO dropped below 50%, then first increase airflow sparging up to 40 mL/min and then increase agitation up to 400 RPM to maintain this set-point.

Upon addition of 2-MEA, the DO dropped and the airflow and agitation immediately increased both to maximum levels (FIGS. 81-82). However, due to the observation of foaming, the maximum sparge rate was lowered to 30 mL/min. At this rate, the DO could not be maintained at 50%; instead, it dropped to near 25% and then increased to 50% by the end of the reduction phase. Some entrainment of air through the surface was still observed under these conditions.

As observed in the run at 100 RPM (example 53, FIG. 66), the addition of 2-MEA resulted in an immediate drop in redox potential from 155 mV to −285 MV (FIG. 81); however, with increased oxygen transfer, the redox only dropped further to −323 mV within an hour, whereas at 100 RPM the redox dropped further to −416 mV within an hour. Furthermore, the redox had increased to −261 mV by the end of the three-hour reduction period. With increased agitation and sparge, the pH dropped from pH 7.4 to 6.9 and rose over the three-hour reduction period to pH 7.0, presumably due to oxidation of 2-MEA to the less acidic form cystamine (FIG. 83).

During diafiltration, the DO increased upon 2-MEA removal and due to introduction of more oxygen through the diafiltration buffer. The increased DO resulted in reduced agitation and sparge rates. By the end of diafiltration, the pH had returned to the start value. The DO and redox were near the start values after diafiltration and gradually reached the start values by the end of the O/N incubation.

The rate and extent of 2-MEA auto-oxidation during the reduction phase was determined as described in the example 53. At the increased agitation rate of 400 RPM and 30 mL/min sparge, the kla value was 5.2/h, resulting in the consumption of 1.94 mM of oxygen during the reduction phase. This corresponds to auto-oxidation of 3.88 mM 2-MEA, or 7.8% of the reductant, which is unexpectedly slightly lower than that determined for agitation alone of 9.2%. This discrepancy may be due to slight variations in the process conditions (most notably liquid height which was near the top of the impeller) which can alter the kla, leading to error in the calculation. Regardless, both numbers are considerably higher than the 2.6% calculated for conditions at 100 RPM and without sparging (example 53).

In contrast to the condition at 100 RPM, increased agitation and sparging resulted in the appearance of inter-chain heavy chain bonds (at redox of −323 mV) and inter heavy and light chain bonds (at redox −261 mV) prior to the end of the reduction period, as assessed by SDS-PAGE (FIG. 84). This is likely due to the elevated redox potential under these conditions. Through the diafiltration process, all expected forms of the antibody were observed (L, H, HL, HH, HHL, LHHL). The extent of oxidation was complete after 5 L diafiltered buffer, at which time the redox potential was 28 mV. The banding pattern suggests there were some inter-chain disulfide bonds that did not reform, which is more likely to be an assay artifact as this was also present in the IgG1 control.

Similar to the example at 100 RPM (example 53, FIG. 70), CIEX analysis for the present example demonstrated that substantial exchange already had occurred within 30 min of reduction (FIG. 85). However, in contrast to the 100 RPM conditions, during the present run the homodimer peaks increased during diafiltration. As a result, the O/N sample contained only 80.2% heterodimer with 9.8% residual homodimer 7D8 and 10.1% residual homodimer 2F8. Determination of the concentration of these same samples by OD280 measurement demonstrated complete recovery (103%). HP-SEC analysis of the final sample demonstrated that the process did not induce product aggregation or degradation; the sample was >99% intact monomer (data not shown).

The finding of the low percentage of exchange for the final sample in this example could be due to increased shear and/or increased oxygen transfer during the reduction phase. These results are similar to the example that used increased agitation without sparging; the primary difference between the example without sparging (example 55) and the present example, was the further increase in DO, pH and redox over the reduction period, corresponding to the appearance of heavy/light inter-chain bonds.

Example 57: Impact of Nitrogen on Generation of Bispecific Antibody at 1-L Scale The experiment of Example 53 was repeated with the following changes. The system was purged of oxygen from the time prior to reduction to just after the completion of diafiltration.

The homodimers were placed in the system at 25° C. with agitation at 200 RPM; the headspace was gassed with nitrogen at 300 mL/min together with sparging of nitrogen at 15 mL/min. The homodimer mixture was slowly circulated through the diafiltration cartridge O/N, to purge the entire system of oxygen. These parameters were maintained throughout the reduction and diafiltration steps except for the increase in circulation rate required for diafiltration. The diafiltration buffer was also sparged at 300 mL/min with nitrogen. Pharmed masterflex tubing (Saint Gobain) was used and wrapped in parafilm to minimize air exchange. The diafiltration cartridge was placed in a bag to provide a nitrogen blanket around that system. Samples with IAA were taken by drawing the sample from the reactor into a syringe devoid of air and already containing IAA to minimize oxygen exposure. These measures were required to prevent oxygen from leaking into the system to demonstrate the oxygen requirement for the re-oxidation process. For commercial manufacture, such conditions may be used but others may suffice, e.g. a simple nitrogen overlay. At the completion of diafiltration, nitrogen gassing (sparge and overlay) was discontinued and an air overlay was initiated at 500 mL/min for 5 min and at 15 mL/min for the remainder of the run.

The initial redox potential in this run was 84 mV, compared to 156 mV in Example 53. The difference is attributed to the difference in initial DO of 0% in the present example versus 100% in example 53. In the present example, addition of 2-MEA resulted in a rapid drop in redox to −447 mV and a drop in pH to from 7.4 to 7.0 (FIGS. 86-87). Both the pH and redox values remained stable over the three-hour reduction phase; these results support that lack of oxygen prevents 2-MEA auto-oxidation and thereby increases robustness of the reduction step.

The pH had increased to the final value close to 7.4 by the end of diafiltration, but the redox had increased to only −268 mV (FIGS. 86-87). The low redox value likely results from a combination of low DO combined with still reduced protein and potentially still reduced residual 2-MEA. Following diafiltration, air was introduced in the headspace and DO and redox rose rapidly and remained relatively stable for several hours and, subsequently, increased to new stable values of 102% DO and 178 mV for redox.

SDS-PAGE analysis demonstrated complete reduction of the inter-chain disulfide bonds within 30 min (FIG. 88). The antibody remained reduced during the remainder of the reduction period and throughout the entire period of diafiltration, despite a redox potential (−268 mV) in the range where partial oxidation was observed in the other examples (example 53-56). These results confirm the need for oxygen to reform the inter-chain disulfide bonds. Inter-chain disulfide bond formation was apparent within one hour after introducing oxygen, but re-oxidation was not complete after three hours, at which time the redox potential was −83 mV. Faster disulfide bond formation occurred during the examples where oxygen was present during diafiltration (examples 53-56). This is likely due to the higher concentration of oxygen and higher redox potential in those examples during diafiltration. The O/N sample showed increased oxidation of the antibody. The residual minor low molecular weight bands are possibly caused by the continuous circulation of the material through the cartridge. Some cloudiness of the solution was observed prior to 2-MEA addition, indicating that the overnight circulation had an impact on the product. The cloudiness disappeared upon addition of 2-MEA, but re-appeared after continuous circulation O/N, after the completion of diafiltration. Protein recovery (96%) was slightly lower in this example than in examples 55-56.

CIEX analysis demonstrated efficient exchange of the homodimers into the heterodimer product (FIG. 89); substantial exchange had already occurred within 30 min of reduction. The final product was 94.8% bispecific, 4.0% 7D8 homodimer, and 1.2% 2F8 homodimer. HP-SEC analysis of the final sample demonstrated that the process did not induce product aggregation (>99% intact monomer).

Using mathematical procedures similar to that in Example 53, data were analyzed to determine the calculated oxygen consumption after diafiltration (FIG. 90). The calculated total amount of oxygen consumed increased to 0.33 mM initially, and then decreased and stabilized to 0.30 mM. The drop in calculated total oxygen consumed could be due to oxygen liberation or, more likely, to experimental error. The calculations are quite sensitive to the kla used in the calculation, and the kla was determined in a separate experiment in PBS. Another theoretical possibility is release of oxygen from peroxide that has been shown to form from metal-catalyzed auto-oxidation of sulfhydryls at low reductant concentration (Fedorcsak et al., Exp Cell Res 108: 331-339, 1977; Jeitner and Lawrence, Toxicological Sciences 63: 57-64, 2001). More likely, besides an error in the estimated kla, there may be other factors which complicate the interpretation. For example, it is likely that the 2 L of headspace in the reactor was not immediately converted from nitrogen to air with a 500 mL/min air purge for 5 min followed by a 15 mL/min air overlay. Also it is possible that a low level of 2-MEA remained and contributed to oxygen consumption. Last, it is possible that other cysteines in the molecule were reduced and then re-oxidized, though typically for these disulfides to be reduced requires denaturation in a strong solution such as 6M urea.

Example 58: Impact of Low pH on Re-Oxidation of Bispecific Antibody at 1-L Scale The experiment of example 53 was repeated until the end of the reduction period. At that point, just prior to diafiltration, and just prior to taking the 3-hour reduction sample, the pH was reduced to 5.0 using 6.4 mL of 2 M acetic acid; agitation was increased to 200 RPM while adding the acid and then reduced back to 100 RPM prior to diafiltration. PBS, adjusted to pH 5.0 by adding 2 M acetic acid, was used as diafiltration buffer. As in example 53 the product was kept O/N (at 25° C., 100 RPM, 15 ml/min headspace gassing). The next day, a sample was taken, the product was adjusted back to pH 7.4 using a solution of 8.8 mL 2N Tris base adjusted to pH 9 with HCl, and samples were taken just after pH adjustment and then 1 and 2 hours post pH adjustment.

As expected, the redox, DO, pH, SDS-PAGE, and CIEX profiles during the reduction period (FIGS. 91-94) were similar to that from example 53 (FIGS. 66-67; 69-70). At the end of the three-hour reduction period, the redox increased from −423 mV to −144 mV as the pH was adjusted from 6.99 to 5.03. Before and after pH adjustment, the inter-chain bonds remained completely reduced. In other examples in pH 7.4 buffer (e.g. examples 53, 55 and 56), disulfide bonds between heavy chains were observed as the redox approached approximately −360 mV, even prior to 2-MEA removal, and disulfide bonds between heavy and light chains were apparent as the redox approached −280 mV. During diafiltration at pH 5.0, the redox increased to 28 mV and all expected combinations of heavy and light chains were apparent (L, H, HL, HH, HHL, LHHL). However, in contrast to other examples with diafiltration at higher pH, a substantial portion of the inter-chain bonds remained unformed. The redox increased further to 51 mV within an hour after diafiltration and then to 53 mV after O/N incubation. By this time, inter-chain bond formation had increased slightly. The DO increased from 0% to 83% during diafiltration and stabilized at 80% two hours following diafiltration. The off-set from the original DO value of 100% could be due the impact of pH on the equilibrium value of dissolved oxygen and further could be impacted by the volatility of acetic acid which could potentially cross the silicone membrane and impact probe calibration. Upon neutralization to pH 7.4, the redox dropped to −109 mV as a result of the pH adjustment. Despite the lower redox, the increased pH resulted in an immediate increase in inter-chain bond formation. Oxygen consumption was apparent, as the DO dropped following pH adjustment. Following the pH increase, the redox increased over the next two hours to −78 mV, by which time the product was almost completely oxidized. After further incubation, the DO returned to 80% and the redox stabilized at 135 mV, likely indicating that product oxidation was complete (sample not analyzed). The slight off-set between the initial and final redox may be due to differences in buffer composition.

CIEX analysis demonstrated efficient exchange of the homodimers into the heterodimer product (FIG. 94); substantial exchange had already occurred within 30 min of reduction. The final product was 93.7% bispecific, 4.8% IgG1-7D8-K409R homodimer, and 1.5% IgG1-2F8-F405L homodimer. Determination of the concentration of these same samples by OD280 measurement demonstrated complete recovery of 103%. HP-SEC analysis of the final sample demonstrated that the process did not induce product aggregation or degradation; the sample was >99% intact monomer (data not shown).

These results demonstrate that the re-oxidation process is slower and less complete at pH 5 compared to pH 7.4. The pH may impact the kinetics and/or the equilibrium of the process.

Example 59: Impact of Cystamine on the Exchange Process

Cystamine is the oxidized dimer of cysteamine (2-MEA).
The experiment of Example 53 was repeated, except that exchange was performed in a smaller volume of 99 mL containing 10 g/L human IgG1-7D8-K409R and 10 g/L IgG1-2F8-F405L plus 1 mL 5 M cystamine (final concentration 50 mM cystamine) in PBS pH 7.4, for five hours. Upon addition of cystamine, the redox dropped from 194 mV to 130 mV and the pH dropped from 7.41 to 7.07 (FIG. 95). Samples were taken at the start and after 0.5, 1, 3, and 5 hours of incubation of the homodimers in cystamine, and analyzed by CIEX. No formation of bispecific antibody was observed (FIG. 96). These results confirm that cystamine does not induce IgG1 Fab-arm exchange or that only the reduced form of the reagent can reduce the disulfide bonds of the antibody.

Example 60: Use of Cysteine as Reductant and Ion Exchange to Remove Reductant

Cysteine is a natural, compendial, non-toxic compound, readily available in large quantities suitable for GMP production; cysteine may also be used as a reductant/reducing agent. The efficacy of cysteine as reductant was tested. The redox potential of cysteine (Sigma C5360) was compared to that of 2-MEA in the 1-L reactor system, as described in example 53. The reactor was filled with 990 mL PBS pH 7.4 (P. Braun) and the DO was brought to 0% using nitrogen. A stock solution of 5 M 2-MEA was added gradually to the reactor (up to 45 mM end concentration) and the pH, DO, and redox were recorded. The redox of PBS alone was 87.5 mV (Table 13). The redox initially dropped rapidly to −218.7 mV at 0.5 mM 2-MEA and then more gradually −345 mV at 45 mM 2-MEA. At this point, the pH had dropped to 6.92 due to the acidity of 2-MEA.

The experiment was repeated with 0.5 M stock solution of cysteine instead of 2-MEA. The cysteine stock was adjusted to pH 7.4 with 2 M NaOH prior to use, since this solution has very low acidity. The redox of PBS alone was 102.5 mV (Table 14). The redox initially dropped rapidly to −186.2 mV at 1 mM cysteine and then more gradually −309.6 mV at 45.9 mM cysteine.

In summary, a 412 mV total drop in redox was observed for 45.9 mM cysteine at pH 7.4 and a 433 mV drop in redox for 45.0 mM 2-MEA at pH 6.92 (Table 13-14). Based on the redox potential observed in 1-L exchange experiments performed using 2-MEA, as described in previous examples, cysteine should support homodimer reduction and exchange into the bispecific antibody.

To evaluate the ability of cysteine to support exchange, a time-course study was performed using varying concentrations of cysteine. IgG1-7D8-K409R (1.8 mg) and IgG1-2F8-F405L (1.8 mg) were incubated in cation-exchange (CIEX) buffer (10 mM sodium phosphate, pH 7.0) plus 10-100 mM cysteine in a total volume of 1.0 mL. The reaction mixture was placed at 30° C. within the HPLC chamber and 28.0 μL of the mixture was loaded onto the column every 55 minutes up to 385 minutes. Before each injection cycle, the column (Dionex ProPac WCX-10 column, 4 mm diameter 250 mm length) was equilibrated in CIEX buffer. The temperature of the column was maintained at 30° C. Following the wash with CIEX buffer for 3 minutes, a linear salt gradient from 0 to 60 mM NaCl in CIEX buffer was applied at a flow rate of 1.0 mL/min for 18.5 minutes. The column was regenerated with 750 mM NaCl in CIEX buffer for 5 minutes, followed by equilibration for 18.5 minutes in CIEX buffer in preparation for injection of the next sample. The UV absorbance of the effluent was monitored at a wavelength of 280 nm.

FIGS. 97-101 show the CIEX traces for 10 mM, 25 mM, 50 mM, 75 mM and 100 mM cysteine, from 0-385 min. Based on preliminary injections of cysteine without protein and blank buffer injections, the early peak, eluting near 1 min in each trace, was assigned to the presence of cysteine in the sample and/or to cystine, the oxidized dimeric form of cysteine. The homodimers and bispecific antibody, labeled in each graph, eluted much later. These results demonstrate that a CIEX column can be used for reductant removal.

At 10 mM cysteine (FIG. 97), reduction was slow and not yet complete by 385 min. In contrast, exchange was faster and complete by 385 min at 25 mM (FIG. 98), 50 mM (FIG. 99), and 75 mM (FIG. 100) cysteine. Exchange appeared to be even faster at 100 mM cysteine (FIG. 101); however, at 385 min the bispecific antibody peak was a doublet. This doublet was also observed at the intermediate time points at lower cysteine concentrations. In each case, a higher concentration of cysteine resulted in a higher initial proportion of the more basic doublet peak (retention time 14.3 min); over time, the more basic peak shifted into the more acidic peak (retention time 14.0 min), which was the expected retention time for the bispecific antibody. The most likely interpretation is that the more basic peak from the doublet is an intermediate form, where reformation of the inter-chain disulfide bonds had not yet occurred. The final amount of bispecific antibody formed at 385 minutes is shown in Table 15. At 10 mM cysteine, there was only 54.9% conversion of homodimers into the bispecific antibody. At 25 mM, this increased to 91.0% and further increased to 93.5% and 94.7% at 50 mM and 75 mM cysteine. The exchange at 100 mM cysteine was the highest, 95.1%; however, both acidic and basic doublet peaks were designated as bispecific antibody.

The use of cysteine as reductant was further explored using a desalting column for reductant removal. The same conditions, as described supra, were applied for the reduction (CIEX buffer, 1 mL sample, 30° C., 3.6 mg/mL total protein) using 50 mM cysteine as the reductant for 385 minutes. Following removal of cysteine using size exclusion (G-25 microspin columns from GE Healthcare), the bispecific antibody was re-oxidized at RT in CIEX equilibration buffer at 30° C. for two hours or at RT for 18 hours. The CIEX profiles are shown in FIG. 102. Table 16 shows the percentages residual homodimers and bispecific antibody that were formed after re-oxidation. The results show that exchange was efficient and that re-oxidation for at 30° C. for two hours was equivalent to re-oxidation at RT for 18 hours, although the traces indicate the presence of residual cysteine/cystine.

TABLE 13

Redox potential of 2-MEA and cysteine in PBS buffer under nitrogen.

| Volume (mL) | 5M 2-MEA Stock (mL) | [2-MEA] (mM) | pH | Redox (mV) | DO (%) |
|---|---|---|---|---|---|
| 990 | 0 | 0.0 | 7.40 | 87.5 | 0 |
| 990 | 0.1 | 0.5 | 7.39 | −218.7 | 0 |
| 990.1 | 0.1 | 1.0 | 7.38 | −245.9 | 0 |
| 990.2 | 0.3 | 2.5 | 7.34 | −275.6 | 0 |
| 990.5 | 0.5 | 5.0 | 7.28 | −297.8 | 0 |
| 991 | 1 | 10.1 | 7.20 | −317.8 | 0 |
| 992 | 2 | 20.1 | 7.09 | −332.6 | 0 |
| 994 | 5 | 45.0 | 6.92 | −345.0 | 0 |

TABLE 14

| Volume (mL) | 0.5M Cysteine Stock (ml) | [Cysteine] (mM) | pH | Redox (mV) | DO (%) |
|---|---|---|---|---|---|
| 990 | 0 | 0.0 | 7.40 | 102.5 | 0 |
| 990 | 2 | 1.0 | 7.38 | −186.2 | 0 |
| 992 | 2 | 2.0 | 7.37 | −207.9 | 0 |
| 994 | 4 | 4.0 | 7.36 | −231.4 | 0 |
| 998 | 12 | 9.9 | 7.34 | −260.9 | 0 |
| 1010 | 20 | 19.4 | 7.32 | −289.8 | 0 |
| 1030 | 20 | 28.6 | 7.32 | −300.6 | 0 |
| 1050 | 20 | 37.4 | 7.32 | −307.9 | 0 |
| 1070 | 20 | 45.9 | 7.32 | −309.6 | 0 |

TABLE 15

Percentages of bispecific antibody and homodimers after 385 minutes of incubation with different concentrations of cysteine. Percentages were determined using the peak area of the main peak for each of the three species.

| Cysteine concentration (mM) | Percentage IgG1-7D8-K409R | Percentage IgG1-2F8-F405L | Total percentage bispecific antibody |
|---|---|---|---|
| 10 | 23.0 | 22.1 | 54.9 |
| 25 | 5.9 | 3.1 | 91.0 |
| 50 | 4.9 | 1.5 | 93.5 |
| 75 | 3.9 | 1.5 | 94.7 |
| 100 | 3.5 | 1.4 | 95.1 |

TABLE 16

Percentages of bispecific antibody and homodimers after re-oxidation at 30° C. for two hours or at RT for 18 hours using 50 mM cysteine.

| Re-oxidation | Percentage IgG1-7D8-K409R | Percentage IgG1-2F8-F405L | Total percentage bispecific antibody |
|---|---|---|---|
| 2 h, 30° C. | 4.4 | 1.3 | 94.3 |
| 18 h, RT | 4.5 | 1.2 | 94.3 |

Example 61: Formation and Purification of Heterodimeric Protein Using Immobilized Reductant Columns To enable formation of and reductant removal from bispecific antibodies in one step, immobilized reductant columns were used. A mixture of homodimers IgG1-2F8-F405L and IgG1-7D8-K409R were added to an immobilized reductant column (Thermo Scientific/Pierce, Rockford, Ill., USA; cat. no 77701), prepared according to the manufacturer's instructions, in the molar ratio 1:1 at a concentration of 2.5 mg/mL each in PBS (P. Braun) and incubated at RT for 3 hours. Antibodies were eluted by applying 2 mL of PBS and collected. Samples were analyzed by HPLC-CIEX. FIG. 103 shows the formation of the bispecific antibody in between the the originating homodimers (25.3% bispecific, 36.4% IgG1-2F8-F405L and 38.3% IgG1-7D8-K409%).

Example 62: Evaluation of Bispecific IgG1 Using Allotype Differences

To enable removal of residual amounts of homodimer in a bispecific antibody preparation, it was investigated whether bispecific antibodies could be produced from two homodimers of different allotypes.

Expression vectors for anti-CD20 antibody 7D8 in an IgG1m(f) allotype backbone, including the K409R mutation, and anti-EGFR antibody 2F8 in an IgG1m(za) allotype backbone, including the F405L mutation, were prepared by methods known in the art (SEQ ID NO.s: 8 and 9, described below). The proteins were expressed and purified as described in Examples 1, 2 and 5. Equimolar amounts of the resulting IgG1m(f)-K409R-CD20 and IgG1m(za)-F405L-EGFR proteins were incubated in the presence of 25 mM 2-MEA in a total volume of 1 mL, at 37° C. for 90 min. The final concentration of total antibody was 1 mg/mL. Next, 2-MEA was removed from the mixture by buffer exchange to PBS (B. Braun) using a PD-10 desalting column (GE Healthcare Europe GmbH, Diegem, Belgium). Serially diluted samples (ranging from 2.3-5,000 ng/mL) of the bispecific antibodies were compared to the parental antibodies in the ELISA described below. An antibody with a backbone containing both allotypes, IgGm(fa), was included as control antibody. Bispecific antibody formation was determined using a sandwich ELISA. For this assay, an ELISA plate (Greiner bio-one, Frickenhausen, Germany) was coated with 1 μg/mL (100 μL/well) of mouse anti-human G1m(f) antibody 5F10 (Sanquin, Amsterdam, The Netherlands; Jefferis, R., et al. Immunol. Lett. 1992 31: 143-168; de Lange, G. G., Exp. Clin. Immunogenet. 1989 6: 7-17) in PBS at 4° C., O/N. The plate was washed three times with PBST and blocked with PBST by incubating on a plate shaker (300 RPM) at RT for 60 min. The plate was washed three times with PBST and samples were diluted in PBST and transferred to the ELISA plate (100 μL/well). After incubation on a plate shaker (300 rpm) at RT for 60 min, the plate was washed three times with PBST. Next, 100 μL of the HRP-labelled mouse anti-human G1m(a) antibody 4E3 (Southern Biotech, Birmingham, Ala., USA; cat. no 9052-05; at a 10,000-fold dilution in PBST) was added and incubated on a plate shaker (300 rpm) at RT for 60 min. The plate was washed three times with PBST. A 50 mg ABTS tablet (Roche Diagnostics GmbH, Mannheim, Germany) was dissolved in ABTS buffer (Roche) and added to the ELISA plate (100 μL/well). The plate was incubated on a plate shaker (300 rpm) in the dark at RT for 30 min (or longer if desired). The reaction was stopped with 100 μL 2% oxalic acid (final concentration 1%, Riedel de Haen Seelze, Germany) per well. The ELISA plate was left at RT for 10 min before reading absorbance at 405 nm in an ELISA plate reader. FIG. 104 shows concentration-dependent detection of the bispecific antibody, whereas the two parental antibodies were not detected. The control antibody IgG1m(fa) generated a higher signal in the ELISA, since it contained both allotypic determinants on each heavy chain.

(IgG1m(za)-F405L)

SEQ ID NO.: 8

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKKDTLMISRTPEVTCVVVDVSH

EDPPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFLLYSKLTVDKSRW

QQGNVFSCSVMHEALHNHYTQKSLSLSPGK

-continued (IgG1m(f)-K409R)

SEQ ID NO.: 9

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDK<u>R</u>VEP

KSCDKTHTCPPCPAPELLGGPSVFLFPPKPKDTLMISRTPEVTCVVVAVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYS<u>R</u>LTVDKSRW

QQGNVFSCSVMHEALHNHYTQKSLSLSPGK

Example 63: Purification of Bispecific IgG1 by Allotype-Specific Antibodies

Antibodies expressed in IgG1m(f) and IgG1m(za) allotype backbones will be prepared by methods known in the art, including the K409R and F405L mutations. The proteins will be subsequently expressed and purified as described in Examples 1, 2 and 5. Bispecific antibodies will be generated by steered non-equimolar exchange as described in Example 64. This will result in a reaction mixture containing bispecific IgG1m(f,za) antibodies and the remainder of the parental antibody that was added in excess (SNEEP).

Affinity chromatography will be used to specifically purify the bispecific IgG1m(f,za) antibodies. Therefore, mouse anti-human G1m(f) antibody 5F10 (Sanquin) or mouse anti-human G1m(a) antibody 4E3 (Southern Biotech) will be coupled to beads according to the manufacturer's instructions. The reaction mixture containing the bispecific IgG1m(f,za) antibodies and the remainder of the parental antibody that was added in excess, will be loaded onto a column containing the appropriate beads (specific for the allotypic determinant present on the bispecific IgG1m(f,za) antibodies, but not on the parental antibody that was added in excess). The column will be washed thoroughly to get rid of the excess parental antibody, and the bispecific IgG1m (f,za) antibodies will then be eluted from the column, according to the manufacturer's instructions.

Example 64: Combination of Steered Non-Equimolar Exchange Process (SNEEP) with a Mutation in One of the Homodimers that Eliminates the Protein A Binding Site It was investigated whether the presence of one homodimer in the exchanged product could be diminished by using an excess of the other homodimer in the exchange process (steered non-equimolar exchange process; SNEEP). SNEEP, using an excess of IgG1-7D8-K409R (purified on protein A) to diminish the presence of IgG1-2F8-F405L (purified on protein A) homodimer in the exchanged product, resulted in only 0.1% IgG1-2F8-F405L homodimer in the exchanged product (FIG. 105). Conditions used were 7.2 mg IgG1-7D8-K409R, 6.0 mg IgG1-2F8-F405L, 75 mM 2-MEA in 3 mL PBS, incubation at 31° C. for five hours. Using an excess of the IgG1-2F8-F405L homodimer, the percentage of IgG1-7D8-K409R in the exchanged product was only 0.4% (FIG. 106) (same conditions, with 6 mg of the IgG1-7D8-K409R and 7.2 mg IgG1-2F8-F405L).

Next, it was investigated whether highly pure bispecific antibody could be produced using a combination of SNEEP and Protein A chromatography, using one homodimer that was mutated to eliminate the protein A binding site; the following mutations were introduced: I253A, H310A, and H435A (AAA mutant), and one that can still bind to Protein A. To test whether the homodimer mutated to lack the protein A binding site could be exchanged with a homodimer containing the protein A binding site, the homodimers IgG1-7D8-AAA-K409R and IgG1-2F8-F405L were purified on Protein G and on protein A, respectively. For SNEEP, the following conditions were used: 1 mg IgG1-7D8-AAA-K409R and 0.5 mg IgG1-2F8-F405L in 1.2 mL PBS containing 25 mM 2-MEA, 37° C., 90 min. Using this procedure, the percentage of IgG1-2F8-F405L mutant in the exchanged product was 1.2% (FIG. 107). The bispecific antibody, containing a low percentage of the IgG1-7D8-AAA-K409R homodimer (that was used in excess in the exchange reaction), was purified using a 1 mL MabSelect-Sure column pre-equilibrated with PBS (B. Braun). The resulting CIEX chromatogram (FIG. 108) showed a peak in the flow-through fractions (Peak FT) and a peak in the elution fractions (Peak E), indicating a non-binding and a binding fraction. The ratio of the non-binding and binding fractions was roughly in correspondence with the 50% excess of the IgG1-7D8-AAA-K409R homodimer that was used in the SNEEP.

Analysis of Peak FT by CIEX (FIG. 109) showed that this fraction contained exclusively IgG1-7D8-AAA-K409R homodimer, with undetectably low amounts of the bispecific antibody and the IgG1-2F8-F405L homodimer. This indicates that the bispecific antibody with a single protein A binding site bound well to the MabSelectSure and that the excess IgG1-7D8-AAA-K409R homodimer did not bind to the column, as expected. The low amount of IgG1-2F8-F405L that was left after SNEEP, was not detected in the Peak FT, indicating that it bound to MabSelectSure.

The eluted fractions (Peak E) were analyzed by CIEX (FIG. 110). No IgG1-7D8-AAA-K409R homodimer was detected. The amount of IgG1-2F8-F405L was 2.0%, in good agreement with the 1.2% detected in the intermediate product.

Thus, CIEX analysis after SNEEP demonstrated efficient reduction of the amount of under-abundant homodimer. Further, the over-abundant homodimer, with the eliminated Protein A binding site, was removed via affinity chromatography. No IgG1-7D8-AAA homodimer was detected in the end product. The end product contained 98.0% IgG1-7D8-AAA-K409R×IgG1-2F8-F405L bispecific antibody, and 2.0% IgG1-2F8-F405L homodimer. In summary, SNEEP in combination with one homodimer mutated to lack a protein A binding site, can be used to produce highly pure heterodimeric proteins (98% final purity).

Example 65: Protein A Joint Homodimer Purification and Subsequent Exchange

To investigate whether bispecific antibody could be produced from homodimers that were purified together using a single Protein A capture step, 17.5 mL of the IgG1-b12-F405L (280 µg/mL concentration) was mixed with 66 mL of IgG1-058-K409R (75 µg/mL concentration). The combined supernatants (1:1 mixture, based on total protein) were loaded on a 1-mL protein A column that was equilibrated with 20 mM citrate, 150 mM NaCl, pH 7.0. The bound material was washed and eluted using standard procedures (washing with 7 column volumes (CV) 20 mM citrate, 150 mM NaCl, pH 7.0; pre-elution with 3 CV 20 mM citrate, pH 7.0; elution with 10 mM citrate, pH 3.5).

The fast protein liquid chromatography (FPLC) profile (measured on an ÄKTA FPLC system) of the joint purification of IgG1-b12-F405L, an antibody against gp120, and IgG1-058-K409R, an antibody directed against the c-MET receptor, showed a single peak upon elution at pH 3.5 (FIG. 111). This indicates that the homodimers can be co-purified without adjustments to the standard process for protein A purification. Recoveries (calculated based on OCTET measurements for the supernatant and on A280 measurements for the end product) were >80% for this process, similar to that for IgG1 homodimers without mutations.

The pooled fractions were buffer exchanged to PBS (P. Braun, pH 7.4) using overnight dialysis in a slide-a-lyzer (0.5-3 mL, Thermo). The following day the sample was transferred to a polypropylene tube, final volume was 1.5 mL.

CIEX analysis of the co-purified homodimers showed two peaks, as expected (FIG. 112). The first peak (rT=14.9) corresponds to IgG1-058-K409R the second peak to IgG1-b12-F405L. Quantification of the peak areas, taking into account the specific extinction coefficients, showed that 57% of the IgG was IgG1-b12-F405L and 43% was IgG1-058-K409R, in good agreement with the expected inaccuracy in concentration determination in the supernatant. Subsequently, 0.165 mL 750 mM 2-MEA was added, exchange was carried out at 31° C. for 5 hours. The end product again was dialyzed to PBS (P. Braun, pH 7.4).

The percentage of multimer in the end product, as determined by HP-SEC (2.0%) (FIG. 113), was comparable to that of other IgG1 molecules purified using the same procedure (<1% for IgG1-b12-F405L and 1.8% for IgG1-058-K409R), even though the bispecific product underwent an additional protein A purification step compared to the homodimers. This indicates that the product quality of jointly purified homodimers was not affected by their mutual presence. No IgG1-058-K409R homodimer was detected in the CIEX profile of the end product, and the percentages of heterodimeric protein and IgG1-b12-F405L homodimer were 86% and 14% (FIG. 114).

Example 66: Post-Exchange Polishing CIEX in Combination with SNEEP

It was investigated whether it is possible to remove both homodimers from a bispecific product using a combination of SNEEP and of weak cation exchange (WCIEX) chromatography in isocratic mode. The homodimers were successfully purified on Protein A using the standard approach described for joint purification (Example 65). SNEEP was described in example 64 and showed 0.1% (IgG1-2F8-F405L; in an exchange reaction with an excess of IgG1-7D8-K409R; FIG. 105) and 0.4% (IgG1-7D8-K409R; in an exchange reaction with an excess of IgG1-2F8-F405L; FIG. 106) homodimers present in the exchanged product. Although this was shown in a separate experiment, it is assumed that these numbers are indicative for the efficiency of SNEEP.

To find the optimal conditions for homodimer removal (polishing) after SNEEP, a 1:1:1 mixture was prepared of IgG1-7D8-K409R, IgG1-7D8-K409Rx2F8-F405L, and IgG1-2F8-F405L. Therefore, this optimization was done on a ternary mixture to make it more generic, whereas SNEEP produces a binary mixture. However it is believed that these conditions are representative for a separation of a binary mixture with two of the three components as well. The mixture was loaded onto a weak cation exchange (WCIEX) column (GE Healthcare), final load 0.4 mg/mL resin and eluted isocratically, using low salt buffer of various compositions (see below). A chromatogram under conditions where good separation was found is shown in FIG. 115. The left peak corresponds to IgG1-7D8-K409R, the middle peak to IgG1-7D8-K409Rx2F8-F405L, and the right peak to IgG1-2F8-F405L. The resolution for the separation of the right peak and the heterodimeric protein was determined using the following equation 5:

$$R = \frac{2(t_b - t_a)}{1.7(W_a + W_b)} \quad \text{(Equation 5)}$$

$t_b$: retention time of the IgG1-2F8-F405L homodimer
$t_a$: retention time of the bispecific antibody
$W_a$: width of the heterodimeric protein peak at half height
$W_b$: width of the IgG1-2F8-F405L homodimer peak at half height.

In FIG. 116, the resolution, calculated using equation 5, was plotted as a function of pH, for two buffers with different ionic strength (10 and 20 mM citrate, pH 6.0-6.8 and 10 mM phosphate pH 6.8 and 7.2) with an overlapping pH region. Resolution was optimal in citrate buffer, pH 6.4. This condition was selected for WCIEX in isocratic mode.

Heterodimeric protein was spiked with 10% IgG1-2F8-F405L homodimer, mimicking a heterodimeric protein product obtained using SNEEP. The cation exchange column (2.5 mL scouting column, 10 cm bed height packed with high-performance Sepharose CM (GE Healthcare) was loaded with 1.0 mL of the mixture in 20 mM citrate, pH 6.4 (4 mg IgG per mL resin).

The FPLC elution profile shows a large peak, followed by a small peak (FIG. 117). In FIG. 118, the analytical CIEX profile of the pooled fractions of the large peak (S0002) is shown. Percentages of IgG1-7D8-K409, IgG1-7D8-K409Rx2F8-F405L, and IgG1-2F8-F405L after elution were 4.3%, 94.8%, and 0.9%, demonstrating that most of the IgG1-2F8-F405L mutant was removed using isocratic elution. As expected, the resolution between the IgG1-7D8-K409R homodimer and the heterodimeric protein was insufficient, as shown by a remaining 4.3% of the IgG1-7D8-K409R homodimer. However, as noted above it is assumed that the amount of IgG1-7D8-K409R homodimer can be reduced using SNEEP.

In summary, SNEEP in combination with isocratic elution on a WCIEX column was used to produce highly pure heterodimeric protein. Alternatively, SNEEP followed by protein A chromatography in combination with an AAA mutation (I253A, H310A, and H435A, as described in Example 64) that eliminates protein A binding can be used to reduce the amount of each homodimer in the bispecific product to below 1%.

Example 67: Bind-and-Elute Chromatography for 2-MEA Removal

It was investigated whether bind-and-elute chromatography (including, but not limited to, CIEX, affinity chromatography, HIC) can be used to remove the reducing agent 2-MEA from a heterodimeric protein preparation. Protein A affinity chromatography was used as a proof-of-principle, the performance of the column prior and after exposure to reducing agent was tested by determination of the point of breakthrough.

The heterodimeric protein product was prepared by incubating 10 mg IgG1-7D8-K409R and 10 mg IgG1-2F8-

F405L in 3 mL with 75 mM 2-MEA, at 31° C. for 5 hours. 3 mL protein product (total protein concentration ~20 mg/mL) was applied to a 5-mL protein A column using PBS for the equilibration and wash steps, and 20 mM citrate, pH 3.0 for elution. The FPLC elution profile was measured on an AKTA is shown in FIG. 119A. At 8 mL, the elution of the protein was marked by a strong increase in $A_{254}$ and $A_{280}$. At approximately 65 mL, the elution of the protein was marked by a strong increase in $A_{254}$. The increase in $A_{280}$ signal is due to the formation of cystamine during the reduction of bispecific antibody. A control run was carried out using PBS with 75 mM 2-MEA without protein (FIG. 119B). The increase in $A_{254}$ at approximately 8 mL marks the elution of 2-MEA. Note that the $A_{280}$ signal was only marginally increased compared to FIG. 119A, due to the absence of cystamine. A peak of equal intensity in the FT fraction was present in both chromatograms, indicating that 2-MEA did not bind to the column and that the protein was eluted.

To test whether column integrity was affected by the presence of 2-MEA, the point of breakthrough of the protein A column was determined before and after removal of 2-MEA (FIG. 120). The point of breakthrough was similar before and after exposure to 2-MEA, indicating that the performance of the column was not affected by the presence of 2-MEA.

To check whether protein A leaked of the column during 2-MEA removal, reduced SDS-PAGE analysis was performed on the purified product (FIG. 121). No bands were observed other than the expected bands of the heavy (50 kDa) and the light chain (25 kDa), indicating no significant loss of protein A upon exposure of the column to 2-MEA.

In summary, the FPLC chromatogram of heterodimeric protein with 75 mM 2-MEA showed a peak with a A280/A215 ratio indicative of the presence of 2-MEA in the flow-through. Point of breakthrough of the protein A column was similar before and after exposure to 2-MEA, indicating that the performance was unaffected by the presence of 2-MEA. Reducing SDS-PAGE showed intact IgG and no signs of protein A leakage, indicating that the column was resistant to 2-MEA. This indicated removal of the 2-MEA from the product.

Example 68: Formation of Bispecific Antibodies Starting with One κ Light Chain- and One λ Light Chain-Containing Homodimer and Purification Using LambdaFabSelect and KappaSelect To enable removal of residual amounts of homodimer in a bispecific antibody preparation, it was investigated whether bispecific antibodies with one κ and one λ light chain could be produced. The possibility of Fab-arm exchange between one IgG4 molecule containing a κ light chain and another IgG4 molecule containing a λ light chain was shown in vivo in patients treated with natalizumab (Labrijn et al. 2009 Nature Biotechnology p 767).

To show that Fab-arm exchange between an IgG1 molecule containing a κ light chain and another IgG1 molecule containing a λ light chain was possible, IgG1 homodimers IgG1-2F8-F405L and BMA 031-N297Q-K409R (IgG1/Lambda antibody against T-cell receptor alpha chain (Shearman et al. 1991 J. Immunol. 147(12): 4366-4373) with N297Q and K409R mutations; the N297Q mutation knocks out a glycosylation site; this does not influence the exchange process) were mixed in the molar ratio 1:1 at a concentration of 0.5 mg/mL each in 150 μL PBS and incubated in the presence of 75 mM 2-MEA at 31° C. for 5 hours. Next, 2-MEA was removed from the mixture by diafiltration to PBS (B. Braun, pH 7.4) using an Amicon Ultra 0.5 (10,000 MWCO, Millipore). FIG. 122 shows that Fab-arm exchange between an IgG1 molecules containing a κ light chain and another IgG1 molecule containing a λ light chain was possible, as analyzed by analytical CIEX.

To purify the bispecific antibodies from contaminating homodimers, neutralization will be performed using Tris, pH 9.0 after elution from protein A. Buffer will be exchanged to PBS by dialysis at 4° C., O/N. To remove non-binding, K light chain-containing homodimer, 4 mg bispecific antibody will loaded per mL LambdaFabSelect resin (1 mL HiTrap column, GE Healthcare Life Sciences, Uppsala, Sweden; cat. no 17-5482) at a loading flow rate of 0.1 mL/min (4 min residence time). Elution will be performed in 0.1 M acetate, pH 3.5. Neutralization will be performed using Tris, pH 9.0. Buffer will be exchanged to PBS by dialysis at at 4° C., O/N. To remove non-binding A light chain-containing homodimer, 4 mg eluted bispefic antibody will be loaded per mL KappaSelect (1 mL HiTrap column, GE Healthcare Life Sciences; cat. no 17-5458) at a loading flow rate of 0.1 mL/min (4 min residence time). Elution will be performed in 0.1 M glycine, pH 2.7, neutralization will be performed using Tris, pH 9.0. Buffer will be exchanged to PBS by dialysis at at 4° C., O/N.

For SNEEP, a 30% molar excess will be used of either the κ light chain-containing homodimer or the λ light chain-containing homodimer. The under-abundant species (i.e. λ light chain- and κ light chain-containing homodimer, respectively) will be bound to LambdaFabSelect or KappaSelect, respectively. In this manner, the excess of κ light chain-containing homodimer or λ light chain-containing homodimer will be removed. Wash and elution conditions as described above for the homodimers will be used for purification of the bispecific antibody.

Alternatively, if no SNEEP is performed, two sequential polishing steps will be performed using KappaSelect and LambdaFabSelect to remove all homodimers.

Example 69: Real Time and Stressed Stability of DuoBody and Homodimers in Phosphate Buffered Saline, pH 7.4

The biochemical stability of heterodimeric protein in PBS buffer was examined upon storage at 2-8° C. and at 25° C. for 12 months, in comparison with the original homodimers. Storage at the elevated temperature of 40° C. for three months was also included. Stability testing was performed with heterodimers formed by exchange of IgG1-2F8-F405L and IgG1-7D8-K409R and the corresponding homodimers IgG1-2F8-F405L and IgG1-7D8-K409R. The three materials were formulated at 5 mg/mL in PBS pH 7.4 (B. Braun, cat. no 3623140; 8.7 mM $HPO_4^{2-}$, 1.8 mM $H_2PO_4^-$, 163.9 mM $Na^+$, 140.3 mM $Cl^-$, pH 7.4). The batches were sterile dispensed as 300 μL aliquots in 1.0 mL cryo vials for incubation at 2-8° C. and in stoppered and capped glass vials for incubation at 25 and 40° C. Materials were analyzed at 0, 1, 2, 3, 6, 9 and 12 months on Nanodrop (A280 and A350), SDS-PAGE, HP-SEC and CIEX.

The measured A280 values were comparable for all samples stored at the different time points and temperatures, as shown in FIG. 123. The absorbance at 350 nm (A350) was also measured in the same sample, providing an indication for sample turbidity. A350 values for the heterodimeric protein and the homodimers did not increase upon storage, indicating that no extensive particulate formation occurred under these conditions.

FIGS. 124 and 125 show the results of non-reduced and reduced SDS-PAGE analysis of the materials at the start of the study and after 12 months storage at 2-8° C. and at 25° C. No significant changes occurred upon storage at 2-8° C. Storage at 25° C. induced small amounts of fragmentation on non-reduced SDS-PAGE and formation of additional bands at 71 and 113 kDa on reduced SDS-PAGE, which seemed to be slightly more for the heterodimeric protein than for the homodimers. The nature of these additional bands could be explained by the formation of non-reducible thio-ether linkages in the IgG molecule upon storage (loss of a sulphur from the disulfide bond). The stressed condition of 40° C. accelerated the fragmentation process and confirmed the results of incubation at 25° C. (FIGS. 126 and 127).

The materials were analyzed for fragmentation and multimerization using HP-SEC and representative chromatograms are shown in FIG. 128. The data summary in Table 17 shows that the heterodimeric protein and the homodimers were monomeric (>99% monomer) at the start of the study and after 12 months storage at 2-8° C. Some fragmentation, but no multimerization, was observed when materials were stored at 25° C. for 12 months. The degree of fragmentation for heterodimeric protein (2.3%) was in between the values of the two respective homodimers, IgG1-7D8-K409R (1.5%) and IgG1-2F8-F405L (6.3%), indicating that the heterodimeric protein was not more labile than the homodimers. Storage at 40° C. induced considerably more fragmentation (hinge fragmentation and loss of Fab fragments), which seemed to be somewhat higher for the heterodimeric protein than for the homodimers (15.6% compared to 3.5% and 10.6%). On the other hand, peak assignment and determination of peak percentages was difficult for these chromatograms, due to inadequate resolution.

The results of the CIEX analysis (charge profiles) at t=0 and t=12 months are shown in FIG. 129. The peak profile of the heterodimeric protein was comparable to that of the homodimers stored under the same conditions. Upon storage at 25° C., an increase in acidic peaks with decreasing neutral peak area was clearly visible for all materials. The acidification of IgG at elevated temperatures and pH is a common phenomenon for IgG and is mainly ascribed to deamidation of Asn residues to form Asp. The peak profiles at 25° C. storage showed that the heterodimeric protein was as susceptible to deamidation as the homodimer materials.

In conclusion, the stability data show that the heterodimeric protein was biochemically stable upon storage at 2-8° C. at 5 mg/mL in PBS pH 7.4 for at least 12 months, based on A280, SDS-PAGE, HP-SEC and CIEX analysis. At elevated temperatures of 25° C. and 40° C., behavior of the heterodimeric protein was comparable to the homodimer materials, but fragmentation seemed to be slightly more. The amount of fragmentation of the heterodimeric protein under stressed conditions can be reduced by formulating the material in other buffers with lower pH (pH 6, data not shown).

TABLE 17

HP-SEC data of heterodimeric protein, IgG1-7D8-K409R and IgG1-2F8-F405L at all time points and temperatures. Percentage of monomer, multimer and degradation are expressed as percentage of total peak height.

| | Incubation time (months) | | | | | | |
|---|---|---|---|---|---|---|---|
| | 0 | 1 | 2 | 3 | 6 | 9 | 12 |
| 2-8° C. | % monomer | | | | | | |
| Bispecific antibody | >99 | >99 | >99 | >99 | >99 | >99 | >99 |
| IgG1-7D8-K409R | >99 | >99 | >99 | >99 | >99 | >99 | >99 |
| IgG1-2F8-F405L | >99 | >99 | >99 | >99 | >99 | >99 | >99 |
| 25° C. | % monomer | | | | | | |
| Bispecific antibody | >99 | >99 | 98.7 | 98.6 | 98.1 | 97.5 | 96.9 |
| IgG1-7D8-K409R | >99 | >99 | >99 | >99 | 98.7 | 98.3 | 97.6 |
| IgG1-2F8-F405L | >99 | >99 | >99 | 99.0 | 98.6 | 94.3 | 93.1 |
| 25° C. | % fragmentation | | | | | | |
| Bispecific antibody | <1 | <1 | <1 | <1 | 1.2 | 1.8 | 2.3 |
| IgG1-7D8-K409R | <1 | <1 | <1 | <1 | <1 | 1.1 | 1.5 |
| IgG1-2F8-F405L | <1 | <1 | <1 | <1 | <1 | 5.2 | 6.3 |
| 40° C. | % monomer | | | | | | |
| Bispecific antibody | >99 | 96.9 | 93.4 | 83.3 | | | |
| IgG1-7D8-K409R | >99 | 98.0 | 95.9 | 95.4 | | | |
| IgG1-2F8-F405L | >99 | 94.7 | 90.8 | 88.6 | | | |
| 40° C. | % fragmentation | | | | | | |
| Bispecific antibody | <1 | 2.1 | 4.5 | 15.6 | | | |
| IgG1-7D8-K409R | <1 | 1.0 | 2.4 | 3.5 | | | |
| IgG1-2F8-F405L | <1 | 4.6 | 8.3 | 10.6 | | | |
| 40° C. | % multimer | | | | | | |
| Bispecific antibody | <1 | <1 | <1 | 1.1 | | | |
| IgG1-7D8-K409R | <1 | <1 | <1 | 1.1 | | | |
| IgG1-2F8-F405L | <1 | <1 | <1 | <1 | | | |

Percentages multimer were <1 for all materials stored at 2-8° C. and at 25° C.
Percentages fragmentation were <1 for all materials stored at 2-8° C.

The invention claimed is:

1. An in vitro method for production of a heterodimeric antibody comprising the following steps:
   a) incubating in a composition a first homodimeric antibody with a second homodimeric antibody under reducing conditions sufficient to allow reduction of the inter-chain disulfide bonds in the hinge region, wherein said first homodimeric antibody comprises an Fc region of an immunoglobulin, said Fc region comprising a first human IgG1 CH3 region, and said second homodimeric antibody comprises an Fc region of an immunoglobulin, said Fc region comprising a second human IgG1 CH3 region, wherein said first homodimeric antibody has a K409R amino acid substitution (numbering according to the EU Index), and said second homodimeric antibody has an amino acid substitution selected from the group consisting of: L368A, L368D, L368E, L368G, L368H, L368I, L368N, L368Q, L368R, L368S, L368T, L368V, L368W, D399A, D399F, D399H, D399K, D399R, D399Y, F405A, F405D, F405E, F405H, F405I, F405K, F405L, F405M, F405N, F405Q, F405S, F405T, F405V, F405W, F405Y, Y407G, Y407L, Y407M, and Y407W (numbering according to the EU Index), and wherein the reducing conditions comprise adding a reducing agent,
   b) subjecting the composition obtained from step a) to oxidizing conditions sufficient to allow oxidation of cysteines in the antibodies to inter-chain disulfide bonds, thereby obtaining a heterodimeric antibody.

2. The method according to claim 1, wherein the reducing conditions in step a) comprise adding a reducing agent.

3. The method according to claim 2, wherein the reducing agent is selected from the group consisting of: 2-mercaptoethylamine, a chemical derivative of 2-mercaptoethylamine, L-cysteine, and D-cysteine.

4. The method according to claim 1, wherein step a) comprises adding a metal chelating agent.

5. The method according to claim 4, wherein the metal chelating agent is EDTA, EGTA or citric acid.

6. The method according to claim 1, wherein the reducing conditions in step a) comprise reducing the amount of oxygen in the composition in step a).

7. The method according to claim 1, wherein step a) is performed under reducing conditions with a redox potential between −150 and −600 mV.

8. The in vitro method according to claim 1, wherein step a) comprises incubation for at least 30 min at a temperature of at least 20° C. in the presence of at least 25 mM of a reducing agent selected from the group consisting of 2-mercaptoethylamine, L-cysteine and D-cysteine.

9. The method according to claim 1, wherein the first and second homodimeric antibodies are in a buffer selected from the group consisting of a) 8.1 mM sodium phosphate ($Na_2HPO_4$-$7H_2O$), 1.5 mM potassium phosphate ($KH_2PO_4$), 138 mM sodium chloride (NaCl), 2.7 mM potassium chloride (KCl) pH 5.0; b) 8.1 mM sodium phosphate ($Na_2HPO_4$-$7H_2O$), 1.5 mM potassium phosphate ($KH_2PO_4$), 138 mM sodium chloride (NaCl), 2.7 mM potassium chloride (KCl) pH 7.0; and c) 20 mM Tris-HCl, pH 7.8.

10. The method according to claim 1, wherein step b) comprises a pH in the range of 6-8.5.

11. The method according to claim 1, wherein the oxidizing conditions in step b) comprise adding oxygen or an oxidizing agent.

12. The method according to claim 11, wherein the oxidizing agent is dehydroascorbic acid (dhAA).

13. The method according to claim 1, wherein step b) comprises separating the heterodimeric antibody and the reducing agent.

14. The method according to claim 1, wherein the oxidizing conditions in step b) comprise the steps of:
   I) diafiltration of the composition obtained from step a),
   II) incubation of the retentate obtained from step I), and
   III) diafiltration of the composition obtained from step II).

15. The method according to claim 1, wherein the oxidizing conditions in step b) comprise a metal ion or adding a metal ion.

16. The method according to claim 15, wherein the metal ion is selected from the group consisting of: Copper, Manganese, Magnesium, Iron, Nickel and Cobalt.

17. The method according to claim 1, wherein the ratio of first to second homodimeric protein in step a) is in the range of 1:1.01 to 1:2.

18. The method according to claim 1, wherein said first homodimeric antibody has no more than one amino acid substitution in the CH3 region, and the second homodimeric antibody has no more than one amino acid substitution in the CH3 region relative to the wild-type CH3 regions.

19. The method according to claim 1, wherein said first homodimeric antibody has Arg at position 409 and said second homodimeric antibody has Leu at position 405.

20. The method according to claim 1, wherein the first and/or second homodimeric antibody do not contain the c-terminal lysine.

21. The method according to claim 20, wherein the first and/or second homodimeric antibodies are genetically modified to lack the c-terminal lysine in the heavy chain, or wherein the c-terminal lysine is removed from the heavy chain.

* * * * *

UNITED STATES PATENT AND TRADEMARK OFFICE
CERTIFICATE OF CORRECTION

| | |
|---|---|
| PATENT NO. | : 11,492,371 B2 |
| APPLICATION NO. | : 16/426647 |
| DATED | : November 8, 2022 |
| INVENTOR(S) | : Michael Gramer et al. |

It is certified that error appears in the above-identified patent and that said Letters Patent is hereby corrected as shown below:

In the Claims

At Column 149, Claim number 3, Line number 34, delete "The method according to claim 2, wherein the reducing" and insert --The method according to claim 1, wherein the reducing--.

Signed and Sealed this
Seventeenth Day of January, 2023

Katherine Kelly Vidal
*Director of the United States Patent and Trademark Office*